United States Patent
Killmer et al.

(10) Patent No.: US 11,718,851 B2
(45) Date of Patent: *Aug. 8, 2023

(54) METHODS AND COMPOSITIONS FOR INCREASED DOUBLE STRANDED RNA PRODUCTION

(71) Applicant: RNAISSANCE AG LLC, Shawnee Mission, KS (US)

(72) Inventors: John L. Killmer, St. Louis, MO (US); Patrick D. McLaughlin, St. Louis, MO (US); Juan Pedro Humberto Arhancet, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/922,948

(22) Filed: Jul. 7, 2020

(65) Prior Publication Data

US 2022/0145294 A1 May 12, 2022

Related U.S. Application Data

(63) Continuation of application No. 16/084,545, filed as application No. PCT/US2017/021661 on Mar. 9, 2017, now Pat. No. 10,704,045.

(60) Provisional application No. 62/308,381, filed on Mar. 15, 2016.

(51) Int. Cl.
| | | |
|---|---|---|
| *C12N 15/113* | (2010.01) | |
| *C12N 15/11* | (2006.01) | |
| *C07K 14/005* | (2006.01) | |

(52) U.S. Cl.
CPC .......... *C12N 15/113* (2013.01); *C07K 14/005* (2013.01); *C12N 15/111* (2013.01); *C12N 2310/14* (2013.01); *C12N 2330/50* (2013.01); *C12N 2795/18122* (2013.01)

(58) Field of Classification Search
CPC .. C12N 15/113; C12N 15/111; C12N 2330/50
See application file for complete search history.

(56) References Cited

U.S. PATENT DOCUMENTS

| 8,324,149 B2 | 12/2012 | Bundy et al. |
| 10,704,045 B2 | 7/2020 | Killmer et al. |
| 2004/0214318 A1 | 10/2004 | Chapman et al. |
| 2009/0263364 A1 | 10/2009 | Bogaert et al. |
| 2013/0167267 A1 | 6/2013 | Arhancet et al. |
| 2014/0271559 A1 | 9/2014 | Baum et al. |
| 2014/0302593 A1 | 10/2014 | Arhancet et al. |
| 2016/0194613 A1 | 7/2016 | Williams et al. |

FOREIGN PATENT DOCUMENTS

| WO | 2013/117910 A1 | 8/2013 |
| WO | 2014/152432 A2 | 9/2014 |
| WO | 2014/204667 A1 | 12/2014 |
| WO | 2015/042556 A1 | 3/2015 |
| WO | 2015/073720 A1 | 5/2015 |
| WO | 2016/183022 A1 | 11/2016 |
| WO | 2017/160600 A1 | 9/2017 |

OTHER PUBLICATIONS

Dykeman et al., "Packaging Signals in Two Single-Stranded RNA Viruses Imply a Conserved Assembly Mechanism and Geometry of the Packaged Genome," Journal of Molecular Biology, 2013, pp. 3235-3249, vol. 425, No. 17.
International Search Report and Written Opinion relating to International Application No. PCT/US2017/021661, dated May 24, 2017; 13 pgs.
Supplementay European Search Report and Written Opinion relating to EP Application No. 17767194 8, dated Sep. 27, 2019; 7 pgs.
Aalto et al., "Large-scale production of dsRNA and siRNA pools for RNA interference utilizing bacteriophage 6 RNA-dependent RNA polymerase," RNA, 2007, pp. 422-429, vol. 13, No. 3.
Atayde et al., "A single-cloning-step procedure for the generation of RNAi plasmids producing long stem-loop RNA," Molecular and Biochemical Parasitology, 2012, pp. 55-58, vol. 184, No. 1.
Garcia et al., "MS2 coat proteins bound to yeast mRNAs block 5' to 3' degradation and trap mRNA decay products: implications for the localization of mRNAs by MS2-MCP system," RNA, 2015, pp. 1393-1395, vol. 21, No. 8.
Haimovich et al., "Use of the MS2 aptamer and coat protein for RNA localization in yeast: A response to "MS2 coat proteins bound to yeast mRNAs block 5' to 3' degradation and trap mRNA decay products: implications for the localization of mRNAs by MS2-MCP system"," RNA, 2016, pp. 660-666, vol. 22, No. 5.
Huang et al., "Efficient and specific gene knockdown by small interfering RNAs produced in bacteria," Nature Biotechnology, 2013, pp. 350-356, vol. 31, No. 4, with Supplementary Data.
Seroussi et al., "Detection of Killer-Independent dsRNA Plasmids in Ustilago maydis by a Simple and Rapid Method of Extraction of dsRNA," Plasmid, 1989, pp. 216-225, vol. 21, No. 3.
Wei et al., "Construction of Armored RNA Containing Long-Size Chimeric RNA by Increasing the Number and Affinity of the iPac Site in Exogenous RNA and Sequence Coding Coat Protein of the MS2 Bacteriophage," Intervirology, 2008, pp. 144-150, vol. 51, No. 2.
International Search Report and Written Opinion relating to International Application No. PCT/US2020/035339, dated Oct. 8, 2020; 18 pgs.
International Search Report and Written Opinion relating to International Application No. PCT/US2020/035357, dated Sep. 3, 2020; 7 pgs.

*Primary Examiner* — J. E. Angell
(74) *Attorney, Agent, or Firm* — Polsinelli PC; Tara A. Nealey

(57) ABSTRACT

The invention provides methods and compositions for improved production of large quantities of unencapsidated double strand RNA (dsRNA) in vivo. The disclosed methods and compositions, comprising co-expression of genes encoding orotate phosporibosyl transferase, bacteriophage coat protein and dsRNA produce a significant improvement over current in vivo methods of producing unencapsidated dsRNA.

19 Claims, 6 Drawing Sheets

Specification includes a Sequence Listing.

METHODS AND COMPOSITIONS FOR INCREASED DOUBLE STRANDED RNA PRODUCTION

CROSS-REFERENCE TO RELATED APPLICATIONS

This application is a continuation application of U.S. application Ser. No. 16/084,545, filed Sep. 12, 2018, which is a U.S. National Stage Application of International Application Number PCT/US2017/021661, filed Mar. 9, 2017, which claims the benefit of U.S. Provisional Application No. 62/308,381, filed Mar. 15, 2016, the contents of all of which are incorporated herein by reference in their entirety.

SEQUENCE LISTING

This application contains a Sequence Listing that has been submitted in ASCII format via EFS-Web and is hereby incorporated by reference in its entirety. The ASCII copy is named 066803-662723_Sequence_Listing_ST25.txt, and is 409 kilobytes in size.

FIELD OF THE INVENTION

The present invention relates to methods and compositions for increasing in vivo production of double-stranded RNA.

BACKGROUND OF THE INVENTION

The ability to suppress gene expression with RNA homologous to targeted gene sequences has greatly increased demand for large scale production of such RNA. However, the chemical fragility of RNA limits commercial development of many of these techniques. Large scale production of purified RNA is constrained by the high costs associated with in vitro synthesis methods and by the low yields and complex processing requirements associated with in vivo methods.

The susceptibility of RNA to enzymatic and environmental degradation varies widely depending on the nature of the RNA molecule. Single-stranded RNA (ssRNA) is extremely sensitive to degradation and in vivo production of such molecules requires use of production strains lacking endogenous RNAses and benefits by coupling production of the RNA to encapsidation within viral capsid shells to produce Virus-Like Particles (VLPs). Encapsidation reduces degradation of RNA during production and allows more aggressive treatment during purification. VLPs effectively preserve such fragile RNA from degradation by sequestering the RNA within a relatively inert protein shell. Double stranded RNA (dsRNA) are somewhat less susceptible to degradation by cellular and environmental RNAses, although the highest in vivo yields of dsRNA also involve production strains lacking RNAses and many dsRNA also benefit from encapsidation. Unfortunately, the semi-rigid nature of the double-stranded stem region of dsRNA limits the range of dsRNA that can be encapsidated since the length of the double-stranded stem structure cannot exceed the interior diameter of the capsid.

In the course of exploring techniques for increasing the range of dsRNA stems that can be encapsidated, the inventors discovered that under certain conditions a large amount of unencapsidated dsRNA can be recovered directly from cell lysates, but only when the host cells co-express capsid protein or specific portions thereof The presence of high quantities of intact unencapsidated dsRNA in crude cell lysates represents a significant advance in the ability to generate commercial quantities of such RNA for gene suppression and other activities.

Dimers of bacteriophage capsid proteins such as those of the leviviruses MS2 or Q13 recognize and bind with affinity to cognate pac sequences. Such pac sequences comprise approximately 19-21 nucleotides comprising an 8 base pair bulged stem and 4 base loop capable of forming a discrete hairpin structure. Such sequences may be referred to herein as pac-sites, pac sequences, pac-site sequences, pac-site hairpins, or pac-site hairpin sequences. The interaction of capsid dimers with their cognate pac site hairpin is well-characterized and is known to play at least two key roles in the bacteriophage life cycle. Binding of capsid dimers to the cognate pac sites is required for programmed translational repression of the phage encoded replicase, which is only expressed early in infection. In addition, capsid protein binding to both to pac-site sequences and multiple dispersed and degenerate RNA sites with cognate coat protein affinity (the packaging signals described by Dykeman et al., *Packaging Signals in Two Single-Stranded RNA Viruses Imply a Conserved Assembly Mechanism and Geometery of the Packaged* Genome J. Mol. Biol. 425:3235-3249 (2013)) are required for proper assembly into progeny bacteriophage.

The interaction of capsid dimers with cognate pac sites is the subject of a number of different published in vitro and in vivo methods designed to allow encapsidation of heterologous RNAs of various kinds by associating the desired cargo molecule with pac site sequences, either by direct covalent linkage or by various affinity methods. The present invention differs markedly from such approaches in that it comprises co-expression of capsid proteins to produce unencapsidated dsRNA rather than encapsidated RNA. Further, the present invention allows in vivo production of dsRNA entirely lacking pac or any recognized dispersed and degenerate RNA sites with cognate protein affinity. In vivo production of such dsRNA molecules is highly desirable since reducing extraneous sequence reduces the chance of off-target RNAi interactions.

SUMMARY OF THE INVENTION

The invention described in the following embodiments provides methods and compositions for producing large quantities of unencapsidated dsRNA in vivo. The disclosed methods and compositions represent a significant improvement over current in vivo methods of producing dsRNA.

In an embodiment the invention comprises a microbial cell containing a gene encoding a self-complementary stretch of sequence separated by non-complementary sequence such that upon hybridization of the complementary sequences a stem-loop structure is formed, wherein the stem portion of the molecule functions as an RNAi precursor when introduced into the target organism. The microbial cell also contains a bacteriophage coat protein gene encoding a capsid protein. Expression of the dsRNA gene and the coat protein gene results in increased accumulation of un-degraded dsRNA and capsid protein. The amount of dsRNA produced in this way greatly exceeds the amount of dsRNA produced in the absence of capsid protein.

In one embodiment the bacteriophage capsid protein is encoded by the coat protein gene of a species of leviviridae. In a preferred embodiment the coat protein gene encodes the capsid protein of bacteriophage MS2. In another preferred embodiment the coat protein gene encodes the capsid protein of bacteriophage Qbeta.

In an embodiment the capsid protein comprises the N-terminus of the MS2 capsid protein. In another embodiment the capsid protein comprises the N-terminal 41, 35, 25, 21 or 12 amino acids of the MS2 capsid protein. In an embodiment the capsid protein comprises the N-terminus of the Qbeta capsid protein. In another embodiment the capsid protein comprises the N-terminal 41, 35, 25, 21 or 12 amino acids of the Qbeta capsid protein.

In an embodiment the gene encoding the dsRNA may be associated with and expressed from an inducible transcriptional promoter. The coat protein gene may be associated with and expressed from a constitutive or inducible transcriptional promoter. The inducible transcriptional promoter associated with expression of the dsRNA may be the same inducible transcriptional promoter or a different transcriptional promoter from a transcriptional promoter associated with expression of the coat protein gene. In one embodiment the inducible transcriptional promoter associated with expression of the coat protein gene is induced before induction of the inducible transcriptional promoter associated with expression of the dsRNA to allow accumulation of capsid protein prior to production of dsRNA. In another embodiment the transcriptional promoter associated with expression of the coat protein gene is a constitutive transcriptional promoter.

In an embodiment the gene encoding the dsRNA and the coat protein gene encoding the capsid protein are present on a plasmid or extrachromosomal element. The gene encoding the dsRNA and the coat protein gene may be present on the same plasmid or extrachromosomal element or may be present on separate plasmids or extrachromosomal elements. In another embodiment one or both of the genes encoding the dsRNA and the coat protein may be present on the microbial host cell chromosome or chromosomes.

In related embodiments, the dsRNA may be purified from the microbial host cell by lysing the cells to produce a lysate and purifying the dsRNA from the cellular constituents within the lysate prior to processing the purified dsRNA for application. Such processing may include, but is not limited to mixing with excipients, binders or fillers to improve physical handling characteristics, stabilizers to reduce degradation, or other active agents such as chemical pesticides, fungicides, defoliants or other RNAi molecules to broaden the spectrum of application targets, and may include pelletizing, spray drying or dissolving the materials into liquid carriers. In another embodiment the dsRNA is not further purified from the lysate but is processed directly for application. In still another embodiment the microbial host cell is not lysed but is processed directly for application and the dsRNA remains unpurified within the processed cells.

DETAILED DESCRIPTION OF THE INVENTION

The present invention comprises compositions and methods for producing large quantities of dsRNA in vivo and in some embodiments, recovering such dsRNA directly from cell lysates. In its most basic form, the invention involves co-expressing a bacteriophage capsid protein, or a portion thereof, in conjunction with the desired dsRNA for a period of time sufficient to allow accumulation of the dsRNA in a host cell, lysing the host cell, and optionally recovering intact unencapsidated dsRNA directly from the cell lysate. In the absence of bacteriophage capsid protein intact dsRNA is present in cell lysates in only very small quantities, if at all. In contrast, in the presence of bacteriophage capsid protein a relatively large quantity of unencapsidated dsRNA can be recovered from cell lysates.

A number of permutations of RNA structure and coat protein were explored to determine the essential elements of the invention and to optimize the yield of dsRNA produced by the invention. This work is summarized in Table 1 which outlines the various elements of the invention described in detail and in the examples below. The leftmost column of Table 1 refer to individual figures representing cartoon depiction of the predicted RNA structure produced from each of the listed plasmid constructs. In each figure "S" represents the sense strand, "AS" represents antisense strand, and the small hairpin structures represent pac site sequences). The table also lists the coat protein (if any) and the yields of dsRNA (or ssRNA, as indicated) associated with each of the listed plasmid constructs.

TABLE 1

Production of RNA by *E. coli* HT115(DE3) as a function of variation in RNA structure and the presence or absence of coat protein and coat protein variants (n.a. = not applicable; n.d. = not determined).

Figure 1:
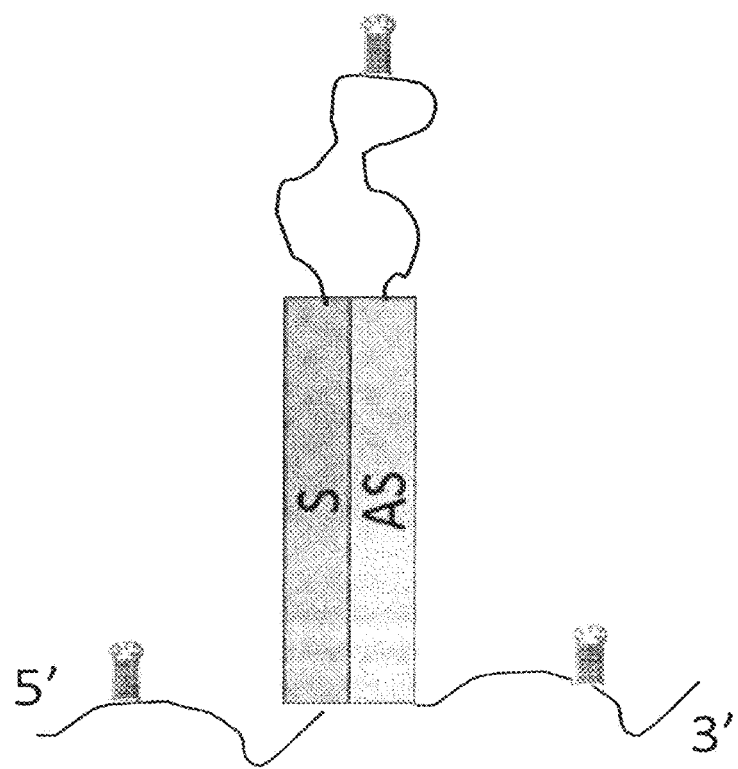
FIG. 1 depicts an RNA stem-loop structure with three pac-site hairpin sequences, one located 5' of the stem-loop structure, one within the loop of the stem-loop structure, and the other 3' of the stem-loop structure.
Figure 2:
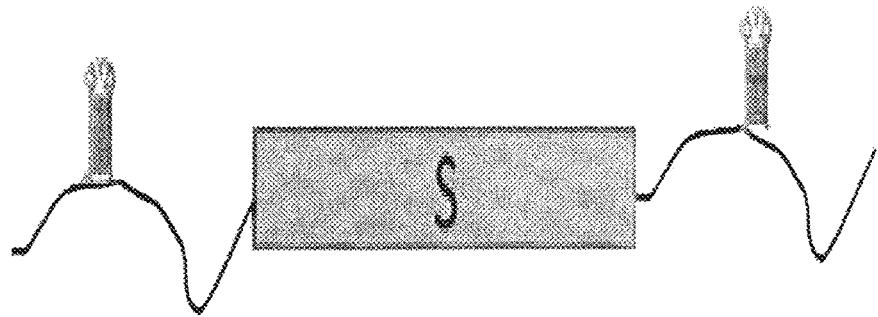
FIG. 2 depicts a single strand (sense) sequence flanked on each side by a pac-site hairpin sequence.
Figure 3:
FIG. 3 depicts a single strand (antisense) sequence flanked on each side by a pac-site hairpin sequence.

| RNA Structure as depicted in | Plasmid | Loop size (bases) | Stem size (bp) | Stem sequence | Coat protein | RNA en capsid (mg/L) | RNA ex capsid (mg/L) |
|---|---|---|---|---|---|---|---|
| FIG. 1 | pAPSE10180 | 139 | 180 | ErkA | M52 | <2 | 75-90 |
| FIG. 1 | pAPSE10181 | 139 | 180 | ErkA | none | n.a | <2 |
| FIG. 2 | pAPSE10189 | n.a. | n.a. | beta actin | MS2 | 20 | <2 |
| FIG. 3 | pAPSE10190 | n.a. | n.a. | beta actin | MS2 | 20 | <2 |
| FIG. 2 | pAPSE10274 | n.a. | n.a. | beta actin | none | n.a. | <2 |
| FIG. 3 | pAPSE10275 | n.a. | n.a. | beta actin | none | n.a. | <2 |

TABLE 1-continued

Production of RNA by *E. coli* HT115(DE3) as a function of variation in RNA structure and the presence or absence of coat protein and coat protein variants (n.a. = not applicable; n.d. = not determined).

Figure 4:
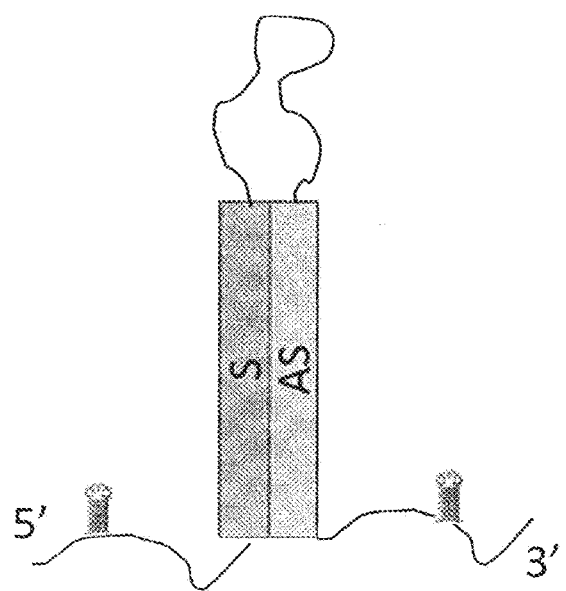
FIG. 4 depicts an RNA stem-loop structure with two pac-site hairpin sequences, one located 5' of the stem-loop structure and the other 3' of the stem-loop structure.
Figure 5:
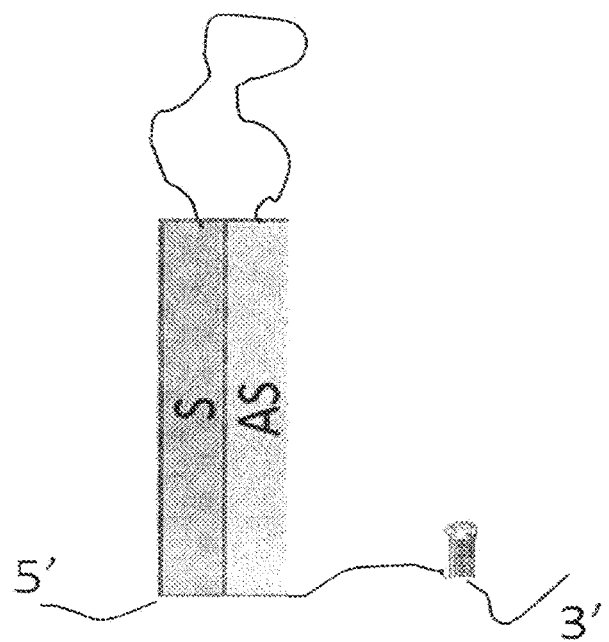
FIG. 5 depicts an RNA stem-loop structure with a single pac-site hairpin sequence located 3' of the stem-loop structure.
Figure 6:
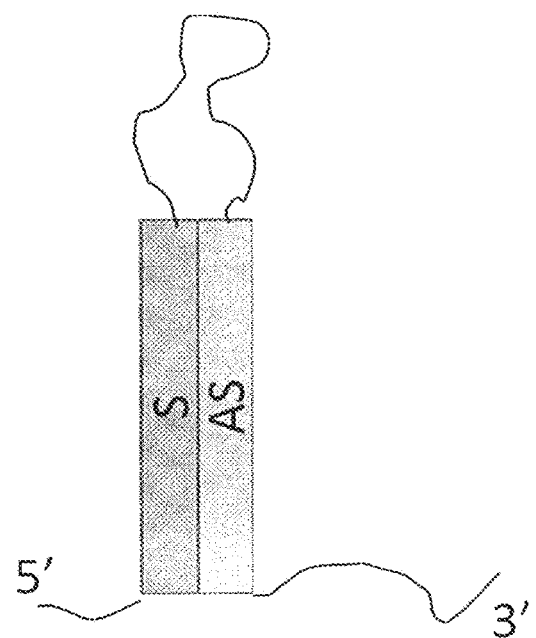
FIG. 6 depicts an RNA stem loop structure lacking any pac site hairpin sequences.

| RNA Structure as depicted in | Plasmid | Loop size (bases) | Stem size (bp) | Stem sequence | Coat protein | RNA en capsid (mg/L) | RNA ex capsid (mg/L) |
|---|---|---|---|---|---|---|---|
| FIG. 1 | pAPSE10269 | 166 | 294 | beta actin | MS2 | 2-10 | 200 |
| FIG. 1 | pAPSE10306 | 166 | 294 | beta actin | none | n.a. | 3 |
| FIG. 4 | pAPSE10216 | 166 | 294 | beta actin | MS2 | 5-20 | 50-250 |
| FIG. 4 | pAPSE10305 | 166 | 294 | beta actin | none | n.a. | 4 |
| FIG. 5 | pAPSE10219 | 166 | 294 | beta actin | MS2 | 5-20 | 30-60 |
| FIG. 5 | pAPSE10304 | 166 | 294 | beta actin | none | n.a. | 3 |
| FIG. 6 | pAPSE10279 | 166 | 294 | beta actin | MS2 | 4 | 65 |
| FIG. 6 | pAPSE10303 | 166 | 294 | beta actin | none | n.a. | 4 |
| FIG. 4 | pAPSE10270 | 116 | 294 | beta actin | MS2 | 2-10 | 200 |
| FIG. 4 | pAPSE10271 | 136 | 294 | beta actin | MS2 | 2-10 | 200 |
| FIG. 4 | pAPSE10272 | 156 | 294 | beta actin | MS2 | 2-10 | 200 |
| FIG. 4 | pAPSE10292 | 131 | 294 | beta actin | MS2 | 2-10 | 150 |
| FIG. 4 | pAPSE10291 | 142 | 294 | beta actin | MS2 | 2-10 | 160 |
| FIG. 4 | pAPSE10276 | 166 | 50 | beta actin | MS2 | 5-10 | 80-120 |
| FIG. 4 | pAPSE10277 | 166 | 75 | beta actin | MS2 | 20-30 | 200-250 |
| FIG. 4 | pAPSE10366 | 166 | 294 | beta actin | MS2 | n.a. | |
| FIG. 4 | pAPSE10181 and pAPSE10149 | 139 | 180 | beta actin | MS2 | n.d. | 200 |
| FIG. 1 | pAPSE10359 | 166 | 294 | beta actin | MS2 | n.d. | n.d. |
| FIG. 4 | pAPSE10357 | 166 | 294 | Beta actin | None (U1A) | n.d. | n.a. |
| FIG. 1 | pAPSE10372 | 139 | 180 | ErkA | None (MS2 N-term fragment | n.d. | 75 |

A. Definitions

As used herein, the term "capsid protein" or "capsid" refers to the coat protein of bacteriophage MS2 or Q13, capable of binding the bacteriophage RNA pac site with high affinity and assembling into a complex hollow tertiary structure in which the bacteriophage RNA is entirely encapsidated within the hollow tertiary structure. In a VLP, the capsid protein forms a hollow tertiary structure in which the heterologous RNA is entirely encapsidated. The term "capsid" also refers to the hollow tertiary structure formed by assembly of individual capsid proteins.

As used herein "ssRNA" and "dsRNA" refer to "single-stranded RNA and double stranded RNA, respectively. An ssRNA is comprised of an RNA sequence of any length that lacks sufficient internal homology to form any significant secondary structures such as hairpins or other structures dependent on hybridization of internal complementary sequences with one another via Watson-Crick base pairing of nucleotide bases between the complementary sequences. In contrast, a dsRNA comprises RNA sequences with sufficient internal homology to form significant secondary structures such as hairpins due to hybridization of internal complementary sequences with one another via Watson-Crick base pairing of nucleotide bases within the complementary sequences. Significant secondary structures generally involve stretches of homology greater than approximately nine bases, but the exact length depends to some extent on context and on whether such secondary structures impart any biological function to the molecule.

As used herein "plasmid" or "extrachromosomal element" refers to any extrachromosomal episome capable of replication or stable maintenance within the host cell. Specifically embraced by this definition are plasmids such as pBR322, pCGl, and pACYC184 which represent the backbones of the described plasmids. Those of ordinary skill in the art will recognize that other plasmids or stably maintained viral episomes can provide the same required functions of maintenance, expression and selection and that alternatives to the basic plasmids described herein may be generated from such other plasmids or stably maintained viral episomes without undue experimentation. A key feature of the present invention is the ability to express the genes encoding a dsRNA and a capsid protein, not specific modes of replication, expression or the selective markers found on episomes containing the genes encoding the dsRNA and capsid protein.

"Substantially similar sequence" refers to sequence variants of the claimed capsid proteins that retain the ability to facilitate accumulation of dsRNA in a microbial host cell as described herein. Such substantially similar sequences include sequences with at least 26% identity and 47% similarity as shown by the differences between MS2 and Qbeta capsid protein sequences (as determined by blastp). Consequentially, substantially similar sequences encompass conserved and homologous substitutions allowing sequence variants with as little as 95%, 90%, 80%, 70%, 60%, 50%, 40%, 30% or 25% identity to, and 95%, 90%, 80%, 70%, 60%, 50% or 40% similarity to, MS2 or Qbeta capsid protein sequences to facilitate accumulation of dsRNA in a microbial host.

B. Common Materials and Methods

Routine microbial and molecular cloning methods and tools, including those for generating and purifying DNA, RNA, and proteins, and for transforming host organisms and expressing recombinant proteins and nucleic acids as described herein, are fully within the capabilities of a person of ordinary skill in the art and are well described in the literature. See, e.g., Sambrook, et al., Molecular Cloning: A Laboratory Manual, 2nd ed., Cold Spring Harbor Laboratory Press, Cold Spring Harbor, N.Y. (1989); Davis, et al., Basic Methods in Molecular Biology, Elsevier Science Publishing Co., Inc., N.Y. (1986); and Ausubel, et al, Current Protocols in Molecular Biology, Greene Publ. Assoc., Wiley-Interscience, NY (1995). The disclosures in each of which are herein incorporated by reference.

Each of the recombinant DNA constructs described in further detail below are based on a common plasmid vector series derived from plasmid pBR322. The first of this plasmid vector series contains a custom synthetic DNA fragment (produced by PCR GenScript, Piscataway, N.J.) comprising a T7 promoter sequence capable of driving transcription of a single copy of the bacteriophage MS2 capsid gene followed by a T7 terminator. This synthetic sequence was inserted as a BamHI-SphI restriction fragment into the corresponding sites of pBR322 to form plasmid pAPSE10118. A second synthetic sequence comprising a T7 promoter sequence followed by an MS2 pac site sequence, a multi-cloning site containing, in order (5' to 3') AsiSI-PmeI-AscI-RsrII-NotI-PacI restriction sites, a second high affinity variant MS2 pac type sequence (C-pac), a T7 terminator and an SphI restriction site was synthesized (PCR Genscript, Piscataway, N.J.) and inserted into the EcoRV site of pAPSE10118 to form pAPSE10136. The two are oriented such that the T7 promoters direct transcription of the same strand of pAPSE10136 (clockwise on the standard pBR322 map) but are separated from one another by a single T7 terminator.

A 180 nucleotide fragment of the ErkA gene of *Drosophila melanogaster* (corresponding to the sequence of GenBank Accession NM_001300706 between nucleotides 156-335) was amplified by PCR incorporating AsiSI and PmeI restriction sites on the 5' and 3' sides, respectively. Insertion of this ErkA gene fragment into the corresponding sites of pAPSE10136 produced pAPSE10169. A second, complimentary copy of the ErkA gene fragment sequence was generated by PCR amplification incorporating a PmeI restriction site on the 5' end, followed by a synthetic loop sequence containing an additional MS2 pac sequence, followed by a NotI restriction site, followed by the complementary (anti-sense) ErkA gene fragment sequence and a PacI restriction site on the 3' end of the PCR fragment. The synthetic loop sequence comprises random sequence incapable of hybridizing with the ErkA gene fragment sequences. This complementary (anti-sense) copy of the ErkA gene fragment is inserted into the PmeI and PacI restriction sites of pAPSE10136 to form pAPSE10180 (SEQ ID NO: 1). A second series of plasmid vectors, lacking the MS2 capsid protein is derived from pAPSE10180 by deleting the MS2 capsid expression sequences by SphI restriction digestion and re-ligation to produce pAPSE 10181 (SEQ ID NO: 2).

Plasmids pAPSE10180 and pAPSE10181 represent the basic platform for expression of the RNA constructs discussed herein. Transcription of the ErkA cassette in these plasmids is predicted to produce an RNA transcript capable of forming a large stem-loop structure comprising a 180 base pair stem and a 139 base loop with 3 individual MS2 pac sequences located 5' and 3' of the stem and within the loop itself. One of ordinary skill in the art will understand that substitution of the ErkA gene fragment sequences by other sequences can be easily accomplished by standard cloning and sub-cloning methods.

Transformation of plasmids pAPSE10180 or pAPSE10181, or any of their derivatives, into host cells capable of inducible expression of T7 polymerase produces cell lines capable of expressing RNA transcripts. All such strains inducibly producing RNA transcripts are referred to generally herein as "expression strains". Unless otherwise indicated, each of the plasmids described herein was electroporated into *E. coli* strain HT115(DE3) with genotype F⁻, mcrA, mcrB, IN (rrnD-rrnE)1, rnc14:: Tn10 (Lambda DE3 lysogen: lacUV 5 promoter-T7 polymerase)) and the resulting recombinant transformants were selected on LB agar plates containing 12 μg/ml tetracycline and/or 100 μg/ml ampicillin. Single colonies were isolated, the presence of intact plasmid confirmed by restriction enzyme analysis and the confirmed transformed cells archived for future use.

Standard expression studies comprised inoculating transformed cells into 100 ml of Super Broth containing 0.1% glucose, 0.4% lactose, 100 μg/ml ampicillin and/or 12.5 μg/ml tetracycline and incubating the cultures with vigorous shaking at 37° C. Expression of the T7 polymerase was achieved by auto-induction by depletion of the available glucose and the presence of the lactose inducer. This ensures that all cultures are induced at the same growth stage. Cells were harvested twelve to eighteen hours post-induction (late stationary phase) by centrifugation at 3,000 g at 4° C. for 30 minutes and stored on ice until lysis.

RNA was isolated from harvested cells by resuspending a 5 ml equivalent of cell culture of harvested cells in sonication buffer comprising Tris-HCl pH 7, 10 mM NaCl and sonicating the suspended cells on ice for 3 minutes. Cell debris was removed by centrifugation at 16,000 g the supernatant (cleared lysate) was immediately processed to recover RNA and VLPs as described. RNA was recovered from half of the cleared lysate using the commercial Purelink RNA Mini Kit method (Ambion Cat. No. 12183018A, Thermo Fisher Scientific Inc., Waltham, Mass.) according to the manufacturer's instructions.

VLPs were purified from the remaining half of the cleared lysate which were diluted to a total volume of 1 ml and treated with 100 units of Benzonase® Nuclease (Sigma Aldrich, St. Louis, Mo.) at 37° C. for two hours. Subsequently, 0.15 mg of Proteinase K was added and the enzymatically treated cleared lysate incubated at 37° C. for an additional three hours. The VLPS were recovered from the enzymatically treated cleared lysate by fractional precipitation. A saturated ammonium sulfate solution was prepared by adding ammonium sulfate to water until it reached saturation (approximately 4.1 M). Fifty microliters of the saturated ammonium sulfate solution was added to the enzymatically treated cleared lysate and the mixture placed on ice and incubated for two hours. Unwanted precipitate was removed from the mixture by centrifugation at 16,000 g and the aqueous solution transferred to a clean Eppendorf tube. The aqueous solution was then subjected to a second precipitation by the addition of 0.171 g of dry ammonium sulfate directly to the aqueous solution. The aqueous solution was vortexed and incubated on ice for two hours. The precipitate was spun down at 16,000 g the aqueous phase discarded and the solid precipitate representing purified VLPs resuspended in 100 microliters of sonication buffer.

RNA was recovered from the resuspended purified VLPs by adding 3 volumes of Trizol LS Reagent (Ambion Cat. No. 10296028, Thermo Fisher Scientific Inc.), vigorously vortexing the mixture, adding 1 ml of chloroform, further vortexing the mixture before pulse centrifugation to separate the aqueous and organic phases of the mixture. The aqueous phase was placed in a clean Eppendorf tube and the RNA purified with a commercial RNA Clean & Concentrator™ kit (Cat. No. R1018, Zymo Research, Irvine, Calif.) according to the manufacturer's instructions.

RNA from bacterial and VLP samples were dissolved in 50 ul of nuclease-free water. To determine the concentration of dsRNA in a sample, the samples were treated with RNAse A (Invitrogen Cat. No. AM2274, Thermo Fisher Scientific Inc.) to degrade single stranded RNA under the manufacturers recommended conditions, the concentration of dsRNA was determined spectrophotmetrically by measuring $OD_{260}$ and 1 µg loaded onto Novex 6% TBE-urea gels (Invitrogen, Thermo Fisher Scientific Inc.). One lane of each gel was loaded with dsDNA size markers of known concentration and the samples were electrophoresed, the gel was stained with ethidium bromide and each band quantitated by densitometry using the dsDNA markers as a standard curve.

RNA yields from constructs producing ssRNA were determined by annealing the sense or anti-sense strand recovered from the induced cells or VLPs with an excess of the cognate strand. The annealed mixture was then treated with RNAse A and the amount of dsRNA incorporating the ssRNA of interest measured as described above.

Little or no differences in final cell densities were observed between any of the cultures from which the samples were harvested and in all cases the cultures appear to have reached stationary phase prior to harvest. To allow direct sample to sample comparison of RNA yields, all dsRNA and ssRNA concentrations are reported as the amount of such RNA present in a 1 L equivalent of culture.

Northern blot analysis was used to verify the identity of bands containing the dsRNA transcripts using a DNA oligonucleotide probe against the random sequence comprising the loop of each dsRNA construct (5'-GGCCGGCGTCT-ATTAGTAGATGCC-3', SEQ ID NO 3). RNA from the 6% polyacrylamide denaturing Urea-TBE gel was transferred to a positively-charged BrightStar-Plus nylon membrane (Ambion Cat. No. 10102, Thermo Fisher Scientific Inc.) using the semi-dry Trans-Blot SD transfer apparatus (BioRad, Hercules, Calif.) for 1 hour at constant current of 0.3 A. RNA was fixed on the membrane by the SpectroLinker XL-1500 UV crosslinking apparatus (Spectronics Corporation, Westbury, N.Y.) using the "optimal crosslink" setting. The membrane was briefly rinsed with water and prehybridized in 50 ml of 5×SSC, 0.1% SDS buffer at 45° C. with gentle shaking. Probe hybridization was carried out overnight at 45° C. in 3 ml of prehybridization buffer with gentle shaking. The oligonucleotide probe targeting the hairpin RNA loop was conjugated with TAMRA. Three washes (for 2 minutes each) with 100 ml of water were completed at room temperature and the blot with a ChemiDoc MP imaging system (BioRad, Hercules, Calif.), using the rhodamine channel.

C. Preferred Embodiments

The following are among the preferred embodiments of the invention.

One embodiment of the present invention comprises a bacterial host cell containing a plasmid encoding both a gene for the desired dsRNA. and a bacteriophage capsid protein gene, such that the dsRNA and the capsid protein genes are transcribed so that the desired dsRNA is produced and the capsid protein gene translated to produce capsid protein and wherein, after a suitable period of time, unencapsidated dsRNA accumulates within the cell to a much higher degree than in the absence of capsid protein. In other embodiments the dsRNA gene and the capsid protein gene may be present on separate compatible plasmids, autonomously maintained phage or other epigenetic elements, or one or both genes may be present within the chromosome of the bacterial host cell.

In an embodiment the dsRNA gene and the capsid protein gene are each transcribed from a transcriptional promoter. The transcriptional promoter may be inducible. In one embodiment the transcriptional promoters are identical; in other embodiments the promoters are different. In still other embodiments the transcriptional promoters may be differentially induced. In such differentially inducible embodiments it may be preferable to induce expression of the capsid protein prior to inducing expression of the dsRNA.

In another embodiment the capsid protein and the dsRNA may be transcribed as a single transcript from a single promoter. The promoter may be inducible. In such embodiments the dsRNA is cleaved from the initial RNA transcript containing the capsid protein coding sequence by post transcriptional processing, such post transcriptional processing may depend on bacterial host cell processes or may be directed by other RNA processing systems such as ribozymes or specific ribonucleases.

In one embodiment one or both of the dsRNA and the capsid protein genes are inducibly transcribed from a transcriptional promoter and transcription is terminated by a transcriptional terminator. In an embodiment the inducible transcriptional promoter is the bacteriophage T7 gene 1 promoter. In other embodiments the inducible transcriptional promoter may be the bacteriophage Lambda $P_L$ or $P_R$ promoters, the lac operon, trp operon, or synthetic tac promoter, or bacteriophage T5 promoter. Other transcription promoters, both constitutive and inducible, known to those of ordinary skill in the art, may also be used in some embodiments. In an embodiment the transcriptional terminator is the bacteriophage T7 late terminator. Other transcription terminators, both rho-dependent and rho-independent, known to those of ordinary skill in the art may also be used in some embodiments.

In an embodiment the coat protein gene encodes a leviviral capsid protein. The coat protein gene may be the MS2 coat protein gene encoding the MS2 capsid protein or substantially similar sequences retaining the ability to allow accumulation of dsRNA in a microbial host cell. The coat protein gene may encode the Qbeta coat protein gene encoding the Qbeta capsid protein or substantially similar sequences retaining the ability to allow accumulation of dsRNA in a microbial host cell.

In an embodiment the dsRNA is recovered from the bacterial host cells co-expressing bacteriophage capsid protein by chemical or mechanical methods to produce a host cell lysate. In an embodiment the dsRNA is further purified from the host cell lysate to remove host cell derived proteins, nucleic acids and membranes including capsid protein. In another embodiment the host cell lysate is directly processed without further purification. In another embodiment bacterial host cells are killed, by chemical or heat or other means without lysis and the intact killed cells processed without further purification.

EXAMPLES

Example 1

Unencapsidated dsRNAs are produced at hither levels in the presence of capsid protein than in the absence of capsid protein.

Expression strains containing pAPSE10180 and pAPSE10181 were constructed and dsRNA production induced by the standard expression procedure described above. The amount of encapsidated and unencapsidated dsRNA each strain produced was measured as described. The initial impetus for this experiment was to determine whether an RNA molecule with a 180 base pair double-stranded stem structure could be packed within a VLP. A 180 bp dsRNA stem is approximately 60 nm in length, whereas the interior diameter of an MS2 capsid is approximately 20 nm. Based on this geometric limitation, little or no encapsidation was expected and, due to host nuclease activity, little or no unencapsidated dsRNA was expected to be recoverable from the cell lysates. As expected only small amounts of encapsidated dsRNA (en capsid) were recovered (<2 mg/L) from the pAPSE10180 expression cells. In contrast, surprisingly large amounts of unencapsidated dsRNA (ex capsid) were recovered (75-90 mg/L) from the pAPSE10180 expression cells. Even more surprisingly, virtually no unencapsidated dsRNA was recovered from the pAPSE10181 expression cells.

To determine whether accumulation of RNA is a specific property of the ErkA sequence, or is a more general property of expressing dsRNA in the presence of capsid protein, a series of expression constructs expressing a 294 base sequence from the beta actin gene of the Colorado potato beetle (*Leptinotarsa deeemlinectta* strain Freeville, GenBank Accession NM 001300706 between nucleotides 156-335) were produced and tested.

Initially, plasmids expressing the 294 base beta actin sequence from Colorado potato beetle in the sense and the anti-sense orientation were constructed from pAPSE10180 by replacing the ErkA sequences, to produce pAPSE10189 (SEQ ID NO: 4 and pAPSE10190 (SEQ ID NO: 5) respectively. The beta actin sense and antisense strand sequences were amplified by PCR (Accuprime Pfx, Invitrogen Cat. No. 12344040, Thermo Fisher Scientific Inc.) from a gBlock template using primers that introduce the AsiSI and PmeI restriction sites at the 5' and 3' ends respectively (gBlock template DNA and PCR primers were synthesized by Integrated DNA Technologies, Coralville Iowa; all restriction endonucleases were from New England BioLabs, Beverly, Mass.). Restriction digest of pAPSE 10180 and the beta actin sense and antisense PCR fragment with AsiSI and PmeI resulted in DNA fragments that could be ligated together in the desired manner. The pAPSE10180 plasmid backbone lacking the ErkA sequence was gel purified and the sense and antisense beta actin sequences were ligated into the gel purified vector to produce pAPSE 10189 and pAPSE 10190, respectively. When transformed into a suitable expression host, such as HT115(DE3) the cells containing pAPSE10189 produces a ssRNA transcript comprising 294 bases of the sense strand of the beta actin gene flanked by pac sequences as well as co-express MS2 capsid protein, when cultured and induced as described above. Likewise, cells containing pAPSE10190 produces a ssRNA transcript comprising 294 bases of the anti-sense strand of the same region of the beta actin gene flanked by pac sequences as well as co-express MS2 capsid protein when transformed into a suitable expression host, cultured and induced as described. A second set of plasmids, lacking the ability to express MS2 capsid protein were also produced by replacing the ErkA sequences of pAPSE10181 with the sense and anti-sense 294 base fragments of the beta actin gene as described above. These plasmids, pASPE10274 (SEQ ID NO: 6) and pAPSE10275 (SEQ ID NO: 7) respectively, were transformed into HT115(DE3) and cultured and induced as described.

Analysis of un-encapsidated RNA recovered from the cells whether co-expressed with capsid protein (as with pAPSE10189 and pAPSE10190) or not (pAPSE10274 and pAPSE10275) showed that virtually no ssRNA can be recovered. However, VLPs recovered from pAPSE10189 and pAPSE10190 yield at least 20 mg/L of ssRNA of sense or anti-sense sequence respectively. This confirms that the plasmid expression systems are capable of producing ssRNA and capsid protein as expected.

A dsRNA expression cassette comprising the 294 base Colorado potato beetle beta actin genes was constructed by a process similar to that described for the dsRNA ErkA expression cassette. In this case, the random DNA sequence comprising the loop between the sense and anti-sense strands of the beta actin sequences comprised 166 bases, including the same internal pac site sequence as found in pAPSE10180 and 10181. This beta actin expression cassette was cloned into pAPSE10180 replacing the ErkA related stem loop sequence to form plasmid pAPSE10269 (SEQ ID NO: 8), and into pAPSE10181 to form plasmid pAPSE10306 (SEQ ID NO: 9). The plasmids were transformed into HT115(DE3), cultured, and induced as described. Analysis of the encapsidated dsRNA produced by the cells containing pAPSE10269 strain showed that 2-10 mg/L dsRNA could be recovered from VLPs. However, much higher levels of the beta actin dsRNA could be recovered from the cells containing pAPSE10269 in unencapsidated form (200 mg/L). Strikingly, analysis of the RNA produced by the pAPSE10306 strain showed that in the absence of co-expressed capsid protein only about 3 mg/L of dsRNA could be recovered.

Thus, the high levels of unencapsidated dsRNA are consistent with a model in which such dsRNA are not packaged efficiently, but for some reason appear to be present within cells co-expressing capsid protein with the dsRNA at much higher levels than in cells which lack capsid protein. One model to account for this observation is that binding of capsid protein to the pac sites inhibits degradation by host cell nucleases.

Example 2

Specific Pac Site-Capsid Protein Interaction is not Required for High Level Production of dsRNA.

To test whether capsid protein bound to pac sites in the dsRNA results in the observed increase in dsRNA production in cells co-expressing capsid protein, perhaps inhibiting endogenous host nuclease degradation of the bound dsRNA, a series of constructs comprising the basic beta actin dsRNA described above were produced with varying numbers and locations of pac sites. Plasmids pAPSE10216 (SEQ ID NO: 10) and pAPSE10305 (SEQ ID NO: 11), are identical to pAPSE10269 and pAPSE10306 respectively, except they lack the internal loop pac site. Plasmids pAPSE10219 (SEQ ID NO: 12) and pAPSE10304 (SEQ ID NO: 13) are identical to pAPSE10217 and pAPSE10306 respectively, except they have only a single pac site located on the 3' end of the stem of the dsRNA. Plasmids pAPSE10279 (SEQ ID NO: 14) and pAPSE10303 (SEQ ID NO: 15) are identical to pAPSE10216 and pAPSE10306 except they lack all pac site sequences entirely. Each of these plasmids was transformed into *E. coli* HTH 5(DE3), cultured and induced as described. Analysis of the encapsidated RNA recovered from VLPs of each of pAPSE10216 and pAPSE10219 show that 5-20 mg/L of dsRNA is encapsidated. Strikingly, even the strain containing pAPSE10279 entirely lacking pac sites produced 4 mg/L of encapsidated dsRNA, indicating that this level of encapsidation may represent non-specific entrainment of dsRNA present in the cells at the time the capsids were formed. Furthermore, the strain containing pAPSE10216 produced as much as 250 mg/L of unencapsidated dsRNA in the presence of capsid protein. The strains containing pAPSE10219 and pAPSE10279 produced 30-60 mg/L and 65 mg/L of unencapsidated dsRNA, respectively in the presence of capsid protein. All of the strains containing plasmids comprising the expression cassettes without co-expression of capsid protein produced <4 mg/L of dsRNA.

Together, these results indicate that the ability of capsid protein to increase the amount of unencapsidated dsRNA that can be recovered from cell lysates is not dependent on the specific binding of capsid protein to its cognate pac site sequence. Although the highest levels of unencapsidated dsRNA are recovered from constructs containing at least 5' and 3' flanking pac sites (approximately 200 mg/L), significant amounts of unencapsidated dsRNA are produced by constructs having only a single 3' flanking pac site, or lacking pac sites entirely. Cells containing plasmids producing dsRNA lacking pac sites altogether produce significantly higher amounts of dsRNA (65 mg/L) when capsid protein is co-expressed with the dsRNA relative to the cell lines lacking capsid protein altogether (3-4 mg/L). The approximately 16× increase in recoverable dsRNA between cells co-expressing capsid protein and those lacking capsid protein (65 mg/L versus 3-4 mg/L) is much more than the approximately 3×-4× increase due to the presence of pac sites (65 mg/L versus 200-250 mg/L). The effect of capsid protein co-expression appears to involve something other than mere binding to cognate pac site sequences that may (or may not) be present on the dsRNA.

Example 3

Loop Size and Structure are Irrelevant to High Level Production of dsRNA.

To test what effect, if any, differences in loop sequence might exert on the production of dsRNA in the presence and absence of co-expressed capsid protein, a series of constructs with different lengths of internal non-homologous loop sequences were inserted between each of the 294 base sense and anti-sense beta actin sequences of pAPSE10269.

Plasmids pAPSE10270 (SEQ ID NO: 16), pAPSE10271 (SEQ ID NO: 17), pAPSE10272 (SEQ ID NO: 18) and pAPSE10292 (SEQ ID NO: 19) have non-homologous loop sizes of 116 bases, 136 bases, 156 bases and 166 bases respectively. Each of these loop sequences has very little propensity for any secondary structure as determined by the m-fold structure prediction program (Zucker and Stiegler (1981) *Optimal computer folding of large RNA sequences using thermodynamics and auxiliary information* Nucl. Acids. Res. 9(1):133-48). In addition, the 139 base loop sequence found associated with the ErkA stem sequences in pAPSE10180 and having a slightly higher propensity for structural interactions within the loop was also placed between the sense and anti-sense beta actin sequences of pAPSE10269, to form pAPSE10292. Additionally, pAPSE10291 (SEQ ID NO: 20) comprising a 142 base loop sequence with a high degree of propensity for forming secondary structure based on internal homology was synthesized and constructed as described.

Each of the plasmids described in this Example were transformed into *E. coli* expression strain HT115(DE3), cultured and induced and the amount of encapsidated and unencapsidated dsRNA determined as described. In each case 2-10 mg/L of dsRNA was recovered from the VITs produced by inducing expression of the plasmid, indicating that loop size or structure had little or no effect on the ability of VLPs to encapsidate the dsRNA. Likewise, expression from each of the plasmids produced between 100 and 200 mg/L unencapsidated dsRNA, indicating that loop size or structure had little or no effect on overall production of unencapsidated dsRNA in the presence of capsid protein.

Example 4

Stem Size is Irrelevant to High Level Production of dsRNA.

Differences in stem sequence derived from the *Drosophila inelanogaster* ErkA gene sequences expressed from pAPSE10180 and the Colorado potato beetle beta actin gene sequences expressed from pAPSE10269 do not make a significant difference in the ability in expression strains to produce large quantities of unencapsidated dsRNA (75-90 mg/L from pAPSE10180 versus 200 mg/L from pAPSE10269). Nor does the length of the dsRNA stem (180 base pairs in the dsRNA produced from pAPSE10180 and 294 base pairs in dsRNA from pAPSE10269). To more systematically test what affect, if any, differences in stem sequence length might exert on the production of dsRNA in the presence and absence of co-expressed capsid protein, a series of expression constructs with different lengths of stem sequences were substituted for each of the 294 base stem forming sense and anti-sense beta actin sequences of pAPSE10269.

Plasmids pAPSE10276 (SEQ ID NO: 21) and pAPSE10277 (SEQ ID NO: 22) encode dsRNA with potential double-stranded stems of 50 and 75 base pairs respectively. The dsRNA expressed by both plasmids comprise 166 bases of non-homologous loop sequence. Although these dsRNA structures are significantly shorter than those in dsRNA from the corresponding ErkA and beta actin constructs, they still exceed the interior diameter of the MS2 VLP.

When transformed into the *E. coli* expression strain HT115(DE3), cultured and induced as described, pAPSE 10276 produces 5-10 mg/L of encapsidated dsRNA and 80-120 mg/L of unencapsidated dsRNA. Plasmid pAPSE 10277 produces 20-30 mg/L encapsidated dsRNA and 200-250 mg/L unencapsidated dsRNA. These values are similar to those observed for pAPSE10180 and pAPSE10269 described earlier in this Example, indicating that differences in stem length and sequence do not play a major role in producing dsRNA in cells co-expressing capsid protein.

Example 5

Capsid Protein is Required for High Level Production of dsRNA.

To confirm the requirement for capsid protein, plasmid pAPSE10216, which produces a dsRNA product at high levels in the presence of capsid protein, was altered to replace the MS2 coat protein gene with eGFP. A gBlock template comprising the T7 promoter to T7 terminator sequences of pAPSE10216 (spanning the sequences between the unique BamHI and SalI sites of the plasmid) in which the coding sequence of MS2 coat protein was replaced with the coding sequence of eGFP was designed, produced and amplified with primers encompassing the BamHI site on the 5' side and the SalI site on the 3' side. The resulting 1 kb fragment was digested with BamHI and SalI and then ligated into BamHI-SalI digested pAPSE10216 to form pAPSE10366 (SEQ ID NO: 24). Plasmid pAPSE10366 was confirmed by restriction digest and transformed into the *E. coli* expression strain HT115(DE3), cultured and induced as described, pAPSE10366 produces <2 mg/L of unencapsidated dsRNA, in contrast to the 200 mg/L produced by pAPSE10216. In addition, the cells expressed high amounts of eGFP as evidenced by the intense fluorescence produced on induction (data not shown) confirming that the basic dual expression plasmid used throughout these studies performs as expected. This result further demonstrates that capsid protein is necessary for accumulation of unencapsidated dsRNA in cells expressing the target RNA gene that otherwise accumulate unencapsidated dsRNA in the presence of capsid protein.

To further confirm that the presence of capsid protein is essential to the high levels of unencapsidated dsRNA production a plasmid compatible with pAPSE10181 and capable of inducible expression of the MS2 capsid protein is constructed. pAPSE10149 (SEQ ID NO: 23) is based on pACYC184. This plasmid comprises a P 15A origin of replication that is not excluded by the colE1 based origin of replication of pAPSE10181 and a chloramphenicol acetyl transferase antibiotic marker to allow selection of co-transformants containing both pAPSE10181 (encoding ampicilin resistance) and pAPSE10149 (encoding chloramphenicol resistance). Plasmid pAPSE10149 also comprises the same T7 promoter sequence capable of driving transcription of a single copy of the bacteriophage MS2 capsid gene followed by a T7 terminator as found in pAPSE10118 cloned into the BamHI and SphI sites of pACYC184. Plasmid pAPSE10149 is transformed into expression strains already containing pAPSE10181 to produce ampicilin and chloramphenicol resistant double transformants. Expression studies of such double transformants show that co-expression of the capsid protein from pAPSE10149 in conjunction with pAPSE10181 produces 200 mg/L of unencapsidated dsRNA whereas cells containing pAPSE10181 alone produce <2 mg/L of unencapsidated dsRNA (see Example 1). This demonstrates that providing capsid protein in trans is sufficient to facilitate production of high levels of unencapsidated dsRNA to host cells containing a plasmid expressing the dsRNA target that otherwise fail to accumulate unencapsidated dsRNA in the absence of capsid protein.

Example 6

Other Capsid Proteins can Induce High Level Production of dsRNA.

To test whether the accumulation of unencapsidated dsRNA is a unique property of bacteriophage MS2 capsid protein, or whether other capsid proteins share this property, a plasmid expression system analogous to pAPSE10216 was constructed. This plasmid, pAPSE10359 (SEQ ID NO: 25) comprises a Qbeta capsid protein and Qbeta pac sites at the 5' and 3' ends of the beta actin dsRNA expression cassette, but is in all other aspects similar to pAPSE10216.

Briefly, the Qbeta coat protein gene sequence (Genebank Accession NC_001890 between nucleotides 1343 and 1744) was synthesized as a gBlock fragment by Integrated DNA Technologies, Coralville, Iowa. The synthetic fragment was amplified with PCR with primers that introduced a BamHI restriction site followed by a T7 promoter sequence upstream of the Qbeta coat protein gene followed by a T7 terminator and a SphI restriction site. The amplified synthetic fragment and plasmid pBR322 were digested with BamHI and SphI and ligated together to form intermediate plasmid pAPSE10358. The beta actin dsRNA sequence of pAPSE10269 was amplified by PCR with primers that introduced an EcoRI restriction site followed by a Qbeta pac sequence followed by the beta actin dsRNA sequence followed by a second copy of the Qbeta pac sequence followed by a BamHI restriction site. This amplified beta actin containing sequence and plasmid pAPSE10358 were digested with EcoRI and BamHI and ligated together to form pAPSE10374. Plasmids pAPSE10374 and pAPSE10216 were digested with AsiSI and NotI. This cleaves pAPSE10374 into two fragments of 4,713 and 113 base pairs and pAPSE10216 into two fragments of 5,204 and 786 base pairs. The 4,713 and 786 base pair fragments were isolated and ligated together to produce pAPSE10359.

When transformed into the *E. coli* expression strain HT115(DE3), cultured and induced as described, pAPSE10359 will produce a large amount of unencapsidated dsRNA relative to the amount of dsRNA produced from a similar construct lacking capsid protein (pAPSE10305). This pattern, similar to that observed for pAPSE10216 and pAPSE10305 described in Example 1, will confirm that expression of the Qbeta capsid protein, like the MS2 capsid protein, is sufficient to increase the amount of dsRNA produced in vivo.

Example 7

RNA Binding Proteins Other than Capsid Proteins are not Sufficient for High Level Production of dsRNA.

To test whether the accumulation of unencapsidated dsRNA is a function of general RNA binding or is specific to bacteriophage capsid proteins, a plasmid expression system, pAPSE10357 (SEQ ID NO: 26) was constructed comprising the RNA binding domain of the human U1A protein and its hairpin cognate binding site from human U 1 snRNA 5' and 3' of the sense and antisense stem loop structure of the beta actin dsRNA. Plasmid pAPSE10357 is similar to pAPSE10216 with the capsid protein replaced by the human U1A RNA binding protein and U1A binding site sequences at the 5' and 3' ends of the beta actin dsRNA expression cassette, but is in all other aspects similar to pAPSE10216.

The DNA sequence encoding the N-terminal 102 amino acids comprising the RNA binding domain of the human U1A protein was amplified from a cloned copy of the U1A protein (Plasmid pAV105, Professor Kathleen Hall, Washington University, St. Louis, Mo.) using PCR primers that introduced a BamIII restriction site followed by a T7 promoter sequence upstream of the U1A gene fragment followed by a T7 terminator and a SphI restriction site. The amplified synthetic fragment and plasmid pBR322 were digested with BamHI and SphI and ligated together to form intermediate plasmid pAPSE10356. The beta actin dsRNA sequence of pAPSE10269 was amplified by PCR with primers that introduced an EcoRI restriction site followed by the hairpin binding site sequence from human U1 snRNA sequence followed by the beta actin dsRNA sequence followed by a second copy of the hairpin binding site sequence from human U1 snRNA sequence followed by a BamHI restriction site. This amplified beta actin containing sequence and plasmid pAPSE10356 were digested with EcoRI and BamHI and ligated together to form pAPSE10373. Plasmids pAPSE10373 and pAPSE10216 were digested with AsiSI and NotI. This cleaves pAPSE10373 into two fragments of 4,627 and 113 base pairs and pAPSE10216 into two fragments of 5,204 and 786 base pairs. The 4,713 and 786 base pair fragments were isolated and ligated together to produce pAPSE10357.

When transformed into the *E. coli* expression strain HT115(DE3), cultured and induced as described, pAPSE10357 will not produce a significant amount of unencapsidated dsRNA relative to the amount of dsRNA produced from a similar construct lacking capsid protein (pAPSE10305). This will confirm that the mere presence of an RNA binding site and binding protein in conjunction with the dsRNA is not sufficient to increase the amount of dsRNA produced in vivo. Alternatively, production of significant amounts of unencapsidated dsRNA will indicate that the presence of RNA binding sites at the 5' and 3' end and the cognate RNA binding protein is sufficient for increasing in vivo production of dsRNA.

Example 8

The N-Terminus of Capsid Protein is Sufficient for High Level Production of dsRNA.

To examine whether the increased production of dsRNA from plasmids containing both the dsRNA gene and the coat protein gene requires the intact capsid protein or whether only a portion of the protein is required, a frame-shift mutation was introduced into the coat protein gene sequence of pAPSE10180. Double digestion of pAPSE10180 with the restriction enzymes StuI and PmlI produces two restriction fragments, a large fragment of 5,485 base pairs and a small thirteen base pair fragment comprising about 4 codons of the capsid protein CDS about 40 codons from the coat protein start codon of pAPSE10180. The restriction enzymes produce blunt-ended termini and the larger fragment was re-ligated to produce plasmid pAPSE10372 (SEQ ID NO: 27), which, in addition to producing an intact inducible dsRNA ErkA-specific sequence, also comprises an inducible frame-shifted protein that includes the N-term 41 codons of the MS2 coat protein followed by 27 codons of frame-shifted sequence before terminating at a stop codon (SEQ ID NO: 28). When pAPSE10372 was transformed into *E. coli* expression strain HTE115(DE3) and cultured and induced as described, 75 mg/L of dsRNA was produced. This indicates that the N terminus of the capsid protein alone is sufficient to increase production of dsRNA as well as the intact capsid protein (compare yields from pAPSE10180 and pAPSE10372 in Table 1).

The N-terminus of the MS2 capsid protein forms a distinctive three-dimensional structure comprised of four separate beta sheets (D. Peabody, *The RNA binding site of bacteriophage MS2 coat protein*, The EMBO Journal 12(2) 595-600 (1993)). Each of these sheets, βD from amino acids 31-35, βC from amino acids 22¬25, βB from amino acids 19-21 and βA amino acids 8-11 may play a role in the ability of the N-terminus capsid protein fragment to improve dsRNA production. Note that the nomenclature is that of Peabody and the numbering includes the N-terminal methionine omitted by Peabody. Progressive deletion of each of these structural motifs can determine the minimum sequence requirement for improving dsRNA production.

Example 9

Fed Batch Fermentation Produces Very High Level Production of dsRNA.

To determine whether quantities of dsRNA could be increased by improving the microbial growth conditions, glucose fed batch fermentations were conducted. Briefly, fed-batch fermentations were carried out in an Eppendorf BioFlo 115 fermenter at 37° C. The pIf was controlled by automatic addition of 30% ammonium hydroxide. The dissolved oxygen probe was calibrated to 0% by unplugging the DO probe and to 100% with air saturation. The vessel was aerated at 2 vvm and dissolved oxygen maintained at 30% by cascade control of agitation. An overnight culture of HT115 (DE3) containing pAPSE10379 was grown in LB containing 100 μg/ul of ampicillin and 12.5 μg/ul of tetracycline at 37° C. to inoculate the seed medium. The seed media is a defined media consisting of 5.68 g/L Na2HPO4, 1.34 g/L KH2PO4, 6.6 g/L (NH4)2SO4, 10 g/L glucose, 1× trace metal and 1× vitamin solutions maintained at a pH of 7.0. To ensure plasmid stability antibiotics are added at 100 μg/ul ampicillin and 12.5 μg/ul tetracycline. At saturation (OD600 3-5) the seed cultures are used to provide 10% inoculum for the fermenter.

During fed batch-cultures a 50% (w/v) solution of glucose was added according to a carbon limiting DO stat feeding strategy. The basal medium consists of 6 g/L $K_2HPO_4$, 3 g/L NaHPO4, 10 g/L $(NH_4)_2SO_4$, 1 g/L $MgSO_4$, 1× trace metal solution with antibiotics added at 100 ug/ul of ampicillin and 12.5 μg/ul of tetracycline. Upon exhaustion of the initial carbon source provided by the glucose the feed solution is added automatically in a manner that maintains the DO level at 30% of saturation.

Once the cell culture has reached an $OD_{600}$ of 60 the cells are induced with 1 mM IPTG or a feed of 20 g/L of lactose by switching the glucose feed to a lactose feed. After induction 1 mL samples are taken at different times post induction. The samples are lysed by sonication of the cell pellet into 20 mM Tris-HCl at pH 7. Total RNA from the cell pellet is purified using well-known Trizol extraction procedures. Briefly 1 volume of cell lysate is added to 1 volumes of Trizol RNA extraction reagent. Addition of 1 volume of chloroform results in the RNA partitioning to the aqueous layer leaving the protein and DNA contaminants behind.

To analyze the yield of dsRNA the total RNA sample is diluted to 1 ug/ul and subjected to RNAseA treatment. The reaction is carried out in 20 mM Tris at pH 7.0 and 37° C. for 40 minutes. Once this is done proteinase K is added to the reaction to remove the nuclease and is allowed to react at 37° C. for 40 minutes. Upon completion of this step the dsRNA remaining is diluted in half, quarters and eighths in order to determine the concentration of the dsRNA using gel densitometry.

Quantification of dsRNA yield by gel densitometry was performed by comparing the intensity of dsRNA bands versus dsDNA bands of known mass and weight on a 1.5% agarose gel containing ethidium bromide. The lambda 100 bp quantifiable DNA marker was used and a standard curve was generated to determine the range in which the dsRNA from the fermentation can be reliably quantified. The computer program calculates the amount of dsRNA in the amount of sample loaded on the gel and a back calculation that considers the dilution steps is performed. Yields of dsRNA at levels as high as 3 g/L have been calculated with both IPTG and lactose as inducers under these conditions. These results indicate that further increases in dsRNA production are possible by improving fermentation conditions.

Example 10

Compositions and Methods for dsRNA Production in Cram Positive Bacteria.

The ability of gram-positive bacteria to produce increased levels of dsRNA by co-expression of capsid proteins can be examined in the following manner. *Corynebacterium glutamicum* MB001(DE3) strain DSM 102071, containing an inducible T7 RNA polymerase gene (described in Kortmann, et al., *A chromosomally encoded T7 RNA polymerase-dependent gene expression system for Corynebacterium glutamicum; construction and comparative evaluation at the single cell level*. Microb Technol. 8(2):253-65. March 2015) is modified to knockout the rile gene homolog encoding RNAse III. Briefly, PCR primers capable of amplifying a 1.2 kb sequence homologous to the sequence present in *C. glutamicum* strain MB001(DE3) immediately upstream of the me gene and PCR primers capable of amplifying a 1.5 kb sequence homologous to the sequence immediately downstream of the me gene are synthesized. A PCR amplification reaction using *C. glutamicum* strain MB001(DE3) genomic DNA and said primers results in a single DNA fragment comprising the 1.2 kb and 1.5 kb target sequences joined together (by standard overlap PCR methods) to produce an approximately 2.7 kb SalI-BamHI synthetic DNA fragment. This SalI-BamHI DNA fragment and plasmid pK18mobsacB (ATCC 87097, described by Schafer, et al., *Small mobilizable multi-purpose cloning vectors derived from the Escherichia coli plasmidspK18 and pK19: selection of defined deletions in the chromosome of Corynebacterium glutamicum*. Gene 145:69-73) are digested with SalI and BamHI and the products ligated together to produce plasmid pAPSE10429 (SEQ ID NO: 29). Plasmid pAPSE10429 is transformed into *C. glutamicum* strain MB001 and transformants selected on kanamycin containing solid LB medium to identify chromosomal integrants. Kanamycin resistant clones are transferred to a solid LB medium containing 20% sucrose. Conversion of sucrose by the sacB gene product is toxic to *C. glutamicum* strain MB001 so only those chromosomal integrants that subsequently delete the sacB gene from the chromosome can survive on such media. Surviving colonies are grown up and screened by PCR to confirm concomitant loss of the mc locus from the chromosome. The desired strain is designated *C. glutamicum* MB001(DE3) rnc. This strain possesses an inducible T7 RNA polymerase and lacks the mc gene and is suitable for testing the efficacy of dsRNA production in the presence and absence of capsid protein.

A shuttle vector capable of expression of capsid coat protein and dsRNA in both *E. coli* and *C. glutamicum* is constructed by synthesizing a DNA comprising the origin of replication of the grain-positive plasmid pCG1 (GeneBank Accession No. AB027714; described by Trautwetter and Blanco, *Structural organization of the Corynebacterium glutamicum plasmid pCG*100. J. Gen. Microbiol. 137:2093-101 1991) and the kanamycin resistance gene of pK18mobsacB. This synthetic DNA (SEQ ID NO: 30) is ligated into the previously described dsRNA containing plasmids at the unique NruI restriction site to allow testing whether the presence of capsid protein in gram-positive *C. glutamicum* MB001(DE3) rnc strain produces dsRNA at high levels as described below.

Insertion of the synthetic DNA comprising the pCG1 origin of replication and the kanamycin resistance gene is accomplished by digesting pAPSE10279 with NruI and ligating the phosphorylated synthetic DNA into the plasmid to produce plasmid pAPSE10430 (SEQ ID NO: 31). Plasmid pAPSE10430 contains the kanamycin resistance gene, the bacteriophage MS2 coat protein, and the dsRNA construct based on the previously described 294 base sense and antisense sequences homologous to the Colorado potato beetle beta actin gene separated by a 166 base non-homologous loop and entirely lacking any pac sequences. In similar fashion, the synthetic DNA comprising the pCG1 origin of replication and the kanamycin resistance gene is also ligated into NruI digested pAPSE10303 to produce pAPSE10431 (SEQ ID NO: 32). Plasmid pAPSE10431 contains resistance genes to ampicillin and kanamycin, as well as the same inducible dsRNA construct as pAPSE10430. However, pAPSE10431 lacks the inducible MS2 coat protein gene of pAPSE10430. The relevant features of pAPSE10430 and pAPSE10431 are presented in Table 2 and the relationship between these two plasmids and their parental plasmids, pAPSE10279 and pAPSE10303, respectively, can be determined by comparing Table 2 and Table 1.

Additional plasmids containing one, two, and three pac sites, with and without MS2 coat protein, are constructed using the same procedure. Plasmid pAPSE10432 (SEQ ID NO: 33) containing a single pac site 3' of the beta actin stem loop structure and encoding the MS2 coat protein gene is produced by ligating the synthetic DNA fragment into the NruI site of pAPSE10219. Plasmid pAPSE10433 (SEQ ID NO: 34) is produced by ligating the synthetic DNA fragment into the NruI site of pAPSE10304. Plasmid pAPSE10433 is identical to pAPSE10432 except it lacks an inducible MS2 coat protein gene. Plasmid pAPSE10434 (SEQ ID NO: 35) containing two pac site sequences located one on either side of the beta actin stem loop and encoding the MS2 coat protein is produced by ligating the synthetic DNA fragment into the NruI site of pAPSE10216. Plasmid pAPSE10435 (SEQ ID NO: 36) is produced by ligating the synthetic DNA fragment into the NruI site of pAPSE10305. Plasmid pAPSE10435 is identical to pAPSE10434 except it lacks an inducible MS2 coat protein gene. Plasmid pAPSE10436 (SEQ ID NO: 37) containing three pac site sequences with one each 5' and 3' of the beta actin stem loop and one within the loop sequence itself (as depicted in FIG. 1) and encoding the MS2 coat protein is produced by ligating the synthetic DNA fragment into the NruI site of pAPSE10269. Plasmid pAPSE10437 (SEQ ID NO: 38) is produced by ligating the synthetic DNA fragment into the NruI site of pAPSE10306. Plasmid pAPSE10437 is identical to pAPSE104360 except it lacks an inducible MS2 coat protein gene.

In each case, following ligation of the synthetic DNA fragment into the NruI site of the target plasmid, transformants the ligation reactions are desalted and transformed in to *C. glutamicum* MB001(DE3) mc and selected for resistance to kanamycin. The selected clones are subsequently grown at 32° C. in 100 ml of LB media containing kanamycin until the culture reaches OD600 0.8, at which time isopropyl β-D-thiogalactopyranoside is added to a final concentration of 1 mM to induce T7 polymerase directed transcription of the MS2 coat protein and the dsRNA, or just the dsRNA precursor in the plasmids lacking coat protein. The induced cultures are allowed to grow for at least 4 hours post-induction to allow sufficient time for accumulation of the MS2 coat protein and dsRNA target. Cells are collected by centrifugation at 3,000 g at 4 C. Each pellet is stored at 4° C. until processing.

The dsRNA is purified by re-suspending each pellet in approximately 0.1 volume of 20 mM Tris-HCl, pH 7.0, containing 10 mM NaCl and sonicated to lyse the cells. Cell debris is removed by centrifugation at 16,000 g. The resulting lysate is mixed with 3 volumes of Trizol (Ambion Life Technologies) and the RNA is extracted by adding 1 volume of chloroform. Addition of NaCl to a final concentration of 500 mM to the aqueous layer and subsequent ethanol precipitation results in a pellet containing the 294 bp siRNA precursor and RNA from the *C. glutamicum* host.

To determine the amount of dsRNA produced by the *C. glutamicum* transformed with plasmids containing various pac site configurations, with and without MS2 coat protein, the ethanol pellets are resuspended and treated with RNAscA for 1 hour at 37° C. followed by Proteinase K digestion for 1 hour at 37° C. Quantification of the dsRNA is accomplished by gel densitometry using a BioRad ChemiDoc MP Imaging System. Several dilutions of the treated dsRNA are run on a 1.5% agarose gel containing 0.001% ethidium bromide. A 100 bp quantifiable dsDNA ladder (QuantiBP DNA ladder Lambda) is used as the standard curve and the dsRNA is quantified at the concentration that falls within the linear range of the standard curve. Software such as Image Lab 4.1 is determined by accounting for the dilutions associated with the dsRNA samples present on the gel.

Table 2 summarizes the predicted results of the dsRNA yield determination of the Colorado potato beetle beta actin dsRNA produced by *C. glutamicum* MB001(DE3) me and the various plasmids described above. Such results confirm that gram positive hosts such as *C. glutamicum* produce large quantities of dsRNA by co-expression of the MS2 coat gene and a dsRNA target of interest.

TABLE 2

Predicted production of dsRNA by *C. glutamicum* MB001(DE3) rnc as a function of variation in dsRNA structure and the presence or absence of coat protein.

| RNA Structure as depicted in | Plasmid | Loop size (bases) | Stem size (bp) | Stem sequence | Coat protein | dsRNA (mg/L) |
|---|---|---|---|---|---|---|
| FIG. 6 | pAPSE10430 | 166 | 294 | beta actin | MS2 | ~60 |
| FIG. 6 | pAPSE10431 | 166 | 294 | beta actin | none | ~4 |
| FIG. 5 | pAPSE10432 | 166 | 294 | beta actin | MS2 | ~120 |
| FIG. 5 | pAPSE10433 | 166 | 294 | beta actin | none | ~4 |
| FIG. 4 | pAPSE10434 | 166 | 294 | beta actin | MS2 | ~250 |
| FIG. 4 | pAPSE10435 | 166 | 294 | beta actin | none | ~4 |
| FIG. 1 | pAPSE10436 | 166 | 294 | beta actin | MS2 | ~250 |
| FIG. 1 | pAPSE10437 | 166 | 294 | beta actin | none | 4 |

Example 11

Compositions and Methods for dsRNA Production in Yeast.

To create a *Saccharomyces cerevisiae* production host suitable for dsRNA accumulation utilizing the MS2 bacteriophage coat protein, the Rnt1 gene of *S cerevisiae* YPH 500 (ATCC 76626) is knocked out according to the procedure of Gardenr and Jasperson (Gardner, J M and Jaspersen, S L, *Manipulating the yeast genome: deletion, mutation and tagging by PCR*. Methods Mol Biol. 1205:45-78, 2014). The KanMx4 gene is amplified from pML104-KanMx4 plasmid (Laughery, et al., *New vectors for simple and streamlined CRISPR-Cas9 genome editing in Saccharomyces cerevisiae.* Yeast 32(12):711-20 Sep. 21, 2015) with PCR primers including 60 base pair (bp) upstream (forward primer) and 60 bp downstream (reverse primer) regions of the *S. cerevisiae* Rnt1 gene. The resulting PCR product is introduced into chemically competent *S. cerevisiae* cells following the established *S. cerevisiae* transformation protocol. The transformed cells are incubated overnight without selection marker to allow for homologous recombination to occur, where in the kanMx4 gene carrying 60 bp upstream and downstream regions of Rnt1 replaced the Rnt1 gene. Following overnight incubation, the transformed cells are plated on YPD plates carrying G418 as selection marker. G418 resistant colonies are screened by PCR to confirm presence of kanMx4 gene and deletion of Rnt1 gene in the YPH 500 genome.

*S. cerevisiae* expression vectors pESC-His, pESC-Leu, pESC-Ura and pESC-Trp are widely used for recombinant protein expression in *S. cerevisiae*. Each of the pESC vectors (Agilent Technologies, Santa Clara Calif.) contains one of four different yeast-selectable markers (HIS3, TRP1, LEU2, or URA3) in the same vector backbone, which allows expression of two different genes in a single yeast cell. The pESC series vectors are used with *S. cerevisiae* strain YPH 500 (MATα ura3-52 lys2-801_amber ade2-101_ochre trp 1-Δ63 his3-Δ200 leu2-Δ1). In this example, the pESC-Trp vector is selected for expression of MS2 coat protein and target dsRNA sequence inside *S. cerevisiae*, although any of the other pESC vectors could be employed using similar methods since these vectors can replicate in *S. cerevisiae* as well as *E. coli*, which facilitates molecular manipulations necessary to produce dsRNA.

The pESC-Tip vector is modified by cloning a 50-base pair multi-cloning site linker containing BamHI, SwaI, AsiSI, NotI, SacII and NheI sites, downstream of the GAL1 promoter into the existing BamHI and NheI sites. Following this, the beta actin stem loop sequence (dsRNA) of pAPSE10279 is excised as an AsiSI/NotI fragment and ligated into the AsiS 1/NotI sites of the modified pESC-Trp vector. Expression of the dsRNA in this plasmid is under the control of galactose inducible promoter GALL The new vector is named pAPSE10439 (SEQ ID NO: 39). Another plasmid, pAPSE10440 (SEQ ID NO: 40), which is identical to pAPSE10439, but also includes the MS2 coat protein. Plasmid pAPSE10440 is constructed by PCR amplifying the MS2 coat protein expression sequences of pAPSE10279 with a forward primer carrying an EcoRI restriction site on the 5' end and the reverse primer carrying SacI site on the 3' end. The PCR product is digested with EcoRI and SacI and cloned into the cognate sites of pAPSE10439. Thus, pAPSE10439 inducibly expresses the dsRNA from the GALL promoter, whereas pAPSE10440 inducibly expresses the dsRNA sequence from the GAL1 promoter and the MS2 coat protein from the GAL10 promoter, Similar plasmid pairs are constructed using this technique. Plasmids pAPSE10441 (SEQ ID NO: 41) and pAPSE10442 (SEQ ID NO: 42) are produced by digesting pAPSE10439 and pAPSE10440 with AsiSI and NotI and isolating the vector fragment. Plasmid pAPSE10219 is also digested with AsiSI and NoII and the dsRNA sequence is isolated. The isolated dsRNA sequence is ligated into the pAPSE10439 vector to form pAPSE10441 and the isolated dsRNA sequence is ligated into the pAPSE10440 vector to form pAPSE10442. Plasmids pAPSE10443 (SEQ ID NO: 43) and pAPSE10444 (SEQ ID NO: 44) are produced by digesting pAPSE10439 and pAPSE10440 with AsiSI and NotI and isolating the vector fragment. Plasmid pAPSE10216 is also digested with AsiSI and NotI and the dsRNA sequence is isolated. The isolated dsRNA sequence is ligated into the pAPSE10439 vector to form pAPSE10443 and the isolated dsRNA sequence is ligated into the pAPSE10440 vector to form pAPSE10444. Plasmids pAPSE10445 (SEQ ID NO: 45) and pAPSE10446 (SEQ ID NO: 46) are produced by digesting pAPSE10439 and pAPSE10440 with AsiSI and NotI and isolating the vector fragment. Plasmid pAPSE10269 is also digested with AsiSI and NotI and the dsRNA sequence is isolated. The isolated dsRNA sequence is ligated into the pAPSE10439 vector to form pAPSE10445 and the isolated dsRNA sequence is ligated into the pAPSE10440 vector to form pAPSE10446.

Chemically competent YPH 500 DRnt1 cells are transformed with each of the above mentioned plasmids (pAPSE10439-46) separately and individual clones selected on synthetic dextrose minimal (SD) tryptophan (trp) drop out plates. After inoculating the 100 ml SD-Trp drop out broth the cultures are grown for 12 to 16 hours. The cells from the culture are then harvested by centrifugation at 3000 g for 5 minutes, the cell pellet is washed once with sterile water and the cells re-suspended in synthetic galactose minimal broth (SG) lacking tryptophan. The cells are grown in the SG-trp drop out broth overnight to induce production and accumulation of dsRNA and MS2 coat protein (where appropriate). Cells are harvested by centrifugation at 3,000 g at 4° C. Each pellet is stored at −20° C. until processing.

The dsRNA is purified by re-suspending each pellet (10 ml culture) in approximately 1.0 ml of yeast cell lysis buffer (Sigma C4482). The resulting lysate is mixed with 3 volumes of Trizol (Ambion Life Technologies) and the RNA extracted by adding 1 volume of chloroform. Addition of NaCl to a final concentration of 500 mM to the aqueous layer and subsequent ethanol precipitation results in a pellet containing the dsRNA and RNA from the S. cerevisiae host. The resulting RNA pellet is dissolved in 20 mM Tris HCl pH 7.0 and RNA concentration of the sample determined. To determine the amount of dsRNA produced by the S. cerevisiae strains, a known amount of RNA (10 µg) from each RNA sample from pAPSE10439-pAPSE10446) are digested with RNAseA for 1 hour at 37° C. followed by Proteinase K digestion for 1 hour at 37° C. The resulting samples contain only the dsRNA target. Quantification of the dsRNA is done by gel densitometry using a BioRad ChemiDoc MP Imaging System. Several dilutions of the RNAse A reaction are run on a gel that contains 1.5% agarose and 0.001% ethidium bromide. A 100 bp quantifiable dsDNA ladder (QuantiBP DNA ladder Lambda) is used as the standard curve and the dsRNA is quantified at the concentration that falls within the linear range of the standard curve. Using Image Lab 4.1 software, the concentration of the dsRNA loaded on the gel is determined and a final yield of dsRNA calculated by accounting for the dilutions of the dsRNA loaded on the gel.

Table 2 summarizes the predicted results of the dsRNA yield determination of the Colorado potato beetle beta actin dsRNA produced by S. cerevisiae YPH-500 and the various plasmids described above. Such results confirm that yeasts such as S. cerevisiae produce large quantities of dsRNA by co-expression of the MS2 coat gene and a dsRNA target of interest.

TABLE 2

Predicted production of dsRNA by S. cerevisiae YPH 500 as a function of variation in dsRNA structure and the presence or absence of coat protein.

| RNA Structure as depicted in (bases) | Plasmid | Loop size | Stem size (bp) | Stem sequence | Coat protein | dsRNA (mg/L) |
| --- | --- | --- | --- | --- | --- | --- |
| FIG. 6 | pAPSE10440 | 166 | 294 | beta actin | MS2 | ~60 |
| FIG. 6 | pAPSE10439 | 166 | 294 | beta actin | none | ~4 |
| FIG. 5 | pAPSE10442 | 166 | 294 | beta actin | MS2 | ~120 |
| FIG. 5 | pAPSE10441 | 166 | 294 | beta actin | none | ~4 |
| FIG. 4 | pAPSE10444 | 166 | 294 | beta actin | MS2 | ~250 |
| FIG. 4 | pAPSE10443 | 166 | 294 | beta actin | none | ~4 |
| FIG. 1 | pAPSE10446 | 166 | 294 | beta actin | MS2 | ~250 |
| FIG. 1 | pAPSE10445 | 166 | 294 | beta actin | none | 4 |

What is claimed is:

1. A method for producing unencapsidated dsRNA in a microbial cell, comprising the step of co-expressing in the microbial cell the dsRNA, and a leviviridae coat protein gene encoding a capsid protein or an amino-terminal fragment of the capsid protein,
   wherein the unencapsidated dsRNA is directly recoverable from a cell lysate; and
   wherein the unencapsidated dsRNA comprises a length exceeding the interior diameter of the leviviridae coat protein.

2. The method of claim 1, wherein the capsid protein is encoded by the coat protein gene of bacteriophage MS2 or the coat protein gene of bacteriophage Qβ.

3. The method of claim 1, wherein the gene encoding the dsRNA and the coat protein gene encoding the capsid protein are expressed from an inducible promoter.

4. The method of claim 3, wherein the coat protein gene encoding the capsid protein is expressed from a constitutive promoter and the gene encoding the dsRNA is expressed from an inducible promoter.

5. The method of claim 1, wherein the coat protein gene encoding the capsid protein is expressed prior to or concomitant with the gene encoding the dsRNA.

6. The method of claim 1, wherein the gene encoding the dsRNA and the coat protein gene encoding the capsid protein are present on one plasmid or extrachromosomal element within the microbial cell.

7. The method of claim 1, wherein the dsRNA is an RNAi precursor.

8. The method of claim 1, wherein after producing the dsRNA the microbial cell is subsequently lysed and the dsRNA purified from the lysate prior to processing for application.

9. The method of claim 1, wherein after producing the dsRNA the microbial cell is lysed and processed for application without further purification of the dsRNA.

10. The method of claim 1, wherein after producing the dsRNA the microbial cells are processed for application without lysis or further purification of the dsRNA.

11. The method of claim 1, wherein the capsid protein comprises a truncated capsid protein.

12. The method of claim 11, wherein the truncated capsid protein consists essentially of the N-terminus of the capsid protein.

13. The method of claim 11, wherein the truncated capsid protein comprises the first 41 amino acids of the capsid protein.

14. The method of claim 11, wherein the truncated capsid protein comprises the first 35 amino acids of the capsid protein.

15. The method of claim 11, wherein the truncated capsid protein comprises the first 25 amino acids of the capsid protein.

16. The method of claim 11, wherein the truncated capsid protein comprises the first 21 amino acids of the capsid protein.

17. The method of claim 11, wherein the truncated capsid protein comprises the first 11 amino acids of the capsid protein.

18. The method of claim 1, wherein the microbial cell is a bacterial cell.

19. The method of claim 1, wherein the microbial cell is a strain of *Escherichia coli*, a strain of *Corynebacterium glutamicum* or a strain of *Saccharomyces cerevisiae*.

* * * * *

SEQUENCE LISTING

```
<160> NUMBER OF SEQ ID NOS: 46

<210> SEQ ID NO 1
<211> LENGTH: 5498
<212> TYPE: DNA
<213> ORGANISM: Artificial Sequence
<220> FEATURE:
<223> OTHER INFORMATION: Recombinant plasmid pAPSE10180; ErkA stem
      loop + capsid protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (127)..(145)
<223> OTHER INFORMATION: bacteriophage MS2 pac sequence
<220> FEATURE:
<221> NAME/KEY: misc_feature
<222> LOCATION: (175)..(182)
<223> OTHER INFORMATION: restriction endonuclease AsiSI recognition site
<220> FEATURE:
<221> NAME/KEY: misc_feature
<222> LOCATION: (179)..(384)
<223> OTHER INFORMATION: ErkA sense strand gene fragment
<220> FEATURE:
<221> NAME/KEY: misc_feature
<222> LOCATION: (436)..(454)
<223> OTHER INFORMATION: bacteriophage MS2 pac sequence
<220> FEATURE:
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
```

```
<223> OTHER INFORMATION: restriction endonuclease PacI recognition site
<220> FEATURE:
<221> NAME/KEY: misc_feature
<222> LOCATION: (709)..(727)
<223> OTHER INFORMATION: bacteriophage MS2 pac sequence
<220> FEATURE:
<221> NAME/KEY: terminator
<222> LOCATION: (743)..(790)
<223> OTHER INFORMATION: bacteriophage T7 transcription terminator
<220> FEATURE:
<221> NAME/KEY: promoter
<222> LOCATION: (1116)..(1134)
<223> OTHER INFORMATION: bacteriophage T7 gene 1 promoter
<220> FEATURE:
<221> NAME/KEY: gene
<222> LOCATION: (1207)..(1596)
<223> OTHER INFORMATION: bacteriophage MS2 coat protein gene
<220> FEATURE:
<221> NAME/KEY: terminator
<222> LOCATION: (1448)..(1495)
<223> OTHER INFORMATION: bacteriophage T7 transcription terminator

<400> SEQUENCE: 1
ttcagatctc gatcccgcga aattaatacg actcactata gggagaccac aacggtttcc      60
ctctagatca caagtttgta caaaaaagca ggctaagaag agatatataca tacgccggcc     120 attcaaacat gaggattacc catgtaacct aaggccggtg tccaggcgcg ctccgcgatc     180
gcacgcggac aaagttcctc aatctaatgc tgaagttata aggggacaaa tatttgaagt     240
tggtcctagg tatattaaac tcgcctatat aggtgaagga gcttatgcca tggttgtgtc     300
tgcggatgac acgctaacaa accaaagagt tgcaataaaa aaatatcgc cctttgaaca     360 ccaaacttat tgctactaca gtttaaacgc aatcgcagca actccggca tctactaata     420 gacgccggcc attcaacatg aggattaccc atgtaaccta agaagacaac aagaagttc     480 aactcttat gtattgatct tccgcggccg ccaataagtt tggtgttcaa agggcgatat     540 ttttttttatt gcaactcttt ggtttgttag cgtgtcatcc gcagacacaa ccatgccata     600
agctccttca cctatatagg cgagttaat atacctagga ccaacttcaa atatttgtcc     660
ccttataact tcagcattag attgaggaac tttaattaag gagttcaaac atgaggatca     720
cccatgtcga agctcccaca ccctagcata accccttggg gcctctaaac gggtcttgag     780
gggttttttg ctgaaaggag gaactatatc cggatatcca caggacgggt gtggtcgcca     840
tgatcgcgta gtcgatagtg gctccaagta gcgaagcgag caggactggg cggcgggcat     900
gcatcgtcca ttccgacagc atcgccagtc actatggcgt gctgctagcg ctatatgcgt     960
tgatgcaatt tctatgcgca cccgttctcg gagcactgtc cgaccgcttt ggccgccgcc     1020
cagtcctgct cgcttcgcta cttggagcca ctatcgacta cgcgatcatg cgaccacac     1080 ccgtcctgtg gatccagatc tcgatccgc gaaattaata cgactcacta tagggagacc     1140
acaacggttt ccctctagat cacaagtttg tacaaaaaag caggctaaga aggagatata     1200
catatggcgt ctaactttac ccaattcgtt ctggttgata acggcggtac gggtgacgtt     1260
accgtagctc cgtccaactt cgccaacggt gttgcgaat ggattagctc taacagccgc     1320
tctcaggcct acaaagtcac gtgctccgtt cgtcagtcta gcgcgcagaa tcgcaaatac     1380
accatcaaag ttgaagtacc gaaagtcgca acgcagaccg taggcggcgt agaactccca     1440
gttgcggcct ggcgctctta cctcaacatg gaactgacta ttccgatttt tgcgacgaac     1500
tccgactgcg aactgattgt taaggcaatg caggcctgc tgaaagacgg taatccgatc     1560
ccatctgcaa tcgctgctaa ctctggcatt tactaataag cggacgcgct gccaccgctg     1620
agcaataact agcataaccc cttggggcct ctaaacgggt cttgaggggt ttttgctga     1680
```

```
aaggaggaac tatatccggc atgcaccatt ccttgcggcg gcggtgctca acggcctcaa   1740
cctactactg ggctgcttcc taatgcagga gtcgcataag ggagagcgtc gaccgatgcc   1800
cttgagagcc ttcaacccag tcagctcctt ccggtgggcg cggggcatga ctatcgtcgc   1860
cgcacttatg actgtcttct ttatcatgca actcgtagga caggtgccgg cagcgctctg   1920
ggtcattttc ggcgaggacc gctttcgctg gagcgcgacg atgatcggcc tgtcgcttgc   1980
ggtattcgga atcttgcacg ccctcgctca agccttcgtc actggtcccg ccaccaaacg   2040
tttcggcgag aagcaggcca ttatcgccgg catggcggcc gacgcgctgg gctacgtctt   2100
gctggcgttc gcgacgcgag gctggatggc cttccccatt atgattcttc tcgcttccgg   2160
cggcatcggg atgcccgcgt tgcaggccat gctgtccagg caggtagatg acgaccatca   2220
gggacagctt caaggatcgc tcgcggctct taccagccta acttcgatca ttggaccgct   2280
gatcgtcacg gcgatttatg ccgcctcggc gagcacatgg aacgggttgg catggattgt   2340
aggcgccgcc ctataccttg tctgcctccc cgcgttgcgt cgcggtgcat ggagccgggc   2400
cacctcgacc tgaatggaag ccggcggcac ctcgctaacg gattcaccac tccaagaatt   2460
ggagccaatc aattcttgcg gagaactgtg aatgcgcaaa ccaacccttg cagaacata   2520 tccatcgcgt ccgccatctc cagcagccgc acgcggcgca tctcgggcag cgttgggtcc   2580
tggccacggg tgcgcatgat cgtgctcctg tcgttgagga cccggctagg ctggcgggt   2640 tgccttactg gttagcagaa tgaatcaccg atacgcgagc gaacgtgaag cgactgctgc   2700
tgcaaaacgt ctgcgacctg agcaacaaca tgaatggtct tcggtttccg tgtttcgtaa   2760
agtctggaaa cgcggaagtc agcgccctgc accattatgt tccggatctg catcgcagga   2820
tgctgctggc tacccgtgg aacacctaca tctgtattaa cgaagcgctg gcattgaccc   2880
tgagtgattt ttctctggtc ccgccgcatc cataccgcca gttgtttacc ctcacaacgt   2940
tccagtaacc gggcatgttc atcatcagta acccgtatcg tgagcatcct ctctcgtttc   3000
atcggtatca ttaccccat gaacagaaat ccccttaca cggaggcatc agtgaccaaa   3060
caggaaaaaa ccgcccttaa catggcccgc tttatcagaa gccagacatt aacgcttctg   3120
gagaaactca acgagctgga cgcggatgaa caggcagaca tctgtgaatc gcttcacgac   3180
cacgctgatg agcttaccg cagctgcctc gcgcgtttcg gtgatgacgg tgaaaacctc   3240
tgacacatgc agctcccgga gacggtcaca gcttgtctgt aagcggatgc cgggagcaga   3300
caagcccgtc agggcgcgtc agcgggtgtt ggcgggtgtc ggggcgcagc catgacccag   3360
tcacgtagcg atagcggagt gtatactggc ttaactatgc ggcatcagag cagattgtac   3420
tgagagtgca ccatatgcgg tgtgaaatac cgcacagatg cgtaaggaga aataccgca   3480 tcaggcgctc ttccgcttcc tcgctcactg actcgctgcg ctcggtcgtt cggctgcggc   3540
gagcggtatc agctcactca aaggcggtaa tacggttatc cacagaatca ggggataacg   3600
caggaaagaa catgtgagca aaaggccagc aaaaggccag gaaccgtaaa aaggccgcgt   3660
tgctggcgtt tttccatagg ctccgccccc ctgacgagca tcacaaaaat cgacgctcaa   3720
gtcagaggtg gcgaaacccg acaggactat aaagatacca ggcgtttccc cctggaagct   3780
ccctcgtgcg ctctcctgtt ccgaccctgc cgcttaccgg atacctgtcc gcctttctcc   3840
cttcgggaag cgtggcgctt tctcatagct cacgctgtag gtatctcagt tcggtgtagg   3900
tcgttcgctc caagctgggc tgtgtgcacg aaccccccgt tcagcccgac cgctgcgcct   3960
tatccggtaa ctatcgtctt gagtccaacc cggtaagaca cgacttatcg ccactggcag   4020
```

```
cagccactgg taacaggatt agcagagcga ggtatgtagg cggtgctaca gagttcttga    4080
agtggtggcc taactacggc tacactagaa ggacagtatt tggtatctgc gctctgctga    4140
agccagttac cttcggaaaa agagttggta gctcttgatc cggcaaacaa accaccgctg    4200
gtagcggtgg ttttttttgtt tgcaagcagc agattacgcg cagaaaaaaa ggatctcaag    4260
aagatccttt gatcttttct acggggtctg acgctcagtg gaacgaaaac tcacgttaag    4320 ggatttttggt catgagatta tcaaaaagga tcttcaccta gatccttttta aattaaaaat    4380 gaagttttaa atcaatctaa agtatatatg agtaaacttg gtctgacagt taccaatgct    4440
taatcagtga ggcacctatc tcagcgatct gtctatttcg ttcatccata gttgcctgac    4500
tccccgtcgt gtagataact acgatacggg agggcttacc atctggcccc agtgctgcaa    4560
tgataccgcg agacccacgc tcaccggctc cagatttatc agcaataaac cagccagccg    4620
gaagggccga gcgcagaagt ggtcctgcaa ctttatccgc ctccatccag tctattaatt    4680
gttgccggga agctagagta agtagttcgc cagttaatag tttgcgcaac gttgttgcca    4740
ttgctgcagg catcgtggtg tcacgctcgt cgtttggtat ggcttcattc agctccggtt    4800
cccaacgatc aaggcgagtt acatgatccc ccatgttgtg caaaaaagcg gttagctcct    4860
tcggtcctcc gatcgttgtc agaagtaagt tggccgcagt gttatcactc atggttatgg    4920
cagcactgca taattctctt actgtcatgc catccgtaag atgcttttct gtgactggtg    4980
agtactcaac caagtcattc tgagaatagt gtatgcggcg accgagttgc tcttgcccgg    5040
cgtcaacacg ggataatacc gcgccacata gcagaacttt aaaagtgctc atcattggaa    5100
aacgttcttc ggggcgaaaa ctctcaagga tcttaccgct gttgagatcc agttcgatgt    5160
aacccactcg tgcacccaac tgatcttcag catctttttac tttcaccagc gtttctgggt    5220
gagcaaaaac aggaaggcaa aatgccgcaa aaaagggaat aagggcgaca cggaaatgtt    5280
gaatactcat actcttcctt tttcaatatt attgaagcat ttatcagggt tattgtctca    5340
tgagcggata catatttgaa tgtatttaga aaaataaaca aatagggggtt ccgcgcacat    5400 ttccccgaaa agtgccacct gacgtctaag aaaccattat tatcatgaca ttaacctata    5460
aaaataggcg tatcacgagg ccctttcgtc ttcaagaa                            5498
```

<210> SEQ ID NO 2  
<211> LENGTH: 4696  
<212> TYPE: DNA  
<213> ORGANISM: Artificial Sequence  
<220> FEATURE:  
<223> OTHER INFORMATION: Recombinant plasmid pAPSE10181; ErkA stem  
      loop - coat protein  
<220> FEATURE:  
<221> NAME/KEY: promoter  
<222> LOCATION: (24)..(42)  
<223> OTHER INFORMATION: bacteriophage T7 gene 1 promoter  
<220> FEATURE:  
<221> NAME/KEY: misc_feature  
<222> LOCATION: (127)..(145)  
<223> OTHER INFORMATION: bacteriophage MS2 pac sequence  
<220> FEATURE:  
<221> NAME/KEY: misc_feature  
<222> LOCATION: (175)..(182)  
<223> OTHER INFORMATION: restriction endonuclease AsiSI recognition site  
<220> FEATURE:  
<221> NAME/KEY: misc_feature  
<222> LOCATION: (179)..(384)  
<223> OTHER INFORMATION: ErkA sense strand gene fragment  
<220> FEATURE:  
<221> NAME/KEY: misc_feature  
<222> LOCATION: (436)..(454)  
<223> OTHER INFORMATION: bacteriophage MS2 pac sequence  
<220> FEATURE:

```
<221> NAME/KEY: misc_feature
<222> LOCATION: (504)..(511)
<223> OTHER INFORMATION: restriction endonuclease NotI recognition site
<220> FEATURE:
<221> NAME/KEY: misc_feature
<222> LOCATION: (505)..(696)
<223> OTHER INFORMATION: ErkA antisense strand gene fragment
<220> FEATURE:
<221> NAME/KEY: misc_feature
<222> LOCATION: (692)..(699)
<223> OTHER INFORMATION: restriction endonuclease PacI recognition site
<220> FEATURE:
<221> NAME/KEY: misc_feature
<222> LOCATION: (709)..(727)
<223> OTHER INFORMATION: bacteriophage MS2 pac sequence
<220> FEATURE:
<221> NAME/KEY: terminator
<222> LOCATION: (743)..(790)
<223> OTHER INFORMATION: bacteriophage T7 transcription terminator
<220> FEATURE:
<221> NAME/KEY: misc_feature
<222> LOCATION: (897)..(902)
<223> OTHER INFORMATION: restriction endonuclease SphI recognition site

<400> SEQUENCE: 2
ttcagatctc gatcccgcga aattaatacg actcactata gggagaccac aacggtttcc      60
ctctagatca caagtttgta caaaaaagca ggctaagaag gagatataca tacgccggcc     120
attcaaacat gaggattacc catgtaacct aaggccggtg tccaggcgcg ctccgcgatc     180
gcacgcggac aaagttcctc aatctaatgc tgaagttata aggggacaaa tatttgaagt     240
tggtcctagg tatattaaac tcgcctatat aggtgaagga gcttatggca tggttgtgtc     300
tgcggatgac acgctaacaa accaaagagt tgcaataaaa aaaatatcgc cctttgaaca     360
ccaaacttat tgctactaca gtttaaacgc aatcgcagca aactccggca tctactaata     420
gacgccggcc attcaacatg aggattaccc atgtaaccta agaagacaac aaagaagttc     480
aactctttat gtattgatct tccgcggccg ccaataagtt tggtgttcaa agggcgatat     540 ttttttatt gcaactcttt ggtttgttag cgtgtcatcc gcagacacaa ccatgccata     600
agctccttca cctatatagg cgagtttaat tacctagga ccaacttcaa atatttgtcc      660
ccttataact tcagcattag attgaggaac tttaattaag gagttcaaac atgaggatca     720
cccatgtcga agctcccaca ccctagcata accccttggg gcctctaaac gggtcttgag     780 gggtttttg ctgaaaggag gaactatatc cggatatcca caggacgggt gtggtcgcca      840
tgatcgcgta gtcgatagtg gctccaagta gcgaagcgag caggactggg cggcgggcat     900
gcaccattcc ttgcggcggc ggtgctcaac ggcctcaacc tactactggg ctgcttccta     960
atgcaggagt cgcataaggg agagcgtcga ccgatgccct tgagagcctt caacccagtc    1020
agctccttcc ggtgggcgcg ggcatgact atcgtcgccg cacttatgac tgtcttcttt     1080
atcatgcaac tcgtaggaca ggtgccggca gcgctctggg tcattttcgg cgaggaccgc    1140
tttcgctgga gcgcgacgat gatcggcctg tcgcttgcgg tattcggaat cttgcacgcc    1200
ctcgctcaag ccttcgtcac tggtcccgcc accaaacgtt tcggcgagaa gcaggccatt    1260
atcgccggca tggcggccga cgcgctgggc tacgtcttgc tggcgttcgc gacgcgaggc    1320
tggatggcct tccccattat gattcttctc gcttccggcg catcgggat gcccgcgttg     1380 caggccatgc tgtccaggca ggtagatgac gaccatcagg acagcttca aggatcgctc     1440 gcggctctta ccagcctaac ttcgatcatt ggaccgctga tcgtcacggc gatttatgcc    1500
gcctcggcga gcatggaa cgggttggca tggattgtag gcgccgccct ataccttgtc      1560
tgcctccccg cgttgcgtcg cggtgcatgg agccgggcca cctcgacctg aatggaagcc    1620
```

```
ggcggcacct cgctaacgga ttcaccactc caagaattgg agccaatcaa ttcttgcgga   1680
gaactgtgaa tgcgcaaacc aaccctcggc agaacatatc catcgcgtcc gccatctcca   1740
gcagccgcac gcggcgcatc tcgggcagcg ttgggtcctg ccacgggtg cgcatgatcg    1800 tgctcctgtc gttgaggacc cggctaggct ggcggggttg ccttactggt tagcagaatg   1860
aatcaccgat acgcgagcga acgtgaagcg actgctgctg caaaacgtct gcgacctgag   1920
caacaacatg aatggtcttc ggtttccgtg tttcgtaaag tctggaaacg cggaagtcag   1980
cgccctgcac cattatgttc cggatctgca tcgcaggatg ctgctggcta ccctgtggaa   2040
cacctacatc tgtattaacg aagcgctggc attgaccctg agtgattttt ctctggtccc   2100
gccgcatcca taccgccagt tgtttaccct cacaacgttc cagtaaccgg gcatgttcat   2160
catcagtaac ccgtatcgtg agcatcctct ctcgtttcat cggtatcatt accccatga    2220 acagaaatcc cccttacacg gaggcatcag tgaccaaaca ggaaaaaacc gcccttaaca   2280
tggcccgctt tatcagaagc cagacattaa cgcttctgga gaaactcaac gagctggacg   2340
cggatgaaca ggcagacatc tgtgaatcgc ttcacgacca cgctgatgag ctttaccgca   2400
gctgcctcgc gcgtttcggt gatgacggtg aaaacctctg acacatgcag ctcccggaga   2460
cggtcacagc ttgtctgtaa gcggatgccg ggagcagaca agcccgtcag ggcgcgtcag   2520
cgggtgttgg cgggtgtcgg ggcgcagcca tgacccagtc acgtagcgat agcggagtgt   2580
atactggctt aactatgcgg catcagagca gattgtactg agagtgcacc atatgcggtg   2640
tgaaataccg cacagatgcg taaggagaaa ataccgcatc aggcgctctt ccgcttcctc   2700
gctcactgac tcgctgcgct cggtcgttcg gctgcggcga cggtatcag ctcactcaaa    2760 ggcggtaata cggttatcca cagaatcagg ggataacgca ggaaagaaca tgtgagcaaa   2820
aggccagcaa aaggccagga accgtaaaaa ggccgcgttg ctggcgtttt tccataggct   2880
ccgcccccct gacgagcatc acaaaaatcg acgctcaagt cagaggtggc gaaacccgac   2940
aggactataa agataccagg cgtttccccc tggaagctcc ctcgtgcgct ctcctgttcc   3000
gaccctgccg cttaccggat acctgtccgc ctttctccct cgggaagcg tggcgctttc    3060 tcatagctca cgctgtaggt atctcagttc ggtgtaggtc gttcgctcca agctgggctg   3120
tgtgcacgaa ccccccgttc agcccgaccg ctgcgcctta ccggtaact atcgtcttga    3180 gtccaacccg gtaagacacg acttatcgcc actggcagca gccactggta acaggattag   3240
cagagcgagg tatgtaggcg gtgctacaga gttcttgaag tggtggccta actacggcta   3300
cactagaagg acagtatttg gtatctgcgc tctgctgaag ccagttacct tcggaaaaag   3360
agttggtagc tcttgatccg gcaaacaaac caccgctggt agcggtggtt ttttgtttg    3420 caagcagcag attacgcgca gaaaaaaagg atctcaagaa gatcctttga tcttttctac   3480
ggggtctgac gctcagtgga acgaaaactc acgttaaggg attttggtca tgagattatc   3540
aaaaaggatc ttcacctaga tccttttaaa ttaaaatga agttttaaat caatctaaag    3600
tatatatgag taaacttggt ctgacagtta ccaatgctta atcagtgagg cacctatctc   3660
agcgatctgt ctatttcgtt catccatagt tgcctgactc cccgtcgtgt agataactac   3720
gatacgggag ggcttaccat ctggccccag tgctgcaatg ataccgcgag acccacgctc   3780
accggctcca gatttatcag caataaacca gccagccgga agggccgagc gcagaagtgg   3840
tcctgcaact ttatccgcct ccatccagtc tattaattgt tgccgggaag ctagagtaag   3900
tagttcgcca gttaatagtt tgcgcaacgt tgttgccatt gctgcaggca tcgtggtgtc   3960
```

```
acgctcgtcg tttggtatgg cttcattcag ctccggttcc caacgatcaa ggcgagttac      4020
atgatccccc atgttgtgca aaaaagcggt tagctccttc ggtcctccga tcgttgtcag      4080
aagtaagttg gccgcagtgt tatcactcat ggttatggca gcactgcata attctcttac      4140
tgtcatgcca tccgtaagat gcttttctgt gactggtgag tactcaacca agtcattctg      4200
agaatagtgt atgcggcgac cgagttgctc ttgcccggcg tcaacacggg ataataccgc      4260
gccacatagc agaactttaa aagtgctcat cattggaaaa cgttcttcgg ggcgaaaact      4320
ctcaaggatc ttaccgctgt tgagatccag ttcgatgtaa cccactcgtg cacccaactg      4380
atcttcagca tcttttactt tcaccagcgt ttctgggtga gcaaaaacag gaaggcaaaa      4440
tgccgcaaaa aagggaataa gggcgacacg gaaatgttga atactcatac tcttcctttt      4500
tcaatattat tgaagcattt atcagggtta ttgtctcatg agcggataca tatttgaatg      4560
tatttagaaa aataaacaaa taggggttcc gcgcacattt ccccgaaaag tgccacctga      4620
cgtctaagaa accattatta tcatgacatt aacctataaa aataggcgta tcacgaggcc      4680
ctttcgtctt caagaa                                                     4696

<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide probe

<400> SEQUENCE: 3
ggccggcgtc tattagtaga tgcc                                              24

<210> SEQ ID NO 4
<211> LENGTH: 5591
<212> TYPE: DNA
<213> ORGANISM: Artificial Sequence
<220> FEATURE:
<223> OTHER INFORMATION: Recombinant plasmid pAPSE10189; beta actin
      sense strand + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: promoter
<222> LOCATION: (1209)..(1227)
<223> OTHER INFORMATION: bacteriophage T7 gene 1 promoter
<220> FEATURE:
```

```
<221> NAME/KEY: gene
<222> LOCATION: (1300)..(1689)
<223> OTHER INFORMATION: bacteriophage MS2 cot protein gene
<220> FEATURE:
<221> NAME/KEY: gene
<222> LOCATION: (1300)..(1689)
<223> OTHER INFORMATION: bacteriophage MS2 coat protein gene
<220> FEATURE:
<221> NAME/KEY: terminator
<222> LOCATION: (1722)..(1769)
<223> OTHER INFORMATION: bacteriophage T7 transcription terminator

<400> SEQUENCE: 4
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300 tacgccggcc attcaaacat gaggattacc catgtattta atacccatg tccaggcgcg     360 ctccgcgatc gcgcacgagg ttttctgtc tagtgagcag tgtccaacct caaaagacaa      420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca acatgaggga tcacccatgt cgaagctccc acaccctagc     840
ataacccctt ggggcctcta acgggtctt gaggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcatcgt ccattccgac agcatcgcca    1020
gtcactatgg cgtgctgcta gcgctatatg cgttgatgca atttctatgc gcacccgttc    1080
tcggagcact gtccgaccgc tttggccgcc gcccagtcct gctcgcttcg ctacttggag    1140
ccactatcga ctacgcgatc atggcgacca caccgtcct gtggatccag atctcgatcc    1200
cgcgaaatta atacgactca ctatagggag accacaacgg tttccctcta gatcacaagt    1260
ttgtacaaaa aagcaggcta agaaggagat atacatatgg cgtctaactt tacccaattc    1320
gttctggttg ataacggcgg tacgggtgac gttaccgtag ctccgtccaa cttcgccaac    1380
ggtgttgcgg aatggattag ctctaacagc cgctctcagg cctacaaagt cacgtgctcc    1440
gttcgtcagt ctagcgcgca gaatcgcaaa tacaccatca agttgaagt accgaaagtc    1500 gcaacgcaga ccgtaggcgg cgtagaactc ccagttgcgg cctggcgctc ttacctcaac    1560
atggaactga ctattccgat ttttgcgacg aactccgact cgaactgat tgttaaggca    1620 atgcagggcc tgctgaaaga cggtaatccg atcccatctg caatcgctgc taactctggc    1680
atttactaat aagcggacgc gctgccaccg ctgagcaata actagcataa ccccttgggg    1740
cctctaaacg ggtcttgagg ggttttttgc tgaaaggagg aactatatcc ggcatgcacc    1800
attccttgcg gcggcggtgc tcaacggcct caacctacta ctgggctgct tcctaatgca    1860
ggagtcgcat aagggagagc gtcgaccgat gcccttgaga gccttcaacc cagtcagctc    1920
cttccggtgg gcgcggggca tgactatcgt cgccgcactt atgactgtct tctttatcat    1980
```

```
gcaactcgta ggacaggtgc cggcagcgct ctgggtcatt ttcggcgagg accgctttcg    2040
ctggagcgcg acgatgatcg gcctgtcgct tgcggtattc ggaatcttgc acgccctcgc    2100
tcaagccttc gtcactggtc ccgccaccaa acgtttcggc gagaagcagg ccattatcgc    2160
cggcatggcg gccgacgcgc tgggctacgt cttgctggcg ttcgcgacgc gaggctggat    2220
ggccttcccc attatgattc ttctcgcttc cggcggcatc gggatgcccg cgttgcaggc    2280
catgctgtcc aggcaggtag atgacgacca tcagggacag cttcaaggat cgctcgcggc    2340
tcttaccagc ctaacttcga tcattggacc gctgatcgtc acggcgattt atgccgcctc    2400
ggcgagcaca tggaacgggt tggcatggat tgtaggcgcc gccctatacc ttgtctgcct    2460
ccccgcgttg cgtcgcggtg catggagccg ggccacctcg acctgaatgg aagccggcgg    2520
cacctcgcta acggattcac cactccaaga attggagcca atcaattctt gcggagaact    2580
gtgaatgcgc aaaccaaccc ttggcagaac atatccatcg cgtccgccat ctccagcagc    2640
cgcacgcggc gcatctcggg cagcgttggg tcctggccac gggtgcgcat gatcgtgctc    2700
ctgtcgttga ggacccggct aggctggcgg ggttgcctta ctggttagca gaatgaatca    2760
ccgatacgcg agcgaacgtg aagcgactgc tgctgcaaaa cgtctgcgac ctgagcaaca    2820
acatgaatgg tcttcggttt ccgtgtttcg taaagtctgg aaacgcggaa gtcagcgccc    2880
tgcaccatta tgttccggat ctgcatcgca ggatgctgct ggctaccctg tggaacacct    2940
acatctgtat taacgaagcg ctggcattga ccctgagtga tttttctctg gtcccgccgc    3000
atccataccg ccagttgttt accctcacaa cgttccagta accgggcatg ttcatcatca    3060
gtaacccgta tcgtgagcat cctctctcgt ttcatcggta tcattacccc catgaacaga    3120
aatccccctt acacggaggc atcagtgacc aaacaggaaa aaaccgccct taacatggcc    3180
cgctttatca gaagccagac attaacgctt ctggagaaac tcaacgagct ggacgcggat    3240
gaacaggcag acatctgtga atcgcttcac gaccacgctg atgagcttta ccgcagctgc    3300
ctcgcgcgtt tcggtgatga cggtgaaaac ctctgacaca tgcagctccc ggagacggtc    3360
acagcttgtc tgtaagcgga tgccgggagc agacaagccc gtcagggcgc gtcagcgggt    3420
gttggcgggt gtcggggcgc agccatgacc cagtcacgta gcgatagcgg agtgtatact    3480
ggcttaacta tgcggcatca gagcagattg tactgagagt gcaccatatg cggtgtgaaa    3540
taccgcacag atgcgtaagg agaaaatacc gcatcaggcg ctcttccgct tcctcgctca    3600
ctgactcgct gcgctcggtc gttcggctgc ggcgagcggt atcagctcac tcaaaggcgg    3660
taatacggtt atccacagaa tcaggggata acgcaggaaa gaacatgtga gcaaaaggcc    3720
agcaaaaggc caggaaccgt aaaaaggccg cgttgctggc gtttttccat aggctccgcc    3780
cccctgacga gcatcacaaa aatcgacgct caagtcagag gtggcgaaac ccgacaggac    3840
tataaagata ccaggcgttt ccccctggaa gctccctcgt gcgctctcct gttccgaccc    3900
tgccgcttac cggatacctg tccgcctttc tcccttcggg aagcgtggcg ctttctcata    3960
gctcacgctg taggtatctc agttcggtgt aggtcgttcg ctccaagctg ggctgtgtgc    4020 acgaacccc cgttcagccc gaccgctgcg ccttatccgg taactatcgt cttgagtcca    4080
acccggtaag acacgactta tcgccactgg cagcagccac tggtaacagg attagcagag    4140
cgaggtatgt aggcggtgct acagagttct tgaagtggtg gcctaactac ggctacacta    4200
gaaggacagt atttggtatc tgcgctctgc tgaagccagt taccttcgga aaaagagttg    4260
gtagctcttg atccggcaaa caaaccaccg ctggtagcgg tggttttttt gtttgcaagc    4320
```

```
agcagattac gcgcagaaaa aaaggatctc aagaagatcc tttgatcttt tctacggggt    4380
ctgacgctca gtggaacgaa aactcacgtt aagggatttt ggtcatgaga ttatcaaaaa    4440
ggatcttcac ctagatcctt ttaaattaaa aatgaagttt taaatcaatc taaagtatat    4500
atgagtaaac ttggtctgac agttaccaat gcttaatcag tgaggcacct atctcagcga    4560
tctgtctatt tcgttcatcc atagttgcct gactccccgt cgtgtagata actacgatac    4620
gggagggctt accatctggc cccagtgctg caatgatacc gcgagaccca cgctcaccgg    4680
ctccagattt atcagcaata aaccagccag ccggaagggc cgagcgcaga gtggtcctg     4740 caactttatc cgcctccatc cagtctatta attgttgccg ggaagctaga gtaagtagtt    4800
cgccagttaa tagtttgcgc aacgttgttg ccattgctgc aggcatcgtg gtgtcacgct    4860
cgtcgtttgg tatggcttca ttcagctccg gttcccaacg atcaaggcga gttacatgat    4920
cccccatgtt gtgcaaaaaa gcggttagct ccttcggtcc tccgatcgtt gtcagaagta    4980
agttggccgc agtgttatca ctcatggtta tggcagcact gcataattct cttactgtca    5040
tgccatccgt aagatgcttt tctgtgactg gtgagtactc aaccaagtca ttctgagaat    5100
agtgtatgcg gcgaccgagt tgctcttgcc cggcgtcaac acgggataat accgcgccac    5160
atagcagaac tttaaaagtg ctcatcattg gaaaacgttc ttcggggcga aaactctcaa    5220
ggatcttacc gctgttgaga tccagttcga tgtaacccac tcgtgcaccc aactgatctt    5280
cagcatcttt tactttcacc agcgtttctg ggtgagcaaa aacaggaagg caaaatgccg    5340
caaaaaaggg aataagggcg acacggaaat gttgaatact catactcttc ctttttcaat    5400
attattgaag catttatcag ggttattgtc tcatgagcgg atacatattt gaatgtattt    5460
agaaaaataa acaaataggg gttccgcgca catttccccg aaaagtgcca cctgacgtct    5520
aagaaaccat tattatcatg acattaacct ataaaaatag gcgtatcacg aggccctttc    5580
gtcttcaaga a                                                         5591
```

<210> SEQ ID NO 5
<211> LENGTH: 5591
<212> TYPE: DNA
<213> ORGANISM: Artificial Sequence
<220> FEATURE:
<223> OTHER INFORMATION: Recombinant plasmid pAPSE10190; beta actin
      antisense strand + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin antisense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)

<223> OTHER INFORMATION: bacteriophage T7 transcription terminator
<220> FEATURE:
<221> NAME/KEY: promoter
<222> LOCATION: (1209)..(1227)
<223> OTHER INFORMATION: bacteriophage T7 gene 1 promoter
<220> FEATURE:
<221> NAME/KEY: gene
<222> LOCATION: (1300)..(1689)
<223> OTHER INFORMATION: bacteriophage MS2 coat protein gene
<220> FEATURE:
<221> NAME/KEY: terminator
<222> LOCATION: (1722)..(1769)
<223> OTHER INFORMATION: bacteriophage T7 transcription terminator

<400> SEQUENCE: 5

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300
tacgccggcc attcaaacat gaggattacc catgtattta ataccccatg tccaggcgcg     360
ctccgcgatc gctcatccca gttggtgatg ataccgtgtt cgatgggta tttcaggtg     420
aggatacctc ttttgctttg ggcttcatct cctacgtatg agtccttttg tcccataccg     480
accatgactc cttgatgcct tgggcgaccg acgatcgagg ggaagacggc acggggtgcg     540
tcatctcctg cgaaaccggc tttgcacata ccggatccat tgtctacgac aagagccgct     600
acatcgtcgt cacacatgtt gtcttttgag gttggacact gctcactaga cagaaaaacc     660
tcgtgcgttt aaacctttcg gattataaca tcacatctag gcgcgcctga cgatcaacca     720
taccagacgg accgaatacc cggtctgaac gagggcggcc gcgtaccca agaagtactt     780
agagttaatt aaggagttca aacatgagga tcacccatgt cgaagctccc acccctagc     840
ataaccccctt ggggcctcta acgggtctt gaggggtttt ttgctgaaag gaggaactat     900
atccggatat ccacaggacg ggtgtggtcg ccatgatcgc gtagtcgata gtggctccaa     960
gtagcgaagc gagcaggact gggcggcggg catgcatcgt ccattccgac agcatcgcca    1020
gtcactatgg cgtgctgcta gcgctatatg cgttgatgca atttctatgc gcaccgttc    1080
tcggagcact gtccgaccgc tttggccgcc gcccagtcct gctcgcttcg ctacttggag    1140
ccactatcga ctacgcgatc atggcgacca caccgtcct gtggatccag atctcgatcc    1200
cgcgaaatta atacgactca ctatagggag accacaacgg tttccctcta gatcacaagt    1260
ttgtacaaaa agcaggcta agaaggagat atacatatg cgtctaactt acccaattc    1320
gttctggttg ataacggcgg tacgggtgac gttaccgtag ctccgtccaa cttcgccaac    1380
ggtgttgcgg aatggattag ctctaacagc cgctctcagg cctacaaagt cacgtgctcc    1440
gttcgtcagt ctagcgcgca gaatcgcaaa tacaccatca agttgaagt accgaaagtc    1500
gcaacgcaga ccgtaggcgg cgtagaactc ccagttgcgg cctggcgctc ttacctcaac    1560
atggaactga ctattccgat ttttgcgacg aactccgact gcgaactgat tgttaaggca    1620
atgcagggcc tgctgaaaga cggtaatccg atcccatctg caatcgctgc taactctggc    1680
atttactaat aagcggacgc gctgccaccg ctgagcaata actagcataa ccccttgggg    1740
cctctaaacg ggtcttgagg ggttttttgc tgaaggagg aactatatcc ggcatgcacc    1800
attccttgcg gcgcggtgc tcaacggcct caacctacta ctgggctgct tcctaatgca    1860
ggagtcgcat aagggagagc gtcgaccgat gcccttgaga gccttcaacc cagtcagctc    1920
```

```
cttccggtgg gcgcggggca tgactatcgt cgccgcactt atgactgtct tctttatcat   1980
gcaactcgta ggacaggtgc cggcagcgct ctgggtcatt ttcggcgagg accgctttcg   2040
ctggagcgcg acgatgatcg gcctgtcgct tgcggtattc ggaatcttgc acgccctcgc   2100
tcaagccttc gtcactggtc ccgccaccaa acgtttcggc gagaagcagg ccattatcgc   2160
cggcatggcg gccgacgcgc tgggctacgt cttgctggcg ttcgcgacgc gaggctggat   2220
ggccttcccc attatgattc ttctcgcttc cggcggcatc gggatgcccg cgttgcaggc   2280
catgctgtcc aggcaggtag atgacgacca tcagggacag cttcaaggat cgctcgcggc   2340
tcttaccagc ctaacttcga tcattggacc gctgatcgtc acggcgattt atgccgcctc   2400
ggcgagcaca tggaacgggt tggcatggat tgtaggcgcc gccctatacc ttgtctgcct   2460
ccccgcgttg cgtcgcggtg catggagccg ggccacctcg acctgaatgg aagccggcgg   2520
cacctcgcta acggattcac cactccaaga attggagcca atcaattctt gcggagaact   2580
gtgaatgcgc aaaccaaccc ttggcagaac atatccatcg cgtccgccat ctccagcagc   2640
cgcacgcggc gcatctcggg cagcgttggg tcctggccac gggtgcgcat gatcgtgctc   2700
ctgtcgttga ggacccggct aggctggcgg ggttgcctta ctggttagca gaatgaatca   2760
ccgatacgcg agcgaacgtg aagcgactgc tgctgcaaaa cgtctgcgac ctgagcaaca   2820
acatgaatgg tcttcggttt ccgtgtttcg taaagtctgg aaacgcggaa gtcagcgccc   2880
tgcaccatta tgttccggat ctgcatcgca ggatgctgct ggctaccctg tggaacacct   2940
acatctgtat taacgaagcg ctggcattga ccctgagtga ttttctctg gtcccgccgc   3000 atccataccg ccagttgttt accctcacaa cgttccagta accgggcatg ttcatcatca   3060
gtaacccgta tcgtgagcat cctctctcgt ttcatcggta tcattacccc catgaacaga   3120
aatccccctt acacggaggc atcagtgacc aaacaggaaa aaaccgccct aacatggcc   3180 cgctttatca gaagccagac attaacgctt ctggagaaac tcaacgagct ggacgcggat   3240
gaacaggcag acatctgtga atcgcttcac gaccacgctg atgagcttta ccgcagctgc   3300
ctcgcgcgtt tcggtgatga cggtgaaaac ctctgacaca tgcagctccc ggagacggtc   3360
acagcttgtc tgtaagcgga tgccgggagc agacaagccc gtcagggcgc gtcagcgggt   3420
gttggcgggt gtcggggcgc agccatgacc cagtcacgta gcgatagcgg agtgtatact   3480
ggcttaacta tgcggcatca gagcagattg tactgagagt gcaccatatg cggtgtgaaa   3540
taccgcacag atgcgtaagg agaaaatacc gcatcaggcg ctcttccgct tcctcgctca   3600
ctgactcgct gcgctcggtc gttcggctgc ggcgagcggt atcagctcac tcaaaggcgg   3660
taatacggtt atccacagaa tcaggggata acgcaggaaa gaacatgtga gcaaaaggcc   3720
agcaaaaggc caggaaccgt aaaaaggccg cgttgctggc gtttttccat aggctccgcc   3780
cccctgacga gcatcacaaa aatcgacgct caagtcagag gtggcgaaac ccgacaggac   3840
tataaagata ccaggcgttt ccccctggaa gctccctcgt gcgctctcct gttccgaccc   3900
tgccgcttac cggatacctg tccgcctttc tcccttcggg aagcgtggcg ctttctcata   3960
gctcacgctg taggtatctc agttcggtgt aggtcgttcg ctccaagctg ggctgtgtgc   4020
acgaaccccc cgttcagccc gaccgctgcg ccttatccgg taactatcgt cttgagtcca   4080
acccggtaag acacgactta tcgccactgg cagcagccac tggtaacagg attagcagag   4140
cgaggtatgt aggcggtgct acagagttct tgaagtggtg gcctaactac ggctacacta   4200
gaaggacagt atttggtatc tgcgctctgc tgaagccagt taccttcgga aaagagttg   4260
```

```
gtagctcttg atccggcaaa caaaccaccg ctggtagcgg tggttttttt gtttgcaagc    4320
agcagattac gcgcagaaaa aaaggatctc aagaagatcc tttgatcttt tctacggggt    4380
ctgacgctca gtggaacgaa aactcacgtt aagggatttt ggtcatgaga ttatcaaaaa    4440
ggatcttcac ctagatcctt ttaaattaaa aatgaagttt taaatcaatc taaagtatat    4500
atgagtaaac ttggtctgac agttaccaat gcttaatcag tgaggcacct atctcagcga    4560
tctgtctatt tcgttcatcc atagttgcct gactccccgt cgtgtagata actacgatac    4620
gggagggctt accatctggc cccagtgctg caatgatacc gcgagaccca cgctcaccgg    4680
ctccagattt atcagcaata aaccagccag ccggaagggc cgagcgcaga agtggtcctg    4740
caactttatc cgcctccatc cagtctatta attgttgccg ggaagctaga gtaagtagtt    4800
cgccagttaa tagtttgcgc aacgttgttg ccattgctgc aggcatcgtg gtgtcacgct    4860
cgtcgtttgg tatggcttca ttcagctccg gttcccaacg atcaaggcga gttacatgat    4920
cccccatgtt gtgcaaaaaa gcggttagct ccttcggtcc tccgatcgtt gtcagaagta    4980
agttggccgc agtgttatca ctcatggtta tggcagcact gcataattct cttactgtca    5040
tgccatccgt aagatgcttt tctgtgactg gtgagtactc aaccaagtca ttctgagaat    5100
agtgtatgcg gcgaccgagt tgctcttgcc cggcgtcaac acgggataat accgcgccac    5160
atagcagaac tttaaaagtg ctcatcattg gaaaacgttc ttcggggcga aaactctcaa    5220
ggatcttacc gctgttgaga tccagttcga tgtaacccac tcgtgcaccc aactgatctt    5280
cagcatcttt tactttcacc agcgtttctg ggtgagcaaa aacaggaagg caaaatgccg    5340
caaaaaaggg aataagggcg acacggaaat gttgaatact catactcttc cttttttcaat    5400 attattgaag catttatcag ggttattgtc tcatgagcgg atacatattt gaatgtattt    5460
agaaaaataa acaaataggg gttccgcgca catttccccg aaaagtgcca cctgacgtct    5520
aagaaaccat tattatcatg acattaacct ataaaaatag gcgtatcacg aggccctttc    5580
gtcttcaaga a                                                         5591
```

<210> SEQ ID NO 6
<211> LENGTH: 4789
<212> TYPE: DNA
<213> ORGANISM: Artificial Sequence
<220> FEATURE:
<223> OTHER INFORMATION: Recombinant plasmid pAPSE10274; beta actin
      sense strand - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (802)..(820)
<223> OTHER INFORMATION: bacteriophage MS2 pac sequence
<220> FEATURE:

```
<221> NAME/KEY: terminator
<222> LOCATION: (836)..(883)
<223> OTHER INFORMATION: bacteriophage T7 transcription terminator
<220> FEATURE:
<221> NAME/KEY: misc_feature
<222> LOCATION: (990)..(995)
<223> OTHER INFORMATION: restriction endonuclease SphI  recognition site

<400> SEQUENCE: 6
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300 tacgccggcc attcaaacat gaggattacc catgtattta atacccatg tccaggcgcg      360 ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacctttcg gattataaca tcacatctag gcgcgcctga cgatcaacca     720
taccagacgg accgaatacc cggtctgaac gagggcggcc gcggtaccca agaagtactt     780
agagttaatt aaggagttca acatgagga tcacccatgt cgaagctccc acaccctagc      840 ataaccccctt ggggcctcta acgggtctt gagggggttt t tgctgaaag gaggaactat      900 atccggatat ccacaggacg ggtgtggtcg ccatgatcgc gtagtcgata gtggctccaa     960
gtagcgaagc gagcaggact gggcggcggg catgcaccat tccttgcggc ggcggtgctc    1020
aacggcctca acctactact gggctgcttc ctaatgcagg agtcgcataa gggagagcgt    1080
cgaccgatgc ccttgagagc cttcaaccca gtcagctcct tccggtgggc gcggggcatg    1140
actatcgtcg ccgcacttat gactgtcttc tttatcatgc aactcgtagg acaggtgccg    1200
gcagcgctct gggtcatttt cggcgaggac cgctttcgct ggagcgcgac gatgatcggc    1260
ctgtcgcttg cggtattcgg aatcttgcac gccctcgctc aagccttcgt cactggtccc    1320
gccaccaaac gtttcggcga aagcaggcc attatcgccg gcatggcggc cgacgcgctg    1380
ggctacgtct tgctggcgtt cgcgacgcga ggctggatgg ccttcccat tatgattctt    1440 ctcgcttccg gcggcatcgg gatgcccgcg ttgcaggcca tgctgtccag gcaggtagat    1500
gacgaccatc agggacagct tcaaggatcg ctcgcggctc ttaccagcct aacttcgatc    1560
attggaccgc tgatcgtcac ggcgatttat gccgcctcgg cgagcacatg gaacgggttg    1620
gcatggattg taggcgccgc cctataccct gtctgcctcc ccgcgttgcg tcgcggtgca    1680
tggagccggg ccacctcgac ctgaatggaa gccggcggca cctcgctaac ggattcacca    1740
ctccaagaat tggagccaat caattcttgc ggagaactgt gaatgcgcaa accaaccctt    1800
ggcagaacat atccatcgcg tccgccatct ccagcagccg cacgcggcgc atctcgggca    1860
gcgttgggtc ctggccacgg gtgcgcatga tcgtgctcct gtcgttgagg accggctag    1920 gctgcgggg ttgccttact ggttagcaga atgaatcacc gatacgcgag cgaacgtgaa    1980
gcgactgctg ctgcaaaacg tctgcgacct gagcaacaac atgaatgtc ttcggtttcc    2040 gtgtttcgta aagtctggaa acgcggaagt cagcgccctg caccattatg ttccggatct    2100
```

```
gcatcgcagg atgctgctgg ctaccctgtg aacacctac atctgtatta acgaagcgct    2160
ggcattgacc ctgagtgatt tttctctggt cccgccgcat ccataccgcc agttgtttac    2220
cctcacaacg ttccagtaac cgggcatgtt catcatcagt aacccgtatc gtgagcatcc    2280
tctctcgttt catcggtatc attacccca tgaacagaaa tcccccttac acggaggcat     2340
cagtgaccaa acaggaaaaa accgcccttta catggcccg ctttatcaga agccagacat     2400
taacgcttct ggagaaactc aacgagctgg acgcggatga acaggcagac atctgtgaat    2460
cgcttcacga ccacgctgat gagctttacc gcagctgcct cgcgcgtttc ggtgatgacg    2520
gtgaaaacct ctgacacatg cagctcccgg agacggtcac agcttgtctg taagcggatg    2580
ccgggagcag acaagcccgt cagggcgcgt cagcgggtgt tggcgggtgt cggggcgcag    2640
ccatgaccca gtcacgtagc gatagcggag tgtatactgg cttaactatg cggcatcaga    2700
gcagattgta ctgagagtgc accatatgcg gtgtgaaata ccgcacagat gcgtaaggag    2760
aaaataccgc atcaggcgct cttccgcttc ctcgctcact gactcgctgc gctcggtcgt    2820
tcggctgcgg cgagcggtat cagctcactc aaaggcggta atacggttat ccacagaatc    2880
aggggataac gcaggaaaga acatgtgagc aaaaggccag caaaaggcca ggaaccgtaa    2940
aaaggccgcg ttgctggcgt ttttccatag gctccgcccc cctgacgagc atcacaaaaa    3000
tcgacgctca agtcagaggt ggcgaaaccc gacaggacta taaagatacc aggcgtttcc    3060
ccctggaagc tccctcgtgc gctctcctgt tccgaccctg ccgcttaccg gatacctgtc    3120
cgcctttctc ccttcgggaa gcgtggcgct ttctcatagc tcacgctgta ggtatctcag    3180
ttcggtgtag gtcgttcgct ccaagctggg ctgtgtgcac gaaccccccg ttcagcccga    3240
ccgctgcgcc ttatccggta actatcgtct tgagtccaac ccggtaagac acgacttatc    3300
gccactggca gcagccactg gtaacaggat tagcagagcg aggtatgtag gcggtgctac    3360
agagttcttg aagtggtggc ctaactacgg ctacactaga aggacagtat ttggtatctg    3420
cgctctgctg aagccagtta ccttcggaaa aagagttggt agctcttgat ccggcaaaca    3480
aaccaccgct ggtagcggtg gtttttttgt ttgcaagcag cagattacgc gcagaaaaaa    3540
aggatctcaa gaagatcctt tgatcttttc tacggggtct gacgctcagt ggaacgaaaa    3600
ctcacgttaa gggattttgg tcatgagatt atcaaaaagg atcttcacct agatcctttt    3660
aaattaaaaa tgaagtttta atcaatcta agtatatat gagtaaactt ggtctgacag      3720
ttaccaatgc ttaatcagtg aggcacctat ctcagcgatc tgtctatttc gttcatccat    3780
agttgcctga ctccccgtcg tgtagataac tacgatacgg gagggcttac catctggccc    3840
cagtgctgca atgataccgc gagacccacg ctcaccggct ccagatttat cagcaataaa    3900
ccagccagcc ggaagggccg agcgcagaag tggtcctgca actttatccg cctccatcca    3960
gtctattaat tgttgccggg aagctagagt aagtagttcg ccagttaata gtttgcgcaa    4020
cgttgttgcc attgctgcag gcatcgtggt gtcacgctcg tcgtttggta tggcttcatt    4080
cagctccggt tcccaacgat caaggcgagt tacatgatcc cccatgttgt gcaaaaaagc    4140
ggttagctcc ttcggtcctc cgatcgttgt cagaagtaag ttggccgcag tgttatcact    4200
catggttatg gcagcactgc ataattctct tactgtcatg ccatccgtaa gatgcttttc    4260
tgtgactggt gagtactcaa ccaagtcatt ctgagaatag tgtatgcggc gaccgagttg    4320
ctcttgcccg gcgtcaacac gggataatac cgcgccacat agcagaactt taaaagtgct    4380
catcattgga aaacgttctt cggggcgaaa actctcaagg atcttaccgc tgttgagatc    4440
```

```
cagttcgatg taacccactc gtgcacccaa ctgatcttca gcatctttta ctttcaccag    4500
cgtttctggg tgagcaaaaa caggaaggca aaatgccgca aaaaaggaa taagggcgac     4560 acggaaatgt tgaatactca tactcttcct ttttcaatat tattgaagca tttatcaggg    4620
ttattgtctc atgagcggat acatatttga atgtatttag aaaaataaac aaataggggt    4680
tccgcgcaca tttccccgaa aagtgccacc tgacgtctaa gaaaccatta ttatcatgac    4740
attaacctat aaaataggc gtatcacgag gccctttcgt cttcaagaa                 4789
```

<210> SEQ ID NO 7
<211> LENGTH: 4789
<212> TYPE: DNA
<213> ORGANISM: Artificial Sequence
<220> FEATURE:
<223> OTHER INFORMATION: Recombinant plasmid pAPSE10275; beta actin
      antisense strand - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin antisense strand gene fragment
<220> FEATURE:
<221> NAME/KEY: misc_feature
<222> LOCATION: (667)..(674)
<223> OTHER INFORMATION: restriction endonuclease PmeI recogntion site
<220> FEATURE:
<221> NAME/KEY: misc_feature
<222> LOCATION: (802)..(820)
<223> OTHER INFORMATION: bacteriophage MS2 pac sequence
<220> FEATURE:
<221> NAME/KEY: terminator
<222> LOCATION: (836)..(883)
<223> OTHER INFORMATION: bacteriophage T7 transcription terminator
<220> FEATURE:
<221> NAME/KEY: misc_feature
<222> LOCATION: (990)..(995)
<223> OTHER INFORMATION: restriction endonuclease SphI recognition site

<400> SEQUENCE: 7

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatgaa ttcagatctc gatcccgcga aattaatacg actcactata ggagaccac    240 aacggtttcc ctctagatca caagtttgta caaaaaagca ggctaagaag gagatataca    300
tacgccggcc attcaaacat gaggattacc catgtattta atacccatg tccaggcgcg    360 ctccgcgatc gctcatccca gttggtgatg ataccgtgtt cgatggggta tttcagggtg    420
aggatacctc ttttgctttg ggcttcatct cctacgtatg agtcctttg tcccataccg    480 accatgactc cttgatgcct tgggcgaccg acgatcgagg ggaagacggc acgggtgcg    540 tcatctcctg cgaaaccggc tttgcacata ccggatccat tgtctacgac aagagccgct    600
acatcgtcgt cacacatgtt gtcttttgag gttggacact gctcactaga cagaaaaacc    660
tcgtgcgttt aaacctttcg gattataaca tcacatctag gcgcgcctga cgatcaacca    720
```

```
taccagacgg accgaatacc cggtctgaac gagggcggcc gcggtaccca agaagtactt    780
agagttaatt aaggagttca aacatgagga tcacccatgt cgaagctccc acaccctagc    840
ataacccctt ggggcctcta acgggtctt gaggggtttt ttgctgaaag gaggaactat     900
atccggatat ccacaggacg ggtgtggtcg ccatgatcgc gtagtcgata gtggctccaa    960
gtagcgaagc gagcaggact gggcggcggg catgcaccat tccttgcggc ggcggtgctc   1020
aacggcctca acctactact gggctgcttc ctaatgcagg agtcgcataa gggagagcgt   1080
cgaccgatgc ccttgagagc cttcaaccca gtcagctcct tccggtgggc gcggggcatg   1140
actatcgtcg ccgcacttat gactgtcttc tttatcatgc aactcgtagg acaggtgccg   1200
gcagcgctct gggtcatttt cggcgaggac cgctttcgct ggagcgcgac gatgatcggc   1260
ctgtcgcttg cggtattcgg aatcttgcac gccctcgctc aagccttcgt cactggtccc   1320
gccaccaaac gtttcggcga aagcaggcc attatcgccg gcatggcggc cgacgcgctg   1380
ggctacgtct tgctggcgtt cgcgacgcga ggctggatgg ccttccccat tatgattctt   1440
ctcgcttccg gcggcatcgg gatgcccgcg ttgcaggcca tgctgtccag gcaggtagat   1500
gacgaccatc agggacagct tcaaggatcg ctcgcggctc ttaccagcct aacttcgatc   1560
attggaccgc tgatcgtcac ggcgatttat gccgcctcgg cgagcacatg gaacgggttg   1620
gcatggattg taggcgccgc cctataccct tgtctgcctcc ccgcgttgcg tcgcggtgca   1680
tggagccggg ccacctcgac ctgaatggaa ccggcggca cctcgctaac ggattcacca    1740
ctccaagaat tggagccaat caattcttgc ggagaactgt gaatgcgcaa accaacccctt   1800
ggcagaacat atccatcgcg tccgccatct ccagcagccg cacgcggcgc atctcgggca   1860
gcgttgggtc ctggccacgg gtgcgcatga tcgtgctcct gtcgttgagg acccggctag   1920
gctggcgggg ttgccttact ggttagcaga atgaatcacc gatacgcgag cgaacgtgaa   1980
gcgactgctg ctgcaaaacg tctgcgacct gagcaacaac atgaatggtc ttcggtttcc   2040
gtgtttcgta aagtctggaa acgcggaagt cagcgccctg caccattatg ttccggatct   2100
gcatcgcagg atgctgctgg ctaccctgtg gaacacctac atctgtatta acgaagcgct   2160
ggcattgacc ctgagtgatt tttctctggt cccgccgcat ccataccgcc agttgtttac   2220
cctcacaacg ttccagtaac cgggcatgtt catcatcagt aacccgtatc gtgagcatcc   2280
tctctcgttt catcggtatc attaccccca tgaacagaaa tccccttac acggaggcat    2340
cagtgaccaa acaggaaaaa accgccctta acatggcccg ctttatcaga agccagacat   2400
taacgcttct ggagaaactc aacgagctgg acgcggatga acaggcagac atctgtgaat   2460
cgcttcacga ccacgctgat gagctttacc gcagctgcct cgcgcgtttc ggtgatgacg   2520
gtgaaaacct ctgacacatg cagctcccgg agacggtcac agcttgtctg taagcggatg   2580
ccgggagcag acaagcccgt cagggcgcgt cagcgggtgt tggcgggtgt cggggcgcag   2640
ccatgaccca gtcacgtagc gatagcggag tgtatactgg cttaactatg cggcatcaga   2700
gcagattgta ctgagagtgc accatatgcg gtgtgaaata ccgcacagat gcgtaaggag   2760
aaaataccgc atcaggcgct cttccgcttc ctcgctcact gactcgctgc gctcggtcgt   2820
tcggctgcgg cgagcggtat cagctcactc aaaggcggta atacggttat ccacagaatc   2880
aggggataac gcaggaaaga acatgtgagc aaaaggccag caaaaggcca ggaaccgtaa   2940
aaaggccgcg ttgctggcgt ttttccatag gctccgcccc cctgacgagc atcacaaaaa   3000
tcgacgctca agtcagaggt ggcgaaaccc gacaggacta taaagatacc aggcgtttcc   3060
ccctggaagc tccctcgtgc gctctcctgt tccgaccctg ccgcttaccg gatacctgtc   3120
```

```
cgcctttctc ccttcgggaa gcgtggcgct ttctcatagc tcacgctgta ggtatctcag   3180
ttcggtgtag gtcgttcgct ccaagctggg ctgtgtgcac gaaccccccg ttcagcccga   3240
ccgctgcgcc ttatccggta actatcgtct tgagtccaac ccggtaagac acgacttatc   3300
gccactggca gcagccactg gtaacaggat tagcagagcg aggtatgtag gcggtgctac   3360
agagttcttg aagtggtggc ctaactacgg ctacactaga aggacagtat ttggtatctg   3420
cgctctgctg aagccagtta ccttcggaaa aagagttggt agctcttgat ccggcaaaca   3480
aaccaccgct ggtagcggtg gttttttgt ttgcaagcag cagattacgc gcagaaaaaa   3540
aggatctcaa gaagatcctt tgatcttttc tacgggtct gacgctcagt ggaacgaaaa   3600
ctcacgttaa gggattttgg tcatgagatt atcaaaaagg atcttcacct agatcctttt   3660
aaattaaaaa tgaagtttta atcaatcta agtatatat gagtaaactt ggtctgacag   3720
ttaccaatgc ttaatcagtg aggcacctat ctcagcgatc tgtctatttc gttcatccat   3780
agttgcctga ctccccgtcg tgtagataac tacgatacgg gagggcttac catctggccc   3840
cagtgctgca atgataccgc gagacccacg ctcaccggct ccagatttat cagcaataaa   3900
ccagccagcc ggaagggccg agcgcagaag tggtcctgca actttatccg cctccatcca   3960
gtctattaat tgttgccggg aagctagagt aagtagttcg ccagttaata gtttgcgcaa   4020
cgttgttgcc attgctgcag gcatcgtggt gtcacgctcg tcgtttggta tggcttcatt   4080
cagctccggt tcccaacgat caaggcgagt tacatgatcc cccatgttgt gcaaaaaagc   4140
ggttagctcc ttcggtcctc cgatcgttgt cagaagtaag ttggccgcag tgttatcact   4200
catggttatg gcagcactgc ataattctct tactgtcatg ccatccgtaa gatgcttttc   4260
tgtgactggt gagtactcaa ccaagtcatt ctgagaatag tgtatgcggc gaccgagttg   4320
ctcttgcccg gcgtcaacac gggataatac cgcgccacat agcagaactt taaaagtgct   4380
catcattgga aaacgttctt cggggcgaaa actctcaagg atcttaccgc tgttgagatc   4440
cagttcgatg taacccactc gtgcacccaa ctgatcttca gcatctttta ctttcaccag   4500
cgtttctggg tgagcaaaaa caggaaggca aaatgccgca aaaaagggaa taagggcgac   4560
acggaaatgt tgaatactca tactcttcct ttttcaatat tattgaagca tttatcaggg   4620
ttattgtctc atgagcggat acatatttga atgtatttag aaaaataaac aataggggt   4680 tccgcgcaca tttccccgaa aagtgccacc tgacgtctaa gaaaccatta ttatcatgac   4740
attaacctat aaaaataggc gtatcacgag gcccttcgt cttcaagaa                4789
```

```
<210> SEQ ID NO 8
<211> LENGTH: 3864
<212> TYPE: DNA
<213> ORGANISM: Artificial Sequence
<220> FEATURE:
<223> OTHER INFORMATION: Recombinant plasmid pAPSE10269; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
```

```
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator

<400> SEQUENCE: 8
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatatacaa     300
tacgccggcc attcaaacat gaggattacc catgtattta ataccccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg cacccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttccctttcc agcgggatgc     720
tttatctaaa cgcaacatga ggatcaccca tgtcgccaca tcgcttccta gttccgctgg     780
gatccatcgt tggcggccga agccgccatt ccatagtgag ttctggcgcg cctcatccca     840
gttggtgatg ataccgtgtt cgatgggta tttcagggtg aggataccct ttttgctttg     900
ggcttcatct cctacgtatg agtccttttg tcccataccg accatgactc cttgatgcct     960
tgggcgaccg acgatcgagg ggaagacggc acggggtgcg tcatctcctg cgaaaccggc    1020
tttgcacata ccggatccat tgtctacgac aagagccgct acatcgtcgt cacacatgtt    1080
gtcttttgag gttggacact gctcactaga cagaaaaacc tcgtgccgga ccgaataccc    1140
ggtctgaacg agggcggccg cggtacccaa gaagtactta gagttaatta aggagttcaa    1200
acatgaggat cacccatgtc gaagctccca caccctagca taaccccttg gggcctctaa    1260
```

```
acgggtcttg aggggttttt tgctgaaagg aggaactata tccggatatc cacaggacgg    1320
gtgtggtcgc catgatcgcg tagtcgatag tggctccaag tagcgaagcg agcaggactg    1380
ggcggcgggc atgcatcgtc cattccgaca gcatcgccag tcactatggc gtgctgctag    1440
cgctatatgc gttgatgcaa tttctatgcg cacccgttct cggagcactg tccgaccgct    1500
ttggccgccg cccagtcctg ctcgcttcgc tacttggagc cactatcgac tacgcgatca    1560
tggcgaccac acccgtcctg tggatccaga tctcgatccc gcgaaattaa tacgactcac    1620
tatagggaga ccacaacggt ttccctctag atcacaagtt tgtacaaaaa agcaggctaa    1680
gaaggagata tacatatggc gtctaacttt acccaattcg ttctggttga taacggcggt    1740
acgggtgacg ttaccgtagc tccgtccaac ttcgccaacg gtgttgcgga atggattagc    1800
tctaacagcc gctctcaggc ctacaaagtc acgtgctccg ttcgtcagtc tagcgcgcag    1860
aatcgcaaat acaccatcaa agttgaagta ccgaaagtcg caacgcagac cgtaggcggc    1920
gtagaactcc cagttgcggc ctggcgctct tacctcaaca tggaactgac tattccgatt    1980
tttgcgacga actccgactg cgaactgatt gttaaggcaa tgcagggcct gctgaaagac    2040
ggtaatccga tcccatctgc aatcgctgct aactctggca tttactaata agcggacgcg    2100
ctgccaccgc tgagcaataa ctagcataac cccttggggc tctaaacgg tcttgaggg    2160 gttttttgct gaaggagga actatatccg gcatgcacca ttccttgcgg cggcggtgct    2220
caacggcctc aacctactac tgggctgctt cctaatgcag gagtcgcata agggagagcg    2280
tcgaccgatg cccttgagag ccttcaaccc agtcagctcc ttccggtggg cgcggggcat    2340
gactatcgtc gccgcactta tgactgtctt ctttatcatg caactcgtag acaggtgcc    2400 ggcagcgctc tgggtcattt tcggcgagga ccgctttcgc tggagcgcga cgatgatcgg    2460
cctgtcgctt gcggtattcg gaatcttgca cgccctcgct caagccttcg tcactggtcc    2520
cgccaccaaa cgtttcggcg agaagcaggc cattatcgcc ggcatggcgg ccgacgcgct    2580
gggctacgtc ttgctggcgt cgcgacgcg aggctggatg ccttccccca ttatgattct    2640
tctcgcttcc ggcggcatcg ggatgcccgc gttgcaggcc atgctgtcca ggcaggtaga    2700
tgacgaccat cagggacagc ttcaaggatc gctcgcggct cttaccagcc taacttcgat    2760
cattggaccg ctgatcgtca cggcgattta tgccgcctcg gcgagcacat ggaacgggtt    2820
ggcatggatt gtaggcgccg ccctatacct tgtctgcctc cccgcgttgc gtcgcggtgc    2880
atggagccgg gccacctcga cctgaatgga agccggcggc acctcgctaa cggattcacc    2940
actccaagaa ttggagccaa tcaattcttg cggagaactg tgaatgcgca aaccaaccct    3000
tggcagaaca tatccatcgc gtccgccatc tccagcagcc gcacgcggcg catctcgggc    3060
agcgttgggt cctggccacg ggtgcgcatg atcgtgctcc tgtcgttgag gacccggcta    3120
ggctggcggg gttgccttac tggttagcag aatgaatcac cgatacgcga gcgaacgtga    3180
agcgactgct gctgcaaaac gtctgcgacc tgagcaacaa catgaatggt cttcggtttc    3240
cgtgtttcgt aaagtctgga aacgcggaag tcagcgccct gcaccattat gttccggatc    3300
tgcatcgcag gatgctgctg gctaccctgt ggaacaccta catctgtatt aacgaagcgc    3360
tggcattgac cctgagtgat ttttctctgg tcccgccgca tccataccgc cagttgttta    3420
ccctcacaac gttccagtaa ccgggcatgt tcatcatcag taacccgtat cgtgagcatc    3480
ctctctcgtt tcatcggtat cattacccc atgaacagaa atccccctta cacggaggca    3540
tcagtgacca aacaggaaaa aaccgccctt aacatggccc gctttatcag aagccagaca    3600
ttaacgcttc tggagaaact caacgagctg gacgcggatg aacaggcaga catctgtgaa    3660
```

```
tcgcttcacg accacgctga tgagctttac cgcagctgcc tcgcgcgttt cggtgatgac    3720
ggtgaaaacc tctgacacat gcagctcccg gagacggtca cagcttgtct gtaagcggat    3780
gccgggagca gacaagcccg tcagggcgcg tcagcgggtg ttggcgggtg tcggggcgca    3840
gccatgaccc agtcacgtag cgat                                          3864

<210> SEQ ID NO 9
<211> LENGTH: 5375
<212> TYPE: DNA
<213> ORGANISM: Artificial Sequence
<220> FEATURE:
<223> OTHER INFORMATION: Recombinant plasmid pAPSE10306; beta actin stem
      loop - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1389)..(1394)
<223> OTHER INFORMATION: restriction endonuclease SphI recognition site

<400> SEQUENCE: 9
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatgaa ttcagatctc gatcccgcga aattaatacg actcactata ggagaccac     240 aacggtttcc ctctagatca caagtttgta caaaaaagca ggctaagaag gagatataca    300
tacgccggcc attcaaacat gaggattacc catgtattta ataccatg tccaggcgcg     360 ctccgcgatc gcgcacgagg ttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg cacccgtgc cgtcttcccc tcgatcgtcg gtcgcccaag    540
gcatcaagga gtcatggtcg gtatgggaca aaaggactca tacgtaggag atgaagccca    600
```

```
aagcaaaaga ggtatcctca ccctgaaata ccccatcgaa cacgtatca tcaccaactg      660 ggatgagttt aaaccctcta gctgctttac aaagtactgg ttcccttttcc agcgggatgc    720 tttatctaaa cgcaacatga ggatcaccca tgtcgccaca tcgcttccta gttccgctgg    780
gatccatcgt tggcggccga agccgccatt ccatagtgag ttctggcgcg cctcatccca    840
gttggtgatg ataccgtgtt cgatgggta tttcagggtg aggatacctc ttttgctttg     900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac accgtcctg taccattcct tgcggcggcg gtgctcaacg gcctcaacct    1620
actactgggc tgcttcctaa tgcaggagtc gcataaggga gagcgtcgac cgatgcccttt 1680 gagagccttc aacccagtca gctccttccg gtgggcgcgg ggcatgacta tcgtcgccgc   1740
acttatgact gtcttctta tcatgcaact cgtaggacag gtgccggcag cgctctgggt    1800
cattttcggc gaggaccgct ttcgctggag cgcgacgatg atcggcctgt cgcttgcggt   1860
attcggaatc ttgcacgccc tcgctcaagc cttcgtcact ggtcccgcca ccaaacgttt   1920
cggcgagaag caggccatta tcgccggcat ggcggccgac gcgctgggct acgtcttgct   1980
ggcgttcgcg acgcgaggct ggatggcctt ccccattatg attcttctcg cttccggcgg   2040
catcgggatg cccgcgttgc aggccatgct gtccaggcag gtagatgacg accatcaggg   2100
acagcttcaa ggatcgctcg cggctcttac cagcctaact tcgatcattg gaccgctgat   2160
cgtcacggcg atttatgccg cctcggcgag cacatggaac gggttggcat ggattgtagg   2220
cgccgcccta taccttgtct gcctccccgc gttgcgtcgc ggtgcatgga gccgggccac   2280
ctcgacctga atggaagccg gcggcacctc gctaacggat tcaccactcc aagaattgga   2340
gccaatcaat tcttgcggag aactgtgaat gcgcaaacca acccttggca gaacatatcc   2400
atcgcgtccg ccatctccag cagccgcacg cggcgcatct cgggcagcgt tgggtcctgg   2460
ccacgggtgc gcatgatcgt gctcctgtcg ttgaggaccc ggctaggctg gcggggttgc   2520
cttactggtt agcagaatga atcaccgata cgcgagcgaa cgtgaagcga ctgctgctgc   2580
aaaacgtctg cgacctgagc aacaacatga atggtcttcg gtttccgtgt ttcgtaaagt   2640
ctggaaacgc ggaagtcagc gccctgcacc attatgttcc ggatctgcat cgcaggatgc   2700
tgctggctac cctgtggaac acctacatct gtattaacga agcgctggca ttgaccctga   2760 gtgattttc tctggtcccg ccgcatccat accgccagtt gtttacccttc acaacgttcc   2820 agtaaccggg catgttcatc atcagtaacc cgtatcgtga gcatcctctc tcgtttcatc   2880
ggtatcatta cccccatgaa cagaaatccc ccttacacgg aggcatcagt gaccaaacag   2940
```

```
gaaaaaaccg cccttaacat ggcccgcttt atcagaagcc agacattaac gcttctggag    3000
aaactcaacg agctggacgc ggatgaacag gcagacatct gtgaatcgct tcacgaccac    3060
gctgatgagc tttaccgcag ctgcctcgcg cgtttcggtg atgacggtga aaacctctga    3120
cacatgcagc tcccggagac ggtcacagct tgtctgtaag cggatgccgg gagcagacaa    3180
gcccgtcagg gcgcgtcagc gggtgttggc gggtgtcggg gcgcagccat gacccagtca    3240
cgtagcgata gcggagtgta tactggctta actatgcggc atcagagcag attgtactga    3300
gagtgcacca tatgcggtgt gaaataccgc acagatgcgt aaggagaaaa taccgcatca    3360
ggcgctcttc cgcttcctcg ctcactgact cgctgcgctc ggtcgttcgg ctgcggcgag    3420
cggtatcagc tcactcaaag gcggtaatac ggttatccac agaatcaggg gataacgcag    3480
gaaagaacat gtgagcaaaa ggccagcaaa aggccaggaa ccgtaaaaag gccgcgttgc    3540
tggcgttttt ccataggctc cgcccccctg acgagcatca caaaaatcga cgctcaagtc    3600
agaggtggcg aaacccgaca ggactataaa gataccaggc gtttccccct ggaagctccc    3660
tcgtgcgctc tcctgttccg accctgccgc ttaccggata cctgtccgcc tttctccctt    3720
cgggaagcgt ggcgctttct catagctcac gctgtaggta tctcagttcg gtgtaggtcg    3780
ttcgctccaa gctgggctgt gtgcacgaac cccccgttca gcccgaccgc tgcgccttat    3840
ccggtaacta tcgtcttgag tccaacccgg taagacacga cttatcgcca ctggcagcag    3900
ccactggtaa caggattagc agagcgaggt atgtaggcgg tgctacagag ttcttgaagt    3960
ggtggcctaa ctacggctac actagaagga cagtatttgg tatctgcgct ctgctgaagc    4020
cagttacctt cggaaaaaga gttggtagct cttgatccgg caaacaaacc accgctggta    4080
gcggtggttt ttttgtttgc aagcagcaga ttacgcgcag aaaaaaagga tctcaagaag    4140
atcctttgat cttttctacg gggtctgacg ctcagtggaa cgaaaactca cgttaaggga    4200
ttttggtcat gagattatca aaaaggatct tcacctagat ccttttaaat taaaaatgaa    4260
gttttaaatc aatctaaagt atatatgagt aaacttggtc tgacagttac caatgcttaa    4320
tcagtgaggc acctatctca gcgatctgtc tatttcgttc atccatagtt gcctgactcc    4380
ccgtcgtgta gataactacg atacgggagg gcttaccatc tggccccagt gctgcaatga    4440
taccgcgaga cccacgctca ccggctccag atttatcagc aataaaccag ccagccggaa    4500
gggccgagcg cagaagtggt cctgcaactt tatccgcctc catccagtct attaattgtt    4560
gccgggaagc tagagtaagt agttcgccag ttaatagttt gcgcaacgtt gttgccattg    4620
ctgcaggcat cgtggtgtca cgctcgtcgt ttggtatggc ttcattcagc tccggttccc    4680
aacgatcaag gcgagttaca tgatccccca tgttgtgcaa aaaagcggtt agctccttcg    4740
gtcctccgat cgttgtcaga agtaagttgg ccgcagtgtt atcactcatg gttatggcag    4800
cactgcataa ttctcttact gtcatgccat ccgtaagatg cttttctgtg actggtgagt    4860
actcaaccaa gtcattctga atagtgta tgcggcgacc gagttgctct tgcccggcgt    4920
caacacggga taataccgcg ccacatagca gaactttaaa agtgctcatc attggaaaac    4980
gttcttcggg gcgaaaactc tcaaggatct taccgctgtt gagatccagt tcgatgtaac    5040
ccactcgtgc acccaactga tcttcagcat cttttacttt caccagcgtt tctgggtgag    5100
caaaaacagg aaggcaaaat gccgcaaaaa agggaataag ggcgacacgg aaatgttgaa    5160
tactcatact cttcctttttt caatattatt gaagcattta tcagggttat tgtctcatga    5220
gcggatacat atttgaatgt atttagaaaa ataaacaaat aggggttccg cgcacatttc    5280
cccgaaaagt gccacctgac gtctaagaaa ccattattat catgacatta acctataaaa    5340
```
ataggcgtat cacgaggccc tttcgtcttc aagaa                          5375

<210> SEQ ID NO 10
<211> LENGTH: 5990
<212> TYPE: DNA
<213> ORGANISM: Artificial Sequence
<220> FEATURE:
<223> OTHER INFORMATION: Recombinant plasmid pAPSE10216; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator

<400> SEQUENCE: 10
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660

```
ggatgagttt aaaccctcta gctgctttac aaagtactgg ttcccttcc agcgggatgc      720
tttatctaaa cgcaatgaga gaggtattcc tcaggccaca tcgcttccta gttccgctgg     780
gatccatcgt tggcggccga agccgccatt ccatagtgag ttctggcgcg cctcatccca    840
gttggtgatg ataccgtgtt cgatggggta tttcagggtg aggatacctc ttttgctttg    900
ggcttcatct cctacgtatg agtccttttg tcccataccg accatgactc cttgatgcct   960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca cacccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggc gtctaacttt acccaattcg ttctggttga taacggcggt   1740
acgggtgacg ttaccgtagc tccgtccaac ttcgccaacg gtgttgcgga atggattagc   1800
tctaacagcc gctctcaggc ctacaaagtc acgtgctccg ttcgtcagtc tagcgcgcag   1860
aatcgcaaat acaccatcaa agttgaagta ccgaaagtcg caacgcagac cgtaggcggc   1920
gtagaactcc cagttgcggc ctggcgctct tacctcaaca tggaactgac tattccgatt   1980
tttgcgacga actccgactg cgaactgatt gttaaggcaa tgcagggcct gctgaaagac   2040
ggtaatccga tcccatctgc aatcgctgct aactctggca tttactaata agcggacgcg   2100
ctgccaccgc tgagcaataa ctagcataac cccttggggc tctaaacgg tcttgaggg   2160
gttttttgct gaaaggagga actatatccg gcatgcacca ttccttgcgg cggcggtgct   2220
caacggcctc aacctactac tgggctgctt cctaatgcag gagtcgcata agggagagcg   2280
tcgaccgatg cccttgagag ccttcaaccc agtcagctcc ttccggtggg cgcggggcat   2340
gactatcgtc gccgcactta tgactgtctt ctttatcatg caactcgtag acaggtgcc    2400
ggcagcgctc tgggtcattt tcggcgagga ccgctttcgc tggagcgcga cgatgatcgg   2460
cctgtcgctt gcgtattcg gaatcttgca cgccctcgct caagccttcg tcactggtcc   2520
cgccaccaaa cgtttcggcg agaagcaggc cattatcgcc ggcatggcgg ccgacgcgct   2580
gggctacgtc ttgctggcgt tcgcgacgcg aggctggatg gccttcccca ttatgattct   2640
tctcgcttcc ggcggcatcg gatgcccgc gttgcaggcc atgctgtcca ggcaggtaga    2700
tgacgaccat cagggacagc ttcaaggatc gctcgcggct cttaccagcc taacttcgat   2760
cattggaccg ctgatcgtca cggcgattta tgccgcctcg gcgagcacat ggaacgggtt   2820
ggcatggatt gtaggcgccg ccctatacct tgtctgcctc cccgcgttgc gtcgcggtgc   2880
atggagccgg gccacctcga cctgaatgga agccggcggc acctcgctaa cggattcacc   2940
actccaagaa ttggagccaa tcaattcttg cggagaactg tgaatgcgca aaccaaccct   3000
```

```
tggcagaaca tatccatcgc gtccgccatc tccagcagcc gcacgcggcg catctcgggc    3060
agcgttgggt cctggccacg ggtgcgcatg atcgtgctcc tgtcgttgag gacccggcta    3120
ggctggcggg gttgccttac tggttagcag aatgaatcac cgatacgcga gcgaacgtga    3180
agcgactgct gctgcaaaac gtctgcgacc tgagcaacaa catgaatggt cttcggtttc    3240
cgtgtttcgt aaagtctgga aacgcggaag tcagcgccct gcaccattat gttccggatc    3300
tgcatcgcag gatgctgctg gctaccctgt ggaacaccta catctgtatt aacgaagcgc    3360
tggcattgac cctgagtgat ttttctctgg tcccgccgca tccataccgc cagttgttta    3420
ccctcacaac gttccagtaa ccgggcatgt tcatcatcag taacccgtat cgtgagcatc    3480
ctctctcgtt tcatcggtat cattaccccc atgaacagaa atcccccttc acggaggca    3540 tcagtgacca acaggaaaaa aaccgcccct aacatggccc gctttatcag aagccagaca    3600
ttaacgcttc tggagaaact caacgagctg gacgcggatg aacaggcaga catctgtgaa    3660
tcgcttcacg accacgctga tgagctttac cgcagctgcc tcgcgcgttt cggtgatgac    3720
ggtgaaaacc tctgacacat gcagctcccg gagacggtca cagcttgtct gtaagcggat    3780
gccgggagca gacaagcccg tcagggcgcg tcagcgggtg ttggcgggtg tcggggcgca    3840
gccatgaccc agtcacgtag cgatagcgga gtgtatactg gcttaactat gcggcatcag    3900
agcagattgt actgagagtg caccatatgc ggtgtgaaat accgcacaga tgcgtaagga    3960
gaaaataccg catcaggcgc tcttccgctt cctcgctcac tgactcgctg cgctcggtcg    4020
ttcggctgcg gcgagcggta tcagctcact caaaggcggt aatacggtta tccacagaat    4080
caggggataa cgcaggaaag aacatgtgag caaaaggcca gcaaaaggcc aggaaccgta    4140
aaaaggccgc gttgctggcg tttttccata ggctccgccc ccctgacgag catcacaaaa    4200
atcgacgctc aagtcagagg tggcgaaacc cgacaggact ataaagatac caggcgtttc    4260
cccctggaag ctccctcgtg cgctctcctg ttccgaccct gccgcttacc ggatacctgt    4320
ccgcctttct cccttcggga agcgtggcgc tttctcatag ctcacgctgt aggtatctca    4380
gttcggtgta ggtcgttcgc tccaagctgg gctgtgtgca cgaaccccc gttcagcccg    4440 accgctgcgc cttatccggt aactatcgtc ttgagtccaa cccggtaaga cacgacttat    4500
cgccactggc agcagccact ggtaacagga ttagcagagc gaggtatgta ggcggtgcta    4560
cagagttctt gaagtggtgg cctaactacg gctacactag aaggacagta tttggtatct    4620
gcgctctgct gaagccagtt accttcggaa aaagagttgg tagctcttga tccggcaaac    4680
aaaccaccgc tggtagcggt ggtttttttg tttgcaagca gcagattacg cgcagaaaaa    4740
aaggatctca agaagatcct ttgatctttt ctacggggtc tgacgctcag tggaacgaaa    4800
actcacgtta agggatttg gtcatgagat tatcaaaaag gatcttcacc tagatccttt    4860
taaattaaaa atgaagtttt aaatcaatct aaagtatata tgagtaaact tggtctgaca    4920
gttaccaatg cttaatcagt gaggcaccta tctcagcgat ctgtctattt cgttcatcca    4980
tagttgcctg actccccgtc gtgtagataa ctacgatacg ggagggctta ccatctggcc    5040
ccagtgctgc aatgataccg cgagacccac gctcaccggc tccagattta tcagcaataa    5100
accagccagc cggaagggcc gagcgcagaa gtggtcctgc aactttatcc gcctccatcc    5160
agtctattaa ttgttgccgg gaagctagag taagtagttc gccagttaat agtttgcgca    5220
acgttgttgc cattgctgca ggcatcgtgg tgtcacgctc gtcgtttggt atggcttcat    5280
tcagctccgg ttcccaacga tcaaggcgag ttacatgatc cccatgttg tgcaaaaaag    5340 cggttagctc cttcggtcct ccgatcgttg tcagaagtaa gttggccgca gtgttatcac    5400
```

```
tcatggttat ggcagcactg cataattctc ttactgtcat gccatccgta agatgctttt      5460
ctgtgactgg tgagtactca accaagtcat tctgagaata gtgtatgcgg cgaccgagtt      5520
gctcttgccc ggcgtcaaca cgggataata ccgcgccaca tagcagaact ttaaaagtgc      5580
tcatcattgg aaaacgttct cggggcgaaa actctcaag gatcttaccg ctgttgagat       5640
ccagttcgat gtaacccact cgtgcaccca actgatcttc agcatctttt actttcacca      5700
gcgtttctgg gtgagcaaaa acaggaaggc aaaatgccgc aaaaaaggga ataagggcga      5760
cacggaaatg ttgaatactc atactcttcc tttttcaata ttattgaagc atttatcagg      5820
gttattgtct catgagcgga tacatatttg aatgtattta gaaaaataaa caatagggg       5880 ttccgcgcac atttccccga aaagtgccac ctgacgtcta agaaaccatt attatcatga      5940
cattaaccta taaaaatagg cgtatcacga ggccctttcg tcttcaagaa                 5990
```

```
<210> SEQ ID NO 11
<211> LENGTH: 5188
<212> TYPE: DNA
<213> ORGANISM: Artificial Sequence
<220> FEATURE:
<223> OTHER INFORMATION: Recombinant plasmid pAPSE10305; beta actin stem
      loop - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (373)..(667)
<223> OTHER INFORMATION: beta actin sense strand gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophageT7 transcription terminator
<220> FEATURE:
<221> NAME/KEY: misc_feature
<222> LOCATION: (1389)..(1394)
<223> OTHER INFORMATION: restriction endonuclease SphI recognition site

<400> SEQUENCE: 11
ttctcatgtt tgacagctta tcatcgataa gctttaatgc ggtagtttat cacagttaaa        60
ttgctaacgc agtcaggcac cgtgtatgaa atctaacaat gcgctcatcg tcatcctcgg       120
caccgtcacc ctggatgctg taggcatagg cttggttatg ccggtactgc cgggcctctt      180
gcgggatgaa ttcagatctc gatcccgcga aattaatacg actcactata ggagaccac       240 aacggtttcc ctctagatca caagtttgta caaaaaagca ggctaagaag agatataca       300 tacgccggcc attcaaacat gaggattacc catgtattta aatacccatg tccaggcgcg      360
ctccgcgatc gcgcacgagg ttttctgtc tagtgagcag tgtccaacct caaaagacaa      420
catgtgtgac gacgatgtag cggctcttgt cgtagacaat ggatccggta tgtgcaaagc      480
```

-continued

```
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttccgctgg    780
gatccatcgt tggcggccga agccgccatt ccatagtgag ttctggcgcg cctcatccca    840
gttggtgatg ataccgtgtt cgatgggta tttcagggtg aggatacctc ttttgctttg     900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca cacctagca taaccccttg gggcctctaa    1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcaccatt ccttgcggcg gcggtgctca acggcctcaa cctactactg   1440
ggctgcttcc taatgcagga gtcgcataag ggagagcgtc gaccgatgcc cttgagagcc   1500
ttcaacccag tcagctcctt ccggtgggcg cggggcatga ctatcgtcgc cgcacttatg   1560
actgtcttct ttatcatgca actcgtagga caggtgccgg cagcgctctg ggtcattttc   1620
ggcgaggacc gctttcgctg gagcgcgacg atgatcggcc tgtcgcttgc ggtattcgga   1680
atcttgcacg ccctcgctca agccttcgtc actggtcccg ccaccaaacg tttcggcgag   1740
aagcaggcca ttatcgccgg catggcggcc gacgcgctgg gctacgtctt gctggcgttc   1800
gcgacgcgag gctggatggc cttccccatt atgattcttc tcgcttccgg cggcatcggg   1860
atgcccgcgt tgcaggccat gctgtccagg caggtagatg acgaccatca gggacagctt   1920
caaggatcgc tcgcggctct taccagccta acttcgatca ttggaccgct gatcgtcacg   1980
gcgatttatg ccgcctcggc gagcacatgg aacgggttgg catggattgt aggcgccgcc   2040
ctataccttg tctgcctccc cgcgttgcgt cgcggtgcat ggagccgggc cacctcgacc   2100
tgaatggaag ccggcggcac ctcgctaacg gattcaccac tccaagaatt ggagccaatc   2160
aattcttgcg gagaactgtg aatgcgcaaa ccaaccctttg gcagaacata tccatcgcgt   2220
ccgccatctc cagcagccgc acgcggcgca tctcgggcag cgttgggtcc tggccacggg   2280
tgcgcatgat cgtgctcctg tcgttgagga cccggctagg ctggcggggt tgccttactg   2340
gttagcagaa tgaatcaccg atacgcgagc gaacgtgaag cgactgctgc tgcaaaacgt   2400
ctgcgacctg agcaacaaca tgaatggtct tcggtttccg tgtttcgtaa agtctggaaa   2460
cgcggaagtc agcgccctgc accattatgt tccggatctg catcgcagga tgctgctggc   2520
taccctgtgg aacacctaca tctgtattaa cgaagcgctg gcattgaccc tgagtgattt   2580
ttctctggtc ccgccgcatc cataccgcca gttgtttacc ctcacaacgt tccagtaacc   2640
gggcatgttc atcatcagta acccgtatcg tgagcatcct ctctcgtttc atcggtatca   2700 ttaccccccat gaacagaaat ccccttaca cggaggcatc agtgaccaaa caggaaaaaa   2760
ccgcccttaa catggcccgc tttatcagaa gccagacatt aacgcttctg gagaaactca   2820
```

```
acgagctgga cgcggatgaa caggcagaca tctgtgaatc gcttcacgac cacgctgatg    2880
agctttaccg cagctgcctc gcgcgtttcg gtgatgacgg tgaaaacctc tgacacatgc    2940
agctcccgga gacggtcaca gcttgtctgt aagcggatgc cgggagcaga caagcccgtc    3000
agggcgcgtc agcgggtgtt ggcggtgtc ggggcgcagc catgacccag tcacgtagcg    3060
atagcggagt gtatactggc ttaactatgc ggcatcagag cagattgtac tgagagtgca    3120
ccatatgcgg tgtgaaatac cgcacagatg cgtaaggaga aaataccgca tcaggcgctc    3180
ttccgcttcc tcgctcactg actcgctgcg ctcggtcgtt cggctgcggc gagcggtatc    3240
agctcactca aaggcggtaa tacgttatc cacagaatca ggggataacg caggaaagaa     3300
catgtgagca aaaggccagc aaaaggccag gaaccgtaaa aaggccgcgt tgctggcgtt    3360
tttccatagg ctccgccccc ctgacgagca tcacaaaaat cgacgctcaa gtcagaggtg    3420
gcgaaacccg acaggactat aaagatacca ggcgtttccc cctggaagct ccctcgtgcg    3480
ctctcctgtt ccgaccctgc cgcttaccgg atacctgtcc gcctttctcc cttcgggaag    3540
cgtggcgctt tctcatagct cacgctgtag gtatctcagt tcggtgtagg tcgttcgctc    3600
caagctgggc tgtgtgcacg aaccccccgt tcagcccgac cgctgcgcct tatccggtaa    3660
ctatcgtctt gagtccaacc cggtaagaca cgacttatcg ccactggcag cagccactgg    3720
taacaggatt agcagagcga ggtatgtagg cggtgctaca gagttcttga agtggtggcc    3780
taactacggc tacactagaa ggacagtatt tggtatctgc gctctgctga gccagttac     3840
cttcggaaaa agagttggta gctcttgatc cggcaaacaa accaccgctg gtagcggtgg    3900
tttttttgtt tgcaagcagc agattacgcg cagaaaaaaa ggatctcaag aagatccttt    3960
gatcttttct acggggtctg acgctcagtg gaacgaaaac tcacgttaag ggattttggt    4020
catgagatta tcaaaaagga tcttcaccta gatcctttta aattaaaaat gaagttttaa    4080
atcaatctaa agtatatatg agtaaacttg gtctgacagt taccaatgct taatcagtga    4140
ggcacctatc tcagcgatct gtctatttcg ttcatccata gttgcctgac tccccgtcgt    4200
gtagataact acgatacggg agggcttacc atctggcccc agtgctgcaa tgataccgcg    4260
agacccacgc tcaccggctc cagatttatc agcaataaac cagccagccg gaagggccga    4320
gcgcagaagt ggtcctgcaa ctttatccgc ctccatccag tctattaatt gttgccggga    4380
agctagagta agtagttcgc cagttaatag tttgcgcaac gttgttgcca ttgctgcagg    4440
catcgtggtg tcacgctcgt cgtttggtat ggcttcattc agctccggtt cccaacgatc    4500
aaggcgagtt acatgatccc ccatgttgtg caaaaaagcg gttagctcct tcggtcctcc    4560
gatcgttgtc agaagtaagt tggccgcagt gttatcactc atggttatgg cagcactgca    4620
taattctctt actgtcatgc catccgtaag atgcttttct gtgactggtg agtactcaac    4680
caagtcattc tgagaatagt gtatgcggcg accgagttgc tcttgcccgg cgtcaacacg    4740
ggataatacc gcgccacata gcagaacttt aaaagtgctc atcattggaa aacgttcttc    4800
ggggcgaaaa ctctcaagga tcttaccgct gttgagatcc agttcgatgt aacccactcg    4860
tgcacccaac tgatcttcag catcttttac tttcaccagc gtttctgggt gagcaaaaac    4920
aggaaggcaa aatgccgcaa aaagggaat aagggcgaca cggaaatgtt gaatactcat     4980
actcttcctt tttcaatatt attgaagcat ttatcagggt tattgtctca tgagcggata    5040
catatttgaa tgtatttaga aaaataaaca ataggggtt ccgcgcacat ttccccgaaa     5100
agtgccacct gacgtctaag aaaccattat tatcatgaca ttaacctata aaaataggcg    5160
tatcacgagg ccctttcgtc ttcaagaa                                        5188
```

```
<210> SEQ ID NO 12
<211> LENGTH: 5657
<212> TYPE: DNA
<213> ORGANISM: Artificial Sequence
<220> FEATURE:
<223> OTHER INFORMATION: Recombinant plasmid pAPSE10219; beta actin stem
      loop + coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
      sequence
<220> FEATURE:
<221> NAME/KEY: misc_feature
<222> LOCATION: (40)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (497)..(791)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: promoter
<222> LOCATION: (1275)..(1293)
<223> OTHER INFORMATION: bacteriophage T7 gene 1 promoter
<220> FEATURE:
<221> NAME/KEY: gene
<222> LOCATION: (1366)..(1755)
<223> OTHER INFORMATION: bacteriophage MS2 coat protein gene
<220> FEATURE:
<221> NAME/KEY: terminator
<222> LOCATION: (1788)..(1835)
<223> OTHER INFORMATION: bacteriophage T7 transcription terminator

<400> SEQUENCE: 12
ttccgaaatt aatacgactc actataggga ggcgatcgcg cacgaggttt ttctgtctag      60
tgagcagtgt ccaacctcaa aagacaacat gtgtgacgac gatgtagcgg ctcttgtcgt     120
agacaatgga tccggtatgt gcaaagccgg tttcgcagga gatgacgcac cccgtgccgt     180
cttcccctcg atcgtcggtc gcccaaggca tcaaggagtc atggtcggta tgggacaaaa     240
ggactcatac gtaggagatg aagcccaaag caaaagaggt atcctcaccc tgaaatatcc     300
catcgaacac ggtatcatca ccaactggga tgagtttaaa ccctctagct gctttacaaa     360
gtactggttc ccttttccagc gggatgcttt atctaaacgc aatgagagag gtattcctca     420
ggccacatcg cttcctagtt ccgctgggat ccatcgttgg cggccgaagc cgccattcca     480
tagtgagttc tggcgcgcct catcccagtt ggtgatgata ccgtgttcga tggggtattt     540
cagggtgagg atacctcttt tgctttgggc ttcatctcct acgtatgagt ccttttgtcc     600
cataccgacc atgactcctt gatgccttgg gcgaccgacg atcgagggga agacggcacg     660
gggtgcgtca tctcctgcga aaccggcttt gcacataccg gatccattgt ctacgacaag     720
agccgctaca tcgtcgtcac acatgttgtc ttttgaggtt ggacactgct cactagacag     780
```

```
aaaaacctcg tgccggaccg aatacccggt ctgaacgagg gcggccgcgg tacccaagaa    840
gtacttagag ttaattaagg agttcaaaca tgaggatcac ccatgtcgaa gctcccacac    900
cctagcataa cccccttggg cctctaaacg ggtcttgagg ggttttttgc tgaaaggagg    960
aactatatcc ggatatccac aggacgggtg tggtcgccat gatcgcgtag tcgatagtgg   1020
ctccaagtag cgaagcgagc aggactgggc ggcgggcatg catcgtccat tccgacagca   1080
tcgccagtca ctatggcgtg ctgctagcgc tatatgcgtt gatgcaattt ctatgcgcac   1140
ccgttctcgg agcactgtcc gaccgctttg gccgccgccc agtcctgctc gcttcgctac   1200
ttggagccac tatcgactac gcgatcatgg cgaccacacc cgtcctgtgg atccagatct   1260
cgatcccgcg aaattaatac gactcactat agggagacca caacggtttc cctctagatc   1320
acaagtttgt acaaaaaagc aggctaagaa ggagatatac atatggcgtc taactttacc   1380
caattcgttc tggttgataa cggcggtacg ggtgacgtta ccgtagctcc gtccaacttc   1440
gccaacggtg ttgcggaatg gattagctct aacagccgct ctcaggccta caaagtcacg   1500
tgctccgttc gtcagtctag cgcgcagaat cgcaaataca ccatcaaagt tgaagtaccg   1560
aaagtcgcaa cgcagaccgt aggcggcgta gaactcccag ttgcggcctg gcgctcttac   1620
ctcaacatgg aactgactat tccgattttt gcgacgaact ccgactgcga actgattgtt   1680
aaggcaatgc agggcctgct gaaagacggt aatccgatcc catctgcaat cgctgctaac   1740
tctggcattt actaataagc ggacgcgctg ccaccgctga gcaataacta gcataacccc   1800
ttggggcctc taaacgggtc ttgagggggtt ttttgctgaa aggaggaact atatccggca   1860
tgcaccattc cttgcggcgg cggtgctcaa cggcctcaac ctactactgg gctgcttcct   1920
aatgcaggag tcgcataagg gagagcgtcg accgatgccc ttgagagcct tcaacccagt   1980
cagctccttc cggtgggcgc ggggcatgac tatcgtcgcc gcacttatga ctgtcttctt   2040
tatcatgcaa ctcgtaggac aggtgccggc agcgctctgg gtcattttcg gcgaggaccg   2100 cttcgctgg agcgcgacga tgatcggcct gtcgcttgcg gtattcggaa tcttgcacgc   2160
cctcgctcaa gccttcgtca ctggtcccgc caccaaacgt ttcggcgaga agcaggccat   2220
tatcgccggc atggcggccg acgcgctggg ctacgtcttg ctggcgttcg cgacgcgagg   2280
ctggatggcc ttccccatta tgattcttct cgcttccggc ggcatcggga tgcccgcgtt   2340
gcaggccatg ctgtccaggc aggtagatga cgaccatcag ggacagcttc aaggatcgct   2400
cgcggctctt accagcctaa cttcgatcat tggaccgctg atcgtcacgg cgatttatgc   2460
cgcctcggcg agcacatgga acgggttggc atggattgta ggcgccgccc tataccttgt   2520
ctgcctcccc gcgttgcgtc gcggtgcatg gagccgggcc acctcgacct gaatggaagc   2580
cggcggcacc tcgctaacgg attcaccact ccaagaattg gagccaatca attcttgcgg   2640
agaactgtga atgcgcaaac caacccttgg cagaacatat ccatcgcgtc cgccatctcc   2700
agcagccgca cgcggcgcat ctcgggcagc gttgggtcct ggccacgggt gcgcatgatc   2760
gtgctcctgt cgttgaggac ccggctaggc tggcggggtt gccttactgg ttagcagaat   2820
gaatcaccga tacgcgagcg aacgtgaagc gactgctgct gcaaaacgtc tgcgacctga   2880
gcaacaacat gaatggtctt cggtttccgt gtttcgtaaa gtctggaaac gcggaagtca   2940
gcgccctgca ccattatgtt ccggatctgc atcgcaggat gctgctggct accctgtgga   3000
acacctacat ctgtattaac gaagcgctgg cattgaccct gagtgatttt tctctggtcc   3060
cgccgcatcc ataccgccag ttgtttaccc tcacaacgtt ccagtaaccg ggcatgttca   3120
tcatcagtaa cccgtatcgt gagcatcctc tctcgtttca tcggtatcat tacccccatg   3180
```

```
aacagaaatc cccttacac ggaggcatca gtgaccaaac aggaaaaaac cgcccttaac    3240
atggcccgct ttatcagaag ccagacatta acgcttctgg agaaactcaa cgagctggac    3300
gcggatgaac aggcagacat ctgtgaatcg cttcacgacc acgctgatga gctttaccgc    3360
agctgcctcg cgcgtttcgg tgatgacggt gaaaacctct gacacatgca gctcccggag    3420
acggtcacag cttgtctgta agcggatgcc gggagcagac aagcccgtca gggcgcgtca    3480
gcgggtgttg gcgggtgtcg gggcgcagcc atgacccagt cacgtagcga tagcggagtg    3540
tatactggct taactatgcg gcatcagagc agattgtact gagagtgcac catatgcggt    3600
gtgaaatacc gcacagatgc gtaaggagaa aataccgcat caggcgctct ccgcttcct     3660 cgctcactga ctcgctgcgc tcggtcgttc ggctgcggcg agcggtatca gctcactcaa    3720
aggcggtaat acggttatcc acagaatcag gggataacgc aggaaagaac atgtgagcaa    3780
aaggccagca aaaggccagg aaccgtaaaa aggccgcgtt gctggcgttt ttccataggc    3840
tccgcccccc tgacgagcat cacaaaaatc gacgctcaag tcagaggtgg cgaaacccga    3900
caggactata aagataccag gcgtttcccc ctggaagctc cctcgtgcgc tctcctgttc    3960
cgaccctgcc gcttaccgga tacctgtccg cctttctccc ttcgggaagc gtggcgcttt    4020
ctcatagctc acgctgtagg tatctcagtt cggtgtaggt cgttcgctcc aagctgggct    4080
gtgtgcacga accccccgtt cagcccgacc gctgcgcctt atccggtaac tatcgtcttg    4140
agtccaaccc ggtaagacac gacttatcgc cactggcagc agccactggt aacaggatta    4200
gcagagcgag gtatgtaggc ggtgctacag agttcttgaa gtggtggcct aactacggct    4260
acactagaag gacagtattt ggtatctgcg ctctgctgaa gccagttacc ttcggaaaaa    4320
gagttggtag ctcttgatcc ggcaaacaaa ccaccgctgg tagcggtggt ttttttgttt    4380
gcaagcagca gattacgcgc agaaaaaaag gatctcaaga agatcctttg atcttttcta    4440
cggggtctga cgctcagtgg aacgaaaact cacgttaagg gattttggtc atgagattat    4500
caaaaaggat cttcacctag atccttttaa attaaaaatg aagttttaaa tcaatctaaa    4560
gtatatatga gtaaacttgg tctgacagtt accaatgctt aatcagtgag gcacctatct    4620
cagcgatctg tctatttcgt tcatccatag ttgcctgact ccccgtcgtg tagataacta    4680
cgatacggga gggcttacca tctggcccca gtgctgcaat gataccgcga cccacgct     4740 caccggctcc agatttatca gcaataaacc agccagccgg aagggccgag cgcagaagtg    4800
gtcctgcaac tttatccgcc tccatccagt ctattaattg ttgccgggaa gctagagtaa    4860
gtagttcgca gttaatagt ttgcgcaacg ttgttgccat tgctgcaggc atcgtggtgt     4920
cacgctcgtc gtttggtatg gcttcattca gctccggttc ccaacgatca aggcgagtta    4980
catgatcccc catgttgtgc aaaaaagcgg ttagctcctt cggtcctccg atcgttgtca    5040
gaagtaagtt ggccgcagtg ttatcactca tggttatggc agcactgcat aattctctta    5100
ctgtcatgcc atccgtaaga tgcttttctg tgactggtga gtactcaacc aagtcattct    5160
gagaatagtg tatgcggcga ccgagttgct cttgcccggc gtcaacacgg ataataccg     5220 cgccacatag cagaacttta aaagtgctca tcattggaaa acgttcttcg ggcgaaaac     5280 tctcaaggat cttaccgctg ttgagatcca gttcgatgta acccactcgt gcacccaact    5340
gatcttcagc atcttttact ttcaccagcg tttctgggtg agcaaaaaca ggaaggcaaa    5400
atgccgcaaa aaagggaata agggcgacac ggaaatgttg aatactcata ctcttccttt    5460
ttcaatatta ttgaagcatt tatcagggtt attgtctcat gagcggatac atatttgaat    5520
```

```
gtatttagaa aaataaacaa ataggggttc cgcgcacatt tccccgaaaa gtgccacctg    5580
acgtctaaga aaccattatt atcatgacat taacctataa aaataggcgt atcacgaggc    5640
cctttcgtct tcaagaa                                                   5657

<210> SEQ ID NO 13
<211> LENGTH: 4855
<212> TYPE: DNA
<213> ORGANISM: Artificial Sequence
<220> FEATURE:
<223> OTHER INFORMATION: Recombinant plasmid pAPSE10304; beta actin stem
      loop - coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (40)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI recognition site
<220> FEATURE:
<221> NAME/KEY: misc_feature
<222> LOCATION: (497)..(791)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: misc_feature
<222> LOCATION: (1056)..(1061)
<223> OTHER INFORMATION: restriction endonuclease SphI recognition site

<400> SEQUENCE: 13
ttccgaaatt aatacgactc actatagggg ggcgatcgcg cacgaggttt ttctgtctag     60
tgagcagtgt ccaacctcaa aagacaacat gtgtgacgac gatgtagcgg ctcttgtcgt   120
agacaatgga tccggtatgt gcaaagccgg tttcgcagga gatgacgcac cccgtgccgt   180
cttcccctcg atcgtcggtc gcccaaggca tcaaggagtc atggtcggta tgggacaaaa   240
ggactcatac gtaggagatg aagcccaaag caaaagaggt atcctcaccc tgaaatacc    300 catcgaacac ggtatcatca ccaactggga tgagtttaaa ccctctagct gctttacaaa   360
gtactggttc ccttttccagc gggatgcttt atctaaacgc aatgagagag gtattcctca   420
ggccacatcg cttcctagtt ccgctgggat ccatcgttgg cggccgaagc cgccattcca   480
tagtgagttc tggcgcgcct catcccagtt ggtgatgata ccgtgttcga tgggtattt    540 cagggtgagg atacctcttt tgctttgggc ttcatctcct acgtatgagt ccttttgtcc   600
cataccgacc atgactcctt gatgccttgg gcgaccgacg atcgagggga agacggcacg   660
gggtgcgtca tctcctgcga aaccggcttt gcacataccg gatccattgt ctacgacaag   720
agccgctaca tcgtcgtcac acatgttgtc ttttgaggtt ggacactgct cactagacag   780 aaaaaccctcg tgccggaccg aatacccggt ctgaacgagg gcggccgcgg tacccaagaa   840
gtacttagag ttaattaagg agttcaaaca tgaggatcac ccatgtcgaa gctcccacac   900
```

```
cctagcataa ccccttgggg cctctaaacg ggtcttgagg ggttttttgc tgaaaggagg    960
aactatatcc ggatatccac aggacgggtg tggtcgccat gatcgcgtag tcgatagtgg   1020
ctccaagtag cgaagcgagc aggactgggc ggcgggcatg caccattcct tgcggcggcg   1080
gtgctcaacg gcctcaacct actactgggc tgcttcctaa tgcaggagtc gcataaggga   1140
gagcgtcgac cgatgccctt gagagccttc aacccagtca gctccttccg gtgggcgcgg   1200
ggcatgacta tcgtcgccgc acttatgact gtcttcttta tcatgcaact cgtaggacag   1260
gtgccggcag cgctctgggt cattttcggc gaggaccgct ttcgctggag cgcgacgatg   1320
atcggcctgt cgcttgcggt attcggaatc ttgcacgccc tcgctcaagc cttcgtcact   1380
ggtcccgcca ccaaacgttt cggcgagaag caggccatta tcgccggcat ggcggccgac   1440
gcgctgggct acgtcttgct ggcgttcgcg acgcgaggct ggatggcctt ccccattatg   1500
attcttctcg cttccggcgg catcgggatg cccgcgttgc aggccatgct gtccaggcag   1560
gtagatgacg accatcaggg acagcttcaa ggatcgctcg cggctcttac cagcctaact   1620
tcgatcattg gaccgctgat cgtcacggcg atttatgccg cctcggcgag cacatggaac   1680
gggttggcat ggattgtagg cgccgcccta taccttgtct gcctccccgc gttgcgtcgc   1740
ggtgcatgga gccgggccac ctcgacctga atggaagccg gcggcacctc gctaacggat   1800
tcaccactcc aagaattgga gccaatcaat tcttgcggag aactgtgaat gcgcaaacca   1860
acccttggca gaacatatcc atcgcgtccg ccatctccag cagcccgcacg cggcgcatct   1920
cgggcagcgt tgggtcctgg ccacgggtgc gcatgatcgt gctcctgtcg ttgaggaccc   1980
ggctaggctg gcggggttgc cttactggtt agcagaatga atcaccgata cgcgagcgaa   2040
cgtgaagcga ctgctgctgc aaaacgtctg cgacctgagc aacaacatga atggtcttcg   2100
gtttccgtgt ttcgtaaagt ctggaaacgc ggaagtcagc gccctgcacc attatgttcc   2160
ggatctgcat cgcaggatgc tgctggctac cctgtggaac acctacatct gtattaacga   2220
agcgctggca ttgaccctga gtgattttc tctggtcccg ccgcatccat accgccagtt   2280
gtttaccctc acaacgttcc agtaaccggg catgttcatc atcagtaacc cgtatcgtga   2340
gcatcctctc tcgtttcatc ggtatcatta ccccccatgaa cagaaatccc ccttacacgg   2400
aggcatcagt gaccaaacag gaaaaaaccg cccttaacat ggcccgcttt atcagaagcc   2460
agacattaac gcttctggag aaactcaacg agctggacgc ggatgaacag gcagacatct   2520
gtgaatcgct tcacgaccac gctgatgagc tttaccgcag ctgcctcgcg cgtttcggtg   2580
atgacggtga aaacctctga cacatgcagc tcccggagac ggtcacagct tgtctgtaag   2640
cggatgccgg gagcagacaa gcccgtcagg gcgcgtcagc gggtgttggc gggtgtcggg   2700
gcgcagccat gacccagtca cgtagcgata gcggagtgta tactggctta actatgcggc   2760
atcagagcag attgtactga gagtgcacca tatgcggtgt gaaataccgc acagatgcgt   2820
aaggagaaaa taccgcatca ggcgctcttc cgcttcctcg ctcactgact cgctgcgctc   2880
ggtcgttcgg ctgcggcgag cggtatcagc tcactcaaag gcggtaatac ggttatccac   2940
agaatcaggg gataacgcag gaaagaacat gtgagcaaaa ggccagcaaa aggccaggaa   3000
ccgtaaaaag gccgcgttgc tggcgttttt ccataggctc cgcccccctg acgagcatca   3060
caaaaatcga cgctcaagtc agaggtggcg aaacccgaca ggactataaa gataccaggc   3120
gtttccccct ggaagctccc tcgtgcgctc tcctgttccg accctgccgc ttaccggata   3180
cctgtccgcc tttctccctt cgggaagcgt ggcgctttct catagctcac gctgtaggta   3240
tctcagttcg gtgtaggtcg ttcgctccaa gctgggctgt gtgcacgaac cccccgttca   3300
```

```
gcccgaccgc tgcgccttat ccggtaacta tcgtcttgag tccaacccgg taagacacga      3360
cttatcgcca ctggcagcag ccactggtaa caggattagc agagcgaggt atgtaggcgg      3420
tgctacagag ttcttgaagt ggtggcctaa ctacggctac actagaagga cagtatttgg      3480
tatctgcgct ctgctgaagc cagttacctt cggaaaaaga gttggtagct cttgatccgg      3540
caaacaaacc accgctggta gcggtggttt ttttgtttgc aagcagcaga ttacgcgcag      3600
aaaaaaagga tctcaagaag atcctttgat cttttctacg gggtctgacg ctcagtggaa      3660
cgaaaactca cgttaaggga ttttggtcat gagattatca aaaaggatct cacctagat       3720 cctttaaat taaaaatgaa gttttaaatc aatctaaagt atatatgagt aaacttggtc       3780
tgacagttac caatgcttaa tcagtgaggc acctatctca gcgatctgtc tatttcgttc      3840
atccatagtt gcctgactcc ccgtcgtgta gataactacg atacgggagg gcttaccatc      3900
tggccccagt gctgcaatga taccgcgaga cccacgctca ccggctccag atttatcagc      3960
aataaaccag ccagccggaa gggccgagcg cagaagtggt cctgcaactt tatccgcctc      4020
catccagtct attaattgtt gccgggaagc tagagtaagt agttcgccag ttaatagttt      4080
gcgcaacgtt gttgccattg ctgcaggcat cgtggtgtca cgctcgtcgt ttggtatggc      4140
ttcattcagc tccggttccc aacgatcaag gcgagttaca tgatccccca tgttgtgcaa      4200
aaaagcggtt agctccttcg gtcctccgat cgttgtcaga agtaagttgg ccgcagtgtt      4260
atcactcatg gttatggcag cactgcataa ttctcttact gtcatgccat ccgtaagatg      4320
cttttctgtg actggtgagt actcaaccaa gtcattctga atagtgta tgcggcgacc        4380 gagttgctct tgcccggcgt caacacggga taataccgcg ccacatagca gaactttaaa      4440
agtgctcatc attggaaaac gttcttcggg gcgaaaactc tcaaggatct taccgctgtt      4500
gagatccagt tcgatgtaac ccactcgtgc acccaactga tcttcagcat cttttacttt      4560
caccagcgtt tctgggtgag caaaaacagg aaggcaaaat gccgcaaaaa agggaataag      4620
ggcgacacgg aaatgttgaa tactcatact cttccttttt caatattatt gaagcattta      4680
tcagggttat tgtctcatga gcggatacat atttgaatgt atttagaaaa ataaacaaat      4740
aggggttccg cgcacatttc cccgaaaagt gccacctgac gtctaagaaa ccattattat      4800
catgacatta acctataaaa ataggcgtat cacgaggccc tttcgtcttc aagaa           4855
```

<210> SEQ ID NO 14
<211> LENGTH: 5367
<212> TYPE: DNA
<213> ORGANISM: Artificial Sequence
<220> FEATURE:
<223> OTHER INFORMATION: Recombinant plasmid pAPSE10279; beta actin stem
      loop + capsid
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature

```
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: promoter
<222> LOCATION: (985)..(1003)
<223> OTHER INFORMATION: bacteriophage T7 gene 1 promoter
<220> FEATURE:
<221> NAME/KEY: gene
<222> LOCATION: (1076)..(1465)
<223> OTHER INFORMATION: bacteriophage MS2 coat protein gene
<220> FEATURE:
<221> NAME/KEY: terminator
<222> LOCATION: (1498)..(1545)
<223> OTHER INFORMATION: bacteriophage T7 transcription terminator

<400> SEQUENCE: 14
```

| | | | |
|---|---|---|---|
| ttcttagctc cggcaagcaa ttaagaactt ccgaaattaa tacgactcac tatagggagg | | | 60 |
| cgatcgcgca cgaggttttt ctgtctagtg agcagtgtcc aacctcaaaa gacaacatgt | | | 120 |
| gtgacgacga tgtagcggct cttgtcgtag acaatggatc cggtatgtgc aaagccggtt | | | 180 |
| tcgcaggaga tgacgcaccc cgtgccgtct tcccctcgat cgtcggtcgc caaggcatc | | | 240 |
| aaggagtcat ggtcggtatg gacaaaagg actcatacgt aggagatgaa gcccaaagca | | | 300 |
| aaagaggtat cctcaccctg aaataccca tcgaacacgg tatcatcacc aactgggatg | | | 360 |
| agtttaaacc ctctagctgc tttacaaagt actggttccc tttccagcgg gatgctttat | | | 420 |
| ctaaacgcaa tgagagaggt attcctcagg ccacatcgct tcctagttcc gctgggatcc | | | 480 |
| atcgttggcg gccgaagccg ccattccata gtgagttctg gcgcgcctca tcccagttgg | | | 540 |
| tgatgatacc gtgttcgatg gggtatttca gggtgaggat acctcttttg ctttgggctt | | | 600 |
| catctcctac gtatgagtcc ttttgtccca taccgaccat gactccttga tgccttgggc | | | 660 |
| gaccgacgat cgaggggaag acggcacggg gtgcgtcatc tcctgcgaaa ccggctttgc | | | 720 |
| acataccgga tccattgtct acgacaagag ccgctacatc gtcgtcacac atgttgtctt | | | 780 |
| ttgaggttgg acactgctca ctagacagaa aaacctcgtg ccggaccgaa tacccggtct | | | 840 |
| gaacgaggtt aattaaggta cccaagaagt acttagaggc ggccgcctag cataaccct | | | 900 |
| tggggcctct aaacgggtct tgaggggttt tttgagaaac ggccgaatac acctgttcgg | | | 960 |
| atccagatct cgatcccgcg aaattaatac gactcactat agggagacca acggtttc | | | 1020 |
| cctctagatc acaagtttgt acaaaaaagc aggctaagaa ggagatatac atatggcgtc | | | 1080 |
| taactttacc caattcgttc tggttgataa cggcggtacg ggtgacgtta ccgtagctcc | | | 1140 |
| gtccaacttc gccaacggtg ttgcggaatg gattagctct aacagccgct ctcaggccta | | | 1200 |
| caaagtcacg tgctccgttc gtcagtctag cgcgcagaat cgcaaataca ccatcaaagt | | | 1260 |
| tgaagtaccg aaagtcgcaa cgcagaccgt aggcggcgta gaactcccag ttgcggcctg | | | 1320 |
| gcgctcttac ctcaacatgg aactgactat tccgattttt gcgacgaact ccgactgcga | | | 1380 |
| actgattgtt aaggcaatgc agggcctgct gaaagacggt aatccgatcc catctgcaat | | | 1440 |
| cgctgctaac tctggcattt actaataagc ggacgcgctg ccaccgctga gcaataacta | | | 1500 |
| gcataacccc ttggggcctc taaacgggtc ttgagggggtt ttttgctgaa aggaggaact | | | 1560 |
| atatccggca tgcaccattc cttgcggcgg cggtgctcaa cggcctcaac ctactactgg | | | 1620 |
| gctgcttcct aatgcaggag tcgcataagg gagagcgtcg accgatgccc ttgagagcct | | | 1680 |
| tcaacccagt cagctccttc cggtgggcgc ggggcatgac tatcgtcgcc gcacttatga | | | 1740 |

```
ctgtcttctt tatcatgcaa ctcgtaggac aggtgccggc agcgctctgg gtcatttttcg    1800 gcgaggaccg ctttcgctgg agcgcgacga tgatcggcct gtcgcttgcg gtattcggaa    1860
tcttgcacgc cctcgctcaa gccttcgtca ctggtcccgc caccaaacgt ttcggcgaga    1920
agcaggccat tatcgccggc atggcggccg acgcgctggg ctacgtcttg ctggcgttcg    1980
cgacgcgagg ctggatggcc ttccccatta tgattcttct cgcttccggc ggcatcggga    2040
tgcccgcgtt gcaggccatg ctgtccaggc aggtagatga cgaccatcag ggacagcttc    2100
aaggatcgct cgcggctctt accagcctaa cttcgatcat tggaccgctg atcgtcacgg    2160
cgatttatgc cgcctcggcg agcacatgga acgggttggc atggattgta ggcgccgccc    2220
tataccttgt ctgcctcccc gcgttgcgtc gcggtgcatg gagccgggcc acctcgacct    2280
gaatggaagc cggcggcacc tcgctaacgg attcaccact ccaagaattg gagccaatca    2340
attcttgcgg agaactgtga atgcgcaaac caacccttgg cagaacatat ccatcgcgtc    2400
cgccatctcc agcagccgca cgcggcgcat ctcgggcagc gttgggtcct ggccacgggt    2460
gcgcatgatc gtgctcctgt cgttgaggac ccggctaggc tggcggggtt gccttactgg    2520
ttagcagaat gaatcaccga tacgcgagcg aacgtgaagc gactgctgct gcaaaacgtc    2580
tgcgacctga gcaacaacat gaatggtctt cggtttccgt gtttcgtaaa gtctggaaac    2640
gcggaagtca gcgccctgca ccattatgtt ccggatctgc atcgcaggat gctgctggct    2700
accctgtgga acacctacat ctgtattaac gaagcgctgg cattgaccct gagtgatttt    2760
tctctggtcc cgccgcatcc ataccgccag ttgtttaccc tcacaacgtt ccagtaaccg    2820
ggcatgttca tcatcagtaa cccgtatcgt gagcatcctc tctcgtttca tcggtatcat    2880 taccccccatg aacagaaatc ccccttacac ggaggcatca gtgaccaaac aggaaaaaac    2940
cgcccttaac atgccccgct ttatcagaag ccagacatta acgcttctgg agaaactcaa    3000
cgagctggac gcggatgaac aggcagacat ctgtgaatcg cttcacgacc acgctgatga    3060
gctttaccgc agctgcctcg cgcgtttcgg tgatgacggt gaaaacctct gacacatgca    3120
gctcccggag acggtcacag cttgtctgta agcggatgcc gggagcagac aagcccgtca    3180
gggcgcgtca gcgggtgttg gcgggtgtcg ggcgcagcc atgacccagt cacgtagcga    3240
tagcggagtg tatactggct taactatgcg gcatcagagc agattgtact gagagtgcac    3300
catatgcggt gtgaaatacc gcacagatgc gtaaggagaa aataccgcat caggcgctct    3360
tccgcttcct cgctcactga ctcgctgcgc tcggtcgttc ggctgcggcg agcggtatca    3420
gctcactcaa aggcggtaat acggttatcc acagaatcag gggataacgc aggaaagaac    3480
atgtgagcaa aaggccagca aaaggccagg aaccgtaaaa aggccgcgtt gctggcgttt    3540
ttccataggc tccgcccccc tgacgagcat cacaaaaatc gacgctcaag tcagaggtgg    3600
cgaaacccga caggactata aagataccag gcgtttcccc ctggaagctc cctcgtgcgc    3660
tctcctgttc cgaccctgcc gcttaccgga tacctgtccg cctttctccc ttcgggaagc    3720
gtggcgcttt ctcatagctc acgctgtagg tatctcagtt cggtgtaggt cgttcgctcc    3780
aagctgggct gtgtgcacga acccccgtt cagcccgacc gctgcgcctt atccggtaac    3840
tatcgtcttg agtccaaccc ggtaagacac gacttatcgc cactggcagc agccactggt    3900
aacaggatta gcagagcgag gtatgtaggc ggtgctacag agttcttgaa gtggtggcct    3960
aactacggct acactagaag gacagtattt ggtatctgcg ctctgctgaa gccagttacc    4020
ttcggaaaaa gagttggtag ctcttgatcc ggcaaacaaa ccaccgctgg tagcggtggt    4080
ttttttgttt gcaagcagca gattacgcgc agaaaaaaag gatctcaaga agatcctttg    4140
```

```
atcttttcta cggggtctga cgctcagtgg aacgaaaact cacgttaagg gattttggtc    4200
atgagattat caaaaaggat cttcacctag atccttttaa attaaaaatg aagttttaaa    4260
tcaatctaaa gtatatatga gtaaacttgg tctgacagtt accaatgctt aatcagtgag    4320
gcacctatct cagcgatctg tctatttcgt tcatccatag ttgcctgact ccccgtcgtg    4380
tagataacta cgatacggga gggcttacca tctggcccca gtgctgcaat gataccgcga    4440
gacccacgct caccggctcc agatttatca gcaataaacc agccagccgg aagggccgag    4500
cgcagaagtg gtcctgcaac tttatccgcc tccatccagt ctattaattg ttgccgggaa    4560
gctagagtaa gtagttcgcc agttaatagt ttgcgcaacg ttgttgccat tgctgcaggc    4620
atcgtggtgt cacgctcgtc gtttggtatg gcttcattca gctccggttc ccaacgatca    4680
aggcgagtta catgatcccc catgttgtgc aaaaaagcgg ttagctcctt cggtcctccg    4740
atcgttgtca gaagtaagtt ggccgcagtg ttatcactca tggttatggc agcactgcat    4800
aattctctta ctgtcatgcc atccgtaaga tgcttttctg tgactggtga gtactcaacc    4860
aagtcattct gagaatagtg tatgcggcga ccgagttgct cttgcccggc gtcaacacgg    4920
gataataccg cgccacatag cagaacttta aaagtgctca tcattggaaa acgttcttcg    4980
gggcgaaaac tctcaaggat cttaccgctg ttgagatcca gttcgatgta acccactcgt    5040
gcacccaact gatcttcagc atcttttact ttcaccagcg tttctgggtg agcaaaaaca    5100
ggaaggcaaa atgccgcaaa aaagggaata agggcgacac ggaaatgttg aatactcata    5160
ctcttccttt ttcaatatta ttgaagcatt tatcagggtt attgtctcat gagcggatac    5220
atatttgaat gtatttagaa aaataaacaa ataggggttc cgcgcacatt tccccgaaaa    5280
gtgccacctg acgtctaaga aaccattatt atcatgacat taacctataa aaataggcgt    5340
atcacgaggc cctttcgtct tcaagaa                                        5367

<210> SEQ ID NO 15
<211> LENGTH: 4764
<212> TYPE: DNA
<213> ORGANISM: Artificial Sequence
<220> FEATURE:
<223> OTHER INFORMATION: Recombinant plasmid pAPSE10303; beta actin stem
      loop - coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator

<400> SEQUENCE: 15
ttcttagctc cggcaagcaa ttaagaactt ccgaaattaa tacgactcac tatagggagg    60
```

```
cgatcgcgca cgaggttttt ctgtctagtg agcagtgtcc aacctcaaaa gacaacatgt    120
gtgacgacga tgtagcggct cttgtcgtag acaatggatc cggtatgtgc aaagccggtt    180
tcgcaggaga tgacgcaccc cgtgccgtct tcccctcgat cgtcggtcgc ccaaggcatc    240
aaggagtcat ggtcggtatg ggacaaaagg actcatacgt aggagatgaa gcccaaagca    300
aaagaggtat cctcaccctg aaataccccca tcgaacacgg tatcatcacc aactgggatg    360
agtttaaacc ctctagctgc tttacaaagt actggttccc tttccagcgg gatgctttat    420
ctaaacgcaa tgagagaggt attcctcagg ccacatcgct tcctagttcc gctgggatcc    480
atcgttggcg gccgaagccg ccattccata gtgagttctg gcgcgcctca tcccagttgg    540
tgatgatacc gtgttcgatg gggtatttca gggtgaggat acctcttttg ctttgggctt    600
catctcctac gtatgagtcc ttttgtccca taccgaccat gactccttga tgccttgggc    660
gaccgacgat cgaggggaag acggcacggg gtgcgtcatc tcctgcgaaa ccggctttgc    720
acataccgga tccattgtct acgacaagag ccgctacatc gtcgtcacac atgttgtctt    780
ttgaggttgg acactgctca ctagacagaa aaacctcgtg ccggaccgaa tacccggtct    840
gaacgaggtt aattaaggta cccaagaagt acttagaggc ggccgcctag cataacccct    900
tggggcctct aaacgggtct tgaggggttt tttgagaaac ggccgaatac acctgttcgg    960
atccagatcc accattcctt gcggcggcgg tgctcaacgg cctcaaccta ctactgggct    1020
gcttcctaat gcaggagtcg cataagggag agcgtcgacc gatgcccttg agagccttca    1080
acccagtcag ctccttccgg tgggcgcggg gcatgactat cgtcgccgca cttatgactg    1140
tcttctttat catgcaactc gtaggacagg tgccggcagc gctctgggtc attttcggcg    1200
aggaccgctt tcgctggagc gcgacgatga tcggcctgtc gcttgcggta ttcggaatct    1260
tgcacgccct cgctcaagcc ttcgtcactg gtcccgccac caaacgtttc ggcgagaagc    1320
aggccattat cgccggcatg gcggccgacg cgctgggcta cgtcttgctg gcgttcgcga    1380
cgcgaggctg gatggccttc cccattatga ttcttctcgc ttccggcggc atcgggatgc    1440
ccgcgttgca ggccatgctg tccaggcagg tagatgacga ccatcaggga cagcttcaag    1500
gatcgctcgc ggctcttacc agcctaactt cgatcattgg accgctgatc gtcacggcga    1560
tttatgccgc ctcggcgagc acatggaacg ggttggcatg gattgtaggc gccgccctat    1620
accttgtctg cctccccgcg ttgcgtcgcg gtgcatggag ccgggccacc tcgacctgaa    1680
tggaagccgg cggcacctcg ctaacggatt caccactcca agaattggag ccaatcaatt    1740
cttgcggaga actgtgaatg cgcaaaccaa cccttggcag aacatatcca tcgcgtccgc    1800
catctccagc agccgcacgc ggcgcatctc gggcagcgtt gggtcctggc cacgggtgcg    1860
catgatcgtg ctcctgtcgt tgaggacccg gctaggctgg cggggttgcc ttactggtta    1920
gcagaatgaa tcaccgatac gcgagcgaac gtgaagcgac tgctgctgca aacgtctgc    1980 gacctgagca caacatgaa tggtcttcgg tttccgtgtt tcgtaaagtc tggaaacgcg    2040
gaagtcagcg ccctgcacca ttatgttccg gatctgcatc gcaggatgct gctggctacc    2100
ctgtggaaca cctacatctg tattaacgaa gcgctggcat tgaccctgag tgattttttct    2160 ctggtcccgc cgcatccata ccgccagttg tttaccctca caacgttcca gtaaccgggc    2220
atgttcatca tcagtaaccc gtatcgtgag catcctctct cgtttcatcg gtatcattac    2280
ccccatgaac agaaatcccc cttacacgga ggcatcagtg accaaacagg aaaaaaccgc    2340
ccttaacatg gcccgcttta tcagaagcca gacattaacg cttctggaga aactcaacga    2400
```

```
gctggacgcg gatgaacagg cagacatctg tgaatcgctt cacgaccacg ctgatgagct    2460
ttaccgcagc tgcctcgcgc gtttcggtga tgacggtgaa aacctctgac acatgcagct    2520
cccggagacg gtcacagctt gtctgtaagc ggatgccggg agcagacaag cccgtcaggg    2580
cgcgtcagcg ggtgttggcg ggtgtcgggg cgcagccatg acccagtcac gtagcgatag    2640
cggagtgtat actggcttaa ctatgcggca tcagagcaga ttgtactgag agtgcaccat    2700
atgcggtgtg aaataccgca cagatgcgta aggagaaaat accgcatcag cgctcttcc     2760 gcttcctcgc tcactgactc gctgcgctcg tcgttcggc tgcggcgagc ggtatcagct    2820
cactcaaagg cggtaatacg gttatccaca gaatcagggg ataacgcagg aaagaacatg    2880
tgagcaaaag gccagcaaaa ggccaggaac cgtaaaaagg ccgcgttgct ggcgttttc    2940 cataggctcc gcccccctga cgagcatcac aaaaatcgac gctcaagtca gaggtggcga    3000
aacccgacag gactataaag ataccaggcg tttccccctg gaagctccct cgtgcgctct    3060
cctgttccga ccctgccgct taccggatac ctgtccgcct ttctcccttc gggaagcgtg    3120
gcgctttctc atagctcacg ctgtaggtat ctcagttcgg tgtaggtcgt tcgctccaag    3180
ctgggctgtg tgcacgaacc ccccgttcag cccgaccgct gcgccttatc cggtaactat    3240
cgtcttgagt ccaacccggt aagacacgac ttatcgccac tggcagcagc cactggtaac    3300
aggattagca gagcgaggta tgtaggcggt gctacagagt tcttgaagtg gtggcctaac    3360
tacggctaca ctagaaggac agtatttggt atctgcgctc tgctgaagcc agttaccttc    3420
ggaaaaagag ttggtagctc ttgatccggc aaacaaacca ccgctggtag cggtggtttt    3480
tttgtttgca agcagcagat tacgcgcaga aaaaaggat ctcaagaaga tcctttgatc     3540
ttttctacgg ggtctgacgc tcagtggaac gaaaactcac gttaagggat tttggtcatg    3600
agattatcaa aaaggatctt cacctagatc cttttaaatt aaaaatgaag ttttaaatca    3660
atctaaagta tatatgagta aacttggtct gacagttacc aatgcttaat cagtgaggca    3720
cctatctcag cgatctgtct atttcgttca tccatagttg cctgactccc cgtcgtgtag    3780
ataactacga tacgggaggg cttaccatct ggccccagtg ctgcaatgat accgcgagac    3840
ccacgctcac cggctccaga tttatcagca ataaaccagc cagccggaag ggccgagcgc    3900
agaagtggtc ctgcaacttt atccgcctcc atccagtcta ttaattgttg ccgggaagct    3960
agagtaagta gttcgccagt taatagtttg cgcaacgttg ttgccattgc tgcaggcatc    4020
gtggtgtcac gctcgtcgtt tggtatggct tcattcagct ccggttccca acgatcaagg    4080
cgagttacat gatccccat gttgtgcaaa aaagcggtta gctccttcgg tcctccgatc      4140
gttgtcagaa gtaagttggc cgcagtgtta tcactcatgg ttatggcagc actgcataat    4200
tctcttactg tcatgccatc cgtaagatgc ttttctgtga ctggtgagta ctcaaccaag    4260
tcattctgag aatagtgtat gcggcgaccg agttgctctt gcccggcgtc aacacgggat    4320
aataccgcgc cacatagcag aactttaaaa gtgctcatca ttggaaaacg ttcttcgggg    4380
cgaaaactct caaggatctt accgctgttg agatccagtt cgatgtaacc cactcgtgca    4440
cccaactgat cttcagcatc ttttactttc accagcgttt ctgggtgagc aaaaacagga    4500
aggcaaaatg ccgcaaaaaa gggaataagg gcgacacgga aatgttgaat actcatactc    4560
ttcctttttc aatattattg aagcatttat cagggttatt gtctcatgag cggatacata    4620
tttgaatgta tttagaaaaa taaacaaata ggggttccgc gcacatttcc ccgaaaagtg    4680
ccacctgacg tctaagaaac cattattatc atgacattaa cctataaaaa taggcgtatc    4740
acgaggccct ttcgtcttca agaa                                           4764
```

<210> SEQ ID NO 16
<211> LENGTH: 5940
<212> TYPE: DNA
<213> ORGANISM: Artificial Sequence
<220> FEATURE:
<223> OTHER INFORMATION: Recombinant plasmid pAPSE10270; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (782)..(1076)
<223> OTHER INFORMATION: beta actin antisense gene fragment
<220> FEATURE:
<221> NAME/KEY: misc_feature
<222> LOCATION: (1151)..(1169)
<223> OTHER INFORMATION: Bacteriophage MS2 pac sequence
<220> FEATURE:
<221> NAME/KEY: terminator
<222> LOCATION: (1185)..(1232)
<223> OTHER INFORMATION: bacteriophage T7 transcription terminator
<220> FEATURE:
<221> NAME/KEY: promoter
<222> LOCATION: (1558)..(1576)
<223> OTHER INFORMATION: bacteriophage T7 gene 1 promoter
<220> FEATURE:
<221> NAME/KEY: gene
<222> LOCATION: (1649)..(2038)
<223> OTHER INFORMATION: bacteriophage MS2 coat protein gene
<220> FEATURE:
<221> NAME/KEY: terminator
<222> LOCATION: (2071)..(2118)
<223> OTHER INFORMATION: bacteriophage T7 transcription terminator

<400> SEQUENCE: 16
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatatacca     300
tacgccggcc attcaaacat gaggattacc catgtattta atacccatg tccaggcgcg     360 ctccgcgatc gcgcacgagg ttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttcccttttcc agcgggatgc     720 tttatctaaa cgcaatgaga gaggtattcc tcaggccaca tcgcttccta gttcggcgcg     780
cctcatccca gttggtgatg ataccgtgtt cgatgggta tttcagggtg aggatacctc     840

```
ttttgctttg ggcttcatct cctacgtatg agtccttttg tcccataccg accatgactc    900
cttgatgcct tgggcgaccg acgatcgagg ggaagacggc acggggtgcg tcatctcctg    960
cgaaaccggc tttgcacata ccggatccat tgtctacgac aagagccgct acatcgtcgt   1020
cacacatgtt gtcttttgag gttggacact gctcactaga cagaaaaacc tcgtgccgga   1080
ccgaataccc ggtctgaacg agggcggccg cggtacccaa gaagtactta gagttaatta   1140
aggagttcaa acatgaggat cacccatgtc gaagctccca cccctagca taaccccttg    1200
gggcctctaa acgggtcttg aggggttttt tgctgaaagg aggaactata tccggatatc   1260
cacaggacgg gtgtggtcgc catgatcgcg tagtcgatag tggctccaag tagcgaagcg   1320
agcaggactg ggcggcgggc atgcatcgtc cattccgaca gcatcgccag tcactatggc   1380
gtgctgctag cgctatatgc gttgatgcaa tttctatgcg cacccgttct cggagcactg   1440
tccgaccgct ttggccgccg cccagtcctg ctcgcttcgc tacttggagc cactatcgac   1500
tacgcgatca tggcgaccac acccgtcctg tggatccaga tctcgatccc gcgaaattaa   1560
tacgactcac tatagggaga ccacaacggt ttccctctag atcacaagtt tgtacaaaaa   1620
agcaggctaa gaaggagata tacatatggc gtctaacttt acccaattcg ttctggttga   1680
taacggcggt acgggtgacg ttaccgtagc tccgtccaac ttcgccaacg gtgttgcgga   1740
atggattagc tctaacagcc gctctcaggc ctacaaagtc acgtgctccg ttcgtcagtc   1800
tagcgcgcag aatcgcaaat acaccatcaa agttgaagta ccgaaagtcg caacgcagac   1860
cgtaggcggc gtagaactcc cagttgcggc ctggcgctct tacctcaaca tggaactgac   1920
tattccgatt tttgcgacga actccgactg cgaactgatt gttaaggcaa tgcagggcct   1980
gctgaaagac ggtaatccga tcccatctgc aatcgctgct aactctggca tttactaata   2040
agcggacgcg ctgccaccgc tgagcaataa ctagcataac cccttggggc ctctaaacgg   2100
gtcttgaggg gttttttgct gaaaggagga actatatccg gcatgcacca ttccttgcgg   2160
cggcggtgct caacggcctc aacctactac tgggctgctt cctaatgcag gagtcgcata   2220
agggagagcg tcgaccgatg cccttgagag ccttcaaccc agtcagctcc ttccggtggg   2280
cgcggggcat gactatcgtc gccgcactta tgactgtctt ctttatcatg caactcgtag   2340
gacaggtgcc ggcagcgctc tgggtcattt tcggcgagga ccgctttcgc tggagcgcga   2400
cgatgatcgg cctgtcgctt gcggtattcg gaatcttgca cgcccgcct caagccttcg    2460
tcactggtcc cgccaccaaa cgtttcggcg agaagcaggc cattatcgcc ggcatggcgg   2520
ccgacgcgct gggctacgtc ttgctggcgt tcgcgacgcg aggctggatg gccttcccca   2580
ttatgattct tctcgcttcc ggcggcatcg ggatgcccgc gttgcaggcc atgctgtcca   2640
ggcaggtaga tgacgaccat cagggacagc ttcaaggatc gctcgcggct cttaccagcc   2700
taacttcgat cattggaccg ctgatcgtca cggcgattta tgccgcctcg gcgagcacat   2760
ggaacgggtt ggcatggatt gtaggcgccg ccctatacct tgtctgcctc cccgcgttgc   2820
gtcgcggtgc atggagccgg gccacctcga cctgaatgga agccggcggc acctcgctaa   2880
cggattcacc actccaagaa ttggagccaa tcaattcttg cggagaactg tgaatgcgca   2940
aaccaacctt ggcagaaca tatccatcgc gtccgccatc tccagcagcc gcacgcggcg   3000
catctcgggc agcgttgggt cctggccacg ggtgcgcatg atcgtgctcc tgtcgttgag   3060
gacccggcta ggctggcggg gttgccttac tggttagcag aatgaatcac cgatacgcga   3120
gcgaacgtga agcgactgct gctgcaaaac gtctgcgacc tgagcaacaa catgaatggt   3180
```

```
cttcggtttc cgtgtttcgt aaagtctgga aacgcggaag tcagcgccct gcaccattat    3240
gttccggatc tgcatcgcag gatgctgctg gctaccctgt ggaacaccta catctgtatt    3300
aacgaagcgc tggcattgac cctgagtgat ttttctctgg tcccgccgca tccataccgc    3360
cagttgttta ccctcacaac gttccagtaa ccgggcatgt tcatcatcag taacccgtat    3420
cgtgagcatc ctctctcgtt tcatcggtat cattaccccc atgaacagaa atccccctta    3480 cacgaggca tcagtgacca aacaggaaaa aaccgccctt aacatggccc gctttatcag    3540
aagccagaca ttaacgcttc tggagaaact caacgagctg gacgcggatg aacaggcaga    3600
catctgtgaa tcgcttcacg accacgctga tgagctttac cgcagctgcc tcgcgcgttt    3660
cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggcgca gccatgaccc agtcacgtag cgatagcgga gtgtatactg gcttaactat    3840
gcggcatcag agcagattgt actgagagtg caccatatgc ggtgtgaaat accgcacaga    3900
tgcgtaagga gaaaataccg catcaggcgc tcttccgctt cctcgctcac tgactcgctg    3960
cgctcggtcg ttcggctgcg gcgagcggta tcagctcact caaaggcggt aatacggtta    4020
tccacagaat caggggataa cgcaggaaag aacatgtgag caaaaggcca gcaaaaggcc    4080
aggaaccgta aaaaggccgc gttgctggcg ttttttccata ggctccgccc ccctgacgag    4140
catcacaaaa atcgacgctc aagtcagagg tggcgaaacc cgacaggact ataaagatac    4200
caggcgtttc ccctggaag ctccctcgtg cgctctcctg ttccgaccct gccgcttacc    4260
ggatacctgt ccgcctttct cccttcggga agcgtggcgc tttctcatag ctcacgctgt    4320
aggtatctca gttcggtgta ggtcgttcgc tccaagctgg gctgtgtgca cgaaccccc    4380 gttcagcccg accgctgcgc cttatccggt aactatcgtc ttgagtccaa cccggtaaga    4440
cacgacttat cgccactggc agcagccact ggtaacagga ttagcagagc gaggtatgta    4500
ggcggtgcta cagagttctt gaagtggtgg cctaactacg gctacactag aaggacagta    4560
tttggtatct gcgctctgct gaagccagtt accttcggaa aaagagttgg tagctcttga    4620
tccggcaaac aaaccaccgc tggtagcggt ggtttttttg tttgcaagca gcagattacg    4680
cgcagaaaaa aaggatctca agaagatcct ttgatctttt ctacggggtc tgacgctcag    4740
tggaacgaaa actcacgtta agggattttg gtcatgagat tatcaaaaag gatcttcacc    4800
tagatccttt taaattaaaa atgaagtttt aaatcaatct aaagtatata tgagtaaact    4860
tggtctgaca gttaccaatg cttaatcagt gaggcaccta tctcagcgat ctgtctattt    4920
cgttcatcca tagttgcctg actccccgtc gtgtagataa ctacgatacg ggagggctta    4980
ccatctggcc ccagtgctgc aatgatacc g cgagacccac gctcaccggc tccagattta    5040
tcagcaataa accagccagc cggaagggcc gagcgcagaa gtggtcctgc aactttatcc    5100
gcctccatcc agtctattaa ttgttgccgg gaagctagag taagtagttc gccagttaat    5160
agtttgcgca acgttgttgc cattgctgca ggcatcgtgg tgtcacgctc gtcgtttggt    5220
atggcttcat tcagctccgg ttcccaacga tcaaggcgag ttacatgatc ccccatgttg    5280
tgcaaaaaag cggttagctc cttcggtcct ccgatcgttg tcagaagtaa gttggccgca    5340
gtgttatcac tcatggttat ggcagcactg cataattctc ttactgtcat gccatccgta    5400
agatgctttt ctgtgactgg tgagtactca accaagtcat tctgagaata gtgtatgcgg    5460
cgaccgagtt gctcttgccc ggcgtcaaca cgggataata ccgcgccaca tagcagaact    5520
ttaaaagtgc tcatcattgg aaaacgttct tcggggcgaa aactctcaag gatcttaccg    5580
```

```
ctgttgagat ccagttcgat gtaacccact cgtgcaccca actgatcttc agcatctttt    5640
actttcacca gcgtttctgg gtgagcaaaa acaggaaggc aaaatgccgc aaaaaaggga    5700
ataagggcga cacggaaatg ttgaatactc atactcttcc tttttcaata ttattgaagc    5760
atttatcagg gttattgtct catgagcgga tacatatttg aatgtattta gaaaaataaa    5820
caaatagggg ttccgcgcac atttccccga aaagtgccac ctgacgtcta agaaaccatt    5880
attatcatga cattaaccta taaaaatagg cgtatcacga ggccctttcg tcttcaagaa    5940
```

<210> SEQ ID NO 17
<211> LENGTH: 5960
<212> TYPE: DNA
<213> ORGANISM: Artificial Sequence
<220> FEATURE:
<223> OTHER INFORMATION: Recombinant plasmid pAPSE10271; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (802)..(1096)
<223> OTHER INFORMATION: beta actin antisense gene fragment
<220> FEATURE:
<221> NAME/KEY: misc_feature
<222> LOCATION: (1171)..(1189)
<223> OTHER INFORMATION: bacteriophage MS2 pac sequence
<220> FEATURE:
<221> NAME/KEY: terminator
<222> LOCATION: (1205)..(1252)
<223> OTHER INFORMATION: bacteriophage T7 transcription terminator
<220> FEATURE:
<221> NAME/KEY: promoter
<222> LOCATION: (1578)..(1596)
<223> OTHER INFORMATION: bacteriophage T7 gene 1 promoter
<220> FEATURE:
<221> NAME/KEY: gene
<222> LOCATION: (1669)..(2058)
<223> OTHER INFORMATION: bacteriophage MS2 coat protein gene
<220> FEATURE:
<221> NAME/KEY: terminator
<222> LOCATION: (2091)..(2138)
<223> OTHER INFORMATION: bacteriophage T7 transcription terminator

<400> SEQUENCE: 17

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300 tacgccggcc attcaaacat gaggattacc catgtattta aatacccatg tccaggcgcg     360
ctccgcgatc gcgcacgagg tttttctgtc tagtgagcag tgtccaacct caaaagacaa     420
catgtgtgac gacgatgtag cggctcttgt cgtagacaat ggatccggta tgtgcaaagc     480
```

```
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttcccttttcc agcgggatgc   720 tttatctaaa cgcaatgaga gaggtattcc tcaggccaca tcgcttccta gttccgctgg    780
gatccatcgt tggcggcgcg cctcatccca gttggtgatg ataccgtgtt cgatggggta    840
tttcagggtg aggatacctc ttttgctttg ggcttcatct cctacgtatg agtccttttg    900
tcccataccg accatgactc cttgatgcct tgggcgaccg acgatcgagg ggaagacggc    960
acggggtgcg tcatctcctg cgaaaccggc tttgcacata ccggatccat tgtctacgac   1020
aagagccgct acatcgtcgt cacacatgtt gtcttttgag gttggacact gctcactaga   1080
cagaaaaacc tcgtgccgga ccgaataccc ggtctgaacg agggcggccg cggtacccaa   1140
gaagtactta gagttaatta aggagttcaa acatgaggat cacccatgtc gaagctccca   1200
caccctagca taaccccttg gggcctctaa acgggtcttg aggggttttt tgctgaaagg   1260
aggaactata tccggatatc cacaggacgg gtgtggtcgc catgatcgcg tagtcgatag   1320
tggctccaag tagcgaagcg agcaggactg ggcggcgggc atgcatcgtc cattccgaca   1380
gcatcgccag tcactatggc gtgctgctag cgctatatgc gttgatgcaa tttctatgcg   1440
cacccgttct cggagcactg tccgaccgct ttggccgccg cccagtcctg ctcgcttcgc   1500
tacttggagc cactatcgac tacgcgatca tggcgaccac accgtcctg tggatccaga    1560 tctcgatccc gcgaaattaa tacgactcac tataggagac cacaacggt ttccctctag    1620 atcacaagtt tgtacaaaaa agcaggctaa gaaggagata tacatatggc gtctaacttt   1680
acccaattcg ttctggttga taacggcggt acgggtgacg ttaccgtagc tccgtccaac   1740
ttcgccaacg gtgttgcgga atggattagc tctaacagcc gctctcaggc ctacaaagtc   1800
acgtgctccg ttcgtcagtc tagcgcgcag aatcgcaaat acaccatcaa agttgaagta   1860
ccgaaagtcg caacgcagac cgtaggcggc gtagaactcc cagttgcggc ctggcgctct   1920
tacctcaaca tggaactgac tattccgatt tttgcgacga actccgactg cgaactgatt   1980
gttaaggcaa tgcagggcct gctgaaagac ggtaatccga tcccatctgc aatcgctgct   2040
aactctggca tttactaata gcggacgcg ctgccaccgc tgagcaataa ctagcataac    2100 cccttgggc ctctaaacgg gtcttgaggg gttttttgct gaaaggagga actatatccg    2160
gcatgcacca ttccttgcgg cggcggtgct caacggcctc aacctactac tgggctgctt   2220
cctaatgcag gagtcgcata agggagagcg tcgaccgatg cccttgagag ccttcaaccc   2280
agtcagctcc ttccggtggg cgcggggcat gactatcgtc gccgcactta tgactgtctt   2340
ctttatcatg caactcgtag gacaggtgcc ggcagcgctc tgggtcattt tcggcgagga   2400
ccgctttcgc tggagcgcga cgatgatcgg cctgtcgctt gcggtattcg aatcttgca    2460 cgccctcgct caagccttcg tcactggtcc cgccaccaaa cgtttcggcg agaagcaggc   2520
cattatcgcc ggcatggcgg ccgacgcgct gggctacgtc ttgctggcgt tcgcgacgcg   2580
aggctggatg gccttcccca ttatgattct tctcgcttcc ggcggcatcg gatgcccgc    2640 gttgcaggcc atgctgtcca ggcaggtaga tgacgaccat cagggacagc ttcaaggatc   2700
gctcgcggct cttaccagcc taacttcgat cattggaccg ctgatcgtca cggcgattta   2760
tgccgcctcg gcgagcacat ggaacgggtt ggcatggatt gtaggcgccg ccctatacct   2820
```

```
tgtctgcctc cccgcgttgc gtcgcggtgc atggagccgg gccacctcga cctgaatgga    2880
agccggcggc acctcgctaa cggattcacc actccaagaa ttggagccaa tcaattcttg    2940
cggagaactg tgaatgcgca accaaccct tggcagaaca tatccatcgc gtccgccatc     3000
tccagcagcc gcacgcggcg catctcgggc agcgttgggt cctggccacg ggtgcgcatg    3060
atcgtgctcc tgtcgttgag gacccggcta ggctggcggg gttgccttac tggttagcag    3120
aatgaatcac cgatacgcga gcgaacgtga agcgactgct gctgcaaaac gtctgcgacc    3180
tgagcaacaa catgaatggt cttcggtttc cgtgtttcgt aaagtctgga aacgcggaag    3240
tcagcgccct gcaccattat gttccggatc tgcatcgcag gatgctgctg gctaccctgt    3300
ggaacaccta catctgtatt aacgaagcgc tggcattgac cctgagtgat ttttctctgg    3360
tcccgccgca tccataccgc cagttgttta ccctcacaac gttccagtaa ccgggcatgt    3420
tcatcatcag taacccgtat cgtgagcatc ctctctcgtt tcatcggtat cattacccc     3480
atgaacagaa atccccctta cacggaggca tcagtgacca aacaggaaaa aaccgccctt    3540
aacatggccc gctttatcag aagccagaca ttaacgcttc tggagaaact caacgagctg    3600
gacgcggatg aacaggcaga catctgtgaa tcgcttcacg accacgctga tgagctttac    3660
cgcagctgcc tcgcgcgttt cggtgatgac ggtgaaaacc tctgacacat gcagctcccg    3720
gagacggtca cagcttgtct gtaagcggat gccgggagca gacaagcccg tcagggcgcg    3780
tcagcgggtg ttggcgggtg tcggggcgca gccatgaccc agtcacgtag cgatagcgga    3840
gtgtatactg gcttaactat gcggcatcag agcagattgt actgagagtg caccatatgc    3900
ggtgtgaaat accgcacaga tgcgtaagga gaaataccg catcaggcgc tcttccgctt     3960
cctcgctcac tgactcgctg cgctcggtcg ttcggctgcg gcgagcggta tcagctcact    4020
caaaggcggt aatacggtta tccacagaat caggggataa cgcaggaaag aacatgtgag    4080
caaaaggcca gcaaaaggcc aggaaccgta aaaaggccgc gttgctggcg ttttttccata   4140
ggctccgccc ccctgacgag catcacaaaa atcgacgctc aagtcagagg tggcgaaacc    4200
cgacaggact ataaagatac caggcgtttc ccctggaagc tccctcgtg cgctctcctg     4260
ttccgaccct gccgcttacc ggatacctgt ccgcctttct cccttcggga agcgtggcgc    4320
tttctcatag ctcacgctgt aggtatctca gttcggtgta ggtcgttcgc tccaagctgg    4380
gctgtgtgca cgaaccccc gttcagcccg accgctgcgc cttatccggt aactatcgtc     4440
ttgagtccaa cccggtaaga cacgacttat cgccactggc agcagccact ggtaacagga    4500
ttagcagagc gaggtatgta ggcggtgcta cagagttctt gaagtggtgg cctaactacg    4560
gctacactag aaggacagta tttggtatct gcgctctgct gaagccagtt accttcggaa    4620
aaagagttgg tagctcttga tccggcaaac aaaccaccgc tggtagcggt ggtttttttg    4680
tttgcaagca gcagattacg cgcagaaaaa aaggatctca agaagatcct ttgatctttt    4740
ctacggggtc tgacgctcag tggaacgaaa actcacgtta agggattttg gtcatgagat    4800
tatcaaaaag gatcttcacc tagatccttt taaattaaaa atgaagtttt aaatcaatct    4860
aaagtatata tgagtaaact tggtctgaca gttaccaatg cttaatcagt gaggcaccta    4920
tctcagcgat ctgtctattt cgttcatcca tagttgcctg actccccgtc gtgtagataa    4980
ctacgatacg ggagggctta ccatctggcc ccagtgctgc aatgataccg cgagacccac    5040
gctcaccggc tccagattta tcagcaataa accagccagc cggaagggcc gagcgcagaa    5100
gtggtcctgc aactttatcc gcctccatcc agtctattaa ttgttgccgg gaagctagag    5160
taagtagttc gccagttaat agtttgcgca acgttgttgc cattgctgca ggcatcgtgg    5220
```

```
tgtcacgctc gtcgtttggt atggcttcat tcagctccgg ttcccaacga tcaaggcgag    5280
ttacatgatc ccccatgttg tgcaaaaaag cggttagctc cttcggtcct ccgatcgttg    5340
tcagaagtaa gttggccgca gtgttatcac tcatggttat ggcagcactg cataattctc    5400
ttactgtcat gccatccgta agatgctttt ctgtgactgg tgagtactca accaagtcat    5460
tctgagaata gtgtatgcgg cgaccgagtt gctcttgccc ggcgtcaaca cgggataata    5520
ccgcgccaca tagcagaact ttaaaagtgc tcatcattgg aaaacgttct cggggcgaa     5580 aactctcaag gatcttaccg ctgttgagat ccagttcgat gtaacccact cgtgcaccca    5640
actgatcttc agcatctttt actttcacca gcgtttctgg gtgagcaaaa acaggaaggc    5700
aaaatgccgc aaaaaaggga taagggcga cacggaaatg ttgaatactc atactcttcc     5760
tttttcaata ttattgaagc atttatcagg gttattgtct catgagcgga tacatatttg    5820
aatgtattta gaaaaataaa caaatagggg ttccgcgcac atttccccga aaagtgccac    5880
ctgacgtcta agaaaccatt attatcatga cattaaccta aaaaatagg cgtatcacga     5940 ggcccttcg tcttcaagaa                                                  5960
```

<210> SEQ ID NO 18
<211> LENGTH: 5980
<212> TYPE: DNA
<213> ORGANISM: Artificial Sequence
<220> FEATURE:
<223> OTHER INFORMATION: Recombinant plasmid pAPSE10272; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_features
<222> LOCATION: (317)..(335)
<223> OTHER INFORMATION: bacteriophage MS2 pac sequence
<220> FEATURE:
<221> NAME/KEY: misc_features
<222> LOCATION: (365)..(372)
<223> OTHER INFORMATION: restriction endonuclease AsiSI recognition site
<220> FEATURE:
<221> NAME/KEY: misc_features
<222> LOCATION: (372)..(666)
<223> OTHER INFORMATION: beta actin sense gene fragment
<220> FEATURE:
<221> NAME/KEY: misc_features
<222> LOCATION: (822)..(1116)
<223> OTHER INFORMATION: beta actin antisense gene fragment
<220> FEATURE:
<221> NAME/KEY: misc_feature
<222> LOCATION: (1191)..(1209)
<223> OTHER INFORMATION: bacteriophage MS2 pac sequence
<220> FEATURE:
<221> NAME/KEY: terminator
<222> LOCATION: (1225)..(1272)
<223> OTHER INFORMATION: bacteriophage T7 transcription terminator
<220> FEATURE:
<221> NAME/KEY: promoter
<222> LOCATION: (1598)..(1616)
<223> OTHER INFORMATION: bacteriophage T7 gene 1 promoter
<220> FEATURE:
<221> NAME/KEY: gene
<222> LOCATION: (1689)..(2078)
<223> OTHER INFORMATION: bacteriophage MS2 coat protein gene
<220> FEATURE:
<221> NAME/KEY: terminator
<222> LOCATION: (2111)..(2158)
<223> OTHER INFORMATION: bacteriophage T7 transcription terminator

<400> SEQUENCE: 18

```
ttctcatgtt tgacagctta tcatcgataa gctttaatgc ggtagtttat cacagttaaa    60
```

```
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatgaa ttcagatctc gatcccgcga aattaatacg actcactata gggagaccac    240
aacggtttcc ctctagatca caagtttgta caaaaaagca ggctaagaag agatataca     300 tacgccggcc attcaaacat gaggattacc catgtattta atacccatg tccaggcgcg     360 ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg cacccgtgc cgtcttcccc tcgatcgtcg gtcgcccaag     540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttcccttcc agcgggatgc     720 tttatctaaa cgcaatgaga gaggtattcc tcaggccaca tcgcttccta gttccgctgg    780
gatccatcgt tggcggccga agccgccatt ccatggcgcg cctcatccca gttggtgatg    840
ataccgtgtt cgatgggta tttcaggggtg aggatacctc ttttgcttg ggcttcatct     900 cctacgtatg agtcctttg tcccataccg accatgactc cttgatgcct tgggcgaccg     960
acgatcgagg ggaagacggc acggggtgcg tcatctcctg cgaaaccggc tttgcacata   1020
ccggatccat tgtctacgac aagagccgct acatcgtcgt cacacatgtt gtctttgag    1080 gttggacact gctcactaga cagaaaaacc tcgtgccgga ccgaatacc ggtctgaacg    1140 agggcggccg cggtacccaa gaagtactta gagttaatta aggagttcaa acatgaggat   1200
cacccatgtc gaagctccca cacctagca taacccttg gggcctctaa acgggtcttg    1260
aggggttttt tgctgaaagg aggaactata tccggatatc cacaggacgg gtgtggtcgc   1320
catgatcgcg tagtcgatag tggctccaag tagcgaagcg agcaggactg gcggcgggc    1380 atgcatcgtc cattccgaca gcatcgccag tcactatggc gtgctgctag cgctatatgc   1440
gttgatgcaa tttctatgcg cacccgttct cggagcactg tccgaccgct ttggccgccg   1500
cccagtcctg ctcgcttcgc tacttggagc cactatcgac tacgcgatca tggcgaccac   1560
acccgtcctg tggatccaga tctcgatccc gcgaaattaa tacgactcac tataggaga   1620 ccacaacggt ttccctctag atcacaagtt tgtacaaaaa agcaggctaa gaaggagata   1680
tacatatggc gtctaacttt acccaattcg ttctggttga taacggcggt acgggtgacg   1740
ttaccgtagc tccgtccaac ttcgccaacg gtgttgcgga atggattagc tctaacagcc   1800
gctctcaggc ctacaaagtc acgtgctccg ttcgtcagtc tagcgcgcag aatcgcaaat   1860
acaccatcaa agttgaagta ccgaaagtcg caacgcagac cgtaggcggc gtagaactcc   1920
cagttgcggc ctggcgctct tacctcaaca tggaactgac tattccgatt tttgcgacga   1980
actccgactg cgaactgatt gttaaggcaa tgcaggggcct gctgaaagac ggtaatccga   2040
tcccatctgc aatcgctgct aactctggca tttactaata gcggacgcg ctgccaccgc    2100 tgagcaataa ctagcataac cccttggggc ctctaaacgg gtcttgaggg gttttttgct   2160
gaaaggagga actatatccg gcatgcacca ttccttgcgg cggcggtgct caacggcctc   2220
aacctactac tgggctgctt cctaatgcag gagtcgcata agggagagcg tcgaccgatg   2280
cccttgagag ccttcaaccc agtcagctcc ttccggtggg cgcggggcat gactatcgtc   2340
gccgcactta tgactgtctt ctttatcatg caactcgtag gacaggtgcc ggcagcgctc   2400
```

```
tgggtcattt tcggcgagga ccgctttcgc tggagcgcga cgatgatcgg cctgtcgctt   2460
gcggtattcg gaatcttgca cgccctcgct caagccttcg tcactggtcc cgccaccaaa   2520
cgtttcggcg agaagcaggc cattatcgcc ggcatggcgg ccgacgcgct gggctacgtc   2580
ttgctggcgt tcgcgacgcg aggctggatg gccttcccca ttatgattct tctcgcttcc   2640
ggcggcatcg ggatgcccgc gttgcaggcc atgctgtcca ggcaggtaga tgacgaccat   2700
cagggacagc ttcaaggatc gctcgcggct cttaccagcc taacttcgat cattggaccg   2760
ctgatcgtca cggcgattta tgccgcctcg gcgagcacat ggaacgggtt ggcatggatt   2820
gtaggcgccg ccctatacct tgtctgcctc ccgcgttgc gtcgcggtgc atggagccgg    2880
gccacctcga cctgaatgga agccggcggc acctcgctaa cggattcacc actccaagaa   2940
ttggagccaa tcaattcttg cggagaactg tgaatgcgca aaccaaccct tggcagaaca   3000
tatccatcgc gtccgccatc tccagcagcc gcacgcggcg catctcgggc agcgttgggt   3060
cctggccacg ggtgcgcatg atcgtgctcc tgtcgttgag gacccggcta ggctggcggg   3120
gttgccttac tggttagcag aatgaatcac cgatacgcga gcgaacgtga agcgactgct   3180
gctgcaaaac gtctgcgacc tgagcaacaa catgaatggt cttcggtttc cgtgtttcgt   3240
aaagtctgga aacgcggaag tcagcgccct gcaccattat gttccggatc tgcatcgcag   3300
gatgctgctg gctaccctgt ggaacaccta catctgtatt aacgaagcgc tggcattgac   3360
cctgagtgat ttttctctgg tcccgccgca tccataccgc cagttgttta ccctcacaac   3420
gttccagtaa ccgggcatgt tcatcatcag taacccgtat cgtgagcatc ctctctcgtt   3480
tcatcggtat cattacccccc atgaacagaa atcccccttta cacggaggca tcagtgacca   3540
aacaggaaaa aaccgcccctt aacatggccc gctttatcag aagccagaca ttaacgcttc   3600
tggagaaact caacgagctg gacgcggatg aacaggcaga catctgtgaa tcgcttcacg   3660
accacgctga tgagctttac cgcagctgcc tcgcgcgttt cggtgatgac ggtgaaaacc   3720
tctgacacat gcagctcccg gagacggtca cagcttgtct gtaagcggat gccgggagca   3780
gacaagcccg tcagggcgcg tcagcgggtg ttggcgggtg tcggggcgca gccatgaccc   3840
agtcacgtag cgatagcgga gtgtatactg gcttaactat gcggcatcag agcagattgt   3900
actgagagtg caccatatgc ggtgtgaaat accgcacaga tgcgtaagga gaaaataccg   3960
catcaggcgc tcttccgctt cctcgctcac tgactcgctg cgctcggtcg ttcggctgcg   4020
gcgagcggta tcagctcact caaaggcggt aatacggtta tccacagaat caggggataa   4080
cgcaggaaag aacatgtgag caaaaggcca gcaaaaggcc aggaaccgta aaaaggccgc   4140
gttgctggcg ttttttccata ggctccgccc ccctgacgag catcacaaaa atcgacgctc   4200
aagtcagagg tggcgaaacc cgacaggact ataaagatac caggcgtttc ccctggaag    4260 ctccctcgtg cgctctcctg ttccgaccct gccgcttacc ggatacctgt ccgcctttct   4320
cccttcggga agcgtggcgc tttctcatag ctcacgctgt aggtatctca gttcggtgta   4380
ggtcgttcgc tccaagctgg gctgtgtgca cgaaccccc gttcagcccg accgctgcgc    4440
cttatccggt aactatcgtc ttgagtccaa cccggtaaga cacgacttat cgccactggc   4500
agcagccact ggtaacagga ttagcagagc gaggtatgta ggcggtgcta cagagttctt   4560
gaagtggtgg cctaactacg gctacactag aaggacagta tttggtatct gcgctctgct   4620
gaagccagtt accttcggaa aaagagttgg tagctcttga tccggcaaac aaaccaccgc   4680
tggtagcggt ggtttttttg tttgcaagca gcagattacg cgcagaaaaa aaggatctca   4740
agaagatcct ttgatctttt ctacggggtc tgacgctcag tggaacgaaa actcacgtta   4800
```

```
agggattttg gtcatgagat tatcaaaaag gatcttcacc tagatccttt taaattaaaa    4860
atgaagtttt aaatcaatct aaagtatata tgagtaaact tggtctgaca gttaccaatg    4920
cttaatcagt gaggcaccta tctcagcgat ctgtctattt cgttcatcca tagttgcctg    4980
actccccgtc gtgtagataa ctacgatacg ggagggctta ccatctggcc ccagtgctgc    5040
aatgataccg cgagacccac gctcaccggc tccagattta tcagcaataa accagccagc    5100
cggaagggcc gagcgcagaa gtggtcctgc aactttatcc gcctccatcc agtctattaa    5160
ttgttgccgg gaagctagag taagtagttc gccagttaat agtttgcgca acgttgttgc    5220
cattgctgca ggcatcgtgg tgtcacgctc gtcgtttggt atggcttcat tcagctccgg    5280
ttcccaacga tcaaggcgag ttacatgatc ccccatgttg tgcaaaaaag cggttagctc    5340
cttcggtcct ccgatcgttg tcagaagtaa gttggccgca gtgttatcac tcatggttat    5400
ggcagcactg cataattctc ttactgtcat gccatccgta agatgctttt ctgtgactgg    5460
tgagtactca accaagtcat tctgagaata gtgtatgcgg cgaccgagtt gctcttgccc    5520
ggcgtcaaca cgggataata ccgcgccaca tagcagaact ttaaaagtgc tcatcattgg    5580
aaaacgttct cggggcgaaa actctcaag gatcttaccg ctgttgagat ccagttcgat    5640
gtaacccact cgtgcaccca actgatcttc agcatctttt actttcacca gcgtttctgg    5700
gtgagcaaaa acaggaaggc aaaatgccgc aaaaaaggga ataagggcga cacgaaatg    5760 ttgaatactc atactcttcc ttttcaata ttattgaagc atttatcagg gttattgtct    5820
catgagcgga tacatatttg aatgtattta gaaaaataaa caataggggg ttccgcgcac    5880 atttcccga aaagtgccac ctgacgtcta agaaaccatt attatcatga cattaaccta    5940
taaaaatagg cgtatcacga ggcccttcg tcttcaagaa                          5980
```

<210> SEQ ID NO 19
<211> LENGTH: 6005
<212> TYPE: DNA
<213> ORGANISM: Artificial Sequence
<220> FEATURE:
<223> OTHER INFORMATION: Recombinant plasmid pAPSE10292; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (797)..(1091)
<223> OTHER INFORMATION: beta actin antisense gene fragment
<220> FEATURE:
<221> NAME/KEY: misc_feature
<222> LOCATION: (1166)..(1184)
<223> OTHER INFORMATION: bacteriophage MS2 pac sequence
<220> FEATURE:
<221> NAME/KEY: terminator
<222> LOCATION: (1200)..(1247)
<223> OTHER INFORMATION: bacteriophage T7 transcription terminator
<220> FEATURE:
<221> NAME/KEY: promoter

```
<222> LOCATION: (1573)..(1591)
<223> OTHER INFORMATION: bacteriophage T7 gene 1 promoter
<220> FEATURE:
<221> NAME/KEY: gene
<222> LOCATION: (1664)..(2053)
<223> OTHER INFORMATION: bacteriophage MS2 coat protein gene
<220> FEATURE:
<221> NAME/KEY: terminator
<222> LOCATION: (2086)..(2133)
<223> OTHER INFORMATION: bacteriophage T7 transcription terminator

<400> SEQUENCE: 19
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatataca     300
tacgccggcc attcaaacat gaggattacc catgtattta atacccatg tccaggcgcg     360
ctccgcgatc gcgcacgagg ttttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacgcaatc gcagcaaact ccggcatcta ctaatagacg ccggccattc     720
aacatgagga ttacccatgt aacctaagaa gacaacaaag aagttcaact ctttatgtat     780
tgatcttccg gcgcgcctca tcccagttgg tgatgatacc gtgttcgatg ggtatttca     840
gggtgaggat acctcttttg ctttgggctt catctcctac gtatgagtcc ttttgtccca     900
taccgaccat gactccttga tgccttgggc gaccgacgat cgaggggaag acggcacggg     960
gtgcgtcatc tcctgcgaaa ccggctttgc acataccgga tccattgtct acgacaagag    1020
ccgctacatc gtcgtcacac atgttgtctt ttgaggttgg acactgctca ctagacagaa    1080
aaacctcgtg ccggaccgaa tacccggtct gaacgagggc ggccgcggta cccaagaagt    1140
acttagagtt aattaaggag ttcaaacatg aggatcaccc atgtcgaagc tcccacaccc    1200
tagcataacc ccttggggcc tctaaacggg tcttgagggg ttttttgctg aaaggaggaa    1260
ctatatccgg atatccacag gacgggtgtg gtcgccatga tcgcgtagtc gatagtggct    1320
ccaagtagcg aagcgagcag gactgggcgg cgggcatgca tcgtccattc cgacagcatc    1380
gccagtcact atggcgtgct gctagcgcta tatgcgttga tgcaatttct atgcgcaccc    1440
gttctcggag cactgtccga ccgctttggc cgccgcccag tcctgctcgc ttcgctactt    1500
ggagccacta tcgactacgc gatcatggcg accacacccg tcctgtggat ccagatctcg    1560
atcccgcgaa attaatacga ctcactatag ggagaccaca acggtttccc tctagatcac    1620
aagtttgtac aaaaaagcag gctaagaagg agatatacat atggcgtcta actttaccca    1680
attcgttctg gttgataacg gcggtacggg tgacgttacc gtagctccgt ccaacttcgc    1740
caacggtgtt gcggaatgga ttagctctaa cagccgctct caggcctaca agtcacgtg    1800
ctccgttcgt cagtctagcg cgcagaatcg caaatacacc atcaaagttg aagtaccgaa    1860
agtcgcaacg cagaccgtag gcggcgtaga actcccagtt gcggcctggc gctcttacct    1920
caacatggaa ctgactattc cgattttgc gacgaactcc gactgcgaac tgattgttaa    1980
```

```
ggcaatgcag ggcctgctga aagacggtaa tccgatccca tctgcaatcg ctgctaactc    2040
tggcatttac taataagcgg acgcgctgcc accgctgagc aataactagc ataacccctt    2100
ggggcctcta aacgggtctt gagggggtttt ttgctgaaag gaggaactat atccggcatg   2160
caccattcct tgcggcggcg gtgctcaacg gcctcaacct actactgggc tgcttcctaa    2220
tgcaggagtc gcataaggga gagcgtcgac cgatgcccctt gagagccttc aacccagtca   2280
gctccttccg gtgggcgcgg ggcatgacta tcgtcgccgc acttatgact gtcttcttta    2340
tcatgcaact cgtaggacag gtgccggcag cgctctgggt cattttcggc gaggaccgct    2400
ttcgctggag cgcgacgatg atcggcctgt cgcttgcgt attcggaatc ttgcacgccc     2460
tcgctcaagc cttcgtcact ggtcccgcca ccaaacgttt cggcgagaag caggccatta   2520
tcgccggcat ggcggccgac gcgctgggct acgtcttgct ggcgttcgcg acgcgaggct    2580
ggatggcctt ccccattatg attcttctcg cttccggcgg catcgggatg cccgcgttgc    2640
aggccatgct gtccaggcag gtagatgacg accatcaggg acagcttcaa ggatcgctcg    2700
cggctcttac cagcctaact tcgatcattg gaccgctgat cgtcacggcg atttatgccg    2760
cctcggcgag cacatggaac gggttggcat ggattgtagg cgccgcccta taccttgtct    2820
gcctccccgc gttgcgtcgc ggtgcatgga gccgggccac ctcgacctga atggaagccg    2880
gcggcacctc gctaacggat tcaccactcc aagaattgga gccaatcaat tcttgcggag    2940
aactgtgaat gcgcaaacca acccttggca gaacatatcc atcgcgtccg ccatctccag    3000
cagccgcacg cggcgcatct cgggcagcgt tgggtcctgg ccacgggtgc gcatgatcgt    3060
gctcctgtcg ttgaggaccc ggctaggctg gcggggttgc cttactggtt agcagaatga    3120
atcaccgata cgcgagcgaa cgtgaagcga ctgctgctgc aaaacgtctg cgacctgagc    3180
aacaacatga atggtcttcg gtttccgtgt ttcgtaaagt ctggaaacgc ggaagtcagc    3240
gccctgcacc attatgttcc ggatctgcat cgcaggatgc tgctggctac cctgtggaac    3300
acctacatct gtattaacga agcgctggca ttgaccctga gtgattttc tctggtcccg     3360 ccgcatccat accgccagtt gtttaccctc acaacgttcc agtaaccggg catgttcatc    3420
atcagtaacc cgtatcgtga gcatcctctc tcgtttcatc ggtatcatta cccccatgaa    3480
cagaaatccc ccttacacgg aggcatcagt gaccaaacag gaaaaaaccg cccttaacat    3540
ggcccgcttt atcagaagcc agacattaac gcttctggag aaactcaacg agctggacgc    3600
ggatgaacag gcagacatct gtgaatcgct tcacgaccac gctgatgagc tttaccgcag    3660
ctgcctcgcg cgtttcggtg atgacggtga aaacctctga cacatgcagc tcccggagac    3720
ggtcacagct tgtctgtaag cggatgccgg gagcagacaa gcccgtcagg gcgcgtcagc    3780
gggtgttggc gggtgtcggg gcgcagccat gacccagtca cgtagcgata gcggagtgta    3840
tactggctta actatgcggc atcagagcag attgtactga gagtgcacca tatgcggtgt    3900
gaaataccgc acagatgcgt aaggagaaaa taccgcatca ggcgctcttc cgcttcctcg    3960
ctcactgact cgctgcgctc ggtcgttcgg ctgcggcgag cggtatcagc tcactcaaag    4020
gcggtaatac ggttatccac agaatcaggg gataacgcag gaaagaacat gtgagcaaaa    4080
ggccagcaaa aggccaggaa ccgtaaaaag gccgcgttgc tggcgttttt ccataggctc    4140 cgccccctg acgagcatca caaaaatcga cgctcaagtc agaggtggcg aaacccgaca     4200
ggactataaa gataccaggc gtttccccct ggaagctccc tcgtgcgctc tcctgttccg    4260
accctgccgc ttaccggata cctgtccgcc tttctccctt cgggaagcgt ggcgctttct    4320
catagctcac gctgtaggta tctcagttcg gtgtaggtcg ttcgctccaa gctgggctgt    4380
```

```
gtgcacgaac cccccgttca gcccgaccgc tgcgccttat ccggtaacta tcgtcttgag    4440
tccaacccgg taagacacga cttatcgcca ctggcagcag ccactggtaa caggattagc    4500
agagcgaggt atgtaggcgg tgctacagag ttcttgaagt ggtggcctaa ctacggctac    4560
actagaagga cagtatttgg tatctgcgct ctgctgaagc cagttacctt cggaaaaaga    4620
gttggtagct cttgatccgg caaacaaacc accgctggta gcggtggttt ttttgtttgc    4680
aagcagcaga ttacgcgcag aaaaaaagga tctcaagaag atcctttgat cttttctacg    4740
gggtctgacg ctcagtggaa cgaaaactca cgttaaggga ttttggtcat gagattatca    4800
aaaaggatct tcacctagat ccttttaaat taaaaatgaa gttttaaatc aatctaaagt    4860
atatatgagt aaacttggtc tgacagttac caatgcttaa tcagtgaggc acctatctca    4920
gcgatctgtc tatttcgttc atccatagtt gcctgactcc ccgtcgtgta gataactacg    4980
atacgggagg gcttaccatc tggccccagt gctgcaatga taccgcgaga cccacgctca    5040
ccggctccag atttatcagc aataaaccag ccagccggaa gggccgagcg cagaagtggt    5100
cctgcaactt tatccgcctc catccagtct attaattgtt gccgggaagc tagagtaagt    5160
agttcgccag ttaatagttt gcgcaacgtt gttgccattg ctgcaggcat cgtggtgtca    5220
cgctcgtcgt ttggtatggc ttcattcagc tccggttccc aacgatcaag gcgagttaca    5280
tgatccccca tgttgtgcaa aaaagcggtt agctccttcg gtcctccgat cgttgtcaga    5340
agtaagttgg ccgcagtgtt atcactcatg gttatggcag cactgcataa ttctcttact    5400
gtcatgccat ccgtaagatg cttttctgtg actggtgagt actcaaccaa gtcattctga    5460
gaatagtgta tgcggcgacc gagttgctct tgcccggcgt caacacggga taataccgcg    5520
ccacatagca gaactttaaa agtgctcatc attggaaaac gttcttcggg gcgaaaactc    5580
tcaaggatct taccgctgtt gagatccagt tcgatgtaac ccactcgtgc acccaactga    5640
tcttcagcat cttttacttt caccagcgtt tctgggtgag caaaaacagg aaggcaaaat    5700
gccgcaaaaa agggaataag ggcgacacgg aaatgttgaa tactcatact cttccttttt    5760
caatattatt gaagcattta tcagggttat tgtctcatga gcggatacat atttgaatgt    5820
atttagaaaa ataaacaaat aggggttccg cgcacatttc cccgaaaagt gccacctgac    5880
gtctaagaaa ccattattat catgacatta acctataaaa ataggcgtat cacgaggccc    5940
tttcgtcttc aagaacatta acctataaaa ataggcgtat cacgaggccc tttcgtcttc    6000
aagaa                                                                6005
```

<210> SEQ ID NO 20
<211> LENGTH: 5966
<212> TYPE: DNA
<213> ORGANISM: Artificial Sequence
<220> FEATURE:
<223> OTHER INFORMATION: Recombinant plasmid pAPSE10291; beta actin stem
      loop + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature

```
<222> LOCATION: (372)..(666)
<223> OTHER INFORMATION: beta actin sense gene fragment
<220> FEATURE:
<221> NAME/KEY: misc_feature
<222> LOCATION: (808)..(1102)
<223> OTHER INFORMATION: beta actin antisense gene fragment
<220> FEATURE:
<221> NAME/KEY: misc_feature
<222> LOCATION: (1177)..(1195)
<223> OTHER INFORMATION: bacteriophage MS2 pac sequence
<220> FEATURE:
<221> NAME/KEY: terminator
<222> LOCATION: (1211)..(1258)
<223> OTHER INFORMATION: bacteriophage T7 transcription terminator
<220> FEATURE:
<221> NAME/KEY: promoter
<222> LOCATION: (1584)..(1602)
<223> OTHER INFORMATION: bacteriophage T7 gene 1 promoter
<220> FEATURE:
<221> NAME/KEY: gene
<222> LOCATION: (1675)..(2064)
<223> OTHER INFORMATION: bacteriophage MS2 coat protein gene
<220> FEATURE:
<221> NAME/KEY: terminator
<222> LOCATION: (2097)..(2144)
<223> OTHER INFORMATION: bacteriophage T7 transcription terminator

<400> SEQUENCE: 20
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg ttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaacttaagc ggaacaccag gcggaacgaa gaggagatag agaactagat     720
tgattagaat caaatactag aactactaaa tcgaatcgat acgctaacga aaggacctgg     780
acacgtcgac gagccgctgg ggcgcgcctc atcccagttg gtgatgatac cgtgttcgat     840
ggggtatttc agggtgagga tacctctttt gctttgggct tcatctccta cgtatgagtc     900
cttttgtccc ataccgacca tgactccttg atgccttggg cgaccgacga tcgagggaa     960 gacggcacgg ggtgcgtcat ctcctgcgaa accggctttg cacataccgg atccattgtc    1020
tacgacaaga gccgctacat cgtcgtcaca catgttgtct tttgaggttg gacactgctc    1080
actagacaga aaaacctcgt gccggaccga atacccggtc tgaacgaggg cggccgcggt    1140
acccaagaag tacttagagt taattaagga gttcaaacat gaggatcacc catgtcgaag    1200
ctcccacacc ctagcataac ccctggggc ctctaaacgg gtcttgaggg gttttttgct    1260
gaaaggagga actatatccg gatatccaca ggacgggtgt ggtcgccatg atcgcgtagt    1320
cgatagtggc tccaagtagc gaagcgagca ggactgggcg gcgggcatgc atcgtccatt    1380
ccgacagcat cgccagtcac tatggcgtgc tgctagcgct atatgcgttg atgcaatttc    1440
tatgcgcacc cgttctcgga gcactgtccg accgctttgg ccgccgccca gtcctgctcg    1500
```

-continued

```
cttcgctact tggagccact atcgactacg cgatcatggc gaccacaccc gtcctgtgga    1560
tccagatctc gatcccgcga aattaatacg actcactata gggagaccac aacggtttcc    1620
ctctagatca caagtttgta caaaaaagca ggctaagaag gagatataca tatggcgtct    1680
aactttaccc aattcgttct ggttgataac ggcggtacgg gtgacgttac cgtagctccg    1740
tccaacttcg ccaacggtgt tgcggaatgg attagctcta acagccgctc tcaggcctac    1800
aaagtcacgt gctccgttcg tcagtctagc gcgcagaatc gcaaatacac catcaaagtt    1860
gaagtaccga aagtcgcaac gcagaccgta ggcggcgtag aactcccagt tgcggcctgg    1920
cgctcttacc tcaacatgga actgactatt ccgattttg cgacgaactc cgactgcgaa    1980
ctgattgtta aggcaatgca gggcctgctg aaagacggta atccgatccc atctgcaatc    2040
gctgctaact ctggcattta ctaataagcg gacgcgctgc caccgctgag caataactag    2100
cataacccct tggggcctct aaacgggtct tgaggggttt tttgctgaaa ggaggaacta    2160
tatccggcat gcaccattcc ttgcggcggc ggtgctcaac ggcctcaacc tactactggg    2220
ctgcttccta atgcaggagt cgcataaggg agagcgtcga ccgatgccct tgagagcctt    2280
caacccagtc agctccttcc ggtgggcgcg gggcatgact atcgtcgccg cacttatgac    2340
tgtcttcttt atcatgcaac tcgtaggaca ggtgccggca gcgctctggg tcattttcgg    2400
cgaggaccgc tttcgctgga gcgcgacgat gatcggcctg tcgcttgcgg tattcggaat    2460
cttgcacgcc ctcgctcaag ccttcgtcac tggtcccgcc accaaacgtt tcggcgagaa    2520
gcaggccatt atcgccggca tggcggccga cgcgctgggc tacgtcttgc tggcgttcgc    2580
gacgcgaggc tggatggcct tccccattat gattcttctc gcttccggcg gcatcgggat    2640
gcccgcgttg caggccatgc tgtccaggca ggtagatgac gaccatcagg acagcttca    2700 aggatcgctc gcggctctta ccagcctaac ttcgatcatt ggaccgctga tcgtcacggc    2760
gatttatgcc gcctcggcga gcacatggaa cgggttggca tggattgtag cgccgccct    2820 ataccttgtc tgcctccccg cgttgcgtcg cggtgcatgg agccgggcca cctcgacctg    2880
aatggaagcc ggcggcacct cgctaacgga ttcaccactc caagaattgg agccaatcaa    2940
ttcttgcgga gaactgtgaa tgcgcaaacc aaccccttggc agaacatatc catcgcgtcc    3000
gccatctcca gcagccgcac gcggcgcatc tcgggcagcg ttgggtcctg ccacgggtg    3060 cgcatgatcg tgctcctgtc gttgaggacc cggctaggct ggcggggttg ccttactggt    3120
tagcagaatg aatcaccgat acgcgagcga acgtgaagcg actgctgctg caaaacgtct    3180
gcgacctgag caacaacatg aatggtcttc ggtttccgtg tttcgtaaag tctggaaacg    3240
cggaagtcag cgccctgcac cattatgttc cggatctgca tcgcaggatg ctgctggcta    3300
ccctgtggaa cacctacatc tgtattaacg aagcgctggc attgacctg agtgatttt    3360 ctctggtccc gccgcatcca taccgccagt tgtttaccct cacaacgttc cagtaaccgg    3420
gcatgttcat catcagtaac ccgtatcgtg agcatcctct ctcgtttcat cggtatcatt    3480
acccccatga acagaaatcc cccttacacg gaggcatcag tgaccaaaca ggaaaaaacc    3540
gcccttaaca tggcccgctt tatcagaagc cagacattaa cgcttctgga gaaactcaac    3600
gagctggacg cggatgaaca ggcagacatc tgtgaatcgc ttcacgacca cgctgatgag    3660
ctttaccgca gctgcctcgc gcgtttcggt gatgacggtg aaaacctctg acacatgcag    3720
ctcccgagag cggtcacagc ttgtctgtaa gcggatgccg ggagcagaca agcccgtcag    3780
ggcgcgtcag cgggtgttgg cgggtgtcgg ggcgcagcca tgacccagtc acgtagcgat    3840
agcggagtgt atactggctt aactatgcgg catcagagca gattgtactg agagtgcacc    3900
```

| | | | | |
|---|---|---|---|---|
| atatgcggtg | tgaaataccg | cacagatgcg | taaggagaaa | ataccgcatc aggcgctctt | 3960 |
| ccgcttcctc | gctcactgac | tcgctgcgct | cggtcgttcg | gctgcggcga gcggtatcag | 4020 |
| ctcactcaaa | ggcggtaata | cggttatcca | cagaatcagg | gataacgca ggaaagaaca | 4080 |
| tgtgagcaaa | aggccagcaa | aaggccagga | accgtaaaaa | ggccgcgttg ctggcgtttt | 4140 |
| tccataggct | ccgcccccct | gacgagcatc | acaaaaatcg | acgctcaagt cagaggtggc | 4200 |
| gaaacccgac | aggactataa | agataccagg | cgtttccccc | tggaagctcc ctcgtgcgct | 4260 |
| ctcctgttcc | gaccctgccg | cttaccggat | acctgtccgc | ctttctccct cgggaagcg | 4320 |
| tggcgctttc | tcatagctca | cgctgtaggt | atctcagttc | ggtgtaggtc gttcgctcca | 4380 |
| agctgggctg | tgtgcacgaa | ccccccgttc | agcccgaccg | ctgcgcctta tccggtaact | 4440 |
| atcgtcttga | gtccaacccg | gtaagacacg | acttatcgcc | actggcagca gccactggta | 4500 |
| acaggattag | cagagcgagg | tatgtaggcg | gtgctacaga | gttcttgaag tggtggccta | 4560 |
| actacggcta | cactagaagg | acagtatttg | gtatctgcgc | tctgctgaag ccagttacct | 4620 |
| tcggaaaaag | agttggtagc | tcttgatccg | gcaaacaaac | caccgctggt agcggtggtt | 4680 |
| tttttgtttg | caagcagcag | attacgcgca | gaaaaaaagg | atctcaagaa gatcctttga | 4740 |
| tcttttctac | ggggtctgac | gctcagtgga | acgaaaactc | acgttaaggg attttggtca | 4800 |
| tgagattatc | aaaaaggatc | ttcacctaga | tccttttaaa | ttaaaaatga agttttaaat | 4860 |
| caatctaaag | tatatatgag | taaacttggt | ctgacagtta | ccaatgctta atcagtgagg | 4920 |
| cacctatctc | agcgatctgt | ctatttcgtt | catccatagt | tgcctgactc cccgtcgtgt | 4980 |
| agataactac | gatacgggag | ggcttaccat | ctggccccag | tgctgcaatg ataccgcgag | 5040 |
| acccacgctc | accggctcca | gatttatcag | caataaacca | gccagccgga agggccgagc | 5100 |
| gcagaagtgg | tcctgcaact | ttatccgcct | ccatccagtc | tattaattgt tgccgggaag | 5160 |
| ctagagtaag | tagttcgcca | gttaatagtt | tgcgcaacgt | tgttgccatt gctgcaggca | 5220 |
| tcgtggtgtc | acgctcgtcg | tttggtatgg | cttcattcag | ctccggttcc caacgatcaa | 5280 |
| ggcgagttac | atgatccccc | atgttgtgca | aaaaagcggt | tagctccttc ggtcctccga | 5340 |
| tcgttgtcag | aagtaagttg | gccgcagtgt | tatcactcat | ggttatggca gcactgcata | 5400 |
| attctcttac | tgtcatgcca | tccgtaagat | gcttttctgt | gactggtgag tactcaacca | 5460 |
| agtcattctg | agaatagtgt | atgcggcgac | cgagttgctc | ttgcccggcg tcaacacggg | 5520 |
| ataataccgc | gccacatagc | agaactttaa | aagtgctcat | cattggaaaa cgttcttcgg | 5580 |
| ggcgaaaact | ctcaaggatc | ttaccgctgt | tgagatccag | ttcgatgtaa cccactcgtg | 5640 |
| cacccaactg | atcttcagca | tcttttactt | tcaccagcgt | ttctgggtga gcaaaaacag | 5700 |
| gaaggcaaaa | tgccgcaaaa | aagggaataa | gggcgacacg | gaaatgttga atactcatac | 5760 |
| tcttcctttt | tcaatattat | tgaagcattt | atcagggtta | ttgtctcatg agcggataca | 5820 |
| tatttgaatg | tatttagaaa | aataaacaaa | taggggttcc | gcgcacattt ccccgaaaag | 5880 |
| tgccacctga | cgtctaagaa | accattatta | tcatgacatt | aacctataaa aataggcgta | 5940 |
| tcacgaggcc | ctttcgtctt | caagaa | | | 5966 |

<210> SEQ ID NO 21
<211> LENGTH: 5502
<212> TYPE: DNA
<213> ORGANISM: Artificial Sequence
<220> FEATURE:
<223> OTHER INFORMATION: Recombinant plasmid pAPSE10276; beta actin stem loop + coat protein

```
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(422)
<223> OTHER INFORMATION: beta actin sense gene fragment
<220> FEATURE:
<221> NAME/KEY: misc_feature
<222> LOCATION: (588)..(638)
<223> OTHER INFORMATION: beta actin antisense gene fragment
<220> FEATURE:
<221> NAME/KEY: misc_feature
<222> LOCATION: (713)..(731)
<223> OTHER INFORMATION: bacteriophage MS2 pac sequence
<220> FEATURE:
<221> NAME/KEY: terminator
<222> LOCATION: (747)..(794)
<223> OTHER INFORMATION: bacteriophage T7 transcription terminator
<220> FEATURE:
<221> NAME/KEY: promoter
<222> LOCATION: (1120)..(1138)
<223> OTHER INFORMATION: bacteriophage T7 gene 1 promoter
<220> FEATURE:
<221> NAME/KEY: gene
<222> LOCATION: (1211)..(1600)
<223> OTHER INFORMATION: bacteriophage MS2 coat protein gene
<220> FEATURE:
<221> NAME/KEY: terminator
<222> LOCATION: (1633)..(1680)
<223> OTHER INFORMATION: bacteriophage T7 transcription terminator

<400> SEQUENCE: 21
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta atacccatg tccaggcgcg     360 ctccgcgatc gcgcacgagg ttttctgtc tagtgagcag tgtccaacct caaaagacaa     420
cagtttaaac cctctagctg ctttacaaag tactggttcc ctttccagcg ggatgcttta     480
tctaaacgca atgagagagg tattcctcag gccacatcgc ttcctagttc cgctgggatc     540
catcgttggc ggccgaagcc gccattccat agtgagttct ggcgcgcctg ttgtcttttg     600
aggttggaca ctgctcacta gacagaaaaa cctcgtgccg gaccgaatac ccggtctgaa     660
cgagggcggc gcggtaccc aagaagtact tagagttaat taaggagttc aaacatgagg     720
atcacccatg tcgaagctcc cacaccctag cataacccct tggggcctct aaacgggtct     780
tgaggggttt tttgctgaaa ggaggaacta tatccggata tccacaggac gggtgtggtc     840
gccatgatcg cgtagtcgat agtggctcca agtagcgaag cgagcaggac tgggcggcgg     900
gcatgcatcg tccattccga cagcatcgcc agtcactatg gcgtgctgct agcgctatat     960
gcgttgatgc aatttctatg cgcacccgtt ctcggagcac tgtccgaccg ctttggccgc    1020
cgcccagtcc tgctcgcttc gctacttgga gccactatcg actacgcgat catggcgacc    1080
```

```
acacccgtcc tgtggatcca gatctcgatc ccgcgaaatt aatacgactc actatagggga  1140 gaccacaacg gtttccctct agatcacaag tttgtacaaa aaagcaggct aagaaggaga  1200
tatacatatg gcgtctaact ttacccaatt cgttctggtt gataacggcg gtacgggtga  1260
cgttaccgta gctccgtcca acttcgccaa cggtgttgcg gaatggatta gctctaacag  1320
ccgctctcag gcctacaaag tcacgtgctc cgttcgtcag tctagcgcgc agaatcgcaa  1380
atacaccatc aaagttgaag taccgaaagt cgcaacgcag accgtaggcg cgtagaact  1440 cccagttgcg gcctggcgct cttacctcaa catggaactg actattccga tttttgcgac  1500
gaactccgac tgcgaactga ttgttaaggc aatgcagggc ctgctgaaag acggtaatcc  1560
gatcccatct gcaatcgctg ctaactctgg catttactaa taagcggacg cgctgccacc  1620
gctgagcaat aactagcata acccccttggg gcctctaaac gggtcttgag gggttttttg  1680
ctgaaaggag gaactatatc cggcatgcac cattccttgc ggcggcggtg ctcaacggcc  1740
tcaacctact actgggctgc ttcctaatgc aggagtcgca taaggagag cgtcgaccga  1800 tgcccttgag agccttcaac ccagtcagct ccttccggtg ggcgcgggc atgactatcg  1860 tcgccgcact tatgactgtc ttctttatca tgcaactcgt aggacaggtg ccggcagcgc  1920
tctgggtcat tttcggcgag accgcttttc gctggagcgc gacgatgatc ggcctgtcgc  1980
ttgcggtatt cggaatcttg cacgccctcg ctcaagcctt cgtcactggt cccgccacca  2040
aacgtttcgg cgagaagcag gccattatcg ccggcatggc ggccgacgcg ctgggctacg  2100
tcttgctggc gttcgcgacg cgaggctgga tggccttccc cattatgatt cttctcgctt  2160
ccggcggcat cgggatgccc gcgttgcagg ccatgctgtc caggcaggta gatgacgacc  2220
atcagggaca gcttcaagga tcgctcgcgg ctcttaccag cctaacttcg atcattggac  2280
cgctgatcgt cacggcgatt tatgccgcct cggcgagcac atggaacggg ttggcatgga  2340
ttgtaggcgc cgccctatac cttgtctgcc tccccgcgtt gcgtcgcggt gcatggagcc  2400
gggccacctc gacctgaatg gaagccggcg gcacctcgct aacggattca ccactccaag  2460
aattggagcc aatcaattct gcggagaaac tgtgaatgcg caaaccaacc cttggcagaa  2520
catatccatc gcgtccgcca tctccagcag ccgcacgcgg cgcatctcgg gcagcgttgg  2580
gtcctggcca cgggtgcgca tgatcgtgct cctgtcgttg aggacccggc taggctggcg  2640
gggttgcctt actggttagc agaatgaatc accgatacgc gagcgaacgt gaagcgactg  2700
ctgctgcaaa acgtctgcga cctgagcaac aacatgaatg gtcttcggtt tccgtgtttc  2760
gtaaagtctg gaaacgcgga agtcagcgcc ctgcaccatt atgttccgga tctgcatcgc  2820
aggatgctgc tggctaccct gtggaacacc tacatctgta ttaacgaagc gctggcattg  2880
accctgagtg atttttctct ggtcccgccg catccatacc gccagttgtt taccctcaca  2940
acgttccagt aaccgggcat gttcatcatc agtaacccgt atcgtgagca tcctctctcg  3000
tttcatcggt atcattaccc ccatgaacag aaatcccccct tacacggagg catcagtgac  3060
caaacaggaa aaaaccgccc ttaacatggc ccgctttatc agaagccaga cattaacgct  3120
tctggagaaa ctcaacgagc tggacgcgga tgaacaggca gacatctgtg aatcgcttca  3180
cgaccacgct gatgagcttt accgcagctg cctcgcgcgt ttcggtgatg acggtgaaaa  3240
cctctgacac atgcagctcc cggagacggt cacagcttgt ctgtaagcgg atgccgggag  3300
cagacaagcc cgtcagggcg cgtcagcggg tgttggcggg tgtcggggcg cagccatgac  3360
ccagtcacgt agcgatagcg gagtgtatac tggcttaact atgcggcatc agagcagatt  3420
gtactgagag tgcaccatat gcggtgtgaa ataccgcaca gatgcgtaag gagaaaatac  3480
```

```
cgcatcaggc gctcttccgc ttcctcgctc actgactcgc tgcgctcggt cgttcggctg    3540
cggcgagcgg tatcagctca ctcaaaggcg gtaatacggt tatccacaga atcaggggat    3600
aacgcaggaa agaacatgtg agcaaaaggc cagcaaaagg ccaggaaccg taaaaaggcc    3660
gcgttgctgg cgtttttcca taggctccgc cccctgacg agcatcacaa aaatcgacgc    3720
tcaagtcaga ggtggcgaaa cccgacagga ctataaagat accaggcgtt ccccctgga    3780 agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaaggacag tatttggtat ctgcgctctg    4140
ctgaagccag ttaccttcgg aaaaagagtt ggtagctctt gatccggcaa acaaaccacc    4200
gctggtagcg gtggtttttt tgtttgcaag cagcagatta cgcgcagaaa aaaggatct    4260 caagaagatc ctttgatctt ttctacgggg tctgacgctc agtggaacga aaactcacgt    4320
taagggattt tggtcatgag attatcaaaa aggatcttca cctagatcct tttaaattaa    4380
aaatgaagtt ttaaatcaat ctaaagtata tatgagtaaa cttggtctga cagttaccaa    4440
tgcttaatca gtgaggcacc tatctcagcg atctgtctat ttcgttcatc catagttgcc    4500 tgactcccccg tcgtgtagat aactacgata cgggagggct taccatctgg ccccagtgct    4560
gcaatgatac cgcgagaccc acgctcaccg gctccagatt tatcagcaat aaaccagcca    4620
gccggaaggg ccgagcgcag aagtggtcct gcaactttat ccgcctccat ccagtctatt    4680
aattgttgcc gggaagctag agtaagtagt tcgccagtta atagtttgcg caacgttgtt    4740
gccattgctg caggcatcgt ggtgtcacgc tcgtcgtttg gtatggcttc attcagctcc    4800
ggttcccaac gatcaaggcg agttacatga tcccccatgt tgtgcaaaaa agcggttagc    4860
tccttcggtc ctccgatcgt tgtcagaagt aagttggccg cagtgttatc actcatggtt    4920
atggcagcac tgcataattc tcttactgtc atgccatccg taagatgctt ttctgtgact    4980
ggtgagtact caaccaagtc attctgagaa tagtgtatgc ggcgaccgag ttgctcttgc    5040
ccggcgtcaa cacgggataa taccgcgcca catagcagaa ctttaaaagt gctcatcatt    5100
ggaaaacgtt cttcggggcg aaaactctca aggatcttac cgctgttgag atccagttcg    5160
atgtaaccca ctcgtgcacc caactgatct tcagcatctt ttactttcac cagcgtttct    5220
gggtgagcaa aaacaggaag gcaaaatgcc gcaaaaaagg gaataagggc gacacggaaa    5280
tgttgaatac tcatactctt cctttttcaa tattattgaa gcatttatca gggttattgt    5340
ctcatgagcg gatacatatt tgaatgtatt tagaaaaata aacaaatagg ggttccgcgc    5400
acatttcccc gaaaagtgcc acctgacgtc taagaaacca ttattatcat gacattaacc    5460
tataaaaata ggcgtatcac gaggcccttt cgtcttcaag aa                       5502
```

<210> SEQ ID NO 22
<211> LENGTH: 5552
<212> TYPE: DNA
<213> ORGANISM: Artificial Sequence
<220> FEATURE:
<223> OTHER INFORMATION: Recombinant plasmid pAPSE10277; beta actin stem loop + coat protein
<220> FEATURE:
<221> NAME/KEY: promoter

```
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(447)
<223> OTHER INFORMATION: beta actin sense gene fragment
<220> FEATURE:
<221> NAME/KEY: misc_feature
<222> LOCATION: (613)..(688)
<223> OTHER INFORMATION: beta actin antisense gene fragment
<220> FEATURE:
<221> NAME/KEY: misc_feature
<222> LOCATION: (763)..(781)
<223> OTHER INFORMATION: bacteriophage MS2 pac sequence
<220> FEATURE:
<221> NAME/KEY: terminator
<222> LOCATION: (797)..(844)
<223> OTHER INFORMATION: bacteriophage T7 transcription terminator
<220> FEATURE:
<221> NAME/KEY: promoter
<222> LOCATION: (1170)..(1188)
<223> OTHER INFORMATION: bacteriophage T7 gene 1 promoter
<220> FEATURE:
<221> NAME/KEY: gene
<222> LOCATION: (1261)..(1650)
<223> OTHER INFORMATION: bacteriophage MS2 coat protein gene
<220> FEATURE:
<221> NAME/KEY: terminator
<222> LOCATION: (1683)..(1730)
<223> OTHER INFORMATION: bacteriophage T7 transcription terminator

<400> SEQUENCE: 22
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg   120
caccgtcacc ctggatgctg taggcatagg cttggttatg ccggtactgc cgggcctctt   180
gcgggatgaa ttcagatctc gatcccgcga aattaatacg actcactata gggagaccac   240
aacggtttcc ctctagatca caagtttgta caaaaaagca ggctaagaag gagatataca   300
tacgccggcc attcaaacat gaggattacc catgtattta aatacccatg tccaggcgcg   360
ctccgcgatc gcgcacgagg ttttctgtc tagtgagcag tgtccaacct caaaagacaa   420
catgtgtgac gacgatgtag cggctctgtt taaaccctct agctgcttta caaagtactg   480
gttccctttc cagcgggatg ctttatctaa acgcaatgag agaggtattc ctcaggccac   540
atcgcttcct agttccgctg ggatccatcg ttggcggccg aagccgccat tccatagtga   600
gttctggcgc gccagagccg ctacatcgtc gtcacacatg ttgtcttttg aggttggaca   660
ctgctcacta gacagaaaaa cctcgtgccg gaccgaatac ccggtctgaa cgagggcggc   720
cgcggtaccc aagaagtact tagagttaat taaggagttc aaacatgagg atcacccatg   780
tcgaagctcc cacaccctag cataacccct tggggcctct aaacgggtct tgaggggttt   840
tttgctgaaa ggaggaacta tatccggata tccacaggac gggtgtggtc gccatgatcg   900
cgtagtcgat agtggctcca agtagcgaag cgagcaggac tgggcggcgg gcatgcatcg   960
tccattccga cagcatcgcc agtcactatg gcgtgctgct agcgctatat gcgttgatgc  1020
aatttctatg cgcacccgtt ctcggagcac tgtccgaccg ctttggccgc cgcccagtcc  1080
tgctcgcttc gctacttgga gccactatcg actacgcgat catggcgacc acaccgtcc   1140
```

```
tgtggatcca gatctcgatc ccgcgaaatt aatacgactc actataggga gaccacaacg    1200
gtttccctct agatcacaag tttgtacaaa aaagcaggct aagaaggaga tatacatatg    1260
gcgtctaact ttacccaatt cgttctggtt gataacggcg gtacgggtga cgttaccgta    1320
gctccgtcca acttcgccaa cggtgttgcg gaatggatta gctctaacag ccgctctcag    1380
gcctacaaag tcacgtgctc cgttcgtcag tctagcgcgc agaatcgcaa atacaccatc    1440
aaagttgaag taccgaaagt cgcaacgcag accgtaggcg gcgtagaact cccagttgcg    1500
gcctggcgct cttacctcaa catggaactg actattccga tttttgcgac gaactccgac    1560
tgcgaactga ttgttaaggc aatgcagggc ctgctgaaag acggtaatcc gatcccatct    1620
gcaatcgctg ctaactctgg catttactaa taagcggacg cgctgccacc gctgagcaat    1680
aactagcata accccttggg gcctctaaac gggtcttgag gggttttttg ctgaaaggag    1740
gaactatatc cggcatgcac cattccttgc ggcggcggtg ctcaacggcc tcaacctact    1800
actgggctgc ttcctaatgc aggagtcgca taagggagag cgtcgaccga tgcccttgag    1860
agccttcaac ccagtcagct ccttccgtgt ggcgcggggc atgactatcg tcgccgcact    1920
tatgactgtc ttctttatca tgcaactcgt aggacaggtg ccggcagcgc tctgggtcat    1980
tttcggcgag gaccgctttc gctggagcgc gacgatgatc ggcctgtcgc ttgcggtatt    2040
cggaatcttg cacgccctcg ctcaagcctt cgtcactggt cccgccacca aacgtttcgg    2100
cgagaagcag gccattatcg ccggcatggc ggccgacgcg ctgggctacg tcttgctggc    2160
gttcgcgacg cgaggctgga tggccttccc cattatgatt cttctcgctt ccggcggcat    2220
cgggatgccc gcgttgcagg ccatgctgtc caggcaggta gatgacgacc atcagggaca    2280
gcttcaagga tcgctcgcgg ctcttaccag cctaacttcg atcattggac cgctgatcgt    2340
cacggcgatt tatgccgcct cggcgagcac atggaacggg ttggcatgga ttgtaggcgc    2400
cgccctatac cttgtctgcc tccccgcgtt gcgtcgcggt gcatggagcc gggccacctc    2460
gacctgaatg gaagccggcg gcacctcgct aacggattca ccactccaag aattggagcc    2520
aatcaattct gcggagaaac tgtgaatgcg caaaccaacc cttggcagaa catatccatc    2580
gcgtccgcca tctccagcag ccgcacgcgg cgcatctcgg gcagcgttgg gtcctggcca    2640
cgggtgcgca tgatcgtgct cctgtcgttg aggacccggc taggctggcg gggttgcctt    2700
actggttagc agaatgaatc accgatacgc gagcgaacgt gaagcgactg ctgctgcaaa    2760
acgtctgcga cctgagcaac aacatgaatg gtcttcggtt tccgtgtttc gtaaagtctg    2820
gaaacgcgga agtcagcgcc ctgcaccatt atgttccgga tctgcatcgc aggatgctgc    2880
tggctaccct gtggaacacc tacatctgta ttaacgaagc gctggcattg accctgagtg    2940
atttttctct ggtcccgccg catccatacc gccagttgtt taccctcaca cgttccagt    3000 aaccgggcat gttcatcatc agtaacccgt atcgtgagca tcctctctcg tttcatcggt    3060
atcattaccc ccatgaacag aaatccccct tacacggagg catcagtgac caaacaggaa    3120
aaaaccgccc ttaacatggc ccgctttatc agaagccaga cattaacgct tctggagaaa    3180
ctcaacgagc tggacgcgga tgaacaggca gacatctgtg aatcgcttca cgaccacgct    3240
gatgagcttt accgcagctg cctcgcgcgt ttcggtgatg acggtgaaaa cctctgacac    3300
atgcagctcc cggagacggt cacagcttgt ctgtaagcgg atgccgggag cagacaagcc    3360
cgtcagggcg cgtcagcggg tgttggcggg tgtcggggcg cagccatgac ccagtcacgt    3420
agcgatagcg gagtgtatac tggcttaact atgcggcatc agagcagatt gtactgagag    3480
tgcaccatat gcggtgtgaa ataccgcaca gatgcgtaag gagaaaatac cgcatcaggc    3540
```

```
gctcttccgc ttcctcgctc actgactcgc tgcgctcggt cgttcggctg cggcgagcgg    3600
tatcagctca ctcaaaggcg gtaatacggt tatccacaga atcaggggat aacgcaggaa    3660
agaacatgtg agcaaaaggc cagcaaaagg ccaggaaccg taaaaaggcc gcgttgctgg    3720
cgtttttcca taggctccgc cccctgacg agcatcacaa aaatcgacgc tcaagtcaga    3780
ggtggcgaaa cccgacagga ctataaagat accaggcgtt tccccctgga agctccctcg    3840
tgcgctctcc tgttccgacc ctgccgctta ccggatacct gtccgccttt ctcccttcgg    3900
gaagcgtggc gctttctcat agctcacgct gtaggtatct cagttcggtg taggtcgttc    3960
gctccaagct gggctgtgtg cacgaacccc ccgttcagcc cgaccgctgc gccttatccg    4020
gtaactatcg tcttgagtcc aacccggtaa gacacgactt atcgccactg gcagcagcca    4080
ctggtaacag gattagcaga gcgaggtatg taggcggtgc tacagagttc ttgaagtggt    4140
ggcctaacta cggctacact agaaggacag tatttggtat ctgcgctctg ctgaagccag    4200
ttaccttcgg aaaaagagtt ggtagctctt gatccggcaa acaaaccacc gctggtagcg    4260
gtggtttttt tgtttgcaag cagcagatta cgcgcagaaa aaaaggatct caagaagatc    4320
ctttgatctt ttctacgggg tctgacgctc agtggaacga aaactcacgt taagggattt    4380
tggtcatgag attatcaaaa aggatcttca cctagatcct tttaaattaa aaatgaagtt    4440
ttaaatcaat ctaaagtata tatgagtaaa cttggtctga cagttaccaa tgcttaatca    4500
gtgaggcacc tatctcagcg atctgtctat ttcgttcatc catagttgcc tgactccccg    4560
tcgtgtagat aactacgata cgggagggct taccatctgg ccccagtgct gcaatgatac    4620
cgcgagaccc acgctcaccg gctccagatt tatcagcaat aaaccagcca gccggaaggg    4680
ccgagcgcag aagtggtcct gcaactttat ccgcctccat ccagtctatt aattgttgcc    4740
gggaagctag agtaagtagt tcgccagtta atagtttgcg caacgttgtt gccattgctg    4800
caggcatcgt ggtgtcacgc tcgtcgtttg gtatggcttc attcagctcc ggttcccaac    4860
gatcaaggcg agttacatga tcccccatgt tgtgcaaaaa agcggttagc tccttcggtc    4920
ctccgatcgt tgtcagaagt aagttggccg cagtgttatc actcatggtt atggcagcac    4980
tgcataattc tcttactgtc atgccatccg taagatgctt ttctgtgact ggtgagtact    5040
caaccaagtc attctgagaa tagtgtatgc ggcgaccgag ttgctcttgc ccggcgtcaa    5100
cacgggataa taccgcgcca catagcagaa ctttaaaagt gctcatcatt ggaaaacgtt    5160
cttcggggcg aaaactctca aggatcttac cgctgttgag atccagttcg atgtaaccca    5220
ctcgtgcacc caactgatct tcagcatctt ttactttcac cagcgtttct gggtgagcaa    5280
aaacaggaag gcaaaatgcc gcaaaaaagg gaataagggc gacacggaaa tgttgaatac    5340
tcatactctt cctttttcaa tattattgaa gcatttatca gggttattgt ctcatgagcg    5400
gatacatatt tgaatgtatt tagaaaaata aacaatagg ggttccgcgc acatttcccc    5460
gaaaagtgcc acctgacgtc taagaaacca ttattatcat gacattaacc tataaaaata    5520
ggcgtatcac gaggcccttt cgtcttcaag aa                                  5552
```

<210> SEQ ID NO 23
<211> LENGTH: 4667
<212> TYPE: DNA
<213> ORGANISM: Artificial Sequence
<220> FEATURE:
<223> OTHER INFORMATION: Recombinant plasmid pAPSE10149; coat protein
<220> FEATURE:
<221> NAME/KEY: promoter
<222> LOCATION: (1896)..(1914)

```
<223> OTHER INFORMATION: bacteriophage T7 gene 1 promoter
<220> FEATURE:
<221> NAME/KEY: gene
<222> LOCATION: (1987)..(2376)
<223> OTHER INFORMATION: bacteriophage MS2 coat protein
<220> FEATURE:
<221> NAME/KEY: terminator
<222> LOCATION: (2409)..(2456)
<223> OTHER INFORMATION: bacteriophage T7 transcription terminator

<400> SEQUENCE: 23
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt atgaaatcta acaatgcgct catcgtcatc ctcggcaccg    1620
tcaccctgga tgctgtaggc ataggcttgg ttatgccggt actgccgggc ctcttgcggg    1680
atatcgtcca ttccgacagc atcgccagtc actatggcgt gctgctagcg ctatatgcgt    1740
tgatgcaatt tctatgcgca cccgttctcg gagcactgtc cgaccgcttt ggccgccgcc    1800
cagtcctgct cgcttcgcta cttggagcca ctatcgacta cgcgatcatg gcgaccacac    1860
ccgtcctgtg gatccagatc tcgatcccgc gaaattaata cgactcacta tagggagacc    1920
acaacggttt ccctctagat cacaagtttg tacaaaaaag caggctaaga aggagatata    1980
catatggcgt ctaactttac ccaattcgtt ctggttgata acggcggtac gggtgacgtt    2040
```

```
accgtagctc cgtccaactt cgccaacggt gttgcggaat ggattagctc taacagccgc   2100
tctcaggcct acaaagtcac gtgctccgtt cgtcagtcta gcgcgcagaa tcgcaaatac   2160
accatcaaag ttgaagtacc gaaagtcgca acgcagaccg taggcggcgt agaactccca   2220
gttgcggcct ggcgctctta cctcaacatg gaactgacta ttccgatttt tgcgacgaac   2280
tccgactgcg aactgattgt taaggcaatg cagggcctgc tgaaagacgg taatccgatc   2340
ccatctgcaa tcgctgctaa ctctggcatt tactaataag cggacgcgct gccaccgctg   2400
agcaataact agcataaccc cttggggcct ctaaacgggt cttgaggggt ttttgctga   2460 aaggaggaac tatatccggc atgcaccatt ccttgcggcg gcggtgctca acggcctcaa   2520
cctactactg ggctgcttcc taatgcagga gtcgcataag ggagagcgtc gaccgatgcc   2580
cttgagagcc ttcaacccag tcagctcctt ccggtgggcg cggggcatga ctatcgtcgc   2640
cgcacttatg actgtcttct ttatcatgca actcgtagga caggtgccgg cagcgctctg   2700
ggtcattttc ggcgaggacc gctttcgctg gagcgcgacg atgatcggcc tgtcgcttgc   2760
ggtattcgga atcttgcacg ccctcgctca agccttcgtc actggtcccg ccaccaaacg   2820
tttcggcgag aagcaggcca ttatcgccgg catggcggcc gacgcgctgg gctacgtctt   2880
gctggcgttc gcgacgcgag gctggatggc cttccccatt atgattcttc tcgcttccgg   2940
cggcatcggg atgcccgcgt tgcaggccat gctgtccagg caggtagatg acgaccatca   3000
gggacagctt caaggatcgc tcgcggctct taccagccta acttcgatca ttggaccgct   3060
gatcgtcacg gcgatttatg ccgcctcggc gagcacatgg aacgggttgg catggattgt   3120
aggcgccgcc ctataccttg tctgcctccc cgcgttgcgt cgcggtgcat ggagccgggc   3180
cacctcgacc tgaatggaag ccggcggcac ctcgctaacg gattcaccac tccaagaatt   3240
ggagccaatc aattcttgcg gagaactgtg aatgcgcaaa ccaacccttg gcagaacata   3300
tccatcgcgt ccgccatctc cagcagccgc acgcggcgca tctcgggcag cgttgggtcc   3360
tggccacggg tgcgcatgat cgtgctcctg tcgttgagga cccggctagg ctggcggggt   3420
tgccttactg gttagcagaa tgaatcaccg atacgcgagc gaacgtgaag cgactgctgc   3480
tgcaaaacgt ctgcgacctg agcaacaaca tgaatggtct tcggtttccg tgtttcgtaa   3540
agtctggaaa cgcggaagtc ccctacgtgc tgctgaagtt gcccgcaaca gagagtggaa   3600
ccaaccggtg ataccacgat actatgactg agagtcaacg ccatgagcgg cctcatttct   3660
tattctgagt tacaacagtc cgcaccgctg tccggtagct ccttccggtg ggcgcggggc   3720
atgactatcg tcgccgcact tatgactgtc ttctttatca tgcaactcgt aggacaggtg   3780
ccggcagcgc ccaacagtcc cccggccacg gggcctgcca ccatacccac gccgaaacaa   3840
gcgccctgca ccattatgtt ccggatctgc atcgcaggat gctgctggct accctgtgga   3900
acacctacat ctgtattaac gaagcgctaa ccgtttttat caggctctgg gaggcagaat   3960
aaatgatcat atcgtcaatt attacctcca cggggagagc ctgagcaaac tggcctcagg   4020
catttgagaa gcacacggtc acactgcttc cggtagtcaa taaaccggta aaccagcaat   4080
agacataagc ggctatttaa cgaccctgcc ctgaaccgac gaccgggtcg aatttgcttt   4140
cgaatttctg ccattcatcc gcttattatc acttattcag gcgtagcacc aggcgtttaa   4200
gggcaccaat aactgcctta aaaaaattac gccccgccct gccactcatc gcagtactgt   4260
tgtaattcat taagcattct gccgacatgg aagccatcac agacggcatg atgaacctga   4320
atcgccagcg gcatcagcac cttgtcgcct tgcgtataat atttgcccat ggtgaaaacg   4380
```

```
ggggcgaaga agttgtccat attggccacg tttaaatcaa aactggtgaa actcacccag    4440
ggattggctg agacgaaaaa catattctca ataaaccctt tagggaaata ggccaggttt    4500
tcaccgtaac acgccacatc ttgcgaatat atgtgtagaa actgccggaa atcgtcgtgg    4560
tattcactcc agagcgatga aaacgtttca gtttgctcat ggaaaacggt gtaacaaggg    4620
tgaacactat cccatatcac cagctcaccg tctttcattg ccatacg                 4667

<210> SEQ ID NO 24
<211> LENGTH: 6228
<212> TYPE: DNA
<213> ORGANISM: Artificial Sequence
<220> FEATURE:
<223> OTHER INFORMATION: Recombinant plasmid pAPSE10366; beta actin stem
      loop + eGFP protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (372)..(666)
<223> OTHER INFORMATION: beta actin sense gene fragment
<220> FEATURE:
<221> NAME/KEY: misc_feature
<222> LOCATION: (832)..(1126)
<223> OTHER INFORMATION: beta actin antisense gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1696)..(2415)
<223> OTHER INFORMATION: bacteriophage MS2 coat protein gene
<220> FEATURE:
<221> NAME/KEY: terminator
<222> LOCATION: (2448)..(2495)
<223> OTHER INFORMATION: bacteriophage T7 transcription terminator

<400> SEQUENCE: 24
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccgtactgcc gggcctctt     180 gcgggatgaa ttcagatctc gatcccgcga aattaatacg actcactata gggagaccac    240
aacggtttcc ctctagatca caagtttgta caaaaaagca ggctaagaag agatataca    300 tacgccggcc attcaaacat gaggattacc catgtattta aatacccatg tccaggcgcg    360
ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
```

```
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttcccttttcc agcgggatgc   720 tttatctaaa cgcaatgaga gaggtattcc tcaggccaca tcgcttccta gttccgctgg    780
gatccatcgt tggcggccga agccgccatt ccatagtgag ttctggcgcg cctcatccca    840
gttggtgatg ataccgtgtt cgatggggta tttcagggtg aggataccct ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggt gagcaagggc gaggagctgt tcaccggggt ggtgcccatc   1740
ctggtcgagc tggacggcga cgtaaacggc cacaagttca gcgtgtccgg cgagggcgag   1800
ggcgatgcca cctacggcaa gctgaccctg aagttcatct gcaccaccgg caagctgccc   1860
gtgccctggc ccaccctcgt gaccaccctg acctacggcg tgcagtgctt cagccgctac   1920
cccgaccaca tgaagcagca cgacttcttc aagtccgcca tgcccgaagg ctacgtccag   1980
gagcgcacca tcttcttcaa ggacgacggc aactacaaga cccgcgccga ggtgaagttc   2040
gagggcgaca ccctggtgaa ccgcatcgag ctgaagggca tcgacttcaa ggaggacggc   2100
aacatcctgg ggcacaagct ggagtacaac tacaacagcc acaacgtcta tatcatggcc   2160
gacaagcaga agaacggcat caaggtgaac ttcaagatcc gccacaacat cgaggacggc   2220
agcgtgcagc tcgccgacca ctaccagcag aacacccccca tcggcgacgg ccccgtgctg   2280
ctgcccgaca accactacct gagcacccag tccgccctga gcaaagaccc caacgagaag   2340
cgcgatcaca tggtcctgct ggagttcgtg accgccgccg ggatcactct cggcatggac   2400
gagctgtaca agtaataagc ggacgcgctg ccaccgctga gcaataacta gcataacccc   2460
ttggggcctc taaacgggtc ttgaggggtt ttttgctgaa aggaggaact atatccggtc   2520
gaccgatgcc cttgagagcc ttcaacccag tcagctcctt ccgtgggcg cggggcatga   2580 ctatcgtcgc cgcacttatg actgtcttct ttatcatgca actcgtagga caggtgccgg   2640
cagcgctctg ggtcattttc ggcgaggacc gctttgctg gagcgcgacg atgatcggcc    2700
tgtcgcttgc ggtattcgga atcttgcacg ccctcgctca agccttcgtc actggtcccg   2760
ccaccaaacg tttcggcgag aagcaggcca ttatcgccgg catggcgcc gacgcgctgg    2820 gctacgtctt gctggcgttc gcgacgcgag gctggatggc cttccccatt atgattcttc   2880
tcgcttccgg cggcatcggg atgcccgcgt tgcaggccat gctgtccagg caggtagatg   2940
```

```
acgaccatca gggacagctt caaggatcgc tcgcggctct taccagccta acttcgatca   3000
ttggaccgct gatcgtcacg gcgatttatg ccgcctcggc gagcacatgg aacgggttgg   3060
catggattgt aggcgccgcc ctataccttg tctgcctccc cgcgttgcgt cgcggtgcat   3120
ggagccgggc cacctcgacc tgaatggaag ccggcggcac ctcgctaacg gattcaccac   3180
tccaagaatt ggagccaatc aattcttgcg gagaactgtg aatgcgcaaa ccaacccttg   3240
gcagaacata tccatcgcgt ccgccatctc cagcagccgc acgcggcgca tctcgggcag   3300
cgttgggtcc tggccacggg tgcgcatgat cgtgctcctg tcgttgagga cccggctagg   3360
ctggcggggt tgccttactg gttagcagaa tgaatcaccg atacgcgagc gaacgtgaag   3420
cgactgctgc tgcaaaacgt ctgcgacctg agcaacaaca tgaatggtct tcggtttccg   3480
tgtttcgtaa agtctggaaa cgcggaagtc agcgccctgc accattatgt tccgatctg    3540
catcgcagga tgctgctggc taccctgtgg aacacctaca tctgtattaa cgaagcgctg   3600
gcattgaccc tgagtgattt ttctctggtc ccgccgcatc cataccgcca gttgtttacc   3660
ctcacaacgt tccagtaacc gggcatgttc atcatcagta acccgtatcg tgagcatcct   3720
ctctcgtttc atcggtatca ttaccccat gaacagaaat ccccccttaca cggaggcatc    3780
agtgaccaaa caggaaaaaa ccgcccttaa catggcccgc tttatcagaa gccagacatt   3840
aacgcttctg gagaaactca acgagctgga cgcggatgaa caggcagaca tctgtgaatc   3900
gcttcacgac cacgctgatg agctttaccg cagctgcctc gcgcgtttcg gtgatgacgg   3960
tgaaaacctc tgcacacatgc agctcccgga cacggtcaca gcttgtctgt aagcggatgc   4020
cgggagcaga caagcccgtc agggcgcgtc agcgggtgtt ggcgggtgtc ggggcgcagc   4080
catgacccag tcacgtagcg atagcggagt gtatactggc ttaactatgc ggcatcagag   4140
cagattgtac tgagagtgca ccatatgcgg tgtgaaatac cgcacagatg cgtaaggaga   4200
aaataccgca tcaggcgctc ttccgcttcc tcgctcactg actcgctgcg ctcggtcgtt   4260
cggctgcggc gagcggtatc agctcactca aaggcggtaa tacggttatc cacagaatca   4320
ggggataacg caggaaagaa catgtgagca aaaggccagc aaaaggccag gaaccgtaaa   4380
aaggccgcgt tgctggcgtt tttccatagg ctccgccccc ctgacgagca tcacaaaaat   4440
cgacgctcaa gtcagaggtg gcgaaacccg acaggactat aaagatacca ggcgtttccc   4500
cctggaagct ccctcgtgcg ctctcctgtt ccgaccctgc cgcttaccgg atacctgtcc   4560
gcctttctcc cttcgggaag cgtggcgctt tctcatagct cacgctgtag gtatctcagt   4620
tcggtgtagg tcgttcgctc caagctgggc tgtgtgcacg aaccccccgt tcagcccgac   4680
cgctgcgcct tatccggtaa ctatcgtctt gagtccaacc cggtaagaca cgacttatcg   4740
ccactggcag cagccactgg taacaggatt agcagagcga ggtatgtagg cggtgctaca   4800
gagttcttga agtggtggcc taactacggc tacactagaa ggacagtatt tggtatctgc   4860
gctctgctga agccagttac cttcggaaaa agagttggta gctcttgatc cggcaaacaa   4920
accaccgctg gtagcggtgg tttttttgtt tgcaagcagc agattacgcg cagaaaaaaa   4980
ggatctcaag aagatccttt gatcttttct acggggtctg acgctcagtg gaacgaaaac   5040
tcacgttaag ggattttggt catgagatta tcaaaaagga tcttcaccta gatcctttta   5100
aattaaaaat gaagttttaa atcaatctaa agtatatatg agtaaacttg gtctgacagt   5160
taccaatgct taatcagtga ggcacctatc tcagcgatct gtctatttcg ttcatccata   5220
gttgcctgac tccccgtcgt gtagataact acgatacggg agggcttacc atctggcccc   5280
```

```
agtgctgcaa tgataccgcg agacccacgc tcaccggctc cagatttatc agcaataaac   5340
cagccagccg gaagggccga gcgcagaagt ggtcctgcaa ctttatccgc ctccatccag   5400
tctattaatt gttgccggga agctagagta agtagttcgc cagttaatag tttgcgcaac   5460
gttgttgcca ttgctgcagg catcgtggtg tcacgctcgt cgtttggtat ggcttcattc   5520
agctccggtt cccaacgatc aaggcgagtt acatgatccc ccatgttgtg caaaaaagcg   5580
gttagctcct tcggtcctcc gatcgttgtc agaagtaagt tggccgcagt gttatcactc   5640
atggttatgg cagcactgca taattctctt actgtcatgc catccgtaag atgcttttct   5700
gtgactggtg agtactcaac caagtcattc tgagaatagt gtatgcggcg accgagttgc   5760
tcttgcccgg cgtcaacacg ggataatacc gcgccacata gcagaacttt aaaagtgctc   5820
atcattggaa aacgttcttc ggggcgaaaa ctctcaagga tcttaccgct gttgagatcc   5880
agttcgatgt aacccactcg tgcacccaac tgatcttcag catcttttac tttcaccagc   5940
gtttctgggt gagcaaaaac aggaaggcaa aatgccgcaa aaagggaat aagggcgaca   6000 cggaaatgtt gaatactcat actcttcctt tttcaatatt attgaagcat ttatcagggt   6060
tattgtctca tgagcggata catatttgaa tgtatttaga aaataaaca aatagggtt    6120 ccgcgcacat ttccccgaaa agtgccacct gacgtctaag aaaccattat tatcatgaca   6180
ttaacctata aaaataggcg tatcacgagg ccctttcgtc ttcaagaa              6228
```

<210> SEQ ID NO 25
<211> LENGTH: 5499
<212> TYPE: DNA
<213> ORGANISM: Artificial Sequence
<220> FEATURE:
<223> OTHER INFORMATION: Recombinant plasmid pAPSE10359; beta actin stem
      loop + Qbeta coat protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (46)..(65)
<223> OTHER INFORMATION: bacteriophage Qbeta pac sequence
<220> FEATURE:
<221> NAME/KEY: misc_feature
<222> LOCATION: (66)..(73)
<223> OTHER INFORMATION: restriction endonuclease AsiSI recognition site
<220> FEATURE:
<221> NAME/KEY: misc_feature
<222> LOCATION: (74)..(367)
<223> OTHER INFORMATION: beta actin sense strand gene fragment
<220> FEATURE:
<221> NAME/KEY: misc_feature
<222> LOCATION: (534)..(827)
<223> OTHER INFORMATION: beta actin antisense strand gene fragment
<220> FEATURE:
<221> NAME/KEY: misc_feature
<222> LOCATION: (872)..(891)
<223> OTHER INFORMATION: bacteriophage Qbeta pac sequence
<220> FEATURE:
<221> NAME/KEY: terminator
<222> LOCATION: (907)..(954)
<223> OTHER INFORMATION: bacteriophage T7 transcription terminator
<220> FEATURE:
<221> NAME/KEY: promoter
<222> LOCATION: (1108)..(1126)
<223> OTHER INFORMATION: bacteriophage T7 gene 1 promoter
<220> FEATURE:
<221> NAME/KEY: gene
<222> LOCATION: (1196)..(1597)
<223> OTHER INFORMATION: bacteriophage Qbeta coat protein
<220> FEATURE:
<221> NAME/KEY: terminator
<222> LOCATION: (1630)..(1677)

<223> OTHER INFORMATION: bacteriophage T7 transcription terminator

<400> SEQUENCE: 25

```
ttcagatctc gatcccgcga attaatacg actcactata gggagatgca tgtctaagac      60
agcatgcgat cgcgcacgag ttttttctgt ctagtgagca gtgtccaacc tcaaaagaca    120
acatgtgtga cgacgatgta gcggctcttg tcgtagacaa tggatccggt atgtgcaaag    180
ccggtttcgc aggagatgac gcaccccgtg ccgtcttccc ctcgatcgtc ggtcgcccaa    240
ggcatcaagg agtcatggtc ggtatgggac aaaaggactc atacgtagga gatgaagccc    300
aaagcaaaag aggtatcctc accctgaaat accccatcga acacggtatc atcaccaact    360
gggatgagtt taaaccctct agctgcttta caaagtactg gttccctttc cagcgggatg    420
ctttatctaa acgcaatgag agaggtattc ctcaggccac atcgcttcct agttccgctg    480
ggatccatcg ttggcggccg aagccgccat tccatagtga gttctggcgc gcctcatccc    540
agttggtgat gataccgtgt tcgatggggt atttcagggt gaggatacct cttttgcttt    600
gggcttcatc tcctacgtat gagtcctttt gtcccatacc gaccatgact ccttgatgcc    660
ttgggcgacc gacgatcgag gggaagacgg cacggggtgc gtcatctcct gcgaaaccgg    720
cttttgcacat accggatcca ttgtctacga caagagccgc tacatcgtcg tcacacatgt    780
tgtcttttga ggttggacac tgctcactag acagaaaaac ctcgtgccgg accgaatacc    840
cggtctgaac gagggcggcc gcggagttca aatgcatgtc taagacagca tcgaagctcc    900
cacaccctag cataaccct tggggcctct aaacgggtct tgaggggttt tttgctgaaa    960
ggaggaacta tatccggata tccacaggac gggtgtggtc gccatgatcg cgtagtcgat   1020
agtggctcca gtagcgaag cgagcaggac tgggcggcgg gcatgcgcct ccgcctttag   1080
gggatccaga tctcgatccc gcgaaattaa tacgactcac tatagggaga ccacaacggt   1140
ttccctctag atcacaagtt tgtacaaaaa agcaggctaa aaggagata tacatatggc   1200
aaaattagag actgttactt taggtaacat cgggaaagat ggaaaacaaa ctctggtcct   1260
caatccgcgt ggggtaaatc ccactaacgg cgttgcctcg ctttcacaag cgggtgcagt   1320
tcctgcgctg gagaagcgtg ttaccgtttc ggtatctcag ccttctcgca atcgtaagaa   1380
ctacaaggtc caggttaaga tccagaaccc gaccgcttgc actgcaaacg gttcttgtga   1440
cccatccgtt actcgccagg catatgctga cgtgaccttt tcgttcacgc agtatagtac   1500
cgatgaggaa cgagcttttg ttcgtacaga gcttactgct ctgctcgcta gtcctctgct   1560
gatcgatgct attgatcagc tgaacccagc gtattaataa gcggacgcgc tgccaccgct   1620
gagcaataac tagcataacc ccttggggcc tctaaacggg tcttgagggg ttttttgctg   1680
aaaggaggaa ctatatccgg catgcaccat tccttgcggc ggcggtgctc aacggcctca   1740
acctactact gggctgcttc ctaatgcagg agtcgcataa gggagagcgt cgaccgatgc   1800
ccttgagagc cttcaaccca gtcagctcct tccggtgggc gcggggcatg actatcgtcg   1860
ccgcacttat gactgtcttc tttatcatgc aactcgtagg acaggtgccg gcagcgctct   1920
gggtcatttt cggcgaggac cgctttcgct ggagcgcgac gatgatcggc ctgtcgcttg   1980
cggtattcgg aatcttgcac gccctcgctc aagccttcgt cactggtccc gccaccaaac   2040
gtttcggcga aagcaggcc attatcgccg gcatggcggc cgacgcgctg ggctacgtct   2100
tgctggcgtt cgcgacgcga ggctggatgg ccttccccat tatgattctt ctcgcttccg   2160
gcggcatcgg gatgcccgcg ttgcaggcca tgctgtccag gcaggtagat gacgaccatc   2220
agggacagct tcaaggatcg ctcgcggctc ttaccagcct aacttcgatc attggaccgc   2280
```

```
tgatcgtcac ggcgatttat gccgcctcgg cgagcacatg gaacgggttg gcatggattg    2340
taggcgccgc cctataccta gtctgcctcc ccgcgttgcg tcgcggtgca tggagccggg    2400
ccacctcgac ctgaatggaa gccggcggca cctcgctaac ggattcacca ctccaagaat    2460
tggagccaat caattcttgc ggagaactgt gaatgcgcaa accaacccta ggcagaacat    2520
atccatcgcg tccgccatct ccagcagccg cacgcggcgc atctcgggca gcgttgggtc    2580
ctggccacgg gtgcgcatga tcgtgctcct gtcgttgagg acccggctag ctggcgggg    2640 ttgccttact ggttagcaga atgaatcacc gatacgcgag cgaacgtgaa gcgactgctg    2700
ctgcaaaacg tctgcgacct gagcaacaac atgaatggtc ttcggtttcc gtgtttcgta    2760
aagtctggaa acgcggaagt cagcgccctg caccattatg ttccggatct gcatcgcagg    2820
atgctgctgg ctaccctgtg gaacacctac atctgtatta acgaagcgct ggcattgacc    2880
ctgagtgatt tttctctggt cccgccgcat ccataccgcc agttgtttac cctcacaacg    2940
ttccagtaac cgggcatgtt catcatcagt aacccgtatc gtgagcatcc tctctcgttt    3000
catcggtatc attaccccca tgaacagaaa tccccttac acggaggcat cagtgaccaa    3060
acaggaaaaa accgcccta acatggcccg cttatcaga agccagacat taacgcttct    3120
ggagaaactc aacgagctgg acgcggatga acaggcagac atctgtgaat cgcttcacga    3180
ccacgctgat gagctttacc gcagctgcct cgcgcgtttc ggtgatgacg gtgaaaacct    3240
ctgacacatg cagctcccgg agacggtcac agcttgtctg taagcggatg ccgggagcag    3300
acaagcccgt cagggcgcgt cagcgggtgt tggcgggtgt cggggcgcag ccatgaccca    3360
gtcacgtagc gatagcggag tgtatactgg cttaactatg cggcatcaga gcagattgta    3420
ctgagagtgc accatatgcg gtgtgaaata ccgcacagat gcgtaaggag aaaataccgc    3480
atcaggcgct cttccgcttc ctcgctcact gactcgctgc gctcggtcgt tcggctgcgg    3540
cgagcggtat cagctcactc aaaggcggta atacggttat ccacagaatc agggggataac    3600 gcaggaaaga acatgtgagc aaaaggccag caaaaggcca ggaaccgtaa aaaggccgcg    3660
ttgctggcgt ttttccatag gctccgcccc cctgacgagc atcacaaaaa tcgacgctca    3720
agtcagaggt ggcgaaaccc gacaggacta taaagatacc aggcgtttcc ccctggaagc    3780
tccctcgtgc gctctcctgt tccgaccctg ccgcttaccg gatacctgtc cgcctttctc    3840
ccttcgggaa gcgtggcgct ttctcatagc tcacgctgta ggtatctcag ttcggtgtag    3900
gtcgttcgct ccaagctggg ctgtgtgcac gaaccccccg ttcagcccga ccgctgcgcc    3960
ttatccggta actatcgtct tgagtccaac ccggtaagac acgacttatc gccactggca    4020
gcagccactg gtaacaggat tagcagagcg aggtatgtag gcggtgctac agagttcttg    4080
aagtggtggc ctaactacgg ctacactaga aggacagtat ttggtatctg cgctctgctg    4140
aagccagtta ccttcggaaa aagagttggt agctcttgat ccggcaaaca aaccaccgct    4200
ggtagcggtg gtttttttgt ttgcaagcag cagattacgc gcagaaaaaa aggatctcaa    4260
gaagatcctt tgatcttttc tacggggtct gacgctcagt ggaacgaaaa ctcacgttaa    4320
gggattttgg tcatgagatt atcaaaaagg atcttcacct agatcctttt aaattaaaaa    4380
tgaagtttta aatcaatcta agtatatat gagtaaactt ggtctgacag ttaccaatgc    4440
ttaatcagtg aggcacctat ctcagcgatc tgtctatttc gttcatccat agttgcctga    4500
ctccccgtcg tgtagataac tacgatacgg gagggcttac catctggccc cagtgctgca    4560
atgataccgc gagacccacg ctcaccggct ccagatttat cagcaataaa ccagccagcc    4620
```

```
ggaagggccg agcgcagaag tggtcctgca actttatccg cctccatcca gtctattaat    4680
tgttgccggg aagctagagt aagtagttcg ccagttaata gtttgcgcaa cgttgttgcc    4740
attgctgcag gcatcgtggt gtcacgctcg tcgtttggta tggcttcatt cagctccggt    4800
tcccaacgat caaggcgagt tacatgatcc cccatgttgt gcaaaaaagc ggttagctcc    4860
ttcggtcctc cgatcgttgt cagaagtaag ttggccgcag tgttatcact catggttatg    4920
gcagcactgc ataattctct tactgtcatg ccatccgtaa gatgcttttc tgtgactggt    4980
gagtactcaa ccaagtcatt ctgagaatag tgtatgcggc gaccgagttg ctcttgcccg    5040
gcgtcaacac gggataatac cgcgccacat agcagaactt taaaagtgct catcattgga    5100
aaacgttctt cggggcgaaa actctcaagg atcttaccgc tgttgagatc cagttcgatg    5160
taacccactc gtgcacccaa ctgatcttca gcatctttta ctttcaccag cgtttctggg    5220
tgagcaaaaa caggaaggca aaatgccgca aaaagggaa taagggcgac acggaaatgt    5280
tgaatactca tactcttcct ttttcaatat tattgaagca tttatcaggg ttattgtctc    5340
atgagcggat acatatttga atgtatttag aaaaataaac aaataggggt tccgcgcaca    5400
tttccccgaa aagtgccacc tgacgtctaa gaaaccatta ttatcatgac attaacctat    5460
aaaaataggc gtatcacgag gccctttcgt cttcaagaa                          5499
```

<210> SEQ ID NO 26
<211> LENGTH: 5413
<212> TYPE: DNA
<213> ORGANISM: Artificial Sequence
<220> FEATURE:
<223> OTHER INFORMATION: Recombinant plasmid pAPSE10357; beta actin stem
      loop + U1A protein
<220> FEATURE:
<221> NAME/KEY: promoter
<222> LOCATION: (24)..(42)
<223> OTHER INFORMATION: bacteriophage T7 gene 1 promoter
<220> FEATURE:
<221> NAME/KEY: misc_feature
<222> LOCATION: (41)..(66)
<223> OTHER INFORMATION: U1A binding site sequence
<220> FEATURE:
<221> NAME/KEY: misc_feature
<222> LOCATION: (67)..(74)
<223> OTHER INFORMATION: restriction endonuclease AsiSI recognition site
<220> FEATURE:
<221> NAME/KEY: misc_feature
<222> LOCATION: (75)..(368)
<223> OTHER INFORMATION: beta actin sense strand gene fragment
<220> FEATURE:
<221> NAME/KEY: misc_feature
<222> LOCATION: (535)..(828)
<223> OTHER INFORMATION: beta actin antisense strand gene fragment
<220> FEATURE:
<221> NAME/KEY: misc_feature
<222> LOCATION: (873)..(898)
<223> OTHER INFORMATION: U1A binding site sequence
<220> FEATURE:
<221> NAME/KEY: terminator
<222> LOCATION: (914)..(961)
<223> OTHER INFORMATION: bacteriophage T7 transcription terminator
<220> FEATURE:
<221> NAME/KEY: promoter
<222> LOCATION: (1115)..(1133)
<223> OTHER INFORMATION: bacteriophage T7 gene 1 promoter
<220> FEATURE:
<221> NAME/KEY: gene
<222> LOCATION: (1203)..(1511)
<223> OTHER INFORMATION: human U1A protein gene
<220> FEATURE:
<221> NAME/KEY: terminator
<222> LOCATION: (1544)..(1591)
<223> OTHER INFORMATION: bacteriophage T7 transcription terminator

<400> SEQUENCE: 26

```
ttcagatctc gatcccgcga aattaatacg actcactata gggtatccat tgcactccgg      60
atgcccgcga tcgcgcacga ggttttctg tctagtgagc agtgtccaac ctcaaaagac     120
aacatgtgtg acgacgatgt agcggctctt gtcgtagaca atggatccgg tatgtgcaaa     180
gccggtttcg caggagatga cgcaccccgt gccgtcttcc cctcgatcgt cggtcgccca     240
aggcatcaag gagtcatggt cggtatggga caaaaggact catacgtagg agatgaagcc     300
caaagcaaaa gaggtatcct caccctgaaa taccccatcg aacacggtat catcaccaac     360
tgggatgagt ttaaaccctc tagctgcttt acaaagtact ggttcccttt ccagcgggat     420
gctttatcta aacgcaatga gagaggtatt cctcaggcca catcgcttcc tagttccgct     480
gggatccatc gttggcggcc gaagccgcca ttccatagtg agttctggcg cgcctcatcc     540
cagttggtga tgataccgtg ttcgatgggg tatttcaggg tgaggatacc tcttttgctt     600
tgggcttcat ctcctacgta tgagtccttt tgtcccatac cgaccatgac tccttgatgc     660
cttgggcgac cgacgatcga ggggaagacg gcacggggtg cgtcatctcc tgcgaaaccg     720
gctttgcaca taccggatcc attgtctacg acaagagccg ctacatcgtc gtcacacatg     780
ttgtcttttg aggttggaca ctgctcacta gacagaaaaa cctcgtgccg gaccgaatac     840
ccggtctgaa cgagggcggc cgcggagttc aagggtatcc attgcactcc ggatgccccg     900
aagctcccac accctagcat aacccttgg ggcctctaaa cgggtcttga ggggtttttt     960
gctgaaagga ggaactatat ccggatatcc acaggacggg tgtggtcgcc atgatcgcgt    1020
agtcgatagt ggctccaagt agcgaagcga gcaggactgg gcggcgggca tgcgcctccg    1080
cctttagggg atccagatct cgatcccgcg aaattaatac gactcactat agggagacca    1140
caacggtttc cctctagatc acaagtttgt acaaaaaagc aggctaagaa ggagatatac    1200
atatggcagt tcccgagacc cgccctaacc acactattta tatcaacaac ctcaatgaga    1260
agatcaagaa ggatgagcta aaaaagtccc tgtacgccat cttctcccag tttgccaga    1320
tcctggatat cctggtatca cggagcctga agatgagggg ccaggccttt gtcatcttca    1380
aggaggtcag cagcgccacc aacgcccgc gctccatgca gggtttccct ttctatgaca    1440
aacctatgcg tatccagtat gccaagaccg actcagatat cattgccaag atgaaaggca    1500
ccttcgtgta ataagcggac gcgctgccac cgctgagcaa taactagcat aaccccttgg    1560
ggcctctaaa cgggtcttga ggggtttttt gctgaaagga ggaactatat ccggcatgca    1620
ccattccttg cggcggcggt gctcaacggc ctcaacctac tactgggctg cttcctaatg    1680
caggagtcgc ataagggaga gcgtcgaccg atgcccttga gagccttcaa cccagtcagc    1740
tccttccggt gggcgcgggg catgactatc gtcgccgcac ttatgactgt cttctttatc    1800
atgcaactcg taggacaggt gccggcagcg ctctgggtca ttttcggcga ggaccgcttt    1860
cgctggagcg cgacgatgat cggcctgtcg cttgcggtat tcggaatctt gcacgccctc    1920
gctcaagcct tcgtcactgg tcccgccacc aaacgtttcg gcgagaagca ggccattatc    1980
gccggcatgg cggccgacgc gctgggctac gtcttgctgg cgttcgcgac gcgaggctgg    2040
atggccttcc ccattatgat tcttctcgct tccggcggca tcgggatgcc gcgttgcag    2100
gccatgctgt ccaggcaggt agatgacgac catcagggac agcttcaagg atcgctcgcg    2160
gctcttacca gcctaacttc gatcattgga ccgctgatcg tcacggcgat ttatgccgcc    2220
tcggcgagca catggaacgg gttggcatgg attgtaggcg ccgccctata ccttgtctgc    2280
ctccccgcgt tgcgtcgcgg tgcatggagc cgggccacct cgacctgaat ggaagccggc    2340
```

```
ggcacctcgc taacggattc accactccaa gaattggagc caatcaattc ttgcggagaa    2400
ctgtgaatgc gcaaaccaac ccttggcaga acatatccat cgcgtccgcc atctccagca    2460
gccgcacgcg gcgcatctcg ggcagcgttg ggtcctggcc acgggtgcgc atgatcgtgc    2520
tcctgtcgtt gaggacccgg ctaggctggc ggggttgcct tactggttag cagaatgaat    2580
caccgatacg cgagcgaacg tgaagcgact gctgctgcaa aacgtctgcg acctgagcaa    2640
caacatgaat ggtcttcggt ttccgtgttt cgtaaagtct ggaaacgcgg aagtcagcgc    2700
cctgcaccat tatgttccgg atctgcatcg caggatgctg ctggctaccc tgtggaacac    2760
ctacatctgt attaacgaag cgctggcatt gaccctgagt gattttctc tggtcccgcc     2820 gcatccatac cgccagttgt ttaccctcac aacgttccag taaccgggca tgttcatcat    2880
cagtaacccg tatcgtgagc atcctctctc gtttcatcgg tatcattacc cccatgaaca    2940
gaaatccccc ttacacggag gcatcagtga ccaaacagga aaaaccgcc cttaacatgg     3000 cccgctttat cagaagccag acattaacgc ttctggagaa actcaacgag ctggacgcgg    3060
atgaacaggc agacatctgt gaatcgcttc acgaccacgc tgatgagctt taccgcagct    3120
gcctcgcgcg tttcggtgat gacggtgaaa acctctgaca catgcagctc ccggagacgg    3180
tcacagcttg tctgtaagcg gatgccggga gcagacaagc ccgtcagggc gcgtcagcgg    3240
gtgttggcgg gtgtcgggc gcagccatga cccagtcacg tagcgatagc ggagtgtata    3300
ctggcttaac tatgcggcat cagagcagat tgtactgaga gtgcaccata tgcggtgtga    3360
aataccgcac agatgcgtaa ggagaaaata ccgcatcagg cgctcttccg cttcctcgct    3420
cactgactcg ctgcgctcgg tcgttcggct gcggcgagcg gtatcagctc actcaaaggc    3480
ggtaatacgg ttatccacag aatcagggga taacgcagga agaacatgt gagcaaaagg     3540 ccagcaaaag gccaggaacc gtaaaaaggc cgcgttgctg gcgttttcc ataggctccg     3600 cccccctgac gagcatcaca aaaatcgacg ctcaagtcag aggtggcgaa acccgacagg    3660
actataaaga taccaggcgt ttccccctgg aagctccctc gtgcgctctc ctgttccgac    3720
cctgccgctt accggatacc tgtccgcctt tctcccttcg ggaagcgtgg cgctttctca    3780
tagctcacgc tgtaggtatc tcagttcggt gtaggtcgtt cgctccaagc tgggctgtgt    3840
gcacgaaccc cccgttcagc ccgaccgctg cgccttatcc ggtaactatc gtcttgagtc    3900
caacccggta agacacgact tatcgccact ggcagcagcc actggtaaca ggattagcag    3960
agcgaggtat gtaggcggtg ctacagagtt cttgaagtgg tggcctaact acggctacac    4020
tagaaggaca gtatttggta tctgcgctct gctgaagcca gttaccttcg gaaaaagagt    4080
tggtagctct tgatccggca aacaaaccac cgctggtagc ggtggttttt tgtttgcaa     4140 gcagcagatt acgcgcagaa aaaaaggatc tcaagaagat cctttgatct tttctacggg    4200
gtctgacgct cagtggaacg aaaactcacg ttaagggatt ttggtcatga gattatcaaa    4260
aaggatcttc acctagatcc ttttaaatta aaaatgaagt tttaaatcaa tctaaagtat    4320
atatgagtaa acttggtctg acagttacca atgcttaatc agtgaggcac ctatctcagc    4380
gatctgtcta tttcgttcat ccatagttgc ctgactcccc gtcgtgtaga taactacgat    4440
acgggagggc ttaccatctg gccccagtgc tgcaatgata ccgcgagacc cacgctcacc    4500
ggctccagat ttatcagcaa taaaccagcc agccggaagg gccgagcgca gaagtggtcc    4560
tgcaacttta tccgcctcca tccagtctat taattgttgc cgggaagcta gagtaagtag    4620
ttcgccagtt aatagtttgc gcaacgttgt tgccattgct gcaggcatcg tggtgtcacg    4680
```

```
ctcgtcgttt ggtatggctt cattcagctc cggttcccaa cgatcaaggc gagttacatg    4740
atcccccatg ttgtgcaaaa aagcggttag ctccttcggt cctccgatcg ttgtcagaag    4800
taagttggcc gcagtgttat cactcatggt tatggcagca ctgcataatt ctcttactgt    4860
catgccatcc gtaagatgct tttctgtgac tggtgagtac tcaaccaagt cattctgaga    4920
atagtgtatg cggcgaccga gttgctcttg cccggcgtca acacgggata ataccgcgcc    4980
acatagcaga actttaaaag tgctcatcat tggaaaacgt tcttcgggc gaaaactctc    5040 aaggatctta ccgctgttga gatccagttc gatgtaaccc actcgtgcac ccaactgatc    5100
ttcagcatct tttactttca ccagcgtttc tgggtgagca aaaacaggaa ggcaaaatgc    5160
cgcaaaaaag ggaataaggg cgacacggaa atgttgaata ctcatactct tcctttttca    5220
atattattga agcatttatc agggttattg tctcatgagc ggatacatat ttgaatgtat    5280
ttagaaaaat aaacaaatag gggttccgcg cacatttccc cgaaaagtgc cacctgacgt    5340
ctaagaaacc attattatca tgacattaac ctataaaaat aggcgtatca cgaggccctt    5400
tcgtcttcaa gaa                                                       5413
```

<210> SEQ ID NO 27  
<211> LENGTH: 5504  
<212> TYPE: DNA  
<213> ORGANISM: Artificial Sequence  
<220> FEATURE:  
<223> OTHER INFORMATION: Recombinant plasmid pAPSE10372; beta actin stem  
      loop + truncated coat protein  
<220> FEATURE:  
<221> NAME/KEY: promoter  
<222> LOCATION: (24)..(42)  
<223> OTHER INFORMATION: bacteriophage T7 gene 1 promoter  
<220> FEATURE:  
<221> NAME/KEY: misc_feature  
<222> LOCATION: (127)..(145)  
<223> OTHER INFORMATION: bacteriophage MS2 pac sequence  
<220> FEATURE:  
<221> NAME/KEY: misc_feature  
<222> LOCATION: (175)..(182)  
<223> OTHER INFORMATION: restriction endonuclease AsiSI recognition site  
<220> FEATURE:  
<221> NAME/KEY: misc_feature  
<222> LOCATION: (179)..(384)  
<223> OTHER INFORMATION: ErkA sense strand gene fragment  
<220> FEATURE:  
<221> NAME/KEY: misc_feature  
<222> LOCATION: (436)..(454)  
<223> OTHER INFORMATION: bacteriophage MS2 pac sequence  
<220> FEATURE:  
<221> NAME/KEY: misc_feature  
<222> LOCATION: (504)..(511)  
<223> OTHER INFORMATION: restriction endonuclease NotI recognition site  
<220> FEATURE:  
<221> NAME/KEY: misc_feature  
<222> LOCATION: (505)..(696)  
<223> OTHER INFORMATION: ErkA antisense strand gene fragment  
<220> FEATURE:  
<221> NAME/KEY: misc_feature  
<222> LOCATION: (692)..(699)  
<223> OTHER INFORMATION: restriction endonuclease PacI recognition site  
<220> FEATURE:  
<221> NAME/KEY: misc_feature  
<222> LOCATION: (728)..(746)  
<223> OTHER INFORMATION: bacteriophage MS2 pac sequence  
<220> FEATURE:  
<221> NAME/KEY: terminator  
<222> LOCATION: (762)..(809)  
<223> OTHER INFORMATION: bacteriophage T7 transcription terminator  
<220> FEATURE:  
<221> NAME/KEY: promoter  
<222> LOCATION: (1135)..(1153)  
<223> OTHER INFORMATION: bacteriophage T7 gene 1 promoter  
<220> FEATURE:

```
<221> NAME/KEY: misc_feature
<222> LOCATION: (1223)..(1429)
<223> OTHER INFORMATION: bacteriophage MS2 coat protein N-terminal
      fragment
<220> FEATURE:
<221> NAME/KEY: terminator
<222> LOCATION: (1635)..(1682)
<223> OTHER INFORMATION: bacteriophage T7 transcription terminator

<400> SEQUENCE: 27
```

| | | | | | |
|---|---|---|---|---|---|
| ttcagatctc | gatcccgcga | aattaatacg | actcactata | gggagaccac | aacggtttcc | 60 |
| ctctagatca | caagtttgta | caaaaaagca | ggctaagaag | gagatataca | tacgccggcc | 120 |
| attcaaacat | gaggattacc | catgtaacct | aaggccggtg | tccaggcgcg | ctccgcgatc | 180 |
| gcacgcggac | aaagttcctc | aatctaatgc | tgaagttata | aggggacaaa | tatttgaagt | 240 |
| tggtcctagg | tatattaaac | tcgcctatat | aggtgaagga | gcttatggca | tggttgtgtc | 300 |
| tgcggatgac | acgctaacaa | accaaagagt | tgcaataaaa | aaaatatcgc | cctttgaaca | 360 |
| ccaaacttat | tgctactaca | gtttaaacgc | aatcgcagca | actccggca | tctactaata | 420 |
| gacgccggcc | attcaacatg | aggattaccc | atgtaaccta | agaagacaac | aaagaagttc | 480 |
| aactctttat | gtattgatct | tccgcggccg | cggtaccggg | gcaataagtt | tggtgttcaa | 540 |
| agggcgatat | ttttttttatt | gcaactcttt | ggtttgttag | cgtgtcatcc | gcagacacaa | 600 |
| ccatgccata | agctccttca | cctatatagg | cgagtttaat | atacctagga | ccaacttcaa | 660 |
| atatttgtcc | ccttataact | tcagcattag | attgaggaac | tatacgaaaa | ttaattaagg | 720 |
| agttcaaaca | tgaggatcac | ccatgtcgaa | gctcccacac | cctagcataa | ccccttgggg | 780 |
| cctctaaacg | ggtcttgagg | ggttttttgc | tgaaaggagg | aactatatcc | ggatatccac | 840 |
| aggacgggtg | tggtcgccat | gatcgcgtag | tcgatagtgg | ctccaagtag | cgaagcgagc | 900 |
| aggactgggc | ggcgggcatg | catcgtccat | tccgacagca | tcgccagtca | ctatggcgtg | 960 |
| ctgctagcgc | tatatgcgtt | gatgcaattt | ctatgcgcac | ccgttctcgg | agcactgtcc | 1020 |
| gaccgctttg | gccgccgccc | agtcctgctc | gcttcgctac | ttggagccac | tatcgactac | 1080 |
| gcgatcatgg | cgaccacacc | cgtcctgtgg | atccagatct | cgatcccgcg | aaattaatac | 1140 |
| gactcactat | agggagacca | aacggtttc | cctctagatc | acaagtttgt | acaaaaaagc | 1200 |
| aggctaagaa | ggagatatac | atatggcgtc | taactttacc | caattcgttc | tggttgataa | 1260 |
| cggcggtacg | ggtgacgtta | ccgtagctcc | gtccaacttc | gccaacggtg | ttgcggaatg | 1320 |
| gattagctct | aacagccgct | ctcagggtgc | tccgttcgtc | agtctagcgc | gcagaatcgc | 1380 |
| aaatacacca | tcaaagttga | agtaccgaaa | gtcgcaacgc | agaccgtagg | cggcgtagaa | 1440 |
| ctcccagttg | cggcctggcg | ctcttacctc | aacatggaac | tgactattcc | gattttgcg | 1500 |
| acgaactccg | actgcgaact | gattgttaag | gcaatgcagg | gcctgctgaa | agacggtaat | 1560 |
| ccgatcccat | ctgcaatcgc | tgctaactct | ggcatttact | aataagcgga | cgcgctgcca | 1620 |
| ccgctgagca | ataactagca | taaccccttg | gggcctctaa | acgggtcttg | aggggttttt | 1680 |
| tgctgaaagg | aggaactata | tccggcatgc | accattcctt | gcggcggcgg | tgctcaacgg | 1740 |
| cctcaaccta | ctactgggct | gcttcctaat | gcaggagtcg | cataagggag | agcgtcgacc | 1800 |
| gatgcccttg | agagccttca | acccagtcag | ctccttccgg | tgggcgcggg | gcatgactat | 1860 |
| cgtcgccgca | cttatgactg | tcttctttat | catgcaactc | gtaggacagg | tgccggcagc | 1920 |
| gctctgggtc | atttttcggcg | aggaccgctt | cgctggagc | gcgacgatga | tcggcctgtc | 1980 |
| gcttgcggta | ttcggaatct | tgcacgccct | cgctcaagcc | ttcgtcactg | gtcccgccac | 2040 |

-continued

| | |
|---|---|
| caaacgtttc ggcgagaagc aggccattat cgccggcatg gcggccgacg cgctgggcta | 2100 |
| cgtcttgctg gcgttcgcga cgcgaggctg gatggccttc cccattatga ttcttctcgc | 2160 |
| ttccggcggc atcgggatgc ccgcgttgca ggccatgctg tccaggcagg tagatgacga | 2220 |
| ccatcaggga cagcttcaag gatcgctcgc ggctcttacc agcctaactt cgatcattgg | 2280 |
| accgctgatc gtcacggcga tttatgccgc ctcggcgagc acatggaacg ggttggcatg | 2340 |
| gattgtaggc gccgccctat accttgtctg cctccccgcg ttgcgtcgcg gtgcatggag | 2400 |
| ccgggccacc tcgacctgaa tggaagccgg cggcacctcg ctaacggatt caccactcca | 2460 |
| agaattggag ccaatcaatt cttgcggaga actgtgaatg cgcaaaccaa cccttggcag | 2520 |
| aacatatcca tcgcgtccgc catctccagc agccgcacgc ggcgcatctc gggcagcgtt | 2580 |
| gggtcctggc cacgggtgcg catgatcgtg ctcctgtcgt tgaggacccg gctaggctgg | 2640 |
| cggggttgcc ttactggtta gcagaatgaa tcaccgatac gcgagcgaac gtgaagcgac | 2700 |
| tgctgctgca aaacgtctgc gacctgagca acaacatgaa tggtcttcgg tttccgtgtt | 2760 |
| tcgtaaagtc tggaaacgcg gaagtcagcg ccctgcacca ttatgttccg gatctgcatc | 2820 |
| gcaggatgct gctggctacc ctgtggaaca cctacatctg tattaacgaa gcgctggcat | 2880 |
| tgaccctgag tgattttcct ctggtcccgc cgcatccata ccgccagttg tttaccctca | 2940 |
| caacgttcca gtaaccgggc atgttcatca tcagtaaccc gtatcgtgag catcctctct | 3000 |
| cgtttcatcg gtatcattac ccccatgaac agaaatcccc cttacacgga ggcatcagtg | 3060 |
| accaaacagg aaaaaaccgc ccttaacatg gcccgcttta tcagaagcca gacattaacg | 3120 |
| cttctggaga aactcaacga gctggacgcg gatgaacagg cagacatctg tgaatcgctt | 3180 |
| cacgaccacg ctgatgagct ttaccgcagc tgcctcgcgc gtttcggtga tgacggtgaa | 3240 |
| aacctctgac acatgcagct cccggagacg gtcacagctt gtctgtaagc ggatgccggg | 3300 |
| agcagacaag cccgtcaggg cgcgtcagcg ggtgttggcg ggtgtcgggg cgcagccatg | 3360 |
| acccagtcac gtagcgatag cggagtgtat actggcttaa ctatgcggca tcagagcaga | 3420 |
| ttgtactgag agtgcaccat atgcggtgtg aaataccgca cagatgcgta aggagaaaat | 3480 |
| accgcatcag cgctcttcc gcttcctcgc tcactgactc gctgcgctcg tcgttcggc | 3540 |
| tgcggcgagc ggtatcagct cactcaaagg cggtaatacg gttatccaca gaatcagggg | 3600 |
| ataacgcagg aaagaacatg tgagcaaaag gccagcaaaa ggccaggaac cgtaaaaagg | 3660 |
| ccgcgttgct ggcgtttttc cataggctcc gcccccctga cgagcatcac aaaaatcgac | 3720 |
| gctcaagtca gaggtggcga aacccgacag gactataaag ataccaggcg tttccccctg | 3780 |
| gaagctccct cgtgcgctct cctgttccga ccctgccgct taccggatac ctgtccgcct | 3840 |
| ttctcccttc gggaagcgtg gcgctttctc atagctcacg ctgtaggtat ctcagttcgg | 3900 |
| tgtaggtcgt tcgctccaag ctgggctgtg tgcacgaacc ccccgttcag cccgaccgct | 3960 |
| gcgccttatc cggtaactat cgtcttgagt ccaacccggt aagacacgac ttatcgccac | 4020 |
| tggcagcagc cactggtaac aggattagca gagcgaggta tgtaggcggt gctacagagt | 4080 |
| tcttgaagtg gtggcctaac tacggctaca ctagaaggac agtatttggt atctgcgctc | 4140 |
| tgctgaagcc agttaccttc ggaaaaagag ttggtagctc ttgatccggc aaacaaacca | 4200 |
| ccgctggtag cggtggtttt tttgtttgca agcagcagat tacgcgcaga aaaaaggat | 4260 |
| ctcaagaaga tcctttgatc ttttctacgg ggtctgacgc tcagtggaac gaaaactcac | 4320 |
| gttaagggat tttggtcatg agattatcaa aaaggatctt cacctagatc cttttaaatt | 4380 |
| aaaaatgaag ttttaaatca atctaaagta tatatgagta aacttggtct gacagttacc | 4440 |

-continued

```
aatgcttaat cagtgaggca cctatctcag cgatctgtct atttcgttca tccatagttg    4500
cctgactccc cgtcgtgtag ataactacga tacgggaggg cttaccatct ggccccagtg    4560
ctgcaatgat accgcgagac ccacgctcac cggctccaga tttatcagca ataaaccagc    4620
cagccggaag ggccgagcgc agaagtggtc ctgcaacttt atccgcctcc atccagtcta    4680
ttaattgttg ccgggaagct agagtaagta gttcgccagt taatagtttg cgcaacgttg    4740
ttgccattgc tgcaggcatc gtggtgtcac gctcgtcgtt tggtatggct tcattcagct    4800
ccggttccca acgatcaagg cgagttacat gatcccccat gttgtgcaaa aaagcggtta    4860
gctccttcgg tcctccgatc gttgtcagaa gtaagttggc cgcagtgtta tcactcatgg    4920
ttatggcagc actgcataat tctcttactg tcatgccatc cgtaagatgc ttttctgtga    4980
ctggtgagta ctcaaccaag tcattctgag aatagtgtat gcggcgaccg agttgctctt    5040
gcccggcgtc aacacgggat aataccgcgc cacatagcag aactttaaaa gtgctcatca    5100
ttggaaaacg ttcttcgggg cgaaaactct caaggatctt accgctgttg agatccagtt    5160
cgatgtaacc cactcgtgca cccaactgat cttcagcatc ttttactttc accagcgttt    5220
ctgggtgagc aaaaacagga aggcaaaatg ccgcaaaaaa gggaataagg gcgacacgga    5280
aatgttgaat actcatactc ttcctttttc aatattattg aagcatttat cagggttatt    5340
gtctcatgag cggatacata tttgaatgta tttagaaaaa taaacaaata ggggttccgc    5400
gcacatttcc ccgaaaagtg ccacctgacg tctaagaaac cattattatc atgacattaa    5460
cctataaaaa taggcgtatc acgaggccct ttcgtcttca agaa                     5504
```

<210> SEQ ID NO 28
<211> LENGTH: 68
<212> TYPE: PRT
<213> ORGANISM: Artificial Sequence
<220> FEATURE:
<223> OTHER INFORMATION: N-terminus truncated bacteriophage MS2 coat
      protein sequence

<400> SEQUENCE: 28

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Gly Ala Pro Phe Val Ser Leu
        35                  40                  45

Ala Arg Arg Ile Ala Asn Thr Pro Ser Lys Leu Lys Tyr Arg Lys Ser
    50                  55                  60

Gln Arg Arg Pro
65

<210> SEQ ID NO 29
<211> LENGTH: 8339
<212> TYPE: DNA
<213> ORGANISM: Artificial Sequence
<220> FEATURE:
<223> OTHER INFORMATION: Recombinant plasmid pAPSE10429; C. glutamicum
      rnc deletion plasmid
<220> FEATURE:
<221> NAME/KEY: gene
<222> LOCATION: (346)..(1140)
<223> OTHER INFORMATION: Kanamycin resistance gene
<220> FEATURE:
<221> NAME/KEY: promoter
<222> LOCATION: (1186)..(1631)
<223> OTHER INFORMATION: sacB promoter

```
<220> FEATURE:
<221> NAME/KEY: gene
<222> LOCATION: (1632)..(3053)
<223> OTHER INFORMATION: sacB gene
<220> FEATURE:
<221> NAME/KEY: misc_feature
<222> LOCATION: (5504)..(5510)
<223> OTHER INFORMATION: restriction endonuclease BamHI recognition site
<220> FEATURE:
<221> NAME/KEY: misc_feature
<222> LOCATION: (5511)..(8136)
<223> OTHER INFORMATION: PCR fragment comprising 1.5 kb of chromosomal
      sequence downstream of rnc gene (5511-7012) and 1.2 kb of
      chromosomal sequence upstream of rnc gene (7013-8136).
<220> FEATURE:
<221> NAME/KEY: misc_feature
<222> LOCATION: (8136)..(8141)
<223> OTHER INFORMATION: restrcition endonuclease SalI recognition site

<400> SEQUENCE: 29
tgccgcaagc actcagggcg caagggctgc taaaggaagc ggaacacgta gaaagccagt      60
ccgcagaaac ggtgctgacc ccggatgaat gtcagctact gggctatctg gacaagggaa     120
aacgcaagcg caaagagaaa gcaggtagct tgcagtgggc ttacatggcg atagctagac     180
tgggcggttt tatggacagc aagcgaaccg gaattgccag ctgggcgcc ctctggtaag      240 gttgggaagc cctgcaaagt aaactggatg gctttcttgc cgccaaggat ctgatggcgc     300
aggggatcaa gatctgatca agagacagga tgaggatcgt ttcgcatgat tgaacaagat     360
ggattgcacg caggttctcc ggccgcttgg gtggagaggc tattcggcta tgactgggca     420
caacagacaa tcggctgctc tgatgccgcc gtgttccggc tgtcagcgca ggggcgcccg     480 gttcttttg tcaagaccga cctgtccggt gccctgaatg aactccaaga cgaggcagcg     540
cggctatcgt ggctggccac gacgggcgtt ccttgcgcag ctgtgctcga cgttgtcact     600
gaagcgggaa gggactggct gctattgggc gaagtgccgg gcaggatct cctgtcatct     660 caccttgctc ctgccgagaa agtatccatc atggctgatg caatgcggcg gctgcatacg     720
cttgatccgg ctacctgccc attcgaccac caagcgaaac atcgcatcga gcgagcacgt     780
actcggatgg aagccggtct tgtcgatcag gatgatctgg acgaagagca tcaggggctc     840
gcgccagccg aactgttcgc caggctcaag gcgcggatgc ccgacggcga ggatctcgtc     900
gtgacccatg gcgatgcctg cttgccgaat atcatggtgg aaaatggccg cttttctgga     960
ttcatcgact gtggccggct gggtgtggcg gaccgctatc aggacatagc gttggctacc    1020
cgtgatattg ctgaagagct tggcggcgaa tgggctgacc gcttcctcgt gctttacggt    1080
atcgccgctc ccgattcgca gcgcatcgcc ttctatcgcc ttcttgacga gttcttctga    1140
gcgggactct ggggttcgct agaggatcga tccttttaa cccatcacat atacctgccg    1200
ttcactatta tttagtgaaa tgagatatta tgatattttc tgaattgtga ttaaaaaggc    1260
aactttatgc ccatgcaaca gaaactataa aaaatacaga gaatgaaaag aaacagatag    1320
attttttagt tctttaggcc cgtagtctgc aaatccttt atgatttct atcaaacaaa    1380 agaggaaaat agaccagttg caatccaaac gagagtctaa tagaatgagg tcgaaaagta    1440
aatcgcgcgg gtttgttact gataaagcag gcaagaccta aatgtgtaa agggcaaagt    1500 gtatactttg gcgtcacccc ttacatattt taggtctttt tttattgtgc gtaactaact    1560
tgccatcttc aaacaggagg gctggaagaa gcagaccgct aacacagtac ataaaaaagg    1620
agacatgaac gatgaacatc aaaaagtttg caaacaagc aacagtatta accttactta    1680
ccgcactgct ggcaggaggc gcaactcaag cgtttgcgaa agaaacgaac caaaagccat    1740
```

```
ataaggaaac atacggcatt tcccatatta cacgccatga tatgctgcaa atccctgaac    1800
agcaaaaaaa tgaaaaatat caagtttctg aatttgattc gtccacaatt aaaaatatct    1860
cttctgcaaa aggcctggac gtttgggaca gctggccatt acaaaacgct gacggcactg    1920
tcgcaaacta tcacggctac cacatcgtct ttgcattagc cggagatcct aaaaatgcgg    1980
atgacacatc gatttacatg ttctatcaaa aagtcggcga aacttctatt gacagctgga    2040
aaaacgctgg ccgcgtcttt aaagacagcg acaaattcga tgcaaatgat tctatcctaa    2100
aagaccaaac acaagaatgg tcaggttcag ccacatttac atctgacgga aaaatccgtt    2160
tattctacac tgatttctcc ggtaaacatt acggcaaaca aacactgaca actgcacaag    2220
ttaacgtatc agcatcagac agctctttga acatcaacgg tgtagaggat tataaatcaa    2280
tctttgacgg tgacggaaaa acgtatcaaa atgtacagca gttcatcgat gaaggcaact    2340
acagctcagg cgacaaccat acgctgagag atcctcacta cgtagaagat aaaggccaca    2400
aatacttagt atttgaagca aacactggaa ctgaagatgg ctaccaaggc gaagaatctt    2460
tatttaacaa agcatactat ggcaaaagca catcattctt ccgtcaagaa agtcaaaaac    2520
ttctgcaaag cgataaaaaa cgcacggctg agttagcaaa cggcgctctc ggtatgattg    2580
agctaaacga tgattacaca ctgaaaaaag tgatgaaacc gctgattgca tctaacacag    2640
taacagatga aattgaacgc gcgaacgtct ttaaaatgaa cggcaaatgg tacctgttca    2700
ctgactcccg cggatcaaaa atgacgattg acggcattac gtctaacgat atttacatgc    2760
ttggttatgt ttctaattct ttaactggcc catacaagcc gctgaacaaa actggccttg    2820
tgttaaaaat ggatcttgat cctaacgatg taacctttac ttactcacac ttcgctgtac    2880
ctcaagcgaa aggaaacaat gtcgtgatta caagctatat gacaaacaga ggattctacg    2940
cagacaaaca atcaacgttt cgcccgagct tcctgctgaa catcaaaggc aagaaaacat    3000
ctgttgtcaa agacagcatc cttgaacaag acaattaac agttaacaaa taaaaacgca    3060
aaagaaaatg ccgatgggta ccgagcgaaa tgaccgacca agcgacgccc aacctgccat    3120
cacgagattt cgattccacc gccgccttct atgaaaggtt gggcttcgga atcgtttttcc    3180 gggacgccct cgcggacgtg ctcatagtcc acgacgcccg tgattttgta gccctggccg    3240
acggccagca ggtaggccga caggctcatg ccggccgccg ccgcctttc ctcaatcgct    3300 cttcgttcgt ctggaaggca gtacaccttg ataggtgggc tgcccttcct ggttggcttg    3360
gtttcatcag ccatccgctt gccctcatct gttacgccgg cggtagccgg ccagcctcgc    3420
agagcaggat tcccgttgag caccgccagg tgcgaataag ggacagtgaa gaaggaacac    3480
ccgctcgcgg gtgggcctac ttcacctatc ctgcccggct gacgccgttg gatacaccaa    3540
ggaaagtcta cacgaaccct ttggcaaaat cctgtatatc gtgcgaaaaa ggatggatat    3600
accgaaaaaa tcgctataat gaccccgaag cagggttatg cagcggaaaa gcgctgcttc    3660
cctgctgttt tgtggaatat ctaccgactg gaaacaggca atgcaggaa attactgaac    3720 tgagggggaca ggcgagagac gatgccaaag agctcctgaa atctcgata actcaaaaaa    3780 tacgcccggt agtgatctta tttcattatg gtgaaagttg aacctcttac gtgccgatc    3840 aacgtctcat tttcgccaaa agttgggccca gggcttcccg gtatcaacag ggacaccagg    3900
atttatttat tctgcgaagt gatcttccgt cacaggtatt tattcggcgc aaagtgcgtc    3960
gggtgatgct gccaacttac tgatttagtg tatgatggtg ttttttgaggt gctccagtgg    4020 cttctgtttc tatcagctcc tgaaaatctc gataactcaa aaaatacgcc cggtagtgat    4080
cttatttcat tatggtgaaa gttggaacct cttacgtgcc gatcaacgtc tcattttcgc    4140
```

```
caaaagttgg cccagggctt cccggtatca acagggacac caggatttat ttattctgcg    4200
aagtgatctt ccgtcacagg tatttattcg gcgcaaagtg cgtcgggtga tgctgccaac    4260
ttactgattt agtgtatgat ggtgtttttg aggtgctcca gtggcttctg tttctatcag    4320
ggctggatga tcctccagcg cggggatctc atgctggagt tcttcgccca ccccaaaagg    4380
atctaggtga agatccttt tgataatctc atgaccaaaa tcccttaacg tgagttttcg     4440
ttccactgag cgtcagaccc cgtagaaaag atcaaaggat cttcttgaga tccttttttt    4500
ctgcgcgtaa tctgctgctt gcaaacaaaa aaaccaccgc taccagcggt ggtttgtttg    4560
ccggatcaag agctaccaac tcttttccg aaggtaactg gcttcagcag agcgcagata     4620
ccaaatactg ttcttctagt gtagccgtag ttaggccacc acttcaagaa ctctgtagca    4680
ccgcctacat acctcgctct gctaatcctg ttaccagtgg ctgctgccag tggcgataag    4740
tcgtgtctta ccgggttgga ctcaagacga tagttaccgg ataaggcgca gcggtcgggc    4800
tgaacggggg gttcgtgcac acagcccagc ttggagcgaa cgacctacac cgaactgaga    4860
tacctacagc gtgagctatg agaaagcgcc acgcttcccg aagggagaaa ggcggacagg    4920
tatccggtaa gcggcagggt cggaacagga gagcgcacga gggagcttcc aggggggaaac   4980
gcctggtatc tttatagtcc tgtcgggttt cgccacctct gacttgagcg tcgatttttg    5040
tgatgctcgt cagggggggcg gagcctatgg aaaaacgcca gcaacgcggc ctttttacgg   5100
ttcctggcct tttgctggcc ttttgctcac atgttctttc ctgcgttatc ccctgattct    5160
gtggataacc gtattaccgc ctttgagtga gctgataccg ctcgccgcag ccgaacgacc    5220
gagcgcagcg agtcagtgag cgaggaagcg gaagagcgcc caatacgcaa accgcctctc    5280
cccgcgcgtt ggccgattca ttaatgcagc tggcacgaca ggtttcccga ctggaaagcg    5340
ggcagtgagc gcaacgcaat taatgtgagt tagctcactc attaggcacc ccaggcttta    5400
cactttatgc ttccggctcg tatgttgtgt ggaattgtga gcggataaca atttcacaca    5460
ggaaacagct atgacatgat tacgaattcg agctcggtac ccggggatcc caaatccaga    5520
aaagctcata ctgctcccct aatcgatggc ttccccagca agggctttgg aggcgaggcg    5580
ttcttcctca ctgacttccc acacctcgtg agcggcgtgc agtgcgagca gaatgatgaa    5640
acaacctagg atcaaatctg gccatccaga cgtcgtccat gcggtaatta aggccatcat    5700
gatgatggca atgttgatca ggacgtcatt tcgggcggat aggaaggcag cttggccaag    5760
cgagccacca tgttgtcgca ctcgagaaat aatgatggca ctcgcgccgt tgatcacgac    5820
ggcgcccaga gaagcgacga tgatcggaaa cacttcgggc gcttgcggtg cggaaaaccg    5880
ttgaatcgct gcccacgcag caaaagcagc aggtgcaaga atcacaatcg ccataagttt    5940
gcccatcact gcgcgcctcg ccaacggcca tcctagggca atgaaaatga gcaggttgat    6000
ggaggtgtct tcaagaaaat cgacactgtc agccagtaga gaaacggagc ctgcgcttaa    6060
tgcaataaag aattctacaa agaaataagc gaagttaagc agcgcgacgg tgagcacagc    6120
tttgcgcact ttggttgcat caaaagcttc gctcatcagc tagcgccgct tctggcagtt    6180
tgggcagtag tgggagccgc ggttcatgaa actctcccgg atgattaatg ttccgcagcg    6240
tccgcacggc tccccggttt gcgcataagc attcaatgac agcgcaaagt agccggagtt    6300
gccattgacg ttgacataga gcgcgtcgaa agaggtgcca ccttgagcaa gtgctttggt    6360
catcacgtct ttgccagctt gaagaagttc ttccaagcga gctagggaca gtcgatcggc    6420
acgttgcaat gggtgaattt ttgcttgcca gagcatttca tcggcataga tatttccgat    6480
```

```
gccggagacg atctcttggt taagcaggag gcgtttgatc tccgatttcc gagatttcaa   6540
attccgcgca atcgcagaga atcagcaga ctcatccaat acatctgtgg caatgtgaga   6600
gacgcgttcg ggtactccat caactaggtc gccgagccac caataaccga aggtgcgttg   6660
atcgacaaac cacacttcat cgccattatc tagctcgact ttggctcgaa ggtgtggact   6720
aattggtgca tctggttctt tgatgagcat ttgtccactc atcccaaggt gaaccagtag   6780
ccctaaatcg ggacgggttt cgccggaggg tgcgtcgata agctcaagcc agaggaattt   6840
gccgcgtcgc ttggcagcgc tgaccctaag ccctgcgatg ttggcctcga tttcggggcc   6900
accgccgagt tgattgcggg ctgcgcgcgg gtgaagcact gtggcggaca cgatggtgtg   6960
gccgaccata tgatcttcta aaccgcggcg caccacctca acttcaggca gtaggaactt   7020
ctccaaacca gcccagcgcg gatcgacctt ttcctcgtct tctacttctt cagagacacc   7080
gtcaggagct ggcgtttcat catcctggca tgcgccgtac ccaagttctt cgcagacagg   7140
gttaaacggc aaggtcagac cagcttcatc aatgacagac tgaagcagat caatctggtc   7200
ttggttaacc attggcagct catcttcgtc atctgctgca tcttcaccag taacaaagtc   7260
tggatcggca gcaaaaacct cagagacgtg cagcgtcttg gttggggtga gttcgcggag   7320
gcagcgggag cactgtccca gaagctgcgc ttcgatatct gcttcgacgg ccaggcctcc   7380
accgagtgga atgatctggg cttctacgat aacttttccg ccctcgggga tcgcgatcat   7440
ttccggacca atgcgggtcg ggcttggacc tgattgggtg aggtgttccg gaagggcact   7500
tccacgaagg agtgcggcga catcaaaaat aaatggagat tcatgacca ggaagatcct    7560
actcgtacct catcgtgact acatacatca gatgaggatc gctagacgga aaggtgaaaa   7620
agcctaaatg gtttcttgga aactagtagt ctcgatcgtc gcgttcgtag cctcgttcat   7680
aatcacgctc gtagtcccgc tcatattcac cacgcgctgc cggttgctca tcgcgcagct   7740
cgcggccagt agctccagct cctcggcgta gtgcggaacg atcagcagtg acagaacgca   7800
acgtggtgga cagcgaggtt tcaaactctg ccaacttggt atccacgtag tcatcgcatt   7860
cattgcgcag cttgttggag tcagcgtgcg ctgcatccac aatgcggtgt gcttcttccg   7920
tggagcgacg caccacttct gcctcgctga ccaggcgatc ctgctcggcc tggccttcag   7980
caaccgcgcg gcgatacgca tcattgccgg agttgaccag gcgctcagat tcagcctggg   8040
cgcgctcggt gacgctgttt gcttctcgac gagcgtcact cacgatgcga tccgctgtgt   8100
cattagcctt agcaacgaca gaatgcgcat gcttgggtcg acctgcaggc atgcaagctt   8160
ggcactggcc gtcgttttac aacgtcgtga ctgggaaaac cctggcgtta cccaacttaa   8220
tcgccttgca gcacatcccc ctttcgccag ctggcgtaat agcgaagagg cccgcaccga   8280
tcgcccttcc caacagttgc gcagcctgaa tggcgaatgg cgataagcta gcttcacgc    8339
```

<210> SEQ ID NO 30
<211> LENGTH: 3343
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (1)..(301)
<223> OTHER INFORMATION: pCG1 origin of replication
<220> FEATURE:
<221> NAME/KEY: gene
<222> LOCATION: (2269)..(3063)
<223> OTHER INFORMATION: kanamycin resistance gene

<400> SEQUENCE: 30

```
ccatggtcgt cacagagctg gaagcggcag cgagaattat ccgcgatcgt ggcgcggtgc      60
ccgcaggcat gacaaacatc gtaaatgccg cgtttcgtgt ggccgtggcc gcccaggacg     120
tgtcagcgcc gccaccacct gcaccgaatc ggcagcagcg tcgcgcgtcg aaaaagcgca     180
caggcggcaa gaagcgataa gctgcacgaa tacctgaaaa atgttgaacg ccccgtgagc     240
ggtaactcac agggcgtcgg ctaaccccca gtccaaacct gggagaaagc gctcaaaaat     300
gactctagcg gattcacgag acattgacac accggcctgg aaattttccg ctgatctgtt     360
cgacacccat cccgagctcg cgctgcgatc acgtggctgg acgagcgaag accgccgcga     420
attcctcgct cacctgggca gagaaaattt ccagggcagc aagacccgcg acttcgccag     480
cgcttggatc aaagacccgg acacgggaga acacagccg aagttatacc gagttggttc      540
aaaatcgctt gcccggtgcc agtatgttgc tctgacgcac gcgcagcacg cagccgtgct     600
tgtcctggac attgatgtgc cgagccacca ggccggcggg aaaatcgagc acgtaaaccc     660
cgaggtctac gcgattttgg agcgctgggc acgcctggaa aaagcgccag cttggatcgg     720
cgtgaatcca ctgagcggga atgccagct catctggctc attgatccgg tgtatgccgc      780
agcaggcatg agcagcccga atatgcgcct gctggctgca acgaccgagg aaatgacccg     840
cgttttcggc gctgaccagg cttttttcaca taggctgagc cggtggccac tgcacgtctc     900
cgacgatccc accgcgtacc gctggcatgc ccagcacaat cgcgtggatc gcctagctga     960
tcttatggag gttgctcgca tgatctcagg cacagaaaaa cctaaaaaac gctatgagca    1020
ggagtttttct agcggacggg cacgtatcga agcggcaaga aaagccactg cggaagcaaa    1080
agcacttgcc acgcttgaag caagcctgcc gagcgccgct gaagcgtctg gagagctgat    1140
cgacggcgtc cgtgtcctct ggactgctcc agggcgtgcc gcccgtgatg agacggcttt    1200
tcgccacgct ttgactgtgg ataccagtt aaaagcggct ggtgagcgcc taaaagacac    1260
caagatcatc gacgcctacg agcgtgccta caccgtcgct caggcggtcg gagcagacgg    1320
ccgtgagcct gatctgccgc cgatgcgtga ccgccagacg atggcgcgac gtgtgcgcgg    1380
ctacgtcgct aaaggccagc cagtcgtccc tgctcgtcag acagagacgc agagcagccg    1440
agggcgaaaa gctctggcca ctatgggaag acgtggcggt aaaaaggccg cagaacgctg    1500
gaaagaccca aacagtgagt acgcccgagc acagcgagaa aaactagcta agtccagtca    1560
acgacaagct aggaaagcta aggaaatcg cttgaccatt gcaggttggt ttatgactgt     1620
tgagggagag actggctcgt ggcgacaatc aatgaagcta tgtctgaatt tagcgtgtca    1680
cgtcagaccg tgaatagagc acttaagtct gcgggcattg aacttccacg aggacgccgt    1740
aaagcttccc agtaaatgtg ccatctcgta ggcagaaaac ggttccccc gtagggtct     1800
ctctcttggc ctccttttcta ggtcgggctg attgctcttg aagctctcta gggggctca    1860
caccataggc agataacggt tccccaccgg ctcacctcgt aagcgcacaa ggactgctcc    1920
caatgccgca agcactcagg gcgcaagggc tgctaaagga agcggaacac gtagaaagcc    1980
agtccgcaga aacggtgctg accccggatg aatgtcagct actgggctat ctggacaagg    2040
gaaaacgcaa gcgcaaagag aaagcaggta gcttgcagtg gcttacatg gcgatagcta     2100
gactgggcgg ttttatggac agcaagcgaa ccggaattgc cagctgggc gccctctggt     2160
aaggttggga agccctgcaa agtaaactgg atggctttct gccgccaag gatctgatgg     2220
cgcaggggat caagatctga tcaagagaca ggatgaggat cgtttcgcat gattgaacaa    2280
gatggattgc acgcaggttc tccggccgct tgggtggaga ggctattcgg ctatgactgg    2340
```

-continued

```
gcacaacaga caatcggctg ctctgatgcc gccgtgttcc ggctgtcagc gcaggggcgc    2400
ccggttcttt ttgtcaagac cgacctgtcc ggtgccctga atgaactcca agacgaggca    2460
gcgcggctat cgtggctggc cacgacgggc gttccttgcg cagctgtgct cgacgttgtc    2520
actgaagcgg gaagggactg gctgctattg ggcgaagtgc cggggcagga tctcctgtca    2580
tctcaccttg ctcctgccga gaaagtatcc atcatggctg atgcaatgcg gcggctgcat    2640
acgcttgatc cggctacctg cccattcgac caccaagcga acatcgcat cgagcgagca     2700 cgtactcgga tggaagccgg tcttgtcgat caggatgatc tggacgaaga gcatcagggg    2760
ctcgcgccag ccgaactgtt cgccaggctc aaggcgcgga tgcccgacgg cgaggatctc    2820
gtcgtgaccc atggcgatgc ctgcttgccg aatatcatgg tggaaaatgg ccgcttttct    2880
ggattcatcg actgtggccg gctgggtgtg cggaccgct atcaggacat agcgttggct     2940
acccgtgata ttgctgaaga gcttggcggc gaatgggctg accgcttcct cgtgctttac    3000
ggtatcgccg ctcccgattc gcagcgcatc gccttctatc gccttcttga cgagttcttc    3060
tgagcgggac tctggggttc gctagaggat cgatcctttt taacccatca catatacctg    3120
ccgttcacta ttatttagtg aaatgagata ttatgatatt ttctgaattg tgattaaaaa    3180
ggcaacttta tgcccatgca acagaaacta taaaaaatac agagaatgaa agaaacaga     3240 tagatttttt agttctttag gcccgtagtc tgcaaatcct tttatgattt tctatcaaac    3300
aaaagaggaa aatagaccag ttgcaatcca acgagagtc taa                       3343
```

<210> SEQ ID NO 31
<211> LENGTH: 8710
<212> TYPE: DNA
<213> ORGANISM: Artificial Sequence
<220> FEATURE:
<223> OTHER INFORMATION: Recombinant plasmid pAPSE10430; beta actin
hairpin + coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: promoter
<222> LOCATION: (985)..(1003)
<223> OTHER INFORMATION: bacteriophage T7 gene 1 promoter
<220> FEATURE:
<221> NAME/KEY: gene
<222> LOCATION: (1076)..(1465)
<223> OTHER INFORMATION: bacteriophage MS2 coat protein gene
<220> FEATURE:
<221> NAME/KEY: terminator
<222> LOCATION: (1498)..(1545)
<223> OTHER INFORMATION: bacteriophage T7 transcription terminator
<220> FEATURE:

<221> NAME/KEY: misc_feature
<222> LOCATION: (1981)..(5324)
<223> OTHER INFORMATION: synthetic DNA (SEQ ID NO: 30)

<400> SEQUENCE: 31

| | | | | | |
|---|---|---|---|---|---|
| ttcttagctc | cggcaagcaa | ttaagaactt | ccgaaattaa | tacgactcac | tatagggagg | 60 |
| cgatcgcgca | cgaggttttt | ctgtctagtg | agcagtgtcc | aacctcaaaa | gacaacatgt | 120 |
| gtgacgacga | tgtagcggct | cttgtcgtag | acaatggatc | cggtatgtgc | aaagccggtt | 180 |
| tcgcaggaga | tgacgcaccc | cgtgccgtct | tccctcgat | cgtcggtcgc | ccaaggcatc | 240 |
| aaggagtcat | ggtcggtatg | ggacaaaagg | actcatacgt | aggagatgaa | gcccaaagca | 300 |
| aaagaggtat | cctcaccctg | aaataccca | tcgaacacgg | tatcatcacc | aactgggatg | 360 |
| agtttaaacc | ctctagctgc | tttacaaagt | actggttccc | tttccagcgg | gatgctttat | 420 |
| ctaaacgcaa | tgagagaggt | attcctcagg | ccacatcgct | tcctagttcc | gctgggatcc | 480 |
| atcgttggcg | gccgaagccg | ccattccata | gtgagttctg | gcgcgcctca | tcccagttgg | 540 |
| tgatgatacc | gtgttcgatg | gggtatttca | gggtgaggat | acctcttttg | ctttgggctt | 600 |
| catctcctac | gtatgagtcc | ttttgtccca | taccgaccat | gactccttga | tgccttgggc | 660 |
| gaccgacgat | cgaggggaag | acggcacggg | gtgcgtcatc | tcctgcgaaa | ccggctttgc | 720 |
| acataccgga | tccattgtct | acgacaagag | ccgctacatc | gtcgtcacac | atgttgtctt | 780 |
| ttgaggttgg | acactgctca | ctagacagaa | aaacctcgtg | ccggaccgaa | tacccggtct | 840 |
| gaacgaggtt | aattaaggta | cccaagaagt | acttagaggc | ggccgcctag | cataacccct | 900 |
| tggggcctct | aaacgggtct | tgaggggttt | tttgagaaac | ggccgaatac | acctgttcgg | 960 |
| atccagatct | cgatcccgcg | aaattaatac | gactcactat | agggagacca | caacggtttc | 1020 |
| cctctagatc | acaagtttgt | acaaaaaagc | aggctaagaa | ggagatatac | atatggcgtc | 1080 |
| taactttacc | caattcgttc | tggttgataa | cggcggtacg | ggtgacgtta | ccgtagctcc | 1140 |
| gtccaacttc | gccaacggtg | ttgcggaatg | gattagctct | aacagccgct | ctcaggccta | 1200 |
| caaagtcacg | tgctccgttc | gtcagtctag | cgcgcagaat | cgcaaataca | ccatcaaagt | 1260 |
| tgaagtaccg | aaagtcgcaa | cgcagaccgt | aggcggcgta | gaactcccag | ttgcggcctg | 1320 |
| gcgctcttac | ctcaacatgg | aactgactat | tccgattttt | gcgacgaact | ccgactgcga | 1380 |
| actgattgtt | aaggcaatgc | agggcctgct | gaaagacggt | aatccgatcc | catctgcaat | 1440 |
| cgctgctaac | tctggcattt | actaataagc | ggacgcgctg | ccaccgctga | gcaataacta | 1500 |
| gcataacccc | ttggggcctc | taaacgggtc | ttgagggggtt | ttttgctgaa | aggaggaact | 1560 |
| atatccggca | tgcaccattc | cttgcggcgg | cggtgctcaa | cggcctcaac | ctactactgg | 1620 |
| gctgcttcct | aatgcaggag | tcgcataagg | gagagcgtcg | accgatgccc | ttgagagcct | 1680 |
| tcaacccagt | cagctccttc | cggtgggcgc | ggggcatgac | tatcgtcgcc | gcacttatga | 1740 |
| ctgtcttctt | tatcatgcaa | ctcgtaggac | aggtgccggc | agcgctctgg | gtcatttcg | 1800 |
| gcgaggaccg | ctttcgctgg | agcgcgacga | tgatcggcct | gtcgcttgcg | gtattcggaa | 1860 |
| tcttgcacgc | cctcgctcaa | gccttcgtca | ctggtcccgc | caccaaacgt | ttcggcgaga | 1920 |
| agcaggccat | tatcgccggc | atggcggccg | acgcgctggg | ctacgtcttg | ctggcgttcg | 1980 |
| ccatggtcgt | cacagagctg | gaagcggcag | cgagaattat | ccgcgatcgt | ggcgcggtgc | 2040 |
| ccgcaggcat | gacaaacatc | gtaaatgccg | cgtttcgtgt | ggccgtggcc | gcccaggacg | 2100 |
| tgtcagcgcc | gccaccacct | gcaccgaatc | ggcagcagcg | tcgcgcgtcg | aaaaagcgca | 2160 |
| caggcggcaa | gaagcgataa | gctgcacgaa | tacctgaaaa | atgttgaacg | ccccgtgagc | 2220 |

```
ggtaactcac agggcgtcgg ctaaccccca gtccaaacct gggagaaagc gctcaaaaat    2280
gactctagcg gattcacgag acattgacac accggcctgg aaattttccg ctgatctgtt    2340
cgacacccat cccgagctcg cgctgcgatc acgtggctgg acgagcgaag accgccgcga    2400
attcctcgct cacctgggca gagaaaattt ccagggcagc aagacccgcg acttcgccag    2460
cgcttggatc aaagacccgg acacgggaga acacagccg aagttatacc gagttggttc    2520
aaaatcgctt gcccggtgcc agtatgttgc tctgacgcac gcgcagcacg cagccgtgct    2580
tgtcctggac attgatgtgc cgagccacca ggccggcggg aaaatcgagc acgtaaaccc    2640
cgaggtctac gcgattttgg agcgctgggc acgcctggaa aaagcgccag cttggatcgg    2700
cgtgaatcca ctgagcggga aatgccagct catctggctc attgatccgg tgtatgccgc    2760
agcaggcatg agcagcccga atatgcgcct gctggctgca acgaccgagg aaatgacccg    2820
cgttttcggc gctgaccagg cttttcaca taggctgagc cggtggccac tgcacgtctc    2880
cgacgatccc accgcgtacc gctggcatgc ccagcacaat cgcgtggatc gcctagctga    2940
tcttatggag gttgctcgca tgatctcagg cacagaaaaa cctaaaaaac gctatgagca    3000
ggagttttct agcggacggg cacgtatcga agcggcaaga aaagccactg cggaagcaaa    3060
agcacttgcc acgcttgaag caagcctgcc gagcgccgct gaagcgtctg gagagctgat    3120
cgacggcgtc cgtgtcctct ggactgctcc agggcgtgcc gcccgtgatg agacggcttt    3180
tcgccacgct ttgactgtgg ataccagtt aaaagcggct ggtgagcgcc taaaagacac    3240
caagatcatc gacgcctacg agcgtgccta ccgtcgct caggcggtcg gagcagacgg    3300
ccgtgagcct gatctgccgc cgatgcgtga ccgccagacg atggcgcgac gtgtgcgcgg    3360
ctacgtcgct aaaggccagc cagtcgtccc tgctcgtcag acagacgc agagcagccg    3420 agggcgaaaa gctctggcca ctatgggaag acgtggcggt aaaaaggccg cagaacgctg    3480
gaaagaccca acagtgagt acgcccgagc acagcgagaa aaactagcta agtccagtca    3540
acgacaagct aggaaagcta aggaaatcg cttgaccatt gcaggttggt ttatgactgt    3600
tgagggagag actggctcgt ggcgacaatc aatgaagcta tgtctgaatt tagcgtgtca    3660
cgtcagaccg tgaatagagc acttaagtct gcgggcattg aacttccacg aggacgccgt    3720
aaagcttccc agtaaatgtg ccatctcgta ggcagaaaac ggttccccc gtagggtct    3780 ctctcttggc ctccttta ggtcgggctg attgctcttg aagctctcta gggggctca    3840 caccatagc agataacggt tccccaccgg ctcacctcgt aagcgcacaa ggactgctcc    3900
caatgccgca agcactcagg gcgcaagggc tgctaaagga agcggaacac gtagaaagcc    3960
agtccgcaga acggtgctg accccggatg aatgtcagct actgggctat ctggacaagg    4020
gaaaacgcaa gcgcaaagag aaagcaggta gcttgcagtg gcttacatg gcgatagcta    4080 gactgggcgg tttatggac agcaagcgaa ccggaattgc cagctggggc ccctctggt    4140 aaggtgggga gccctgcaa agtaaactgg atggctttct gccgccaag gatctgatgg    4200 cgcaggggat caagatctga tcaagagaca ggatgaggat cgtttcgcat gattgaacaa    4260
gatggattgc acgcaggttc tccggccgct gggtggaga ggctattcgg ctatgactgg    4320
gcacaacaga caatcggctg ctctgatgcc gccgtgttcc ggctgtcagc gcaggggcgc    4380
ccggttcttt ttgtcaagac cgacctgtcc ggtgccctga atgaactcca agacgaggca    4440
gcgcggctat cgtggctggc cacgacgggc gttccttgcg cagctgtgct cgacgttgtc    4500
actgaagcgg gaagggactg gctgctattg ggcgaagtgc cggggcagga tctcctgtca    4560
```

-continued

```
tctcaccttg ctcctgccga gaaagtatcc atcatggctg atgcaatgcg gcggctgcat    4620
acgcttgatc cggctacctg cccattcgac caccaagcga aacatcgcat cgagcgagca    4680
cgtactcgga tggaagccgg tcttgtcgat caggatgatc tggacgaaga gcatcagggg    4740
ctcgcgccag ccgaactgtt cgccaggctc aaggcgcgga tgcccgacgg cgaggatctc    4800
gtcgtgaccc atggcgatgc ctgcttgccg aatatcatgg tggaaaatgg ccgcttttct    4860
ggattcatcg actgtggccg gctgggtgtg cggaccgct atcaggacat agcgttggct    4920
acccgtgata ttgctgaaga gcttggcggc gaatgggctg accgcttcct cgtgctttac    4980
ggtatcgccg ctcccgattc gcagcgcatc gccttctatc gccttcttga cgagttcttc    5040
tgagcgggac tctggggttc gctagaggat cgatcctttt taacccatca catatacctg    5100
ccgttcacta ttatttagtg aaatgagata ttatgatatt ttctgaattg tgattaaaaa    5160
ggcaacttta tgcccatgca acagaaacta taaaaaatac agagaatgaa agaaacaga    5220
tagattttt agttctttag gcccgtagtc tgcaaatcct tttatgattt tctatcaaac    5280
aaaagaggaa aatagaccag ttgcaatcca acgagagtc taacgacgcg aggctggatg    5340
gccttcccca ttatgattct tctcgcttcc ggcggcatcg ggatgcccgc gttgcaggcc    5400
atgctgtcca gcaggtaga tgacgaccat cagggacagc ttcaaggatc gctcgcggct    5460
cttaccagcc taacttcgat cattggaccg ctgatcgtca cggcgattta tgccgcctcg    5520
gcgagcacat ggaacgggtt ggcatggatt gtaggcgccg ccctatacct tgtctgcctc    5580
cccgcgttgc gtcgcggtgc atggagccgg gccacctcga cctgaatgga agccggcggc    5640
acctcgctaa cggattcacc actccaagaa ttggagccaa tcaattcttg cggagaactg    5700
tgaatgcgca aaccaaccct tggcagaaca tatccatcgc gtccgccatc tccagcagcc    5760
gcacgcggcg catctcgggc agcgttgggt cctggccacg ggtgcgcatg atcgtgctcc    5820
tgtcgttgag gacccggcta ggctggcggg gttgccttac tggttagcag aatgaatcac    5880
cgatacgcga cgaacgtga agcgactgct gctgcaaaac gtctgcgacc tgagcaacaa    5940
catgaatggt cttcggtttc cgtgtttcgt aaagtctgga aacgcggaag tcagcgccct    6000
gcaccattat gttccggatc tgcatcgcag gatgctgctg gctaccctgt ggaacaccta    6060
catctgtatt aacgaagcgc tggcattgac cctgagtgat ttttctctgg tcccgccgca    6120
tccataccgc cagttgttta ccctcacaac gttccagtaa ccgggcatgt tcatcatcag    6180
taacccgtat cgtgagcatc ctctctcgtt tcatcggtat cattacccc atgaacagaa    6240
atccccctta cacggaggca tcagtgacca acaggaaaa aaccgcccct aacatggccc    6300
gctttatcag aagccagaca ttaacgcttc tggagaaact caacgagctg acgcggatg    6360
aacaggcaga catctgtgaa tcgcttcacg accacgctga tgagctttac cgcagctgcc    6420
tcgcgcgttt cggtgatgac ggtgaaaacc tctgacacat gcagctcccg gagacggtca    6480
cagcttgtct gtaagcggat gccgggagca gacaagcccg tcaggcgcg tcagcgggtg    6540
ttggcgggtg tcgggcgca gccatgaccc agtcacgtag cgatagcgga gtgtatactg    6600
gcttaactat gcggcatcag agcagattgt actgagagtg caccatatgc ggtgtgaaat    6660
accgcacaga tgcgtaagga gaaaataccg catcaggcgc tcttccgctt cctcgctcac    6720
tgactcgctg cgctcggtcg ttcggctgcg gcgagcggta tcagctcact caaaggcggt    6780
aatacggtta tccacagaat caggggataa cgcaggaaag aacatgtgag caaaaggcca    6840
gcaaaaggcc aggaaccgta aaaaggccgc gttgctggcg ttttccata ggctccgccc    6900
ccctgacgag catcacaaaa atcgacgctc aagtcagagg tggcgaaacc cgacaggact    6960
```

```
ataaagatac caggcgtttc ccctggaag ctccctcgtg cgctctcctg ttccgaccct      7020
gccgcttacc ggatacctgt ccgcctttct ccttcgggaa gcgtggcgc tttctcatag      7080 ctcacgctgt aggtatctca gttcggtgta ggtcgttcgc tccaagctgg gctgtgtgca      7140 cgaaccccc gttcagcccg accgctgcgc cttatccggt aactatcgtc ttgagtccaa      7200
cccggtaaga cacgacttat cgccactggc agcagccact ggtaacagga ttagcagagc      7260
gaggtatgta ggcggtgcta cagagttctt gaagtggtgg cctaactacg gctacactag      7320
aaggacagta tttggtatct gcgctctgct gaagccagtt accttcggaa aaagagttgg      7380
tagctcttga tccggcaaac aaaccaccgc tggtagcggt ggttttttg tttgcaagca      7440 gcagattacg cgcagaaaaa aaggatctca agaagatcct ttgatctttt ctacggggtc      7500
tgacgctcag tggaacgaaa actcacgtta agggattttg gtcatgagat tatcaaaaag      7560
gatcttcacc tagatccttt taaattaaaa atgaagtttt aaatcaatct aaagtatata      7620
tgagtaaact tggtctgaca gttaccaatg cttaatcagt gaggcaccta tctcagcgat      7680
ctgtctattt cgttcatcca tagttgcctg actccccgtc gtgtagataa ctacgatacg      7740
ggagggctta ccatctggcc ccagtgctgc aatgataccg cgagacccac gctcaccggc      7800
tccagattta tcagcaataa accagccagc cggaagggcc gagcgcagaa gtggtcctgc      7860
aactttatcc gcctccatcc agtctattaa ttgttgccgg gaagctagag taagtagttc      7920
gccagttaat agtttgcgca acgttgttgc cattgctgca ggcatcgtgg tgtcacgctc      7980
gtcgtttggt atggcttcat tcagctccgg ttcccaacga tcaaggcgag ttacatgatc      8040
ccccatgttg tgcaaaaaag cggttagctc cttcggtcct ccgatcgttg tcagaagtaa      8100
gttggccgca gtgttatcac tcatggttat ggcagcactg cataattctc ttactgtcat      8160
gccatccgta agatgctttt ctgtgactgg tgagtactca accaagtcat tctgagaata      8220
gtgtatgcgg cgaccgagtt gctcttgccc ggcgtcaaca cgggataata ccgcgccaca      8280
tagcagaact ttaaaagtgc tcatcattgg aaaacgttct cggggcgaaa actctcaag      8340 gatcttaccg ctgttgagat ccagttcgat gtaaccccact cgtgcaccca actgatcttc      8400
agcatctttt actttcacca gcgtttctgg gtgagcaaaa acaggaaggc aaaatgccgc      8460
aaaaaaggga ataagggcga cacggaaatg ttgaatactc atactcttcc ttttcaata      8520 ttattgaagc atttatcagg gttattgtct catgagcgga tacatatttg aatgtattta      8580
gaaaaataaa caaatagggg ttccgcgcac atttccccga aaagtgccac ctgacgtcta      8640
agaaaccatt attatcatga cattaaccta taaaaatagg cgtatcacga ggccctttcg      8700
tcttcaagaa                                                            8710
```

```
<210> SEQ ID NO 32
<211> LENGTH: 8107
<212> TYPE: DNA
<213> ORGANISM: Artificial Sequence
<220> FEATURE:
<223> OTHER INFORMATION: Recombinant plasmid pAPSE10431; beta actin stem
      loop - coat protein
<220> FEATURE:
<221> NAME/KEY: promoter
<222> LOCATION: (38)..(56)
<223> OTHER INFORMATION: bacteriophage T7 gene 1 promoter
<220> FEATURE:
<221> NAME/KEY: misc_feature
<222> LOCATION: (60)..(67)
<223> OTHER INFORMATION: restriction endonuclease AsiSI recognition site
<220> FEATURE:
<221> NAME/KEY: misc_feature
```

```
<222> LOCATION: (68)..(362)
<223> OTHER INFORMATION: beta actin sense gene fragment
<220> FEATURE:
<221> NAME/KEY: misc_feature
<222> LOCATION: (362)..(369)
<223> OTHER INFORMATION: restriction endonuclease PmeI recognition site
<220> FEATURE:
<221> NAME/KEY: misc_feature
<222> LOCATION: (527)..(821)
<223> OTHER INFORMATION: beta actin antisense strand gene fragment
<220> FEATURE:
<221> NAME/KEY: terminator
<222> LOCATION: (887)..(934)
<223> OTHER INFORMATION: bacteriophage T7 transcription terminator
<220> FEATURE:
<221> NAME/KEY: misc_feature
<222> LOCATION: (1378)..(4721)
<223> OTHER INFORMATION: synthetic DNA (SEQ ID NO: 30)

<400> SEQUENCE: 32
ttcttagctc cggcaagcaa ttaagaactt ccgaaattaa tacgactcac tatagggagg    60
cgatcgcgca cgaggttttt ctgtctagtg agcagtgtcc aacctcaaaa gacaacatgt   120
gtgacgacga tgtagcggct cttgtcgtag acaatggatc cggtatgtgc aaagccggtt   180
tcgcaggaga tgacgcaccc cgtgccgtct tcccctcgat cgtcggtcgc ccaaggcatc   240
aaggagtcat ggtcggtatg gacaaaagg actcatacgt aggagatgaa gcccaaagca    300
aaagaggtat cctcaccctg aaataccca tcgaacacgg tatcatcacc aactgggatg    360
agtttaaacc ctctagctgc tttacaaagt actggttccc ttttccagcgg gatgctttat   420 ctaaacgcaa tgagagaggt attcctcagg ccacatcgct tcctagttcc gctgggatcc   480
atcgttggcg gccgaagccg ccattccata gtgagttctg gcgcgcctca tcccagttgg   540
tgatgatacc gtgttcgatg gggtatttca gggtgaggat acctcttttg ctttgggctt   600
catctcctac gtatgagtcc ttttgtccca taccgaccat gactccttga tgccttgggc   660
gaccgacgat cgaggggaag acggcacggg gtgcgtcatc tcctgcgaaa ccggctttgc   720
acataccgga tccattgtct acgacaagag ccgctacatc gtcgtcacac atgttgtctt   780
ttgaggttgg acactgctca ctagacagaa aaacctcgtg ccggaccgaa tacccggtct   840
gaacgaggtt aattaaggta cccaagaagt acttagaggc ggccgcctag cataaccct    900 tggggcctct aaacgggtct tgaggggttt tttgagaaac ggccgaatac acctgttcgg   960
atccagatcc accattcctt gcggcggcgg tgctcaacgg cctcaaccta ctactgggct  1020
gcttcctaat gcaggagtcg cataagggag agcgtcgacc gatgcccttg agagccttca  1080
acccagtcag ctccttccgg tgggcgcggg gcatgactat cgtcgccgca cttatgactg  1140
tcttctttat catgcaactc gtaggacagg tgccggcagc gctctgggtc attttcggcg  1200
aggaccgctt tcgctggagc gcgacgatga tcggcctgtc gcttgcgta ttcggaatct   1260 tgcacgccct cgctcaagcc ttcgtcactg gtcccgccac caaacgtttc ggcgagaagc  1320
aggccattat cgccggcatg gcggccgacg cgctgggcta cgtcttgctg gcgttcgcca  1380
tggtcgtcac agagctggaa gcggcagcga gaattatccg cgatcgtggc gcggtgcccg  1440
caggcatgac aaacatcgta aatgccgcgt tcgtgtggc cgtggccgcc caggacgtgt   1500
cagcgccgcc accacctgca ccgaatcggc agcagcgtcg cgcgtcgaaa aagcgcacag  1560
gcggcaagaa gcgataagct gcacgaatac ctgaaaaatg ttgaacgccc cgtgagcggt  1620
aactcacagg gcgtcggcta accccagtc caaacctggg agaaagcgct caaaatgac   1680 tctagcggat tcacgagaca ttgacacacc ggcctggaaa ttttccgctg atctgttcga  1740
```

```
cacccatccc gagctcgcgc tgcgatcacg tggctggacg agcgaagacc gccgcgaatt    1800
cctcgctcac ctgggcagag aaaatttcca gggcagcaag acccgcgact cgccagcgc    1860
ttggatcaaa gacccggaca cgggagaaac acagccgaag ttataccgag ttggttcaaa    1920
atcgcttgcc cggtgccagt atgttgctct gacgcacgcg cagcacgcag ccgtgcttgt    1980
cctggacatt gatgtgccga gccaccaggc cggcgggaaa atcgagcacg taaaccccga    2040
ggtctacgcg attttggagc gctgggcacg cctggaaaaa gcgccagctt ggatcggcgt    2100
gaatccactg agcgggaaat gccagctcat ctggctcatt gatccggtgt atgccgcagc    2160
aggcatgagc agcccgaata tgcgcctgct ggctgcaacg accgaggaaa tgacccgcgt    2220
tttcggcgct gaccaggctt tttcacatag gctgagccgg tggccactgc acgtctccga    2280
cgatcccacc gcgtaccgct ggcatgccca gcacaatcgc gtggatcgcc tagctgatct    2340
tatggaggtt gctcgcatga tctcaggcac agaaaaacct aaaaaacgct atgagcagga    2400
gttttctagc ggacgggcac gtatcgaagc ggcaagaaaa gccactgcgg aagcaaaagc    2460
acttgccacg cttgaagcaa gcctgccgag cgccgctgaa gcgtctggag agctgatcga    2520
cggcgtccgt gtcctctgga ctgctccagg gcgtgccgcc cgtgatgaga cggcttttcg    2580
ccacgctttg actgtgggat accagttaaa agcggctggt gagcgcctaa aagacaccaa    2640
gatcatcgac gcctacgagc gtgcctacac cgtcgctcag gcggtcggag cagacggccg    2700
tgagcctgat ctgccgccga tgcgtgaccg ccagacgatg gcgcgacgtg tgcgcggcta    2760
cgtcgctaaa ggccagccag tcgtccctgc tcgtcagaca gagacgcaga gcagccgagg    2820
gcgaaaagct ctggccacta tgggaagacg tggcggtaaa aaggccgcag aacgctggaa    2880
agacccaaac agtgagtacg cccgagcaca gcgagaaaaa ctagctaagt ccagtcaacg    2940
acaagctagg aaagctaaag gaaatcgctt gaccattgca ggttggttta tgactgttga    3000
gggagagact ggctcgtggc gacaatcaat gaagctatgt ctgaatttag cgtgtcacgt    3060
cagaccgtga atagagcact taagtctgcg ggcattgaac ttccacgagg acgccgtaaa    3120
gcttcccagt aaatgtgcca tctcgtaggc agaaaacggt tcccccgta ggggtctctc    3180
tcttggcctc cttctaggt cgggctgatt gctcttgaag ctctctaggg gggctcacac    3240
cataggcaga taacggttcc ccaccggctc acctcgtaag cgcacaagga ctgctcccaa    3300
tgccgcaagc actcagggcg caagggctgc taaaggaagc ggaacacgta gaaagccagt    3360
ccgcagaaac ggtgctgacc ccggatgaat gtcagctact gggctatctg gacaagggaa    3420
aacgcaagcg caaagagaaa gcaggtagct tgcagtgggc ttacatggcg atagctagac    3480
tgggcggttt tatggacagc aagcgaaccg gaattgccag ctggggcgcc ctctggtaag    3540
gttgggaagc cctgcaaagt aaactggatg gctttcttgc cgccaaggat ctgatggcgc    3600
aggggatcaa gatctgatca agagacagga tgaggatcgt ttcgcatgat tgaacaagat    3660
ggattgcacg caggttctcc ggccgcttgg gtggagaggc tattcggcta tgactgggca    3720
caacagacaa tcggctgctc tgatgccgcc gtgttccggc tgtcagcgca ggggcgcccg    3780
gttcttttg tcaagaccga cctgtccggt gccctgaatg aactccaaga cgaggcagcg    3840
cggctatcgt ggctggccac gacgggcgtt ccttgcgcag ctgtgctcga cgttgtcact    3900
gaagcgggaa gggactggct gctattgggc gaagtgccgg ggcaggatct cctgtcatct    3960
caccttgctc ctgccgagaa agtatccatc atggctgatg caatgcggcg gctgcatacg    4020
cttgatccgc ctacctgccc attcgaccac caagcgaaac atcgcatcga gcgagcacgt    4080
actcggatgg aagccggtct tgtcgatcag gatgatctgg acgaagagca tcaggggctc    4140
```

```
gcgccagccg aactgttcgc caggctcaag gcgcggatgc ccgacggcga ggatctcgtc      4200
gtgacccatg gcgatgcctg cttgccgaat atcatggtgg aaaatggccg ctttctgga      4260
ttcatcgact gtggccggct gggtgtggcg gaccgctatc aggacatagc gttggctacc      4320
cgtgatattg ctgaagagct tggcggcgaa tgggctgacc gcttcctcgt gctttacggt      4380
atcgccgctc ccgattcgca gcgcatcgcc ttctatcgcc ttcttgacga gttcttctga      4440
gcgggactct ggggttcgct agaggatcga tccttttttaa cccatcacat ataccctgccg     4500
ttcactatta tttagtgaaa tgagatatta tgatattttc tgaattgtga ttaaaaaggc      4560
aactttatgc ccatgcaaca gaaactataa aaaatacaga gaatgaaaag aaacagatag      4620
atttttttagt tctttaggcc cgtagtctgc aaatcctttt atgattttct atcaaacaaa      4680
agaggaaaat agaccagttg caatccaaac gagagtctaa cgacgcgagg ctggatggcc      4740
ttccccatta tgattcttct cgcttccggc ggcatcggga tgcccgcgtt gcaggccatg      4800
ctgtccaggc aggtagatga cgaccatcag ggacagcttc aaggatcgct cgcggctctt      4860
accagcctaa cttcgatcat tggaccgctg atcgtcacgg cgatttatgc cgcctcggcg      4920
agcacatgga acgggttggc atggattgta ggcgccgccc tataccttgt ctgcctcccc      4980
gcgttgcgtc gcggtgcatg gagccgggcc acctcgacct gaatggaagc cggcggcacc      5040
tcgctaacgg attcaccact ccaagaattg gagccaatca attcttgcgg agaactgtga      5100
atgcgcaaac caacccttgg cagaacatat ccatcgcgtc cgccatctcc agcagccgca      5160
cgcggcgcat ctcgggcagc gttgggtcct ggccacgggt gcgcatgatc gtgctcctgt      5220
cgttgaggac ccggctaggc tggcggggtt gccttactgg ttagcagaat gaatcaccga      5280
tacgcgagcg aacgtgaagc gactgctgct gcaaaacgtc tgcgacctga gcaacaacat      5340
gaatggtctt cggtttccgt gtttcgtaaa gtctggaaac gcggaagtca cgcccctgca      5400
ccattatgtt ccggatctgc atcgcaggat gctgctggct accctgtgga acacctacat      5460
ctgtattaac gaagcgctgg cattgaccct gagtgatttt tctctggtcc cgccgcatcc      5520
ataccgccag ttgtttaccc tcacaacgtt ccagtaaccg ggcatgttca tcatcagtaa      5580
cccgtatcgt gagcatcctc tctcgtttca tcggtatcat taccccccatg aacagaaatc      5640
cccccttacac ggaggcatca gtgaccaaac aggaaaaaac cgcccttaac atggcccgct      5700
ttatcagaag ccagacatta acgcttctgg agaaactcaa cgagctggac gcggatgaac      5760
aggcagacat ctgtgaatcg cttcacgacc acgctgatga gctttaccgc agctgcctcg      5820
cgcgtttcgg tgatgacggt gaaaacctct gacacatgca gctcccggag acggtcacag      5880
cttgtctgta gcggatgcc gggagcagac aagcccgtca gggcgcgtca gcgggtgttg      5940
gcgggtgtcg gggcgcagcc atgacccagt cacgtagcga tagcggagtg tatactggct      6000
taactatgcg gcatcagagc agattgtact gagagtgcac catatgcggt gtgaaatacc      6060
gcacagatgc gtaaggagaa aataccgcat caggcgctct ccgcttcct cgctcactga      6120
ctcgctgcgc tcggtcgttc ggctgcggcg agcggtatca gctcactcaa aggcggtaat      6180
acggttatcc acagaatcag gggataacgc aggaaagaac atgtgagcaa aaggccagca      6240
aaaggccagg aaccgtaaaa aggccgcgtt gctggcgttt ttccataggc tccgcccccc      6300
tgacgagcat cacaaaaatc gacgctcaag tcagaggtgg cgaaacccga caggactata      6360
aagataccag gcgtttcccc ctggaagctc cctcgtgcgc tctcctgttc cgaccctgcc      6420
gcttaccgga tacctgtccg cctttctccc ttcgggaagc gtggcgcttt ctcatagctc      6480
```

```
acgctgtagg tatctcagtt cggtgtaggt cgttcgctcc aagctgggct gtgtgcacga    6540
accccccgtt cagcccgacc gctgcgcctt atccggtaac tatcgtcttg agtccaaccc    6600
ggtaagacac gacttatcgc cactggcagc agccactggt aacaggatta gcagagcgag    6660
gtatgtaggc ggtgctacag agttcttgaa gtggtggcct aactacggct acactagaag    6720
gacagtattt ggtatctgcg ctctgctgaa gccagttacc ttcggaaaaa gagttggtag    6780
ctcttgatcc ggcaaacaaa ccaccgctgg tagcggtggt ttttttgttt gcaagcagca    6840
gattacgcgc agaaaaaaag gatctcaaga agatcctttg atcttttcta cggggtctga    6900
cgctcagtgg aacgaaaact cacgttaagg gattttggtc atgagattat caaaaaggat    6960
cttcacctag atccttttaa attaaaaatg aagttttaaa tcaatctaaa gtatatatga    7020
gtaaacttgg tctgacagtt accaatgctt aatcagtgag gcacctatct cagcgatctg    7080
tctatttcgt tcatccatag ttgcctgact ccccgtcgtg tagataacta cgatacggga    7140
gggcttacca tctggcccca gtgctgcaat gataccgcga gacccacgct caccggctcc    7200
agatttatca gcaataaacc agccagccgg aagggccgag cgcagaagtg gtcctgcaac    7260
tttatccgcc tccatccagt ctattaattg ttgccgggaa gctagagtaa gtagttcgcc    7320
agttaatagt ttgcgcaacg ttgttgccat tgctgcaggc atcgtggtgt cacgctcgtc    7380
gtttggtatg gcttcattca gctccggttc ccaacgatca aggcgagtta catgatcccc    7440
catgttgtgc aaaaaagcgg ttagctcctt cggtcctccg atcgttgtca gaagtaagtt    7500
ggccgcagtg ttatcactca tggttatggc agcactgcat aattctctta ctgtcatgcc    7560
atccgtaaga tgcttttctg tgactggtga gtactcaacc aagtcattct gagaatagtg    7620
tatgcggcga ccgagttgct cttgcccggc gtcaacacgg ataataccg cgccacatag    7680
cagaacttta aaagtgctca tcattggaaa acgttcttcg gggcgaaaac tctcaaggat    7740
cttaccgctg ttgagatcca gttcgatgta acccactcgt gcacccaact gatcttcagc    7800
atcttttact ttcaccagcg tttctgggtg agcaaaaaca ggaaggcaaa atgccgcaaa    7860
aaagggaata agggcgacac ggaaatgttg aatactcata ctcttccttt ttcaatatta    7920
ttgaagcatt tatcagggtt attgtctcat gagcggatac atatttgaat gtatttagaa    7980
aaataaacaa ataggggttc cgcgcacatt tccccgaaaa gtgccacctg acgtctaaga    8040
aaccattatt atcatgacat taacctataa aaataggcgt atcacgaggc cctttcgtct    8100
tcaagaa                                                              8107
```

```
<210> SEQ ID NO 33
<211> LENGTH: 9000
<212> TYPE: DNA
<213> ORGANISM: Artificial Sequence
<220> FEATURE:
<223> OTHER INFORMATION: Recombinant plasmid pAPSE10432; beta actin
      hairpin + coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (41)..(334)
<223> OTHER INFORMATION: beta actin sense gene fragment
<220> FEATURE:
<221> NAME/KEY: misc_feature
<222> LOCATION: (334)..(341)
```

```
<223> OTHER INFORMATION: restriction endonuclease PmeI recognition site
<220> FEATURE:
<221> NAME/KEY: misc_feature
<222> LOCATION: (498)..(793)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: promoter
<222> LOCATION: (1275)..(1293)
<223> OTHER INFORMATION: bacteriophage T7 gene 1 promoter
<220> FEATURE:
<221> NAME/KEY: gene
<222> LOCATION: (1366)..(1755)
<223> OTHER INFORMATION: bacteriophage MS2 coat protein gene
<220> FEATURE:
<221> NAME/KEY: terminator
<222> LOCATION: (1788)..(1835)
<223> OTHER INFORMATION: bacteriophage T7 transcription terminator
<220> FEATURE:
<221> NAME/KEY: misc_feature
<222> LOCATION: (2272)..(5614)
<223> OTHER INFORMATION: synthetic DNA (SEQ ID NO: 30)

<400> SEQUENCE: 33
ttccgaaatt aatacgactc actataggga ggcgatcgcg cacgaggttt ttctgtctag      60
tgagcagtgt ccaacctcaa agacaacat gtgtgacgac gatgtagcgg ctcttgtcgt     120
agacaatgga tccggtatgt gcaaagccgg tttcgcagga gatgacgcac cccgtgccgt     180
cttcccctcg atcgtcggtc gcccaaggca tcaaggagtc atggtcggta tgggacaaaa     240
ggactcatac gtaggagatg aagcccaaag caaaagaggg atcctcaccc tgaaataccc     300
catcgaacac ggtatcatca ccaactggga tgagtttaaa ccctctagct gctttacaaa     360
gtactggttc ccttttccagc gggatgcttt atctaaacgc aatgagagag gtattcctca     420
ggccacatcg cttcctagtt ccgctgggat ccatcgttgg cggccgaagc cgccattcca     480
tagtgagttc tggcgcgcct catcccagtt ggtgatgata ccgtgttcga tggggtattt     540
cagggtgagg atacctcttt tgctttgggc ttcatctcct acgtatgagt ccttttgtcc     600
cataccgacc atgactcctt gatgccttgg gcgaccgacg atcgagggga agacggcacg     660
gggtgcgtca tctcctgcga aaccggcttt gcacataccg gatccattgt ctacgacaag     720
agccgctaca tcgtcgtcac acatgttgtc ttttgaggtt ggacactgct cactagacag     780
aaaaacctcg tgccggaccg aatacccggt ctgaacgagg gcggccgcgg tacccaagaa     840
gtacttagag ttaattaagg agttcaaaca tgaggatcac ccatgtcgaa gctcccacac     900
cctagcataa cccccttgggg cctctaaacg ggtcttgagg ggttttttgc tgaaaggagg     960
aactatatcc ggatatccac aggacgggtg tggtcgccat gatcgcgtag tcgatagtgg    1020
ctccaagtag cgaagcgagc aggactgggc ggcgggcatg catcgtccat tccgacagca    1080
tcgccagtca ctatggcgtg ctgctagcgc tatatgcgtt gatgcaattt ctatgcgcac    1140
ccgttctcgg agcactgtcc gaccgctttg gccgccgccc agtcctgctc gcttcgctac    1200
ttggagccac tatcgactac gcgatcatgg cgaccacacc cgtcctgtgg atccagatct    1260
cgatcccgcg aaattaatac gactcactat agggagacca caacggtttc cctctagatc    1320
acaagtttgt acaaaaaagc aggctaagaa ggagatatac atatggcgtc taactttacc    1380
caattcgttc tggttgataa cggcggtacg ggtgacgtta ccgtagctcc gtccaacttc    1440
```

```
gccaacggtg ttgcggaatg gattagctct aacagccgct ctcaggccta caaagtcacg   1500
tgctccgttc gtcagtctag cgcgcagaat cgcaaataca ccatcaaagt tgaagtaccg   1560
aaagtcgcaa cgcagaccgt aggcggcgta gaactcccag ttgcggcctg cgctcttac    1620 ctcaacatgg aactgactat tccgattttt gcgacgaact ccgactgcga actgattgtt   1680
aaggcaatgc agggcctgct gaaagacggt aatccgatcc catctgcaat cgctgctaac   1740
tctggcattt actaataagc ggacgcgctg ccaccgctga gcaataacta gcataacccc   1800
ttggggcctc taaacgggtc ttgaggggtt ttttgctgaa aggaggaact atatccggca   1860
tgcaccattc cttgcggcgg cggtgctcaa cggcctcaac ctactactgg gctgcttcct   1920
aatgcaggag tcgcataagg gagagcgtcg accgatgccc ttgagagcct caacccagt    1980 cagctccttc cggtgggcgc ggggcatgac tatcgtcgcc gcacttatga ctgtcttctt   2040
tatcatgcaa ctcgtaggac aggtgccggc agcgctctgg gtcattttcg gcgaggaccg   2100 cttcgctgg agcgcgacga tgatcggcct gtcgcttgcg gtattcggaa tcttgcacgc     2160
cctcgctcaa gccttcgtca ctggtcccgc caccaaacgt ttcggcgaga agcaggccat   2220
tatcgccggc atggcggccg acgcgctggg ctacgtcttg ctggcgttcg ccatggtcgt   2280
cacagagctg gaagcggcag cgagaattat ccgcgatcgt ggcgcggtgc ccgcaggcat   2340
gacaaacatc gtaaatgccg cgtttcgtgt ggccgtggcc gcccaggacg tgtcagcgcc   2400
gccaccacct gcaccgaatc ggcagcagcg tcgcgcgtcg aaaaagcgca caggcggcaa   2460
gaagcgataa gctgcacgaa tacctgaaaa atgttgaacg ccccgtgagc ggtaactcac   2520
agggcgtcgg ctaaccccca gtccaaacct gggagaaagc gctcaaaaat gactctagcg   2580
gattcacgag acattgacac accggcctgg aaattttccg ctgatctgtt cgacacccat   2640
cccgagctcg cgctgcgatc acgtggctgg acgagcgaag accgccgcga attcctcgct   2700
cacctgggca gagaaaattt ccagggcagc aagaccgcg acttcgccag cgcttggatc     2760
aaagacccgg acacgggaga acacagccg aagttatacc gagttggttc aaaatcgctt     2820
gcccggtgcc agtatgttgc tctgacgcac gcgcagcacg cagccgtgct tgtcctggac   2880
attgatgtgc cgagccacca ggccggcggg aaaatcgagc acgtaaaccc cgaggtctac   2940
gcgattttgg agcgctgggc acgcctggaa aaagcgccag cttggatcgg cgtgaatcca   3000
ctgagcggga aatgccagct catctggctc attgatccgg tgtatgccgc agcaggcatg   3060
agcagcccga atatgcgcct gctggctgca acgaccgagg aaatgacccg cgttttcggc   3120
gctgaccagg ctttttcaca taggctgagc cggtggccac tgcacgtctc cgacgatccc   3180
accgcgtacc gctggcatgc ccagcacaat cgcgtggatc gcctagctga tcttatggag   3240
gttgctcgca tgatctcagg cacagaaaaa cctaaaaaac gctatgagca ggagttttct   3300
agcggacggg cacgtatcga agcggcaaga aaagccactg cggaagcaaa agcacttgcc   3360
acgcttgaag caagcctgcc gagcgccgct gaagcgtctg gagagctgat cgacggcgtc   3420
cgtgtcctct ggactgctcc agggcgtgcc gcccgtgatg agacggcttt tcgccacgct   3480
ttgactgtgg ataccagtt aaaagcggct ggtgagcgcc taaaagacac caagatcatc     3540
gacgcctacg agcgtgccta caccgtcgct caggcggtcg gagcagacgg ccgtgagcct   3600
gatctgccgc cgatgcgtga ccgccagacg atggcgcgac gtgtgcgcgg ctacgtcgct   3660
aaaggccagc cagtcgtccc tgctcgtcag acagagacgc agagcagccg agggcgaaaa   3720
gctctggcca ctatgggaag acgtggcggt aaaaaggccg cagaacgctg gaaagaccca   3780
```

-continued

```
aacagtgagt acgcccgagc acagcgagaa aaactagcta agtccagtca acgacaagct   3840
aggaaagcta aaggaaatcg cttgaccatt gcaggttggt ttatgactgt tgagggagag   3900
actggctcgt ggcgacaatc aatgaagcta tgtctgaatt tagcgtgtca cgtcagaccg   3960
tgaatagagc acttaagtct gcgggcattg aacttccacg aggacgccgt aaagcttccc   4020
agtaaatgtg ccatctcgta ggcagaaaac ggttcccccc gtaggggtct ctctcttggc   4080
ctcctttcta ggtcgggctg attgctcttg aagctctcta gggggctca caccataggc   4140
agataacggt tccccaccgg ctcacctcgt aagcgcacaa ggactgctcc caatgccgca   4200
agcactcagg gcgcaagggc tgctaaagga agcggaacac gtagaaagcc agtccgcaga   4260
aacggtgctg accccggatg aatgtcagct actgggctat ctggacaagg gaaaacgcaa   4320
gcgcaaagag aaagcaggta gcttgcagtg ggcttacatg gcgatagcta gactgggcgg   4380
ttttatggac agcaagcgaa ccggaattgc cagctggggc gccctctggt aaggttggga   4440
agccctgcaa agtaaactgg atggcttttct tgccgccaag gatctgatgg cgcaggggat   4500
caagatctga tcaagagaca ggatgaggat cgtttcgcat gattgaacaa gatgattgc    4560
acgcaggttc tccggccgct tgggtggaga ggctattcgg ctatgactgg gcacaacaga   4620
caatcggctg ctctgatgcc gccgtgttcc ggctgtcagc gcaggggcgc ccggttcttt   4680
ttgtcaagac cgacctgtcc ggtgccctga atgaactcca agacgaggca gcgcggctat   4740
cgtggctggc cacgacgggc gttccttgcg cagctgtgct cgacgttgtc actgaagcgg   4800
gaagggactg gctgctattg ggcgaagtgc cggggcagga tctcctgtca tctcaccttg   4860
ctcctgccga gaaagtatcc atcatggctg atgcaatgcg gcggctgcat acgcttgatc   4920
cggctacctg cccattcgac caccaagcga acatcgcat cgagcgagca cgtactcgga    4980
tggaagccgg tcttgtcgat caggatgatc tggacgaaga gcatcagggg ctcgcgccag   5040
ccgaactgtt cgccaggctc aaggcgcgga tgcccgacgg cgaggatctc gtcgtgaccc   5100
atggcgatgc ctgcttgccg aatatcatgg tggaaaatgg ccgcttttct ggattcatcg   5160
actgtggccg gctgggtgtg gcggaccgct atcaggacat agcgttggct acccgtgata   5220
ttgctgaaga gcttggcggc gaatgggctg accgcttcct cgtgctttac ggtatcgccg   5280
ctcccgattc gcagcgcatc gccttctatc gccttcttga cgagttcttc tgagcgggac   5340
tctgggttc gctagaggat cgatcctttt taacccatca catatacctg ccgttcacta   5400
ttatttagtg aaatgagata ttatgatatt ttctgaattg tgattaaaaa ggcaacttta   5460
tgcccatgca acagaaacta aaaaaatac agagaatgaa aagaaacaga tagattttt    5520
agttctttag gcccgtagtc tgcaaatcct tttatgattt tctatcaaac aaaagaggaa   5580
aatagaccag ttgcaatcca aacgagagtc taacgacgcg aggctggatg gccttcccca   5640
ttatgattct tctcgcttcc ggcggcatcg ggatgcccgc gttgcaggcc atgctgtcca   5700
ggcaggtaga tgacgaccat cagggacagc ttcaaggatc gctcgcggct cttaccagcc   5760
taacttcgat cattggaccg ctgatcgtca cggcgattta tgccgcctcg cgagcacat    5820
ggaacgggtt ggcatggatt gtaggcgccg ccctatacct tgtctgcctc cccgcgttgc   5880
gtcgcggtgc atggagccgg gccacctcga cctgaatgga agccggcggc acctcgctaa   5940
cggattcacc actccaagaa ttggagccaa tcaattcttg cggagaactg tgaatgcgca   6000
aaccaaccct tggcagaaca tatccatcgc gtccgccatc tccagcagcc gcacgcggcg   6060
catctcgggc agcgttgggt cctggccacg ggtgcgcatg atcgtgctcc tgtcgttgag   6120
gacccggcta ggctggcggg gttgccttac tggttagcag aatgaatcac cgatacgcga   6180
```

```
gcgaacgtga agcgactgct gctgcaaaac gtctgcgacc tgagcaacaa catgaatggt   6240
cttcggtttc cgtgtttcgt aaagtctgga acgcggaag tcagcgccct gcaccattat    6300
gttccggatc tgcatcgcag gatgctgctg gctaccctgt ggaacaccta catctgtatt   6360
aacgaagcgc tggcattgac cctgagtgat ttttctctgg tcccgccgca tccataccgc   6420
cagttgttta ccctcacaac gttccagtaa ccgggcatgt tcatcatcag taacccgtat   6480
cgtgagcatc ctctctcgtt tcatcggtat cattaccccc atgaacagaa atccccctta   6540
cacggaggca tcagtgacca aacaggaaaa aaccgccctt aacatggccc gctttatcag   6600
aagccagaca ttaacgcttc tggagaaact caacgagctg gacgcggatg aacaggcaga   6660
catctgtgaa tcgcttcacg accacgctga tgagctttac cgcagctgcc tcgcgcgttt   6720
cggtgatgac ggtgaaaacc tctgacacat gcagctcccg gagacggtca cagcttgtct   6780
gtaagcggat gccgggagca gacaagcccg tcagggcgcg tcagcgggtg ttggcgggtg   6840
tcggggcgca gccatgaccc agtcacgtag cgatagcgga gtgtatactg gcttaactat   6900
gcggcatcag agcagattgt actgagagtg caccatatgc ggtgtgaaat accgcacaga   6960
tgcgtaagga gaaaataccg catcaggcgc tcttccgctt cctcgctcac tgactcgctg   7020
cgctcggtcg ttcggctgcg gcgagcggta tcagctcact caaaggcggt aatacggtta   7080
tccacagaat caggggataa cgcaggaaag aacatgtgag caaaaggcca gcaaaaggcc   7140
aggaaccgta aaaaggccgc gttgctggcg tttttccata ggctccgccc ccctgacgag   7200
catcacaaaa atcgacgctc aagtcagagg tggcgaaacc cgacaggact ataaagatac   7260
caggcgtttc cccctggaag ctccctcgtg cgctctcctg ttccgaccct gccgcttacc   7320
ggatacctgt ccgcctttct cccttcggga agcgtggcgc tttctcatag ctcacgctgt   7380
aggtatctca gttcggtgta ggtcgttcgc tccaagctgg gctgtgtgca cgaaccccccc  7440
gttcagcccg accgctgcgc cttatccggt aactatcgtc ttgagtccaa cccggtaaga   7500
cacgacttat cgccactggc agcagccact ggtaacagga ttagcagagc gaggtatgta   7560
ggcggtgcta cagagttctt gaagtggtgg cctaactacg gctacactag aaggacagta   7620
tttggtatct gcgctctgct gaagccagtt accttcggaa aaagagttgg tagctcttga   7680
tccggcaaac aaaccaccgc tggtagcggt ggttttttg tttgcaagca gcagattacg    7740
cgcagaaaaa aaggatctca agaagatcct ttgatctttt ctacgggtc tgacgctcag    7800
tggaacgaaa actcacgtta agggattttg gtcatgagat tatcaaaaag gatcttcacc   7860
tagatccttt taaattaaaa atgaagtttt aaatcaatct aaagtatata tgagtaaact   7920
tggtctgaca gttaccaatg cttaatcagt gaggcaccta tctcagcgat ctgtctattt   7980
cgttcatcca tagttgcctg actccccgtc gtgtagataa ctacgatacg ggagggctta   8040
ccatctggcc ccagtgctgc aatgataccg cgagacccac gctcaccggc tccagattta   8100
tcagcaataa accagccagc cggaagggcc gagcgcagaa gtggtcctgc aactttatcc   8160
gcctccatcc agtctattaa ttgttgccgg gaagctagag taagtagttc gccagttaat   8220
agtttgcgca acgttgttgc cattgctgca ggcatcgtgg tgtcacgctc gtcgtttggt   8280
atggcttcat tcagctccgg ttcccaacga tcaaggcgag ttacatgatc ccccatgttg   8340
tgcaaaaaag cggttagctc cttcggtcct ccgatcgttg tcagaagtaa gttggccgca   8400
gtgttatcac tcatggttat ggcagcactg cataattctc ttactgtcat gccatccgta   8460
agatgctttt ctgtgactgg tgagtactca accaagtcat tctgagaata gtgtatgcgg   8520
```

-continued

| | |
|---|---|
| cgaccgagtt gctcttgccc ggcgtcaaca cgggataata ccgcgccaca tagcagaact | 8580 |
| ttaaaagtgc tcatcattgg aaaacgttct tcggggcgaa aactctcaag gatcttaccg | 8640 |
| ctgttgagat ccagttcgat gtaacccact cgtgcaccca actgatcttc agcatctttt | 8700 |
| actttcacca gcgtttctgg gtgagcaaaa acaggaaggc aaaatgccgc aaaaaaggga | 8760 |
| ataagggcga cacggaaatg ttgaatactc atactcttcc ttttttcaata ttattgaagc | 8820 |
| atttatcagg gttattgtct catgagcgga tacatatttg aatgtattta gaaaaataaa | 8880 |
| caaatagggg ttccgcgcac atttccccga aaagtgccac ctgacgtcta agaaaccatt | 8940 |
| attatcatga cattaaccta taaaaatagg cgtatcacga ggccctttcg tcttcaagaa | 9000 |

<210> SEQ ID NO 34
<211> LENGTH: 8198
<212> TYPE: DNA
<213> ORGANISM: Artificial Sequence
<220> FEATURE:
<223> OTHER INFORMATION: Recombinant plasmid pAPSE10433; beta actin
      hairpin - coat protein
<220> FEATURE:
<221> NAME/KEY: promoter
<222> LOCATION: (10)..(28)
<223> OTHER INFORMATION: bacteriophage T7 gene 1 promoter
<220> FEATURE:
<221> NAME/KEY: misc_feature
<222> LOCATION: (32)..(39)
<223> OTHER INFORMATION: restriction endonuclease AsiSI recognition site
<220> FEATURE:
<221> NAME/KEY: misc_feature
<222> LOCATION: (41)..(334)
<223> OTHER INFORMATION: beta actin sense gene fragment
<220> FEATURE:
<221> NAME/KEY: misc_feature
<222> LOCATION: (334)..(341)
<223> OTHER INFORMATION: restriction endonuclease PmeI site
<220> FEATURE:
<221> NAME/KEY: misc_feature
<222> LOCATION: (498)..(793)
<223> OTHER INFORMATION: beta actin antisense strand gene fragment
<220> FEATURE:
<221> NAME/KEY: misc_feature
<222> LOCATION: (868)..(886)
<223> OTHER INFORMATION: bacteriophage MS2 pac sequence
<220> FEATURE:
<221> NAME/KEY: terminator
<222> LOCATION: (902)..(949)
<223> OTHER INFORMATION: bacteriophage T7 transcription terminator
<220> FEATURE:
<221> NAME/KEY: misc_feature
<222> LOCATION: (1470)..(4812)
<223> OTHER INFORMATION: bacteriophage T7 transcription terminator

<400> SEQUENCE: 34

| | |
|---|---|
| ttccgaaatt aatacgactc actataggga ggcgatcgcg cacgaggttt ttctgtctag | 60 |
| tgagcagtgt ccaacctcaa aagacaacat gtgtgacgac gatgtagcgg ctcttgtcgt | 120 |
| agacaatgga tccggtatgt gcaaagccgg tttcgcagga gatgacgcac cccgtgccgt | 180 |
| cttcccctcg atcgtcggtc gcccaaggca tcaggagtc atggtcggta tgggacaaaa | 240 |
| ggactcatac gtaggagatg aagcccaaag caaaagaggt atcctcaccc tgaaataccc | 300 |
| catcgaacac ggtatcatca ccaactggga tgagtttaaa ccctctagct gctttacaaa | 360 |
| gtactggttc cctttccagc gggatgcttt atctaaacgc aatgagagag gtattcctca | 420 |
| ggccacatcg cttcctagtt ccgctgggat ccatcgttgg cggccgaagc cgccattcca | 480 |
| tagtgagttc tggcgcgcct catcccagtt ggtgatgata ccgtgttcga tggggtattt | 540 |
| cagggtgagg atacctcttt tgctttgggc ttcatctcct acgtatgagt cctttgtcc | 600 |

```
cataccgacc atgactcctt gatgccttgg gcgaccgacg atcgagggga agacggcacg    660
gggtgcgtca tctcctgcga aaccggcttt gcacataccg gatccattgt ctacgacaag    720
agccgctaca tcgtcgtcac acatgttgtc ttttgaggtt ggacactgct cactagacag    780
aaaaacctcg tgccggaccg aatacccggt ctgaacgagg cggccgcgg tacccaagaa     840 gtacttagag ttaattaagg agttcaaaca tgaggatcac ccatgtcgaa gctcccacac    900
cctagcataa cccttgggg cctctaaacg ggtcttgagg ggttttttgc tgaaaggagg     960
aactatatcc ggatatccac aggacgggtg tggtcgccat gatcgcgtag tcgatagtgg   1020
ctccaagtag cgaagcgagc aggactgggc ggcgggcatg caccattcct tgcggcggcg   1080
gtgctcaacg gcctcaacct actactgggc tgcttcctaa tgcaggagtc gcataaggga   1140
gagcgtcgac cgatgccctt gagagccttc aacccagtca gctccttccg gtgggcgcgg   1200
ggcatgacta tcgtcgccgc acttatgact gtcttcttta tcatgcaact cgtaggacag   1260
gtgccggcag cgctctgggt cattttcggc gaggaccgct ttcgctggag cgcgacgatg   1320
atcggcctgt cgcttgcggt attcggaatc ttgcacgccc tcgctcaagc cttcgtcact   1380
ggtcccgcca ccaaacgttt cggcgagaag caggccatta tcgccggcat ggcggccgac   1440
gcgctgggct acgtcttgct ggcgttcgcc atggtcgtca cagagctgga agcggcagcg   1500
agaattatcc gcgatcgtgg cgcggtgccc gcaggcatga caaacatcgt aaatgccgcg   1560
tttcgtgtgg ccgtggccgc ccaggacgtg tcagcgccgc caccacctgc accgaatcgg   1620
cagcagcgtc gcgcgtcgaa aaagcgcaca ggcggcaaga agcgataagc tgcacgaata   1680
cctgaaaaat gttgaacgcc ccgtgagcgg taactcacag ggcgtcggct aaccccccagt  1740 ccaaacctgg gagaaagcgc tcaaaaatga ctctagcgga ttcacgagac attgacacac   1800
cggcctggaa attttccgct gatctgttcg acacccatcc cgagctcgcg ctgcgatcac   1860
gtggctggac gagcgaagac cgccgcgaat tcctcgctca cctgggcaga gaaaatttcc   1920
agggcagcaa gacccgcgac ttcgccagcg cttggatcaa agaccccggac acggagaaa   1980 cacagccgaa gttataccga gttggttcaa aatcgcttgc ccggtgccag tatgttgctc   2040
tgacgcacgc gcagcacgca gccgtgcttg tcctggacat tgatgtgccg agccaccagg   2100
ccggcgggaa aatcgagcac gtaaaccccg aggtctacgc gattttggag cgctgggcac   2160
gcctggaaaa agcgccagct tggatcggcg tgaatccact gagcgggaaa tgccagctca   2220
tctggctcat tgatccggtg tatgccgcag caggcatgag cagcccgaat atgcgcctgc   2280
tggctgcaac gaccgaggaa atgacccgcg ttttcggcgc tgaccaggct ttttcacata   2340
ggctgagccg gtggccactg cacgtctccg acgatcccac cgcgtaccgc tggcatgccc   2400
agcacaatcg cgtggatcgc ctagctgatc ttatggaggt tgctcgcatg atctcaggca   2460
cagaaaaacc taaaaaacgc tatgagcagg agttttctag cggacgggca cgtatcgaag   2520
cggcaagaaa agccactgcg gaagcaaaag cacttgccac gcttgaagca agcctgccga   2580
gcgccgctga agcgtctgga gagctgatcg acggcgtccg tgtcctctgg actgctccag   2640
ggcgtgccgc ccgtgatgag acggcttttc gccacgcttt gactgtggga taccagttaa   2700
aagcggctgt tgagcgccta aaagacacca agatcatcga cgcctacgag cgtgcctaca   2760
ccgtcgctca ggcggtcgga gcagacggcc gtgagcctga tctgccgccg atgcgtgacc   2820
gccagacgat ggcgcgacgt gtgcgcggct acgtcgctaa aggccagcca gtcgtccctg   2880
ctcgtcagac agagacgcag agcagccgag ggcgaaaagc tctggccact atgggaagac   2940
gtggcggtaa aaaggccgca gaacgctgga aagacccaaa cagtgagtac gcccgagcac   3000
```

```
agcgagaaaa actagctaag tccagtcaac gacaagctag gaaagctaaa ggaaatcgct    3060
tgaccattgc aggttggttt atgactgttg agggagagac tggctcgtgg cgacaatcaa    3120
tgaagctatg tctgaattta gcgtgtcacg tcagaccgtg aatagagcac ttaagtctgc    3180
gggcattgaa cttccacgag gacgccgtaa agcttcccag taaatgtgcc atctcgtagg    3240
cagaaaacgg ttccccccgt aggggtctct ctcttggcct cctttctagg tcgggctgat    3300
tgctcttgaa gctctctagg ggggctcaca ccataggcag ataacggttc cccaccggct    3360
cacctcgtaa gcgcacaagg actgctccca atgccgcaag cactcagggc gcaagggctg    3420
ctaaaggaag cggaacacgt agaaagccag tccgcagaaa cggtgctgac cccggatgaa    3480
tgtcagctac tgggctatct ggacaaggga aaacgcaagc gcaaagagaa agcaggtagc    3540
ttgcagtggg cttacatggc gatagctaga ctgggcggtt ttatggacag caagcgaacc    3600
ggaattgcca gctggggcgc cctctggtaa ggttgggaag ccctgcaaag taaactggat    3660
ggctttcttg ccgccaagga tctgatggcg caggggatca agatctgatc aagagacagg    3720
atgaggatcg tttcgcatga ttgaacaaga tggattgcac gcaggttctc cggccgcttg    3780
ggtggagagg ctattcggct atgactgggc acaacagaca atcggctgct ctgatgccgc    3840
cgtgttccgg ctgtcagcgc aggggcgccc ggttcttttt gtcaagaccg acctgtccgg    3900
tgccctgaat gaactccaag acgaggcagc gcggctatcg tggctggcca cgacgggcgt    3960
tccttgcgca gctgtgctcg acgttgtcac tgaagcggga agggactggc tgctattggg    4020
cgaagtgccg gggcaggatc tcctgtcatc tcaccttgct cctgccgaga agtatccat    4080
catggctgat gcaatgcggc ggctgcatac gcttgatccg gctacctgcc cattcgacca    4140
ccaagcgaaa catcgcatcg agcgagcacg tactcggatg gaagccggtc ttgtcgatca    4200
ggatgatctg gacgaagagc atcaggggct cgcgccagcc gaactgttcg ccaggctcaa    4260
ggcgcggatg cccgacggcg aggatctcgt cgtgacccat ggcgatgcct gcttgccgaa    4320
tatcatggtg gaaaatggcc gcttttctgg attcatcgac tgtggccggc tgggtgtggc    4380
ggaccgctat caggacatag cgttggctac ccgtgatatt gctgaagagc ttggcggcga    4440
atgggctgac cgcttcctcg tgctttacgg tatcgccgct cccgattcgc agcgcatcgc    4500
cttctatcgc cttcttgacg agttcttctg agcgggactc tggggttcgc tagaggatcg    4560
atcctttttta acccatcaca tatacctgcc gttcactatt atttagtgaa atgagatatt    4620
atgatatttt ctgaattgtg attaaaaagg caactttatg cccatgcaac agaaactata    4680
aaaaatacag agaatgaaaa gaaacagata gattttttag ttctttaggc ccgtagtctg    4740
caaatccttt tatgattttc tatcaaacaa aagaggaaaa tagaccagtt gcaatccaaa    4800
cgagagtcta acgacgcgag gctggatggc cttccccatt atgattcttc tcgcttccgg    4860
cggcatcggg atgcccgcgt tgcaggccat gctgtccagg caggtagatg acgaccatca    4920
gggacagctt caaggatcgc tcgcggctct taccagccta acttcgatca ttggaccgct    4980
gatcgtcacg gcgatttatg ccgcctcggc gagcacatgg aacgggttgg catggattgt    5040
aggcgccgcc ctataccttg tctgcctccc cgcgttgcgt cgcggtgcat ggagccgggc    5100
cacctcgacc tgaatggaag ccggcggcac ctcgctaacg gattcaccac tccaagaatt    5160
ggagccaatc aattcttgcg gagaactgtg aatgcgcaaa ccaacccttg gcagaacata    5220
tccatcgcgt ccgccatctc cagcagccgc acgcggcgca tctcgggcag cgttgggtcc    5280
tggccacggg tgcgcatgat cgtgctcctg tcgttgagga cccggctagg ctggcggggt    5340
```

```
tgccttactg gttagcagaa tgaatcaccg atacgcgagc gaacgtgaag cgactgctgc   5400
tgcaaaacgt ctgcgacctg agcaacaaca tgaatggtct tcggtttccg tgtttcgtaa   5460
agtctggaaa cgcggaagtc agcgccctgc accattatgt tccggatctg catcgcagga   5520
tgctgctggc taccctgtgg aacacctaca tctgtattaa cgaagcgctg gcattgaccc   5580
tgagtgattt ttctctggtc ccgccgcatc cataccgcca gttgtttacc ctcacaacgt   5640
tccagtaacc gggcatgttc atcatcagta acccgtatcg tgagcatcct ctctcgtttc   5700
atcggtatca ttaccccat gaacagaaat ccccttaca cggaggcatc agtgaccaaa   5760
caggaaaaaa ccgcccttaa catggcccgc tttatcagaa gccagacatt aacgcttctg   5820
gagaaactca acgagctgga cgcggatgaa caggcagaca tctgtgaatc gcttcacgac   5880
cacgctgatg agctttaccg cagctgcctc gcgcgtttcg gtgatgacgg tgaaaacctc   5940
tgacacatgc agctcccgga cggtcaca gcttgtctgt aagcggatgc cgggagcaga   6000
caagcccgtc agggcgcgtc agcgggtgtt ggcgggtgtc ggggcgcagc catgacccag   6060
tcacgtagcg atagcggagt gtatactggc ttaactatgc ggcatcagag cagattgtac   6120
tgagagtgca ccatatgcgg tgtgaaatac cgcacagatg cgtaaggaga aataccgca   6180 tcaggcgctc ttccgcttcc tcgctcactg actcgctgcg ctcggtcgtt cggctgcggc   6240
gagcggtatc agctcactca aaggcggtaa tacggttatc cacagaatca ggggataacg   6300
caggaaagaa catgtgagca aaaggccagc aaaaggccag gaaccgtaaa aaggccgcgt   6360
tgctggcgtt tttccatagg ctccgccccc ctgacgagca tcacaaaaat cgacgctcaa   6420
gtcagaggtg gcgaaacccg acaggactat aaagatacca ggcgtttccc cctggaagct   6480
ccctcgtgcg ctctcctgtt ccgaccctgc cgcttaccgg atacctgtcc gcctttctcc   6540
cttcgggaag cgtggcgctt tctcatagct cacgctgtag gtatctcagt tcggtgtagg   6600
tcgttcgctc caagctgggc tgtgtgcacg aaccccccgt tcagcccgac cgctgcgcct   6660
tatccggtaa ctatcgtctt gagtccaacc cggtaagaca cgacttatcg ccactggcag   6720
cagccactgg taacaggatt agcagagcga ggtatgtagg cggtgctaca gagttcttga   6780
agtggtggcc taactacggc tacactagaa ggacagtatt tggtatctgc gctctgctga   6840
agccagttac cttcggaaaa agagttggta gctcttgatc cggcaaacaa accaccgctg   6900
gtagcggtgg tttttttgtt tgcaagcagc agattacgcg cagaaaaaaa ggatctcaag   6960
aagatccttt gatcttttct acggggtctg acgctcagtg gaacgaaaac tcacgttaag   7020
ggattttggt catgagatta tcaaaaagga tcttcaccta gatccttttta aattaaaaat   7080 gaagttttaa atcaatctaa agtatatatg agtaaacttg gtctgacagt taccaatgct   7140
taatcagtga ggcacctatc tcagcgatct gtctatttcg ttcatccata gttgcctgac   7200
tccccgtcgt gtagataact acgatacggg agggcttacc atctggcccc agtgctgcaa   7260
tgataccgcg agacccacgc tcaccggctc cagatttatc agcaataaac cagccagccg   7320
gaagggccga gcgcagaagt ggtcctgcaa ctttatccgc ctccatccag tctattaatt   7380
gttgccggga agctagagta agtagttcgc cagttaatag tttgcgcaac gttgttgcca   7440
ttgctgcagg catcgtggtg tcacgctcgt cgtttggtat ggcttcattc agctccggtt   7500
cccaacgatc aaggcgagtt acatgatccc ccatgttgtg caaaaaagcg gttagctcct   7560
tcggtcctcc gatcgttgtc agaagtaagt tggccgcagt gttatcactc atggttatgg   7620
cagcactgca taattctctt actgtcatgc catccgtaag atgcttttct gtgactggtg   7680
agtactcaac caagtcattc tgagaatagt gtatgcggcg accgagttgc tcttgcccgg   7740
```

```
cgtcaacacg ggataatacc gcgccacata gcagaacttt aaaagtgctc atcattggaa    7800
aacgttcttc ggggcgaaaa ctctcaagga tcttaccgct gttgagatcc agttcgatgt    7860
aacccactcg tgcacccaac tgatcttcag catcttttac tttcaccagc gtttctgggt    7920
gagcaaaaac aggaaggcaa aatgccgcaa aaaggggaat aagggcgaca cggaaatgtt    7980
gaatactcat actcttcctt tttcaatatt attgaagcat ttatcagggt tattgtctca    8040
tgagcggata catatttgaa tgtatttaga aaaataaaca aatagggggtt ccgcgcacat    8100 ttccccgaaa agtgccacct gacgtctaag aaaccattat tatcatgaca ttaacctata    8160
aaaataggcg tatcacgagg ccctttcgtc ttcaagaa                            8198
```

<210> SEQ ID NO 35
<211> LENGTH: 9327
<212> TYPE: DNA
<213> ORGANISM: Artificial Sequence
<220> FEATURE:
<223> OTHER INFORMATION: Recombinant plasmid pAPSE10434; beta actin
      hairpin + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1602)..(1620)
<223> OTHER INFORMATION: bacteriophage T7 gene 1 promoter
<220> FEATURE:
<221> NAME/KEY: gene
<222> LOCATION: (1693)..(2082)
<223> OTHER INFORMATION: bacteriophage MS2 coat protein gene
<220> FEATURE:
<221> NAME/KEY: terminator
<222> LOCATION: (2115)..(2162)
<223> OTHER INFORMATION: bacteriophage T7 transcription terminator
<220> FEATURE:
<221> NAME/KEY: misc_feature
<222> LOCATION: (2599)..(5941)
<223> OTHER INFORMATION: synthetic DNA (SEQ ID NO: 30)

<400> SEQUENCE: 35

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
```

```
caccgtcacc ctggatgctg taggcatagg cttggttatg ccggtactgc cgggcctctt    180
gcgggatgaa ttcagatctc gatcccgcga aattaatacg actcactata gggagaccac    240
aacggtttcc ctctagatca caagtttgta caaaaaagca ggctaagaag gagatataca    300
tacgccggcc attcaaacat gaggattacc catgtattta atacccatg tccaggcgcg     360 ctccgcgatc gcgcacgagg tttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttccctttcc agcgggatgc    720
tttatctaaa cgcaatgaga gaggtattcc tcaggccaca tcgcttccta gttccgctgg    780
gatccatcgt tggcggccga agccgccatt ccatagtgag ttctggcgcg cctcatccca    840
gttggtgatg ataccgtgtt cgatgggta tttcagggtg aggatacctc ttttgctttg     900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg ggcctctaa    1260 acgggtcttg aggggttttt tgctgaaagg aggaactata tccgcacagg acgggtgtgg   1320
tcgccatgat cgcgtagtcg atagtggctc caagtagcga agcgagcagg actgggcggc   1380
gggcatgcat cgtccattcc gacagcatcg ccagtcacta tggcgtgctg ctagcgctat   1440
atgcgttgat gcaatttcta tgcgcacccg ttctcggagc actgtccgac cgctttggcc   1500
gccgcccagt cctgctcgct tcgctacttg gagccactat cgactacgcg atcatggcga   1560
ccacacccgt cctgtggatc cagatctcga tcccgcgaaa ttaatacgac tcactatagg   1620
gagaccacaa cggtttccct ctagatcaca gtttgtaca aaaaagcagg ctaagaagga    1680
gatatacata tggcgtctaa ctttacccaa ttcgttctgg ttgataacgg cggtacgggt   1740
gacgttaccg tagctccgtc caacttcgcc aacggtgttg cggaatggat tagctctaac   1800
agccgctctc aggcctacaa agtcacgtgc tccgttcgtc agtctagcgc gcagaatcgc   1860
aaatacacca tcaaagttga agtaccgaaa gtcgcaacgc agaccgtagg cggcgtagaa   1920
ctcccagttg cggcctggcg ctcttacctc aacatggaac tgactattcc gattttgcg    1980 acgaactccg actgcgaact gattgttaag gcaatgcagg gcctgctgaa agacggtaat   2040
ccgatcccat ctgcaatcgc tgctaactct ggcatttact aataagcgga cgcgctgcca   2100
ccgctgagca ataactagca taaccccttg ggcctctaa acgggtcttg aggggttttt   2160
tgctgaaagg aggaactata tccggcatgc accattcctt gcggcggcgg tgctcaacgg   2220
cctcaaccta ctactgggct gcttcctaat gcaggagtcg cataagggag agcgtcgacc   2280
gatgcccttg agagccttca acccagtcag ctccttccgg tgggcgcggg gcatgactat   2340
cgtcgccgca cttatgactg tcttctttat catgcaactc gtaggacagg tgccggcagc   2400
gctctgggtc attttcggcg aggaccgctt tcgctggagc gcgacgatga tcggcctgtc   2460
```

```
gcttgcggta ttcggaatct tgcacgccct cgctcaagcc ttcgtcactg gtcccgccac    2520
caaacgtttc ggcgagaagc aggccattat cgccggcatg gcggccgacg cgctgggcta    2580
cgtcttgctg gcgttcgcca tggtcgtcac agagctggaa gcggcagcga gaattatccg    2640
cgatcgtggc gcggtgcccg caggcatgac aaacatcgta aatgccgcgt tcgtgtggc     2700 cgtggccgcc caggacgtgt cagcgccgcc accacctgca ccgaatcggc agcagcgtcg    2760
cgcgtcgaaa aagcgcacag gcggcaagaa gcgataagct gcacgaatac ctgaaaaatg    2820
ttgaacgccc cgtgagcggt aactcacagg gcgtcggcta accccagtc caaacctggg     2880 agaaagcgct caaaaatgac tctagcggat tcacgagaca ttgacacacc ggcctggaaa    2940
ttttccgctg atctgttcga cacccatccc gagctcgcgc tgcgatcacg tggctggacg    3000
agcgaagacc gccgcgaatt cctcgctcac ctgggcagag aaaatttcca gggcagcaag    3060
acccgcgact tcgccagcgc ttggatcaaa gacccggaca cgggagaaac acagccgaag    3120
ttataccgag ttggttcaaa atcgcttgcc cggtgccagt atgttgctct gacgcacgcg    3180
cagcacgcag ccgtgcttgt cctggacatt gatgtgccga ccaccaggc cggcgggaaa     3240 atcgagcacg taaaccccga ggtctacgcg attttggagc gctgggcacg cctggaaaaa    3300
gcgccagctt ggatcggcgt gaatccactg agcgggaaat gccagctcat ctggctcatt    3360
gatccggtgt atgccgcagc aggcatgagc agcccgaata tgcgcctgct ggctgcaacg    3420
accgaggaaa tgacccgcgt tttcggcgct gaccaggctt tttcacatag gctgagccgg    3480
tggccactgc acgtctccga cgatcccacc gcgtaccgct ggcatgccca gcacaatcgc    3540
gtggatcgcc tagctgatct tatggaggtt gctcgcatga tctcaggcac agaaaaacct    3600
aaaaaacgct atgagcagga gttttctagc ggacgggcac gtatcgaagc ggcaagaaaa    3660
gccactgcgg aagcaaaagc acttgccacg cttgaagcaa gcctgccgag cgccgctgaa    3720
gcgtctggag agctgatcga cggcgtccgt gtcctctgga ctgctccagg gcgtgccgcc    3780
cgtgatgaga cggctttttcg ccacgctttg actgtgggat accagttaaa agcggctggt    3840
gagcgcctaa aagacaccaa gatcatcgac gcctacgagc gtgcctacac cgtcgctcag    3900
gcggtcggag cagacggccg tgagcctgat ctgccgccga tgcgtgaccg ccagacgatg    3960
gcgcgacgtg tgcgcggcta cgtcgctaaa ggccagccag tcgtccctgc tcgtcagaca    4020
gagacgcaga gcagccgagg gcgaaaaagct ctggccacta tgggaagacg tggcggtaaa    4080
aaggccgcag aacgctggaa agacccaaac agtgagtacg cccgagcaca gcgagaaaaa    4140
ctagctaagt ccagtcaacg acaagctagg aaagctaaag gaaatcgctt gaccattgca    4200
ggttggttta tgactgttga gggagagact ggctcgtggc gacaatcaat gaagctatgt    4260
ctgaatttag cgtgtcacgt cagaccgtga atagagcact taagtctgcg ggcattgaac    4320
ttccacgagg acgccgtaaa gcttcccagt aaatgtgcca tctcgtaggc agaaaacggt    4380
tccccccgta ggggtctctc tcttggcctc ctttctaggt cgggctgatt gctcttgaag    4440
ctctctaggg gggctcacac cataggcaga taacggttcc ccaccggctc acctcgtaag    4500
cgcacaagga ctgctcccaa tgccgcaagc actcagggcg caagggctgc taaaggaagc    4560
ggaacacgta gaaagccagt ccgcagaaac ggtgctgacc ccggatgaat gtcagctact    4620
gggctatctg gacaagggaa aacgcaagcg caaagagaaa gcaggtagct tgcagtgggc    4680
ttacatggcg atagctagac tgggcggttt tatggacagc aagcgaaccg gaattgccag    4740
ctggggcgcc ctctggtaag gttgggaagc cctgcaaagt aaactggatg gctttcttgc    4800
cgccaaggat ctgatggcgc aggggatcaa gatctgatca agagacagga tgaggatcgt    4860
```

```
ttcgcatgat tgaacaagat ggattgcacg caggttctcc ggccgcttgg gtggagaggc      4920
tattcggcta tgactgggca acagacaa tcggctgctc tgatgccgcc gtgttccggc        4980
tgtcagcgca ggggcgcccg gttcttttg tcaagaccga cctgtccggt gccctgaatg       5040
aactccaaga cgaggcagcg cggctatcgt ggctggccac gacgggcgtt ccttgcgcag      5100
ctgtgctcga cgttgtcact gaagcgggaa gggactggct gctattgggc gaagtgccgg      5160
ggcaggatct cctgtcatct caccttgctc ctgccgagaa agtatccatc atggctgatg      5220
caatgcggcg gctgcatacg cttgatccgg ctacctgccc attcgaccac caagcgaaac     5280
atcgcatcga gcgagcacgt actcggatgg aagccggtct tgtcgatcag gatgatctgg    5340
acgaagagca tcaggggctc gcgccagccg aactgttcgc caggctcaag gcgcggatgc     5400
ccgacgcgca ggatctcgtc gtgacccatg gcgatgcctg cttgccgaat atcatggtgg     5460
aaaatggccg cttttctgga ttcatcgact gtggccggct gggtgtggcg gaccgctatc     5520
aggacatagc gttggctacc cgtgatattg ctgaagagct tggcggcgaa tgggctgacc     5580
gcttcctcgt gctttacggt atcgccgctc ccgattcgca gcgcatcgcc ttctatcgcc     5640
ttcttgacga gttcttctga gcgggactct ggggttcgct agaggatcga tccttttaa      5700 cccatcacat atacctgccg ttcactatta tttagtgaaa tgagatatta tgatattttc     5760
tgaattgtga ttaaaaggc aactttatgc ccatgcaaca gaaactataa aaatacaga       5820 gaatgaaaag aaacagatag attttttagt tctttaggcc cgtagtctgc aaatccttt      5880 atgattttct atcaaacaaa agaggaaaat agaccagttg caatccaaac gagagtctaa     5940
cgacgcgagg ctgatggcc ttccccatta tgattcttct cgcttccggc ggcatcggga      6000
tgcccgcgtt gcaggccatg ctgtccaggc aggtagatga cgaccatcag ggacagcttc     6060
aaggatcgct cgcggctctt accagcctaa cttcgatcat tggaccgctg atcgtcacgg     6120
cgatttatgc cgcctcggcg agcacatgga acgggttggc atggattgta ggcgccgccc    6180
tataccttgt ctgcctcccc gcgttgcgtc gcggtgcatg gagccgggcc acctcgacct    6240
gaatggaagc cggcggcacc tcgctaacgg attcaccact ccaagaattg gagccaatca    6300
attcttgcgg agaactgtga atgcgcaaac caaccttggg cagaacatat ccatcgcgtc     6360
cgccatctcc agcagccgca cgcggcgcat ctcgggcagc gttgggtcct ggccacgggt    6420
gcgcatgatc gtgctcctgt cgttgaggac ccggctaggc tggcgggggtt gccttactgg    6480 ttagcagaat gaatcaccga tacgcgagcg aacgtgaagc gactgctgct gcaaaacgtc     6540
tgcgacctga gcaacaacat gaatggtctt cggtttccgt gtttcgtaaa gtctggaaac    6600
gcggaagtca gcgccctgca ccattatgtt ccggatctgc atcgcaggat gctgctggct     6660
accctgtgga acacctacat ctgtattaac gaagcgctgg cattgaccct gagtgatttt     6720
tctctggtcc cgccgcatcc ataccgccag ttgtttaccc tcacaacgtt ccagtaaccg     6780
ggcatgttca tcatcagtaa cccgtatcgt gagcatcctc tctcgtttca tcggtatcat     6840
tacccccatg aacagaaatc ccccttacac ggaggcatca gtgaccaaac aggaaaaaac    6900
cgcccttaac atggcccgct ttatcagaag ccagacatta acgcttctgg agaaactcaa     6960
cgagctggac gcggatgaac aggcagacat ctgtgaatcg cttcacgacc acgctgatga    7020
gctttaccgc agctgcctcg cgcgtttcgg tgatgacggt gaaaacctct gacacatgca     7080
gctcccggag acggtcacag cttgtctgta agcggatgcc gggagcagac aagcccgtca     7140
gggcgcgtca gcgggtgttg gcgggtgtcg gggcgcagcc atgacccagt cacgtagcga     7200
```

```
tagcggagtg tatactggct taactatgcg gcatcagagc agattgtact gagagtgcac   7260
catatgcggt gtgaaatacc gcacagatgc gtaaggagaa aataccgcat caggcgctct   7320
tccgcttcct cgctcactga ctcgctgcgc tcggtcgttc ggctgcggcg agcggtatca   7380
gctcactcaa aggcggtaat acggttatcc acagaatcag gggataacgc aggaaagaac   7440
atgtgagcaa aaggccagca aaaggccagg aaccgtaaaa aggccgcgtt gctggcgttt   7500
ttccataggc tccgcccccc tgacgagcat cacaaaaatc gacgctcaag tcagaggtgg   7560
cgaaacccga caggactata aagataccag gcgtttcccc ctggaagctc cctcgtgcgc   7620
tctcctgttc cgaccctgcc gcttaccgga tacctgtccg cctttctccc ttcgggaagc   7680
gtggcgcttt ctcatagctc acgctgtagg tatctcagtt cggtgtaggt cgttcgctcc   7740
aagctgggct gtgtgcacga accccccgtt cagcccgacc gctgcgcctt atccggtaac   7800
tatcgtcttg agtccaaccc ggtaagacac gacttatcgc cactggcagc agccactggt   7860
aacaggatta gcagagcgag gtatgtaggc ggtgctacag agttcttgaa gtggtggcct   7920
aactacggct acactagaag gacagtattt ggtatctgcg ctctgctgaa gccagttacc   7980
ttcggaaaaa gagttggtag ctcttgatcc ggcaaacaaa ccaccgctgg tagcggtggt   8040
tttttttgttt gcaagcagca gattacgcgc agaaaaaaag gatctcaaga agatcctttg   8100
atcttttcta cggggtctga cgctcagtgg aacgaaaact cacgttaagg gattttggtc   8160
atgagattat caaaaaggat cttcacctag atccttttaa attaaaaatg aagttttaaa   8220
tcaatctaaa gtatatatga gtaaacttgg tctgacagtt accaatgctt aatcagtgag   8280
gcacctatct cagcgatctg tctatttcgt tcatccatag ttgcctgact ccccgtcgtg   8340
tagataacta cgatacggga gggcttacca tctggcccca gtgctgcaat gataccgcga   8400
gacccacgct caccggctcc agatttatca gcaataaacc agccagccgg aagggccgag   8460
cgcagaagtg gtcctgcaac tttatccgcc tccatccagt ctattaattg ttgccgggaa   8520
gctagagtaa gtagttcgcc agttaatagt ttgcgcaacg ttgttgccat tgctgcaggc   8580
atcgtggtgt cacgctcgtc gtttggtatg gcttcattca gctccggttc ccaacgatca   8640
aggcgagtta catgatcccc catgttgtgc aaaaaagcgg ttagctcctt cggtcctccg   8700
atcgttgtca gaagtaagtt ggccgcagtg ttatcactca tggttatggc agcactgcat   8760
aattctctta ctgtcatgcc atccgtaaga tgcttttctg tgactggtga gtactcaacc   8820
aagtcattct gagaatagtg tatgcggcga ccgagttgct cttgcccggc gtcaacacgg   8880
gataataccg cgccacatag cagaacttta aaagtgctca tcattggaaa acgttcttcg   8940
gggcgaaaac tctcaaggat cttaccgctg ttgagatcca gttcgatgta acccactcgt   9000
gcacccaact gatcttcagc atcttttact ttcaccagcg tttctgggtg agcaaaaaca   9060
ggaaggcaaa atgccgcaaa aaagggaata agggcgacac ggaaatgttg aatactcata   9120
ctcttccttt ttcaatatta ttgaagcatt tatcagggtt attgtctcat gagcggatac   9180
atatttgaat gtatttagaa aaataaacaa ataggggttc cgcgcacatt tccccgaaaa   9240
gtgccacctg acgtctaaga aaccattatt atcatgacat taacctataa aaataggcgt   9300
atcacgaggc cctttcgtct tcaagaa                                       9327
```

<210> SEQ ID NO 36
<211> LENGTH: 8531
<212> TYPE: DNA
<213> ORGANISM: Artificial Sequence
<220> FEATURE:
<223> OTHER INFORMATION: Recombinant plasmid pAPSE10435; beta actin

```
      hairpin - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1803)..(5145)
<223> OTHER INFORMATION: synthetic DNA (SEQ ID NO: 30)

<400> SEQUENCE: 36
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag agatatacca     300
tacgccggcc attcaaacat gaggattacc catgtattta aatacccatg tccaggcgcg     360
ctccgcgatc gcgcacgagg ttttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttcccttttcc agcgggatgc     720 tttatctaaa cgcaatgaga gaggtattcc tcaggccaca tcgcttccta gttccgctgg     780
gatccatcgt tggcggccga agccgccatt ccatagtgag ttctggcgcg cctcatccca     840
gttggtgatg ataccgtgtt cgatggggta tttcagggtg aggatacctc ttttgctttg     900
ggcttcatct cctacgtatg agtccttttg tcccataccg accatgactc cttgatgcct     960
tgggcgaccg acgatcgagg ggaagacggc acggggtgcg tcatctcctg cgaaaccggc    1020
tttgcacata ccggatccat tgtctacgac aagagccgct acatcgtcgt cacacatgtt    1080
gtcttttgag gttggacact gctcactaga cagaaaaacc tcgtgccgga ccgataccc    1140 ggtctgaacg agggcggccg cggtacccaa gaagtactta gagttaatta aggagttcaa    1200
```

```
acatgaggat cacccatgtc gaagctccca caccctagca taaccccttg gggcctctaa    1260
acgggtcttg aggggttttt tgctgaaagg aggaactata tccggatatc cacaggacgg    1320
gtgtggtcgc catgatcgcg tagtcgatag tggctccaag tagcgaagcg agcaggactg    1380
ggcggcgggc atgcaccatt ccttgcgcg gcggtgctca acggcctcaa cctactactg     1440
ggctgcttcc taatgcagga gtcgcataag ggagagcgtc gaccgatgcc cttgagagcc    1500
ttcaacccag tcagctcctt ccggtgggcg cggggcatga ctatcgtcgc cgcacttatg    1560
actgtcttct ttatcatgca actcgtagga caggtgccgg cagcgctctg ggtcattttc    1620
ggcgaggacc gctttcgctg gagcgcgacg atgatcggcc tgtcgcttgc ggtattcgga    1680
atcttgcacg ccctcgctca agccttcgtc actggtcccg ccaccaaacg tttcggcgag    1740
aagcaggcca ttatcgccgg catggcggcc gacgcgctgg gctacgtctt gctggcgttc    1800
gccatggtcg tcacagagct ggaagcggca gcgagaatta ccgcgatcg tggcgcggtg     1860
cccgcaggca tgacaaacat cgtaaatgcc gcgtttcgtg tggccgtggc cgcccaggac    1920
gtgtcagcgc cgccaccacc tgcaccgaat cggcagcagc gtcgcgcgtc gaaaaagcgc    1980
acaggcggca agaagcgata agctgcacga atacctgaaa aatgttgaac gccccgtgag    2040
cggtaactca cagggcgtcg gctaaccccc agtccaaacc tgggagaaag cgctcaaaaa    2100
tgactctagc ggattcacga gacattgaca caccggcctg gaaattttcc gctgatctgt    2160
tcgacaccca tcccgagctc gcgctgcgat cacgtggctg gacgagcgaa gaccgccgcg    2220
aattcctcgc tcacctgggc agagaaaatt tccaggcag caagacccgc gacttcgcca     2280
gcgcttggat caaagacccg gacacgggag aaacacagcc gaagttatac cgagttggtt    2340
caaaatcgct tgcccggtgc cagtatgttg ctctgacgca cgcgcagcac gcagccgtgc    2400
ttgtcctgga cattgatgtg ccgagccacc aggccggcgg gaaaatcgag cacgtaaacc    2460
ccgaggtcta cgcgattttg gagcgctggg cacgcctgga aaaagcgcca gcttggatcg    2520
gcgtgaatcc actgagcggg aaatgccagc tcatctggct cattgatccg gtgtatgccg    2580
cagcaggcat gagcagcccg aatatgcgcc tgctggctgc aacgaccgag gaaatgaccc    2640
gcgttttcgg cgctgaccag gcttttttcac ataggctgag ccggtggcca ctgcacgtct   2700
ccgacgatcc caccgcgtac cgctggcatg cccagcacaa tcgcgtggat cgcctagctg    2760
atcttatgga ggttgctcgc atgatctcag gcacagaaaa acctaaaaaa cgctatgagc    2820
aggagttttc tagcggacgg gcacgtatcg aagcggcaag aaaagccact gcggaagcaa    2880
aagcacttgc cacgcttgaa gcaagcctgc cgagcgccgc tgaagcgtct ggagagctga    2940
tcgacggcgt ccgtgtcctc tggactgctc cagggcgtgc cgcccgtgat gagacggctt    3000
ttcgccacgc tttgactgtg ggataccagt taaaagcggc tggtgagcgc ctaaaagaca    3060
ccaagatcat cgacgcctac gagcgtgcct acaccgtcgc tcaggcggtc ggagcagacg    3120
gccgtgagcc tgatctgccg ccgatgcgtg accgccagac gatggcgcga cgtgtgcgcg    3180
gctacgtcgc taaaggccag ccagtcgtcc ctgctcgtca gacagagacg cagagcagcc    3240
gagggcgaaa agctctggcc actatgggaa gacgtggcgg taaaaaggcc gcagaacgct    3300
ggaaagaccc aaacagtgag tacgcccgag cacagcgaga aaaactagct aagtccagtc    3360
aacgacaagc taggaaagct aaaggaaatc gcttgaccat tgcaggttgg tttatgactg    3420
ttgagggaga gactggctcg tggcgacaat caatgaagct atgtctgaat ttagcgtgtc    3480
acgtcagacc gtgaatagag cacttaagtc tgcgggcatt gaacttccac gaggacgccg    3540
```

```
taaagcttcc cagtaaatgt gccatctcgt aggcagaaaa cggttccccc cgtagggggtc    3600
tctctcttgg cctcctttct aggtcgggct gattgctctt gaagctctct aggggggctc    3660
acaccatagg cagataacgg ttccccaccg gctcacctcg taagcgcaca aggactgctc    3720
ccaatgccgc aagcactcag ggcgcaaggg ctgctaaagg aagcggaaca cgtagaaagc    3780
cagtccgcag aaacggtgct gaccccggat gaatgtcagc tactgggcta tctggacaag    3840
ggaaaacgca agcgcaaaga gaaagcaggt agcttgcagt gggcttacat ggcgatagct    3900
agactgggcg gttttatgga cagcaagcga accggaattg ccagctgggg cgccctctgg    3960
taaggttggg aagccctgca aagtaaactg gatggctttc ttgccgccaa ggatctgatg    4020
gcgcagggga tcaagatctg atcaagagac aggatgagga tcgtttcgca tgattgaaca    4080
agatggattg cacgcaggtt ctccggccgc ttgggtggag aggctattcg gctatgactg    4140
ggcacaacag acaatcggct gctctgatgc cgccgtgttc cggctgtcag cgcaggggcg    4200
cccggttctt tttgtcaaga ccgacctgtc cggtgccctg aatgaactcc aagacgaggc    4260
agcgcggcta tcgtggctgg ccacgacggg cgttccttgc gcagctgtgc tcgacgttgt    4320
cactgaagcg ggaagggact ggctgctatt gggcgaagtg ccggggcagg atctcctgtc    4380
atctcacctt gctcctgccg agaaagtatc catcatggct gatgcaatgc ggcggctgca    4440
tacgcttgat ccggctacct gcccattcga ccaccaagcg aaacatcgca tcgagcgagc    4500
acgtactcgg atggaagccg gtcttgtcga tcaggatgat ctggacgaag agcatcaggg    4560
gctcgcgcca gccgaactgt tcgccaggct caaggcgcgg atgcccgacg gcgaggatct    4620
cgtcgtgacc catggcgatg cctgcttgcc gaatatcatg gtggaaaatg gccgcttttc    4680
tggattcatc gactgtggcc ggctgggtgt ggcggaccgc tatcaggaca tagcgttggc    4740
tacccgtgat attgctgaag agcttggcgg cgaatgggct gaccgcttcc tcgtgcttta    4800
cggtatcgcc gctcccgatt cgcagcgcat cgccttctat cgccttcttg acgagttctt    4860
ctgagcggga ctctggggtt cgctagagga tcgatccttt ttaacccatc acatatacct    4920
gccgttcact attatttagt gaaatgagat attatgatat tttctgaatt gtgattaaaa    4980
aggcaacttt atgcccatgc aacagaaact ataaaaaata cagagaatga aaagaaacag    5040
atagattttt tagttctttta ggcccgtagt ctgcaaatcc ttttatgatt ttctatcaaa    5100
caaaagagga aaatagacca gttgcaatcc aaacgagagt ctaacgacgc gaggctggat    5160
ggccttcccc attatgattc ttctcgcttc cggcggcatc gggatgcccg cgttgcaggc    5220
catgctgtcc aggcaggtag atgacgacca tcagggacag cttcaaggat cgctcgcggc    5280
tcttaccagc ctaacttcga tcattggacc gctgatcgtc acggcgattt atgccgcctc    5340
ggcgagcaca tggaacgggt tggcatggat tgtaggcgcc gccctatacc ttgtctgcct    5400
ccccgcgttg cgtcgcggtg catggagccg gccacctcg acctgaatgg aagccggcgg    5460
cacctcgcta acggattcac cactccaaga attggagcca atcaattctt gcggagaact    5520
gtgaatgcgc aaaccaaccc ttggcagaac atatccatcg cgtccgccat ctccagcagc    5580
cgcacgcggc gcatctcggg cagcgttggg tcctggccac gggtgcgcat gatcgtgctc    5640
ctgtcgttga ggacccggct aggctggcgg ggttgcctta ctggttagca gaatgaatca    5700
ccgatacgcg agcgaacgtg aagcgactgc tgctgcaaaa cgtctgcgac ctgagcaaca    5760
acatgaatgg tcttcggttt ccgtgtttcg taaagtctgg aaacgcggaa gtcagcgccc    5820
tgcaccatta tgttccggat ctgcatcgca ggatgctgct ggctaccctg tggaacacct    5880
acatctgtat taacgaagcg ctggcattga ccctgagtga ttttctctg gtcccgccgc     5940
```

```
atccataccg ccagttgttt accctcacaa cgttccagta accgggcatg ttcatcatca   6000
gtaacccgta tcgtgagcat cctctctcgt ttcatcggta tcattacccc catgaacaga   6060
aatccccctt acacggaggc atcagtgacc aaacaggaaa aaaccgccct aacatggcc    6120 cgctttatca gaagccagac attaacgctt ctggagaaac tcaacgagct ggacgcggat   6180
gaacaggcag acatctgtga atcgcttcac gaccacgctg atgagcttta ccgcagctgc   6240
ctcgcgcgtt tcggtgatga cggtgaaaac ctctgacaca tgcagctccc ggagacggtc   6300
acagcttgtc tgtaagcgga tgccgggagc agacaagccc gtcagggcgc gtcagcgggt   6360
gttggcgggt gtcggggcgc agccatgacc cagtcacgta gcgatagcgg agtgtatact   6420
ggcttaacta tgcggcatca gagcagattg tactgagagt gcaccatatg cggtgtgaaa   6480
taccgcacag atgcgtaagg agaaaatacc gcatcaggcg ctcttccgct tcctcgctca   6540
ctgactcgct gcgctcggtc gttcggctgc ggcgagcggt atcagctcac tcaaaggcgg   6600
taatacggtt atccacagaa tcaggggata acgcaggaaa gaacatgtga gcaaaaggcc   6660
agcaaaaggc caggaaccgt aaaaaggccg cgttgctggc gtttttccat aggctccgcc   6720
cccctgacga gcatcacaaa aatcgacgct caagtcagag gtggcgaaac ccgacaggac   6780
tataaagata ccaggcgttt ccccctggaa gctccctcgt gcgctctcct gttccgaccc   6840
tgccgcttac cggatacctg tccgcctttc tcccttcggg aagcgtggcg ctttctcata   6900
gctcacgctg taggtatctc agttcggtgt aggtcgttcg ctccaagctg ggctgtgtgc   6960
acgaaccccc cgttcagccc gaccgctgcg ccttatccgg taactatcgt cttgagtcca   7020
acccggtaag acacgactta tcgccactgg cagcagccac tggtaacagg attagcagag   7080
cgaggtatgt aggcggtgct acagagttct tgaagtggtg gcctaactac ggctacacta   7140
gaaggacagt atttggtatc tgcgctctgc tgaagccagt taccttcgga aaaagagttg   7200
gtagctcttg atccggcaaa caaaccaccg ctggtagcgg tggttttttt gtttgcaagc   7260
agcagattac gcgcagaaaa aaaggatctc aagaagatcc tttgatcttt tctacggggt   7320
ctgacgctca gtggaacgaa aactcacgtt aagggatttt ggtcatgaga ttatcaaaaa   7380
ggatcttcac ctagatcctt ttaaattaaa aatgaagttt taaatcaatc taagtatat    7440 atgagtaaac ttggtctgac agttaccaat gcttaatcag tgaggcacct atctcagcga   7500
tctgtctatt tcgttcatcc atagttgcct gactccccgt cgtgtagata actacgatac   7560
gggagggctt accatctggc cccagtgctg caatgatacc gcgagaccca cgctcaccgg   7620
ctccagattt atcagcaata aaccagccag ccggaagggc cgagcgcaga agtggtcctg   7680
caactttatc cgcctccatc cagtctatta attgttgccg ggaagctaga gtaagtagtt   7740
cgccagttaa tagtttgcgc aacgttgttg ccattgctgc aggcatcgtg gtgtcacgct   7800
cgtcgtttgg tatggcttca ttcagctccg gttcccaacg atcaaggcga gttacatgat   7860
cccccatgtt gtgcaaaaaa gcggttagct ccttcggtcc tccgatcgtt gtcagaagta   7920
agttggccgc agtgttatca ctcatggtta tggcagcact gcataattct cttactgtca   7980
tgccatccgt aagatgcttt tctgtgactg gtgagtactc aaccaagtca ttctgagaat   8040
agtgtatgcg gcgaccgagt tgctcttgcc cggcgtcaac acgggataat accgcgccac   8100
atagcagaac tttaaaagtg ctcatcattg gaaaacgttc ttcggggcga aaactctcaa   8160
ggatcttacc gctgttgaga tccagttcga tgtaacccac tcgtgcaccc aactgatctt   8220
cagcatcttt tactttcacc agcgtttctg ggtgagcaaa aacaggaagg caaaatgccg   8280
```

```
caaaaaaggg aataagggcg acacggaaat gttgaatact catactcttc cttttcaat      8340 attattgaag catttatcag ggttattgtc tcatgagcgg atacatattt gaatgtattt     8400
agaaaaataa acaaataggg gttccgcgca catttccccg aaaagtgcca cctgacgtct     8460
aagaaaccat tattatcatg acattaacct ataaaaatag gcgtatcacg aggcccttc      8520 gtcttcaaga a                                                          8531
```

```
<210> SEQ ID NO 37
<211> LENGTH: 9520
<212> TYPE: DNA
<213> ORGANISM: Artificial Sequence
<220> FEATURE:
<223> OTHER INFORMATION: Recombinant plasmid pAPSE10436; beta actin
      hairpin + coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (665)..(672)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: promoter
<222> LOCATION: (1608)..(1626)
<223> OTHER INFORMATION: bacteriophage T7 gene 1 promoter
<220> FEATURE:
<221> NAME/KEY: gene
<222> LOCATION: (1699)..(2088)
<223> OTHER INFORMATION: bacteriophage MS2 coat protein gene
<220> FEATURE:
<221> NAME/KEY: terminator
<222> LOCATION: (2121)..(2168)
<223> OTHER INFORMATION: bacteriophage T7 transcription terminator
<220> FEATURE:
<221> NAME/KEY: misc_feature
<222> LOCATION: (2792)..(6134)
<223> OTHER INFORMATION: synthetic DNA (SEQ ID NO: 30)

<400> SEQUENCE: 37
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
```

```
gcgggatgaa ttcagatctc gatcccgcga aattaatacg actcactata gggagaccac    240
aacggtttcc ctctagatca caagtttgta caaaaaagca ggctaagaag gagatataca    300
tacgccggcc attcaaacat gaggattacc catgtattta aatacccatg tccaggcgcg    360
ctccgcgatc gcgcacgagg ttttttctgtc tagtgagcag tgtccaacct caaaagacaa    420
catgtgtgac gacgatgtag cggctcttgt cgtagacaat ggatccggta tgtgcaaagc    480
cggtttcgca ggagatgacg caccccgtgc cgtcttcccc tcgatcgtcg gtcgcccaag    540
gcatcaagga gtcatggtcg gtatgggaca aaaggactca tacgtaggag atgaagccca    600
aagcaaaaga ggtatcctca ccctgaaata ccccatcgaa cacggtatca tcaccaactg    660
ggatgagttt aaaccctcta gctgctttac aaagtactgg ttcccttttcc agcgggatgc    720 tttatctaaa cgcaacatga ggatcaccca tgtcgccaca tcgcttccta gttccgctgg    780
gatccatcgt tggcggccga agccgccatt ccatagtgag ttctggcgcg cctcatccca    840
gttggtgatg ataccgtgtt cgatgggta tttcagggtg aggatacctc ttttgctttg    900
ggcttcatct cctacgtatg agtccttttg tcccataccg accatgactc cttgatgcct    960
tgggcgaccg acgatcgagg ggaagacggc acggggtgcg tcatctcctg cgaaaccggc   1020
tttgcacata ccggatccat tgtctacgac aagagccgct acatcgtcgt cacacatgtt   1080
gtcttttgag gttggacact gctcactaga cagaaaaacc tcgtgccgga ccgaataccc   1140
ggtctgaacg agggcggccg cggtacccaa gaagtactta gagttaatta aggagttcaa   1200
acatgaggat cacccatgtc gaagctccca caccctagca taaccccttg gggcctctaa   1260
acgggtcttg aggggttttt tgctgaaagg aggaactata tccggatatc cacaggacgg   1320
gtgtggtcgc catgatcgcg tagtcgatag tggctccaag tagcgaagcg agcaggactg   1380
ggcggcgggc atgcatcgtc cattccgaca gcatcgccag tcactatggc gtgctgctag   1440
cgctatatgc gttgatgcaa tttctatgcg cacccgttct cggagcactg tccgaccgct   1500
ttggccgccg cccagtcctg ctcgcttcgc tacttggagc cactatcgac tacgcgatca   1560
tggcgaccac acccgtcctg tggatccaga tctcgatccc gcgaaattaa tacgactcac   1620
tatagggaga ccacaacggt ttccctctag atcacaagtt tgtacaaaaa agcaggctaa   1680
gaaggagata tacatatggc gtctaacttt acccaattcg ttctggttga taacggcggt   1740
acgggtgacg ttaccgtagc tccgtccaac ttcgccaacg tgttgcggga atggattagc   1800
tctaacagcc gctctcaggc ctacaaagtc acgtgctccg ttcgtcagtc tagcgcgcag   1860
aatcgcaaat acaccatcaa agttgaagta ccgaaagtcg caacgcagac cgtaggcggc   1920
gtagaactcc cagttgcggc ctggcgctct tacctcaaca tggaactgac tattccgatt   1980
tttgcgacga actccgactg cgaactgatt gttaaggcaa tgcagggcct gctgaaagac   2040
ggtaatccga tcccatctgc aatcgctgct aactctggca tttactaata gcggacgcg   2100 ctgccaccgc tgagcaataa ctagcataac cccttgggc ctctaaacgg tctgagggg   2160 gtttttttgct gaaaggagga actatatccg gcatgcatcg tccattccga cagcatcgcc   2220
agtcactatg gcgtgctgct agcgctatat gcgttgatgc aatttctatg cgcacccgtt   2280
ctcggagcac tgtccgaccg cttggccgc gcccagtcc tgctcgcttc gctacttgga   2340
gccactatcg actacgcgat catggcgacc acacccgtcc tgtaccattc cttgcggcgg   2400
cggtgctcaa cggcctcaac ctactactgg gctgcttcct aatgcaggag tcgcataagg   2460
gagagcgtcg accgatgccc ttgagagcct tcaacccagt cagctccttc cggtgggcgc   2520
ggggcatgac tatcgtcgcc gcacttatga ctgtcttctt tatcatgcaa ctcgtaggac   2580
```

```
aggtgccggc agcgctctgg gtcattttcg gcgaggaccg ctttcgctgg agcgcgacga   2640
tgatcggcct gtcgcttgcg gtattcggaa tcttgcacgc cctcgctcaa gccttcgtca   2700
ctggtcccgc caccaaacgt ttcggcgaga agcaggccat tatcgccggc atggcggccg   2760
acgcgctggg ctacgtcttg ctggcgttcg ccatggtcgt cacagagctg gaagcggcag   2820
cgagaattat ccgcgatcgt ggcgcggtgc ccgcaggcat gacaaacatc gtaaatgccg   2880
cgtttcgtgt ggccgtggcc gcccaggacg tgtcagcgcc gccaccacct gcaccgaatc   2940
ggcagcagcg tcgcgcgtcg aaaaagcgca caggcggcaa gaagcgataa gctgcacgaa   3000
tacctgaaaa atgttgaacg ccccgtgagc ggtaactcac agggcgtcgg ctaaccccca   3060
gtccaaacct gggagaaagc gctcaaaaat gactctagcg gattcacgag acattgacac   3120
accggcctgg aaattttccg ctgatctgtt cgacacccat cccgagctcg cgctgcgatc   3180
acgtggctgg acgagcgaag accgccgcga attcctcgct cacctgggca gagaaaattt   3240
ccagggcagc aagacccgcg acttcgccag cgcttggatc aaagacccgg acacgggaga   3300
aacacagccg aagttatacc gagttggttc aaaatcgctt gcccggtgcc agtatgttgc   3360
tctgacgcac gcgcagcacg cagccgtgct tgtcctggac attgatgtgc cgagccacca   3420
ggccggcggg aaaatcgagc acgtaaaccc cgaggtctac gcgattttgg agcgctgggc   3480
acgcctggaa aaagcgccag cttggatcgg cgtgaatcca ctgagcggga atgccagct   3540 catctggctc attgatccgg tgtatgccgc agcaggcatg agcagcccga atatgcgcct   3600
gctggctgca acgaccgagg aaatgacccg cgttttcggc gctgaccagg cttttttcaca   3660 taggctgagc cggtggccac tgcacgtctc cgacgatccc accgcgtacc gctggcatgc   3720
ccagcacaat cgcgtggatc gcctagctga tcttatggag gttgctcgca tgatctcagg   3780
cacagaaaaa cctaaaaaac gctatgagca ggagttttct agcggacggg cacgtatcga   3840
agcggcaaga aaagccactg cggaagcaaa agcacttgcc acgcttgaag caagcctgcc   3900
gagcgccgct gaagcgtctg gagagctgat cgacggcgtc cgtgtcctct ggactgctcc   3960
agggcgtgcc gcccgtgatg agacggcttt tcgccacgct ttgactgtgg gataccagtt   4020
aaaagcggct ggtgagcgcc taaaagacac caagatcatc gacgcctacg agcgtgccta   4080
caccgtcgct caggcggtcg gagcagacgg ccgtgagcct gatctgccgc cgatgcgtga   4140
ccgccagacg atggcgcgac gtgtgcgcgg ctacgtcgct aaaggccagc cagtcgtccc   4200
tgctcgtcag acagagacgc agagcagccg agggcgaaaa gctctggcca ctatgggaag   4260
acgtggcggt aaaaaggccg cagaacgctg gaaagaccca acagtgagt acgcccgagc   4320 acagcgagaa aaactagcta agtccagtca acgacaagct aggaaagcta aggaaatcg   4380 cttgaccatt gcaggttggt ttatgactgt tgagggagag actggctcgt ggcgacaatc   4440
aatgaagcta tgtctgaatt tagcgtgtca cgtcagaccg tgaatagagc acttaagtct   4500
gcgggcattg aacttccacg aggacgccgt aaagcttccc agtaaatgtg ccatctcgta   4560
ggcagaaaac ggttcccccc gtaggggtct ctctcttggc ctcctttcta ggtcgggctg   4620
attgctcttg aagctctcta gggggctca caccataggc agataacggt tccccaccgg   4680
ctcacctcgt aagcgcacaa ggactgctcc caatgccgca agcactcagg gcgcaagggc   4740
tgctaaagga agcggaacac gtagaaagcc agtccgcaga aacggtgctg accccggatg   4800
aatgtcagct actgggctat ctggacaagg gaaaacgcaa gcgcaaagag aaagcaggta   4860
gcttgcagtg ggcttacatg gcgatagcta gactgggcgg ttttatggac agcaagcgaa   4920
```

```
ccggaattgc cagctggggc gccctctggt aaggttggga agccctgcaa agtaaactgg    4980
atggctttct tgccgccaag gatctgatgg cgcaggggat caagatctga tcaagagaca    5040
ggatgaggat cgtttcgcat gattgaacaa gatggattgc acgcaggttc tccggccgct    5100
tgggtggaga ggctattcgg ctatgactgg gcacaacaga caatcggctg ctctgatgcc    5160
gccgtgttcc ggctgtcagc gcagggcgc ccggttcttt ttgtcaagac cgacctgtcc     5220
ggtgccctga tgaactcca agacgaggca gcgcggctat cgtggctggc cacgacgggc     5280
gttccttgcg cagctgtgct cgacgttgtc actgaagcgg gaagggactg gctgctattg    5340
ggcgaagtgc cggggcagga tctcctgtca tctcaccttg ctcctgccga gaaagtatcc    5400
atcatggctg atgcaatgcg gcggctgcat acgcttgatc cggctacctg cccattcgac    5460
caccaagcga aacatcgcat cgagcgagca cgtactcgga tggaagccgg tcttgtcgat    5520
caggatgatc tggacgaaga gcatcagggg ctcgcgccag ccgaactgtt cgccaggctc    5580
aaggcgcgga tgcccgacgg cgaggatctc gtcgtgaccc atggcgatgc ctgcttgccg    5640
aatatcatgg tggaaaatgg ccgcttttct ggattcatcg actgtggccg gctgggtgtg    5700
gcggaccgct atcaggacat agcgttggct acccgtgata ttgctgaaga gcttggcggc    5760
gaatgggctg accgcttcct cgtgctttac ggtatcgccg ctcccgattc gcagcgcatc    5820
gccttctatc gccttcttga cgagttcttc tgagcgggac tctggggttc gctagaggat    5880
cgatcctttt taacccatca catatacctg ccgttcacta ttatttagtg aaatgagata    5940
ttatgatatt ttctgaattg tgattaaaaa ggcaacttta tgcccatgca acagaaacta    6000
taaaaaatac agaatgaa aagaaacaga tagatttttt agttctttag gcccgtagtc      6060
tgcaaatcct tttatgattt tctatcaaac aaaagaggaa aatagaccag ttgcaatcca    6120
aacgagagtc taacgacgcg aggctggatg gccttcccca ttatgattct tctcgcttcc    6180
ggcggcatcg ggatgcccgc gttgcaggcc atgctgtcca ggcaggtaga tgacgaccat    6240
cagggacagc ttcaaggatc gctcgcggct cttaccagcc taacttcgat cattggaccg    6300
ctgatcgtca cggcgattta tgccgcctcg gcgagcacat ggaacgggtt ggcatggatt    6360
gtaggcgccg ccctatacct tgtctgcctc ccgcgttgc gtcgcggtgc atggagccgg     6420
gccacctcga cctgaatgga agccggcggc acctcgctaa cggattcacc actccaagaa    6480
ttggagccaa tcaattcttg cggagaactg tgaatgcgca aaccaaccct tggcagaaca    6540
tatccatcgc gtccgccatc tccagcagcc gcacgcggcg catctcgggc agcgttgggt    6600
cctggccacg ggtgcgcatg atcgtgctcc tgtcgttgag gacccggcta ggctggcggg    6660
gttgccttac tggttagcag aatgaatcac cgatacgcga gcgaacgtga agcgactgct    6720
gctgcaaaac gtctgcgacc tgagcaacaa catgaatggt cttcggtttc cgtgtttcgt    6780
aaagtctgga aacgcggaag tcagcgccct gcaccattat gttccggatc tgcatcgcag    6840
gatgctgctg gctaccctgt ggaacaccta catctgtatt aacgaagcgc tggcattgac    6900
cctgagtgat ttttctctgg tcccgccgca tccataccgc cagttgttta ccctcacaac    6960
gttccagtaa ccgggcatgt tcatcatcag taacccgtat cgtgagcatc ctctctcgtt    7020
tcatcggtat cattaccccc atgaacagaa atccccctta cacggaggca tcagtgacca    7080
aacaggaaaa aaccgccctt aacatggccc gctttatcag aagccagaca ttaacgcttc    7140
tggagaaact caacgagctg gacgcggatg aacaggcaga catctgtgaa tcgcttcacg    7200
accacgctga tgagctttac cgcagctgcc tcgcgcgttt cggtgatgac ggtgaaaacc    7260
tctgacacat gcagctcccg gagacggtca cagcttgtct gtaagcggat gccgggagca    7320
```

-continued

```
gacaagcccg tcagggcgcg tcagcgggtg ttggcgggtg tcgggcgcga gccatgaccc    7380
agtcacgtag cgatagcgga gtgtatactg gcttaactat gcggcatcag agcagattgt    7440
actgagagtg caccatatgc ggtgtgaaat accgcacaga tgcgtaagga gaaaataccg    7500
catcaggcgc tcttccgctt cctcgctcac tgactcgctg cgctcggtcg ttcggctgcg    7560
gcgagcggta tcagctcact caaaggcggt aatacggtta ccacagaat cagggataa      7620
cgcaggaaag aacatgtgag caaaaggcca gcaaaaggcc aggaaccgta aaaaggccgc    7680
gttgctggcg ttttttccata ggctccgccc ccctgacgag catcacaaaa atcgacgctc   7740
aagtcagagg tggcgaaacc cgacaggact ataaagatac caggcgtttc ccctggaag    7800
ctccctcgtg cgctctcctg ttccgaccct gccgcttacc ggatacctgt ccgcctttct   7860
cccttcggga agcgtggcgc tttctcatag ctcacgctgt aggtatctca gttcggtgta   7920
ggtcgttcgc tccaagctgg gctgtgtgca cgaaccccc gttcagcccg accgctgcgc    7980
cttatccggt aactatcgtc ttgagtccaa cccggtaaga cacgacttat cgccactggc   8040
agcagccact ggtaacagga ttagcagagc gaggtatgta ggcggtgcta cagagttctt   8100
gaagtggtgg cctaactacg gctacactag aaggacagta tttggtatct gcgtctgct   8160
gaagccagtt accttcggaa aaagagttgg tagctcttga tccggcaaac aaaccaccgc   8220
tggtagcggt ggttttttg tttgcaagca gcagattacg cgcagaaaaa aaggatctca    8280
agaagatcct ttgatctttt ctacggggtc tgacgctcag tggaacgaaa actcacgtta   8340
agggattttg gtcatgagat tatcaaaaag gatcttcacc tagatccttt taaattaaaa    8400
atgaagtttt aaatcaatct aaagtatata tgagtaaact tggtctgaca gttaccaatg   8460
cttaatcagt gaggcaccta tctcagcgat ctgtctattt cgttcatcca tagttgcctg   8520
actccccgtc gtgtagataa ctacgatacg ggagggctta ccatctggcc ccagtgctgc   8580
aatgataccg cgagacccac gctcaccggc tccagattta tcagcaataa accagccagc   8640
cggaagggcc gagcgcagaa gtggtcctgc aactttatcc gcctccatcc agtctattaa   8700
ttgttgccgg gaagctagag taagtagttc gccagttaat agtttgcgca acgttgttgc   8760
cattgctgca ggcatcgtgg tgtcacgctc gtcgtttggt atggcttcat tcagctccgg   8820
ttcccaacga tcaaggcgag ttacatgatc ccccatgttg tgcaaaaag cggttagctc    8880
cttcggtcct ccgatcgttg tcagaagtaa gttggccgca gtgttatcac tcatggttat   8940
ggcagcactg cataattctc ttactgtcat gccatccgta agatgctttt ctgtgactgg   9000
tgagtactca accaagtcat tctgagaata gtgtatgcgg cgaccgagtt gctcttgccc   9060
ggcgtcaaca cgggataata ccgcgccaca tagcagaact ttaaaagtgc tcatcattgg   9120
aaaacgttct cggggcgaaa actctcaag gatcttaccg ctgttgagat ccagttcgat    9180
gtaacccact cgtgcaccca actgatcttc agcatctttt actttcacca gcgtttctgg   9240
gtgagcaaaa acaggaaggc aaaatgccgc aaaaaaggga ataagggcga cacggaaatg   9300
ttgaatactc atactcttcc tttttcaata ttattgaagc atttatcagg gttattgtct   9360
catgagcgga tacatatttg aatgtattta gaaaaataaa caataggggt tccgcgcac    9420
atttccccga aaagtgccac ctgacgtcta agaaaccatt attatcatga cattaaccta   9480
taaaaatagg cgtatcacga ggccctttcg tcttcaagaa                          9520
```

<210> SEQ ID NO 38
<211> LENGTH: 8718
<212> TYPE: DNA

```
<213> ORGANISM: Artificial Sequence
<220> FEATURE:
<223> OTHER INFORMATION: Recombinant plasmid pAPSE10437; beta actin
      hairpin - coat protein
<220> FEATURE:
<221> NAME/KEY: promoter
<222> LOCATION: (214)..(232)
<223> OTHER INFORMATION: bacteriophage T7 gene 1 promoter
<220> FEATURE:
<221> NAME/KEY: misc_feature
<222> LOCATION: (317)..(335)
<223> OTHER INFORMATION: bacteriophage MS2 pac sequence
<220> FEATURE:
<221> NAME/KEY: misc_feature
<222> LOCATION: (365)..(372)
<223> OTHER INFORMATION: restriction endonuclease AsiSI recognition site
<220> FEATURE:
<221> NAME/KEY: misc_feature
<222> LOCATION: (374)..(667)
<223> OTHER INFORMATION: beta actin sense gene fragment
<220> FEATURE:
<221> NAME/KEY: misc_feature
<222> LOCATION: (667)..(674)
<223> OTHER INFORMATION: restriction endonuclease PmeI recognition site
<220> FEATURE:
<221> NAME/KEY: misc_feature
<222> LOCATION: (735)..(753)
<223> OTHER INFORMATION: bacteriophage MS2 pac sequence
<220> FEATURE:
<221> NAME/KEY: misc_feature
<222> LOCATION: (832)..(1126)
<223> OTHER INFORMATION: beta actin antisense strand gene fragment
<220> FEATURE:
<221> NAME/KEY: misc_feature
<222> LOCATION: (1201)..(1219)
<223> OTHER INFORMATION: bacteriophage MS2 pac sequence
<220> FEATURE:
<221> NAME/KEY: terminator
<222> LOCATION: (1235)..(1282)
<223> OTHER INFORMATION: bacteriophage T7 transcription terminator
<220> FEATURE:
<221> NAME/KEY: misc_feature
<222> LOCATION: (1990)..(5332)
<223> OTHER INFORMATION: synthetic DNA (SEQ ID NO: 30)

<400> SEQUENCE: 38
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatgaa ttcagatctc gatcccgcga aattaatacg actcactata gggagaccac     240
aacggtttcc ctctagatca caagtttgta caaaaaagca ggctaagaag gagatataca     300
tacgccggcc attcaaacat gaggattacc catgtattta aatacccatg tccaggcgcg     360
ctccgcgatc gcgcacgagg ttttctgtc tagtgagcag tgtccaacct caaaagacaa     420
catgtgtgac gacgatgtag cggctcttgt cgtagacaat ggatccggta tgtgcaaagc     480
cggtttcgca ggagatgacg caccccgtgc cgtcttcccc tcgatcgtcg gtcgcccaag     540
gcatcaagga gtcatggtcg gtatgggaca aaaggactca tacgtaggag atgaagccca     600
aagcaaaaga ggtatcctca ccctgaaata ccccatcgaa cacggtatca tcaccaactg     660
ggatgagttt aaaccctcta gctgctttac aaagtactgg ttcccttcc agcgggatgc     720 tttatctaaa cgcaacatga ggatcaccca tgtcgccaca tcgcttccta gttccgctgg     780
gatccatcgt tggcggccga agccgccatt ccatagtgag ttctggcgcg cctcatccca     840
gttggtgatg ataccgtgtt cgatggggta tttcagggtg aggataccc ttttgctttg     900 ggcttcatct cctacgtatg agtcctttg tcccataccg accatgactc cttgatgcct     960
```

```
tgggcgaccg acgatcgagg ggaagacggc acggggtgcg tcatctcctg cgaaaccggc    1020
tttgcacata ccggatccat tgtctacgac aagagccgct acatcgtcgt cacacatgtt    1080
gtcttttgag gttggacact gctcactaga cagaaaaacc tcgtgccgga ccgaataccc    1140
ggtctgaacg agggcggccg cggtacccaa gaagtactta gagttaatta aggagttcaa    1200
acatgaggat cacccatgtc gaagctccca caccctagca taaccccttg gggcctctaa    1260
acgggtcttg aggggttttt tgctgaaagg aggaactata tccggatatc cacaggacgg    1320
gtgtggtcgc catgatcgcg tagtcgatag tggctccaag tagcgaagcg agcaggactg    1380
ggcggcgggc atgcatcgtc cattccgaca gcatcgccag tcactatggc gtgctgctag    1440
cgctatatgc gttgatgcaa tttctatgcg cacccgttct cggagcactg tccgaccgct    1500
ttggccgccg cccagtcctg ctcgcttcgc tacttggagc cactatcgac tacgcgatca    1560
tggcgaccac accgtcctg taccattcct tgcggcggcg gtgctcaacg gcctcaacct    1620
actactgggc tgcttcctaa tgcaggagtc gcataaggga gagcgtcgac cgatgccctt    1680
gagagccttc aacccagtca gctccttccg gtgggcgcgg ggcatgacta tcgtcgccgc    1740
acttatgact gtcttcttta tcatgcaact cgtaggacag gtgccggcag cgctctgggt    1800
cattttcggc gaggaccgct ttcgctggag cgcgacgatg atcggcctgt cgcttgcggt    1860
attcggaatc ttgcacgccc tcgctcaagc cttcgtcact ggtcccgcca ccaaacgttt    1920
cggcgagaag caggccatta tcgccggcat ggcggccgac gcgctgggct acgtcttgct    1980
ggcgttcgcc atggtcgtca cagagctgga agcggcagcg agaattatcc gcgatcgtgg    2040
cgcggtgccc gcaggcatga caaacatcgt aaatgccgcg tttcgtgtgg ccgtggccgc    2100
ccaggacgtg tcagcgccgc caccacctgc accgaatcgg cagcagcgtc gcgcgtcgaa    2160
aaagcgcaca ggcggcaaga agcgataagc tgcacgaata cctgaaaaat gttgaacgcc    2220
ccgtgagcgg taactcacag ggcgtcggct aaccccccagt ccaaacctgg gagaaagcgc    2280
tcaaaaatga ctctagcgga ttcacgagac attgacacac cggcctggaa attttccgct    2340
gatctgttcg acacccatcc cgagctcgcg ctgcgatcac gtggctggac gagcgaagac    2400
cgccgcgaat tcctcgctca cctgggcaga gaaaatttcc agggcagcaa gacccgcgac    2460
ttcgccagcg cttggatcaa agacccggac acgggagaaa cacagccgaa gttataccga    2520
gttggttcaa aatcgcttgc ccggtgccag tatgttgctc tgacgcacgc gcagcacgca    2580
gccgtgcttg tcctggacat tgatgtgccg agccaccagg ccggcgggaa aatcgagcac    2640
gtaaaccccg aggtctacgc gattttggag cgctgggcac gcctgaaaaa gcgccagct    2700
tggatcggcg tgaatccact gagcgggaaa tgccagctca tctggctcat tgatccggtg    2760
tatgccgcag caggcatgag cagcccgaat atgcgcctgc tggctgcaac gaccgaggaa    2820
atgacccgcg ttttcggcgc tgaccaggct ttttcacata ggctgagccg gtggccactg    2880
cacgtctccg acgatcccac cgcgtaccgc tggcatgccc agcacaatcg cgtggatcgc    2940
ctagctgatc ttatggaggt tgctcgcatg atctcaggca cagaaaaacc taaaaaacgc    3000
tatgagcagg agttttctag cggacgggca cgtatcgaag cggcaagaaa agccactgcg    3060
gaagcaaaag cacttgccac gcttgaagca agcctgccga gcgccgctga agcgtctgga    3120
gagctgatcg acggcgtccg tgtcctctgg actgctccag ggcgtgccgc ccgtgatgag    3180
acggcttttc gccacgcttt gactgtggga taccagttaa aagcggctgg tgagcgccta    3240
aaagacacca agatcatcga cgcctacgag cgtgcctaca ccgtcgctca ggcggtcgga    3300
gcagacggcc gtgagcctga tctgccgccg atgcgtgacc gccagacgat ggcgcgacgt    3360
```

```
gtgcgcggct acgtcgctaa aggccagcca gtcgtccctg ctcgtcagac agagacgcag      3420
agcagccgag ggcgaaaagc tctggccact atgggaagac gtggcggtaa aaaggccgca      3480
gaacgctgga aagacccaaa cagtgagtac gcccgagcac agcgagaaaa actagctaag      3540
tccagtcaac gacaagctag gaaagctaaa ggaaatcgct tgaccattgc aggttggttt      3600
atgactgttg agggagagac tggctcgtgg cgacaatcaa tgaagctatg tctgaattta      3660
gcgtgtcacg tcagaccgtg aatagagcac ttaagtctgc gggcattgaa cttccacgag      3720
gacgccgtaa agcttcccag taaatgtgcc atctcgtagg cagaaaacgg ttcccccgt       3780 aggggtctct ctcttggcct cctttctagg tcgggctgat tgctcttgaa gctctctagg      3840
ggggctcaca ccataggcag ataacggttc cccaccggct cacctcgtaa gcgcacaagg      3900
actgctccca atgccgcaag cactcagggc gcagggctg ctaaaggaag cggaacacgt       3960
agaaagccag tccgcagaaa cggtgctgac cccggatgaa tgtcagctac tgggctatct      4020
ggacaaggga aaacgcaagc gcaaagagaa agcaggtagc ttgcagtggg cttacatggc      4080
gatagctaga ctgggcggtt ttatggacag caagcgaacc ggaattgcca gctggggcgc      4140
cctctggtaa ggttgggaag ccctgcaaag taaactggat ggcttcttg ccgccaagga      4200 tctgatggcg caggggatca agatctgatc aagagacagg atgaggatcg tttcgcatga      4260
ttgaacaaga tggattgcac gcaggttctc cggccgcttg ggtggagagg ctattcggct      4320
atgactgggc acaacagaca atcggctgct ctgatgccgc cgtgttccgg ctgtcagcgc      4380
aggggcgccc ggttctttt gtcaagaccg acctgtccgg tgccctgaat gaactccaag      4440
acgaggcagc gcggctatcg tggctggcca cgacgggcgt tccttgcgca gctgtgctcg      4500
acgttgtcac tgaagcggga agggactggc tgctattggg cgaagtgccg ggcaggatc      4560 tcctgtcatc tcaccttgct cctgccgaga agtatccat catggctgat gcaatgcggc       4620
ggctgcatac gcttgatccg gctacctgcc cattcgacca ccaagcgaaa catcgcatcg      4680
agcgagcacg tactcggatg aagccggtc ttgtcgatca ggatgatctg gacgaagagc      4740
atcaggggct cgcgccagcc gaactgttcg ccaggctcaa ggcgcggatg cccgacggcg      4800
aggatctcgt cgtgacccat ggcgatgcct gcttgccgaa tatcatggtg aaaatggcc       4860 gcttttctgg attcatcgac tgtggccggc tgggtgtggc ggaccgctat caggacatag      4920
cgttggctac ccgtgatatt gctgaagagc ttggcggcga atgggctgac cgcttcctcg      4980
tgctttacgg tatcgccgct cccgattcgc agcgcatcgc cttctatcgc cttcttgacg      5040
agttcttctg agcgggactc tggggttcgc tagaggatcg atccttttta acccatcaca      5100
tatacctgcc gttcactatt atttagtgaa atgagatatt atgatatttt ctgaattgtg      5160
attaaaaagg caactttatg cccatgcaac agaaactata aaaatacag agaatgaaaa       5220 gaaacagata gatttttag ttctttaggc ccgtagtctg caaatccttt tatgattttc       5280
tatcaaacaa agaggaaaa tagaccagtt gcaatccaaa cgagagtcta acgacgcgag       5340
gctggatggc cttcccccatt atgattcttc tcgcttccgg cggcatcggg atgcccgcgt      5400
tgcaggccat gctgtccagg caggtagatg acgaccatca gggacagctt caaggatcgc      5460
tcgcggctct taccagccta acttcgatca ttggaccgct gatcgtcacg gcgatttatg      5520
ccgcctcggc gagcacatgg aacgggttgg catggattgt aggcgccgcc ctataccttg      5580
tctgcctccc cgcgttgcgt cgcggtgcat ggagccgggc cacctcgacc tgaatggaag      5640
ccggcggcac ctcgctaacg gattcaccac tccaagaatt ggagccaatc aattcttgcg      5700
```

```
gagaactgtg aatgcgcaaa ccaacccttg gcagaacata tccatcgcgt ccgccatctc   5760
cagcagccgc acgcggcgca tctcgggcag cgttgggtcc tggccacggg tgcgcatgat   5820
cgtgctcctg tcgttgagga cccggctagg ctggcggggt tgccttactg gttagcagaa   5880
tgaatcaccg atacgcgagc gaacgtgaag cgactgctgc tgcaaaacgt ctgcgacctg   5940
agcaacaaca tgaatggtct tcggtttccg tgtttcgtaa agtctggaaa cgcggaagtc   6000
agcgccctgc accattatgt tccggatctg catcgcagga tgctgctggc taccctgtgg   6060
aacacctaca tctgtattaa cgaagcgctg gcattgaccc tgagtgattt ttctctggtc   6120
ccgccgcatc cataccgcca gttgtttacc ctcacaacgt tccagtaacc gggcatgttc   6180
atcatcagta acccgtatcg tgagcatcct ctctcgtttc atcggtatca ttaccccat    6240
gaacagaaat cccccttaca cggaggcatc agtgaccaaa caggaaaaaa ccgcccttaa   6300
catggcccgc tttatcagaa gccagacatt aacgcttctg gagaaactca acgagctgga   6360
cgcggatgaa caggcagaca tctgtgaatc gcttcacgac cacgctgatg agctttaccg   6420
cagctgcctc gcgcgtttcg gtgatgacgg tgaaaacctc tgcacacatgc agctcccgga   6480
gacggtcaca gcttgtctgt aagcggatgc cgggagcaga caagcccgtc agggcgcgtc   6540
agcgggtgtt ggcgggtgtc ggggcgcagc catgacccag tcacgtagcg atagcggagt   6600
gtatactggc ttaactatgc ggcatcagag cagattgtac tgagagtgca ccatatgcgg   6660
tgtgaaatac cgcacagatg cgtaaggaga aaataccgca tcaggcgctc ttccgcttcc   6720
tcgctcactg actcgctgcg ctcggtcgtt cggctgcggc gagcggtatc agctcactca   6780
aaggcggtaa tacggttatc cacagaatca ggggataacg caggaaagaa catgtgagca   6840
aaaggccagc aaaaggccag gaaccgtaaa aaggccgcgt tgctggcgtt tttccatagg   6900
ctccgccccc ctgacgagca tcacaaaaat cgacgctcaa gtcagaggtg gcgaaacccg   6960
acaggactat aaagatacca ggcgtttccc cctggaagct ccctcgtgcg ctctcctgtt   7020
ccgaccctgc cgcttaccgg atacctgtcc gcctttctcc cttcgggaag cgtggcgctt   7080
tctcatagct cacgctgtag gtatctcagt tcggtgtagg tcgttcgctc caagctgggc   7140
tgtgtgcacg aaccccccgt tcagcccgac cgctgcgcct tatccggtaa ctatcgtctt   7200
gagtccaacc cggtaagaca cgacttatcg ccactggcag cagccactgg taacaggatt   7260
agcagagcga ggtatgtagg cggtgctaca gagttcttga agtggtggcc taactacggc   7320
tacactagaa ggacagtatt tggtatctgc gctctgctga agccagttac cttcggaaaa   7380
agagttggta gctcttgatc cggcaaacaa accaccgctg gtagcggtgg tttttttgtt   7440
tgcaagcagc agattacgcg cagaaaaaaa ggatctcaag aagatccttt gatcttttct   7500
acggggtctg acgctcagtg gaacgaaaac tcacgttaag gattttggt catgagatta    7560
tcaaaaagga tcttcaccta gatcctttta aattaaaaat gaagttttaa atcaatctaa   7620
agtatatatg agtaaacttg gtctgacagt taccaatgct taatcagtga ggcacctatc   7680
tcagcgatct gtctatttcg ttcatccata gttgcctgac tccccgtcgt gtagataact   7740
acgatacggg agggcttacc atctggcccc agtgctgcaa tgataccgcg agacccacgc   7800
tcaccggctc cagatttatc agcaataaac cagccagccg aagggccga gcgcagaagt    7860
ggtcctgcaa ctttatccgc ctccatccag tctattaatt gttgccggga agctagagta   7920
agtagttcgc cagttaatag tttgcgcaac gttgttgcca ttgctgcagg catcgtggtg   7980
tcacgctcgt cgtttggtat ggcttcattc agctccggtt cccaacgatc aaggcgagtt   8040
acatgatccc ccatgttgtg caaaaaagcg gttagctcct tcggtcctcc gatcgttgtc   8100
```

```
agaagtaagt tggccgcagt gttatcactc atggttatgg cagcactgca taattctctt    8160
actgtcatgc catccgtaag atgcttttct gtgactggtg agtactcaac caagtcattc    8220
tgagaatagt gtatgcggcg accgagttgc tcttgcccgg cgtcaacacg ggataatacc    8280
gcgccacata gcagaacttt aaaagtgctc atcattggaa acgttcttc ggggcgaaaa     8340 ctctcaagga tcttaccgct gttgagatcc agttcgatgt aacccactcg tgcacccaac    8400
tgatcttcag catcttttac tttcaccagc gtttctgggt gagcaaaaac aggaaggcaa    8460
aatgccgcaa aaaagggaat aagggcgaca cggaaatgtt gaatactcat actcttcctt    8520
tttcaatatt attgaagcat ttatcagggt tattgtctca tgagcggata catatttgaa    8580
tgtatttaga aaaataaaca ataggggtt ccgcgcacat tccccgaaa agtgccacct      8640 gacgtctaag aaaccattat tatcatgaca ttaacctata aaaataggcg tatcacgagg    8700
ccctttcgtc ttcaagaa                                                  8718
```

<210> SEQ ID NO 39
<211> LENGTH: 7250
<212> TYPE: DNA
<213> ORGANISM: Artificial Sequence
<220> FEATURE:
<223> OTHER INFORMATION: Recombinant plasmid pAPSE10439; beta actin
      hairpin - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional prmoter
<220> FEATURE:
<221> NAME/KEY: misc_feature
<222> LOCATION: (2844)..(2851)
<223> OTHER INFORMATION: restriction endonuclease AsiSI recognition
      sequence
<220> FEATURE:
<221> NAME/KEY: misc_feature
<222> LOCATION: (2852)..(3146)
<223> OTHER INFORMATION: beta actin sense gene fragment
<220> FEATURE:
<221> NAME/KEY: misc_feature
<222> LOCATION: (3146)..(3153)
<223> OTHER INFORMATION: restriction endonuclease PmeI recognition site
<220> FEATURE:
<221> NAME/KEY: misc_feature
<222> LOCATION: (3311)..(3605)
<223> OTHER INFORMATION: beta actin antisense strand gene fragment
<220> FEATURE:
<221> NAME/KEY: terminator
<222> LOCATION: (3657)..(3846)
<223> OTHER INFORMATION: yeast CYC1 terminator
<220> FEATURE:
<221> NAME/KEY: misc_feature
<222> LOCATION: (5840)..(7182)
<223> OTHER INFORMATION: yeast 2 micron ori

<400> SEQUENCE: 39

-continued

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accataaacg acattactat atatataata taggaagcat ttaatagaca gcatcgtaat | 240 |
| atatgtgtac tttgcagtta tgacgccaga tggcagtagt ggaagatatt ctttattgaa | 300 |
| aaatagcttg tcaccttacg tacaatcttg atccggagct tttctttttt tgccgattaa | 360 |
| gaattaattc ggtcgaaaaa agaaaaggag agggccaaga ggggagggcat tggtgactat | 420 |
| tgagcacgtg agtatacgtg attaagcaca caaaggcagc ttggagtatg tctgttatta | 480 |
| atttcacagg tagttctggt ccattggtga agtttgcgg cttgcagagc acagaggccg | 540 |
| cagaatgtgc tctagattcc gatgctgact tgctgggtat tatatgtgtg cccaatagaa | 600 |
| agagaacaat tgacccggtt attgcaagga aaatttcaag tcttgtaaaa gcatataaaa | 660 |
| atagttcagg cactccgaaa tacttggttg gcgtgtttcg taatcaacct aaggaggatg | 720 |
| ttttggctct ggtcaatgat tacggcattg atatcgtcca actgcatgga gatgagtcgt | 780 |
| ggcaagaata ccaagagttc ctcggtttgc cagttattaa aagactcgta tttccaaaag | 840 |
| actgcaacat actactcagt gcagcttcac agaaaccctca ttcgtttatt cccttgtttg | 900 |
| attcagaagc aggtgggaca ggtgaacttt tggattggaa ctcgatttct gactgggttg | 960 |
| gaaggcaaga gagccccgaa agcttacatt ttatgttagc tggtggactg acgccagaaa | 1020 |
| atgttggtga tgcgcttaga ttaaatggcg ttattggtgt tgatgtaagc ggaggtgtgg | 1080 |
| agacaaatgt tgtaaaagac tctaacaaaa tagcaaattt cgtcaaaaat gctaagaaat | 1140 |
| aggttattac tgagtagtat ttatttaagt attgtttgtg cacttgccta tgcggtgtga | 1200 |
| aataccgcac agatgcgtaa ggagaaaata ccgcatcagg aaattgtaaa cgttaatatt | 1260 |
| ttgttaaaat tcgcgttaaa ttttgttaa atcagctcat ttttaaccaa ataggccgaa | 1320 |
| atcggcaaaa tcccttataa atcaaaagaa tagaccgaga tagggttgag tgttgttcca | 1380 |
| gtttggaaca agagtccact attaaagaac gtggactcca acgtcaaagg gcgaaaaacc | 1440 |
| gtctatcagg gcgatggccc actacgtgaa ccatcaccct aatcaagttt ttgggggtcg | 1500 |
| aggtgccgta aagcactaaa tcggaaccct aaagggagcc cccgatttag agcttgacgg | 1560 |
| ggaaagccgg cgaacgtggc gagaaaggaa gggaagaaag cgaaaggagc gggcgctagg | 1620 |
| gcgctggcaa gtgtagcggt cacgctgcgc gtaaccacca cacccgccgc gcttaatgcg | 1680 |
| ccgctacagg gcgcgtcgcg ccattcgcca ttcaggctgc gcaactgttg gaagggcga | 1740 |
| tcggtgcggg cctcttcgct attacgccag ctgaattgga gcgacctcat gctataccccg | 1800 |
| agaaagcaac ctgacctaca ggaaagagtt actcaagaat aagaattttc gttttaaaac | 1860 |
| ctaagagtca ctttaaaatt tgtatacact tattttttt ataacttatt taataataaa | 1920 |
| aatcataaat cataagaaat tcgcttattt agaagtgtca acaacgtatc taccaacgat | 1980 |
| ttgacccttt tccatctttt cgtaaatttc tggcaaggta gacaagccga caaccttgat | 2040 |
| tggagacttg accaaaccctc tggcgaagaa ttgttaatta agagctcaga tcttatcgtc | 2100 |
| gtcatccttg taatccatcg atactagtgc ggccgcccctt tagtgagggt tgaattcgaa | 2160 |
| ttttcaaaaa ttcttacttt tttttttggat ggacgcaaag aagtttaata atcatattac | 2220 |
| atggcattac caccatatac atatccatat acatatccat atctaatctt acttatatgt | 2280 |
| tgtgaaaatg taaagagccc cattatctta gcctaaaaaa accttctctt tggaactttc | 2340 |
| agtaatacgc ttaactgctc attgctatat tgaagtacgg attagaagcc gccgagcggg | 2400 |

```
tgacagccct ccgaaggaag actctcctcc gtgcgtcctc gtcttcaccg gtcgcgttcc    2460
tgaaacgcag atgtgcctcg cgccgcactg ctccgaacaa taaagattct acaatactag    2520
cttttatggt tatgaagagg aaaaattggc agtaacctgg ccccacaaac cttcaaatga    2580
acgaatcaaa ttaacaacca taggatgata atgcgattag ttttttagcc ttatttctgg    2640
ggtaattaat cagcgaagcg atgattttttg atctattaac agatatataa atgcaaaaac    2700
tgcataacca ctttaactaa tactttcaac attttcggtt tgtattactt cttattcaaa    2760
tgtaataaaa gtatcaacaa aaaattgtta atatacctct atactttaac gtcaaggaga    2820
aaaaaccccg gatccattta aatgcgatcg cgcacgaggt ttttctgtct agtgagcagt    2880
gtccaacctc aaaagacaac atgtgtgacg acgatgtagc ggctcttgtc gtagacaatg    2940
gatccggtat gtgcaaagcc ggtttcgcag gagatgacgc accccgtgcc gtcttcccct    3000
cgatcgtcgg tcgcccaagg catcaaggag tcatggtcgg tatgggacaa aaggactcat    3060
acgtaggaga tgaagcccaa agcaaaagag gtatcctcac cctgaaatac cccatcgaac    3120
acggtatcat caccaactgg gatgagttta aaccctctag ctgctttaca aagtactggt    3180
tccctttcca gcgggatgct ttatctaaac gcaatgagag aggtattcct caggccacat    3240
cgcttcctag ttccgctggg atccatcgtt ggcggccgaa gccgccattc catagtgagt    3300
tctggcgcgc tcatcccag ttggtgatga taccgtgttc gatggggtat ttcagggtga    3360
ggatacctct tttgctttgg gcttcatctc ctacgtatga gtccttttgt cccataccga    3420
ccatgactcc ttgatgcctt gggcgaccga cgatcgaggg gaagacggca cggggtgcgt    3480
catctcctgc gaaaccggct ttgcacatac cggatccatt gtctacgaca agagccgcta    3540
catcgtcgtc acacatgttg tcttttgagg ttggacactg ctcactagac agaaaaacct    3600
cgtgccggac cgaataccg gtctgaacga gggcggccgc ccgcgggcta gctaagatcc    3660
gctctaaccg aaaaggaagg agttagacaa cctgaagtct aggtcccctat ttatttttt    3720 atagttatgt tagtattaag aacgttattt atatttcaaa ttttttctttt ttttctgtac    3780 agacgcgtgt acgcatgtaa cattatactg aaaaccttgc ttgagaaggt tttgggacgc    3840
tcgaagatcc agctgcatta atgaatcggc caacgcgcgg ggagaggcgg tttgcgtatt    3900
gggcgctctt ccgcttcctc gctcactgac tcgctgcgct cggtcgttcg gctgcggcga    3960
gcggtatcag ctcactcaaa ggcggtaata cggttatcca cagaatcagg ggataacgca    4020
ggaaagaaca tgtgagcaaa aggccagcaa aaggccagga accgtaaaaa ggccgcgttg    4080
ctggcgtttt tccataggct ccgcccccct gacgagcatc acaaaaatcg acgctcaagt    4140
cagaggtggc gaaacccgac aggactataa agataccagg cgtttccccc tggaagctcc    4200
ctcgtgcgct ctcctgttcc gaccctgccg cttaccggat acctgtccgc ctttctccct    4260
tcgggaagcg tggcgctttc tcatagctca cgctgtaggt atctcagttc ggtgtaggtc    4320
gttcgctcca agctgggctg tgtgcacgaa ccccccgttc agcccgaccg ctgcgcctta    4380
tccggtaact atcgtcttga gtccaacccg gtaagacacg acttatcgcc actggcagca    4440
gccactggta acaggattag cagagcgagg tatgtaggcg gtgctacaga gttcttgaag    4500
tggtggccta actacggcta cactagaagg acagtatttg gtatctgcgc tctgctgaag    4560
ccagttacct tcggaaaaag agttggtagc tcttgatccg gcaaacaaac caccgctggt    4620
agcggtggtt tttttgtttg caagcagcag attacgcgca gaaaaaaagg atctcaagaa    4680
gatcctttga tcttttctac ggggtctgac gctcagtgga acgaaaactc acgttaaggg    4740
```

```
attttggtca tgagattatc aaaaaggatc ttcacctaga tccttttaaa ttaaaaatga    4800
agttttaaat caatctaaag tatatatgag taaacttggt ctgacagtta ccaatgctta    4860
atcagtgagg cacctatctc agcgatctgt ctatttcgtt catccatagt tgcctgactc    4920
cccgtcgtgt agataactac gatacgggag ggcttaccat ctggcccag tgctgcaatg     4980 ataccgcgag acccacgctc accggctcca gatttatcag caataaacca gccagccgga    5040
agggccgagc gcagaagtgg tcctgcaact ttatccgcct ccatccagtc tattaattgt    5100
tgccgggaag ctagagtaag tagttcgcca gttaatagtt gcgcaacgt tgttgccatt     5160 gctacaggca tcgtggtgtc acgctcgtcg tttggtatgg cttcattcag ctccggttcc    5220
caacgatcaa ggcgagttac atgatccccc atgttgtgca aaaagcggt tagctccttc     5280 ggtcctccga tcgttgtcag aagtaagttg gccgcagtgt tatcactcat ggttatggca    5340
gcactgcata attctcttac tgtcatgcca tccgtaagat gcttttctgt gactggtgag    5400
tactcaacca agtcattctg agaatagtgt atgcggcgac cgagttgctc ttgcccggcg    5460
tcaatacggg ataataccgc gccacatagc agaactttaa aagtgctcat cattggaaaa    5520
cgttcttcgg ggcgaaaact ctcaaggatc ttaccgctgt tgagatccag ttcgatgtaa    5580
cccactcgtg cacccaactg atcttcagca tcttttactt tcaccagcgt ttctgggtga    5640
gcaaaaacag gaaggcaaaa tgccgcaaaa aagggaataa gggcgacacg gaaatgttga    5700
atactcatac tcttcctttt tcaatattat tgaagcattt atcagggtta ttgtctcatg    5760
agcggataca tatttgaatg tatttagaaa aataaacaaa taggggttcc gcgcacattt    5820
ccccgaaaag tgccacctga cgaagcatc tgtgcttcat tttgtagaac aaaaatgcaa     5880
cgcgagagcg ctaattttc aaacaaagaa tctgagctgc attttttacag aacagaaatg    5940 caacgcgaaa gcgctatttt accaacgaag aatctgtgct tcattttgt aaaacaaaaa     6000 tgcaacgcga gagcgctaat ttttcaaaca agaatctga gctgcatttt tacagaacag    6060
aaatgcaacg cgagagcgct attttaccaa caaagaatct atacttcttt tttgttctac    6120
aaaaatgcat cccgagagcg ctatttttct aacaaagcat cttagattac tttttttctc    6180
ctttgtgcgc tctataatgc agtctcttga taacttttttg cactgtaggt ccgttaaggt    6240
tagaagaagg ctactttggt gtctattttc tcttccataa aaaagcctg actccacttc     6300 ccgcgtttac tgattactag cgaagctgcg ggtgcatttt ttcaagataa aggcatcccc    6360
gattatattc tataccgatg tggattgcgc atactttgtg aacagaaagt gatagcgttg    6420
atgattcttc attggtcaga aaattatgaa cggtttcttc tattttgtct ctatatacta    6480
cgtataggaa atgtttacat tttcgtattg ttttcgattc actctatgaa tagttcttac    6540
tacaattttt ttgtctaaag agtaaactaga gagataaaca taaaaatgt agaggtcgag    6600 tttagatgca agttcaagga gcgaaaggtg gatgggtagg ttatataggg atatagcaca    6660
gagatatata gcaaagagat acttttgagc aatgttgtg gaagcggtat tcgcaatatt    6720
ttagtagctc gttacagtcc ggtgcgtttt tggttttttg aaagtgcgtc ttcagagcgc    6780
ttttggtttt caaaagcgct ctgaagttcc tatactttct agagaatagg aacttcggaa    6840
taggaacttc aaagcgtttc cgaaaacgag cgcttccgaa aatgcaacgc gagctgcgca    6900
catacagctc actgttcacg tcgcacctat atctgcgtgt tgcctgtata tatatataca    6960
tgagaagaac ggcatagtgc gtgtttatgc ttaaatgcgt acttatatgc gtctatttat    7020
gtaggatgaa aggtagtcta gtacctcctg tgatattatc ccattccatg cggggtatcg    7080
tatgcttcct tcagcactac cctttagctg ttctatatgc tgccactcct caattggatt    7140
```

```
agtctcatcc ttcaatgcta tcatttcctt tgatattgga tcatattaag aaaccattat      7200
tatcatgaca ttaacctata aaaataggcg tatcacgagg ccctttcgtc                 7250
```

<210> SEQ ID NO 40
<211> LENGTH: 7582
<212> TYPE: DNA
<213> ORGANISM: Artificial Sequence
<220> FEATURE:
<223> OTHER INFORMATION: Recombinant plasmid pAPSE1440; beta actin
      hairpin + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3183)
<223> OTHER INFORMATION: restriction endonuclease AsiSI recognition
      sequence
<220> FEATURE:
<221> NAME/KEY: misc_feature
<222> LOCATION: (3185)..(3478)
<223> OTHER INFORMATION: beta actin sense gene fragment
<220> FEATURE:
<221> NAME/KEY: misc_feature
<222> LOCATION: (3478)..(3485)
<223> OTHER INFORMATION: restriction endonuclease PmeI recognition site
<220> FEATURE:
<221> NAME/KEY: misc_feature
<222> LOCATION: (3643)..(3937)
<223> OTHER INFORMATION: beta actin antisense strand gene fragment
<220> FEATURE:
<221> NAME/KEY: terminator
<222> LOCATION: (3989)..(4178)
<223> OTHER INFORMATION: yeast CYC1 terminator
<220> FEATURE:
<221> NAME/KEY: misc_feature
<222> LOCATION: (6172)..(7514)
<223> OTHER INFORMATION: yeast 2 micron ori

<400> SEQUENCE: 40

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
```

```
tgagcacgtg agtatacgtg attaagcaca caaaggcagc ttggagtatg tctgttatta    480
atttcacagg tagttctggt ccattggtga agtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat ttttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tattttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctctta ttagtaaatg   2100
ccagagttag cagcgattgc agatgggatc ggattaccgt cttttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact tttttttgg   2520
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
```

```
tgctccgaac aataaagatt ctacaatact agcttttatg gttatgaaga ggaaaaattg    2880
gcagtaacct ggccccacaa accttcaaat gaacgaatca aattaacaac cataggatga    2940
taatgcgatt agttttttag ccttatttct ggggtaatta atcagcgaag cgatgatttt    3000
tgatctatta acagatatat aaatgcaaaa actgcataac cactttaact aatactttca    3060
acattttcgg tttgtattac ttcttattca aatgtaataa agtatcaac aaaaaattgt    3120 taatataccct ctatacttta acgtcaagga gaaaaaccc cggatccatt taaatgcgat    3180
cgcgcacgag gttttttctgt ctagtgagca gtgtccaacc tcaaaagaca acatgtgtga    3240
cgacgatgta gcggctcttg tcgtagacaa tggatccggt atgtgcaaag ccggtttcgc    3300
aggagatgac gcaccccgtg ccgtcttccc ctcgatcgtc ggtcgcccaa ggcatcaagg    3360
agtcatggtc ggtatgggac aaaaggactc atacgtagga gatgaagccc aaagcaaaag    3420
aggtatcctc accctgaaat accccatcga acacggtatc atcaccaact gggatgagtt    3480
taaaccctct agctgcttta caaagtactg gttccctttc cagcgggatg ctttatctaa    3540
acgcaatgag agaggtattc ctcaggccac atcgcttcct agttccgctg ggatccatcg    3600
ttggcggccg aagccgccat tccatagtga gttctggcgc gcctcatccc agttggtgat    3660
gataccgtgt tcgatggggt atttcagggt gaggatacct cttttgcttt gggcttcatc    3720
tcctacgtat gagtcctttt gtcccatacc gaccatgact ccttgatgcc ttgggcgacc    3780
gacgatcgag gggaagacgg cacggggtgc gtcatctcct gcgaaaccgg cttttgcacat    3840 accggatcca ttgtctacga caagagccgc tacatcgtcg tcacacatgt tgtcttttga    3900
ggttggacac tgctcactag acagaaaaac ctcgtgccgg accgaatacc cggtctgaac    3960
gagggcggcc gcccgcgggc tagctaagat ccgctctaac cgaaaaggaa ggagttagac    4020
aacctgaagt ctaggtccct atttattttt ttatagttat gttagtatta agaacgttat    4080
ttatatttca aattttttctt tttttttctgt acagacgcgt gtacgcatgt aacattatac    4140 tgaaaaccctt gcttgagaag gttttgggac gctcgaagat ccagctgcat taatgaatcg    4200
gccaacgcgc ggggagaggc ggtttgcgta ttgggcgctc ttccgcttcc tcgctcactg    4260
actcgctgcg ctcggtcgtt cggctgcggc gagcggtatc agctcactca aaggcggtaa    4320
tacggttatc cacagaatca ggggataacg caggaaagaa catgtgagca aaaggccagc    4380
aaaaggccag gaaccgtaaa aaggccgcgt tgctggcgtt tttccatagg ctccgccccc    4440
ctgacgagca tcacaaaaat cgacgctcaa gtcagaggtg gcgaaacccg acaggactat    4500
aaagatacca ggcgtttccc cctggaagct ccctcgtgcg ctctcctgtt ccgaccctgc    4560
cgcttaccgg atacctgtcc gcctttctcc cttcgggaag cgtggcgctt tctcatagct    4620
cacgctgtag gtatctcagt tcggtgtagg tcgttcgctc caagctgggc tgtgtgcacg    4680 aacccccccgt tcagcccgac cgctgcgcct tatccggtaa ctatcgtctt gagtccaacc    4740
cggtaagaca cgacttatcg ccactggcag cagccactgg taacaggatt agcagagcga    4800
ggtatgtagg cggtgctaca gagttcttga agtggtggcc taactacggc tacactagaa    4860
ggacagtatt tggtatctgc gctctgctga agccagttac cttcggaaaa agagttggta    4920
gctcttgatc cggcaaacaa accaccgctg gtagcggtgg ttttttttgtt tgcaagcagc    4980 agattacgcg cagaaaaaaa ggatctcaag aagatccttt gatcttttct acggggtctg    5040
acgctcagtg gaacgaaaac tcacgttaag ggattttggt catgagatta tcaaaaagga    5100
tcttcaccta gatccttta aattaaaaat gaagttttaa atcaatctaa agtatatatg    5160
```

```
agtaaacttg gtctgacagt taccaatgct taatcagtga ggcacctatc tcagcgatct    5220
gtctatttcg ttcatccata gttgcctgac tccccgtcgt gtagataact acgatacggg    5280
agggcttacc atctggcccc agtgctgcaa tgataccgcg agacccacgc tcaccggctc    5340
cagatttatc agcaataaac cagccagccg aagggccga gcgcagaagt ggtcctgcaa     5400
ctttatccgc ctccatccag tctattaatt gttgccggga agctagagta agtagttcgc    5460
cagttaatag tttgcgcaac gttgttgcca ttgctacagg catcgtggtg tcacgctcgt    5520
cgtttggtat ggcttcattc agctccggtt cccaacgatc aaggcgagtt acatgatccc    5580
ccatgttgtg caaaaaagcg gttagctcct tcggtcctcc gatcgttgtc agaagtaagt    5640
tggccgcagt gttatcactc atggttatgg cagcactgca taattctctt actgtcatgc    5700
catccgtaag atgcttttct gtgactggtg agtactcaac caagtcattc tgagaatagt    5760
gtatgcggcg accgagttgc tcttgcccgg cgtcaatacg ggataatacc gcgccacata    5820
gcagaacttt aaaagtgctc atcattggaa aacgttcttc ggggcgaaaa ctctcaagga    5880
tcttaccgct gttgagatcc agttcgatgt aacccactcg tgcacccaac tgatcttcag    5940
catcttttac tttcaccagc gtttctgggt gagcaaaaac aggaaggcaa atgccgcaa     6000
aaagggaat aagggcgaca cggaaatgtt gaatactcat actcttcctt tttcaatatt     6060
attgaagcat ttatcagggt tattgtctca tgagcggata catatttgaa tgtatttaga    6120
aaataaaca ataggggtt ccgcgcacat ttccccgaaa agtgccacct gaacgaagca      6180
tctgtgcttc attttgtaga acaaaaatgc aacgcgagag cgctaatttt tcaaacaaag    6240
aatctgagct gcattttac agaacagaaa tgcaacgcga agcgctatt ttaccaacga      6300
agaatctgtg cttcatttt gtaaaacaaa atgcaacgc gagagcgcta attttcaaa       6360
caaagaatct gagctgcatt tttacagaac agaaatgcaa cgcgagagcg ctattttacc    6420
aacaaagaat ctatacttct ttttgttct acaaaaatgc atcccgagag cgctattttt     6480
ctaacaaagc atcttagatt actttttttc cctttgtgc gctctataat gcagtctctt     6540
gataacttt tgcactgtag gtccgttaag gttagaagaa ggctactttg gtgtctattt     6600
tctcttccat aaaaaaagcc tgactccact tcccgcgttt actgattact agcgaagctg    6660
cgggtgcatt ttttcaagat aaaggcatcc ccgattatat tctataccga tgtggattgc    6720
gcatactttg tgaacagaaa gtgatagcgt tgatgattct tcattggtca gaaaattatg    6780
aacggtttct tctatttgt ctctatatac tacgtatagg aaatgtttac attttcgtat     6840
tgttttcgat tcactctatg aatagttctt actacaattt ttttgtctaa agagtaaatac   6900
tagagataaa cataaaaat gtagaggtcg agtttagatg caagttcaag gagcgaaagg     6960
tggatgggta ggttatatag ggatatagca cagagatata tagcaaagag atacttttga    7020
gcaatgtttg tggaagcggt attcgcaata ttttagtagc tcgttacagt ccggtgcgtt    7080
tttggttttt tgaaagtgcg tcttcagagc gcttttggtt ttcaaaagcg ctctgaagtt    7140
cctatacttt ctagagaata ggaacttcgg aataggaact tcaaagcgtt tccgaaaacg    7200
agcgcttccg aaaatgcaac gcgagctgcg cacatacagc tcactgttca cgtcgcacct    7260
atatctgcgt gttgcctgta tatatatata catgagaaga acggcatagt gcgtgtttat    7320
gcttaaatgc gtacttatat gcgtctattt atgtaggatg aaaggtagtc tagtacctcc    7380
tgtgatatta tcccattcca tgcggggtat cgtatgcttc cttcagcact accctttagc    7440
tgttctatat gctgccactc ctcaattgga ttagtctcat ccttcaatgc tatcatttcc    7500
tttgatattg gatcatatta agaaaccatt attatcatga cattaaccta taaaaatagg    7560
```

```
cgtatcacga ggccctttcg tc                                           7582
```

<210> SEQ ID NO 41
<211> LENGTH: 7269
<212> TYPE: DNA
<213> ORGANISM: Artificial Sequence
<220> FEATURE:
<223> OTHER INFORMATION: Recombinant plasmid pAPSE10441; beta actin stem
      loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional promoter
<220> FEATURE:
<221> NAME/KEY: misc_feature
<222> LOCATION: (2844)..(2851)
<223> OTHER INFORMATION: restriction endonuclease AsiSI recognition
      sequence
<220> FEATURE:
<221> NAME/KEY: misc_feature
<222> LOCATION: (2852)..(3146)
<223> OTHER INFORMATION: beta actin sense gene fragment
<220> FEATURE:
<221> NAME/KEY: misc_feature
<222> LOCATION: (3146)..(3153)
<223> OTHER INFORMATION: restriction endonuclease PmeI recognition site
<220> FEATURE:
<221> NAME/KEY: misc_feature
<222> LOCATION: (3311)..(3605)
<223> OTHER INFORMATION: beta actin antisense strand gene fragment
<220> FEATURE:
<221> NAME/KEY: misc_feature
<222> LOCATION: (3641)..(3659)
<223> OTHER INFORMATION: bacteriophage MS2 pac sequence
<220> FEATURE:
<221> NAME/KEY: terminator
<222> LOCATION: (3676)..(3865)
<223> OTHER INFORMATION: yeast CYC1 terminator
<220> FEATURE:
<221> NAME/KEY: misc_feature
<222> LOCATION: (5859)..(7201)
<223> OTHER INFORMATION: yeast 2 micron ori

<400> SEQUENCE: 41

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accataaacg acattactat atatataata taggaagcat ttaatagaca gcatcgtaat   240
atatgtgtac tttgcagtta tgacgccaga tggcagtagt ggaagatatt ctttattgaa   300
aaatagcttg tcaccttacg tacaatcttg atccggagct tttcttttt tgccgattaa    360 gaattaattc ggtcgaaaaa agaaaaggag agggccaaga gggagggcat tggtgactat   420
tgagcacgtg agtatacgtg attaagcaca caaaggcagc ttggagtatg tctgttatta   480
```

```
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgtta atcagctcat ttttttaacca ataggccgaa   1320 atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaacccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg gaagggcga   1740 tcggtgcggg cctcttcgct attacgccag ctgaattgga gcgacctcat gctatacctg   1800
agaaagcaac ctgacctaca ggaaagagtt actcaagaat aagaatttc gttttaaaac   1860 ctaagagtca ctttaaaatt tgtatacact tattttttt ataacttatt taataataaa   1920
aatcataaat cataagaaat tcgcttattt agaagtgtca acaacgtatc taccaacgat   1980 ttgaccctttt tccatctttt cgtaaatttc tggcaaggta gacaagccga caaccttgat   2040
tggagacttg accaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt tttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520 ctttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgattttg atctattaac agatatataa atgcaaaaac   2700
tgcataacca cttttaactaa tactttcaac attttcggtt tgtattactt cttattcaaa   2760
tgtaataaaa gtatcaacaa aaaattgtta atatacctct atactttaac gtcaaggaga   2820
aaaaaccccg gatccattta aatgcgatcg cgcacgaggt ttttctgtct agtgagcagt   2880
```

```
gtccaacctc aaaagacaac atgtgtgacg acgatgtagc ggctcttgtc gtagacaatg    2940
gatccggtat gtgcaaagcc ggtttcgcag gagatgacgc accccgtgcc gtcttcccct    3000
cgatcgtcgg tcgcccaagg catcaaggag tcatggtcgg tatgggacaa aaggactcat    3060
acgtaggaga tgaagcccaa agcaaaagag gtatcctcac cctgaaatac cccatcgaac    3120
acggtatcat caccaactgg gatgagttta aaccctctag ctgctttaca aagtactggt    3180 tcccttttcca gcgggatgct ttatctaaac gcaatgagag aggtattcct caggccacat   3240
cgcttcctag ttccgctggg atccatcgtt ggcggccgaa gccgccattc catagtgagt    3300
tctggcgcgc ctcatcccag ttggtgatga taccgtgttc gatggggtat ttcagggtga    3360
ggatacctct tttgctttgg gcttcatctc ctacgtatga gtccttttgt cccataccga    3420
ccatgactcc ttgatgcctt gggcgaccga cgatcgaggg gaagacggca cggggtgcgt    3480
catctcctgc gaaaccggct ttgcacatac cggatccatt gtctacgaca agagccgcta    3540
catcgtcgtc acacatgttg tcttttgagg ttggacactg ctcactagac agaaaaacct    3600
cgtgccggac cgaatacccg gtctgaacga gggcggccgc acatgaggat cacccatgtc    3660
cgcgggctag ctaagatccg ctctaaccga aaaggaagga gttagacaac ctgaagtcta    3720
ggtccctatt tattttttta tagttatgtt agtattaaga acgttattta tatttcaaat    3780
tttctttttt tttctgtaca gacgcgtgta cgcatgtaac attatactga aaaccttgct    3840
tgagaaggtt ttgggacgct cgaagatcca gctgcattaa tgaatcggcc aacgcgcggg    3900
gagaggcggt ttgcgtattg ggcgctcttc cgcttcctcg ctcactgact cgctgcgctc    3960
ggtcgttcgg ctgcggcgag cggtatcagc tcactcaaag gcggtaatac ggttatccac    4020
agaatcaggg gataacgcag gaaagaacat gtgagcaaaa ggccagcaaa aggccaggaa    4080
ccgtaaaaag gccgcgttgc tggcgttttt ccataggctc cgcccccctg acgagcatca    4140
caaaaatcga cgctcaagtc agaggtggcg aaacccgaca ggactataaa gataccaggc    4200
gtttccccct ggaagctccc tcgtgcgctc tcctgttccg accctgccgc ttaccggata    4260
cctgtccgcc tttctccctt cgggaagcgt ggcgctttct catagctcac gctgtaggta    4320
tctcagttcg gtgtaggtcg ttcgctccaa gctgggctgt gtgcacgaac cccccgttca    4380
gcccgaccgc tgcgccttat ccggtaacta tcgtcttgag tccaacccgg taagacacga    4440
cttatcgcca ctggcagcag ccactggtaa caggattagc agagcgaggt atgtaggcgg    4500
tgctacagag ttcttgaagt ggtggcctaa ctacggctac actagaagga cagtatttgg    4560
tatctgcgct ctgctgaagc cagttacctt cggaaaaaga gttggtagct cttgatccgg    4620
caaacaaacc accgctggta gcggtggttt ttttgtttgc aagcagcaga ttacgcgcag    4680
aaaaaaagga tctcaagaag atcctttgat cttttctacg gggtctgacg ctcagtggaa    4740
cgaaaactca cgttaaggga ttttggtcat gagattatca aaaaggatct tcacctagat    4800
ccttttaaat taaaaatgaa gttttaaatc aatctaaagt atatatgagt aaacttggtc    4860
tgacagttac caatgcttaa tcagtgaggc acctatctca gcgatctgtc tatttcgttc    4920
atccatagtt gcctgactcc ccgtcgtgta gataactacg atacgggagg gcttaccatc    4980
tggccccagt gctgcaatga taccgcgaga cccacgctca ccggctccag atttatcagc    5040
aataaaccag ccagccggaa gggccgagcg cagaagtggt cctgcaactt tatccgcctc    5100
catccagtct attaattgtt gccgggaagc tagagtaagt agttcgccag ttaatagttt    5160
gcgcaacgtt gttgccattg ctacaggcat cgtggtgtca cgctcgtcgt ttggtatggc    5220
```

```
ttcattcagc tccggttccc aacgatcaag gcgagttaca tgatccccca tgttgtgcaa    5280
aaaagcggtt agctccttcg gtcctccgat cgttgtcaga agtaagttgg ccgcagtgtt    5340
atcactcatg gttatggcag cactgcataa ttctcttact gtcatgccat ccgtaagatg    5400
cttttctgtg actggtgagt actcaaccaa gtcattctga aatagtgta tgcggcgacc      5460
gagttgctct tgcccggcgt caatacggga taataccgcg ccacatagca gaactttaaa    5520
agtgctcatc attggaaaac gttcttcggg gcgaaaactc tcaaggatct taccgctgtt    5580
gagatccagt tcgatgtaac ccactcgtgc acccaactga tcttcagcat cttttacttt    5640
caccagcgtt tctgggtgag caaaaacagg aaggcaaaat gccgcaaaaa agggaataag    5700
ggcgacacgg aaatgttgaa tactcatact cttccttttt caatattatt gaagcattta    5760
tcagggttat tgtctcatga gcggatacat atttgaatgt atttagaaaa ataaacaaat    5820
aggggttccg cgcacatttc cccgaaaagt gccacctgaa cgaagcatct gtgcttcatt    5880
ttgtagaaca aaaatgcaac gcgagagcgc taattttttca aacaaagaat ctgagctgca    5940
tttttacaga acagaaatgc aacgcgaaag cgctatttta ccaacgaaga atctgtgctt    6000
cattttttgta aaacaaaaat gcaacgcgag agcgctaatt tttcaaacaa agaatctgag    6060
ctgcattttt acagaacaga aatgcaacgc gagagcgcta tttaccaac aaagaatcta    6120
tacttctttt ttgttctaca aaatgcatc ccgagagcgc tattttttcta acaaagcatc     6180
ttagattact tttttttctcc tttgtgcgct ctataatgca gtctcttgat aacttttttgc    6240
actgtaggtc cgttaaggtt agaagaaggc tactttggtg tctatttttct cttccataaa    6300
aaaagcctga ctccacttcc cgcgttttact gattactagc gaagctgcgg gtgcattttt    6360
tcaagataaa ggcatccccg attatattct ataccgatgt ggattgcgca ctttgtga     6420
acagaaagtg atagcgttga tgattcttca ttggtcagaa aattatgaac ggtttcttct    6480
attttgtctc tatatactac gtataggaaa tgtttacatt ttcgtattgt tttcgattca    6540
ctctatgaat agttcttact acaatttttt tgtctaaaga gtaatactag agataaacat    6600
aaaaaatgta gaggtcgagt ttagatgcaa gttcaaggag cgaaaggtgg atgggtaggt    6660
tataatggga tatagcacag agatatatag caaagagata cttttgagca atgtttgtgg    6720
aagcggtatt cgcaatattt tagtagctcg ttacagtccg gtgcgttttt ggttttttga    6780
aagtgcgtct tcagagcgct tttggttttc aaaagcgctc tgaagttcct atactttcta    6840
gagaatagga acttcggaat aggaacttca aagcgtttcc gaaaacgagc gcttccgaaa    6900
atgcaacgcg agctgcgcac atacagctca ctgttcacgt cgcacctata tctgcgtgtt    6960
gcctgtatat atatatacat gagaagaacg gcatagtgcg tgtttatgct taaatgcgta    7020
cttatatgcg tctatttatg taggatgaaa ggtagtctag tacctcctgt gatattatcc    7080
cattccatgc ggggtatcgt atgcttcctt cagcactacc ctttagctgt tctatatgct    7140
gccactcctc aattggatta gtctcatcct tcaatgctat catttccttt gatattggat    7200
catattaaga aaccattatt atcatgacat taacctataa aaataggcgt atcacgaggc    7260
cctttcgtc                                                             7269
```

<210> SEQ ID NO 42
<211> LENGTH: 7601
<212> TYPE: DNA
<213> ORGANISM: Artificial Sequence
<220> FEATURE:
<223> OTHER INFORMATION: Recombinant plasmid pAPSE10442; beta actin
      hairpin + coat protein
<220> FEATURE:

```
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3183)
<223> OTHER INFORMATION: restriction endonuclease AsiSI recognition
      sequence
<220> FEATURE:
<221> NAME/KEY: misc_feature
<222> LOCATION: (3185)..(3478)
<223> OTHER INFORMATION: beta actin sense gene fragment
<220> FEATURE:
<221> NAME/KEY: misc_feature
<222> LOCATION: (3478)..(3485)
<223> OTHER INFORMATION: restriction endonuclease PmeI recognition site
<220> FEATURE:
<221> NAME/KEY: misc_feature
<222> LOCATION: (3643)..(3937)
<223> OTHER INFORMATION: beta actin antisense strand gene fragment
<220> FEATURE:
<221> NAME/KEY: misc_feature
<222> LOCATION: (3973)..(3991)
<223> OTHER INFORMATION: bacteriophage MS2 pac sequence
<220> FEATURE:
<221> NAME/KEY: terminator
<222> LOCATION: (4008)..(4197)
<223> OTHER INFORMATION: yeast CYC1 terminator
<220> FEATURE:
<221> NAME/KEY: misc_feature
<222> LOCATION: (6191)..(7533)
<223> OTHER INFORMATION: yeast 2 micron ori

<400> SEQUENCE: 42
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcggggctgg cttaactatg cggcatcaga gcagattgta ctgagagtgc      180
accataaacg acattactat atatataata taggaagcat taatagaca gcatcgtaat      240 atatgtgtac tttgcagtta tgacgccaga tggcagtagt ggaagatatt ctttattgaa      300
aaatagcttg tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta      480
atttcacagg tagttctggt ccattggtga agtttgcgg cttgcagagc acagaggccg      540
cagaatgtgc tctagattcc gatgctgact tgctgggtat tatatgtgtg cccaatagaa      600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
```

```
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttgttaa atcagctcat tttttaaccaa ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttgggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgaccctttt tccatctttt cgtaaatttc tggcaaggta gacaagccga caaccttgat   2040
tggagacttg accaaacctc tggcgaagaa ttgttaatta agagctctta ttagtaaatg   2100
ccagagttag cagcgattgc agatgggatc ggattaccgt ctttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact ttttttttgg   2520
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
tgctccgaac aataaagatt ctacaatact agctttatg gttatgaaga ggaaaaattg   2880
gcagtaaccct ggccccacaa accttcaaat gaacgaatca aattaacaac cataggatga   2940
taatgcgatt agttttttag ccttattttct ggggtaatta atcagcgaag cgatgatttt   3000
tgatctatta acagatatat aaatgcaaaa actgcataac cactttaact aatactttca   3060
acattttcgg tttgtattac ttcttattca aatgtaataa aagtatcaac aaaaaattgt   3120
```

```
taatatacct ctatacttta acgtcaagga gaaaaaaccc cggatccatt taaatgcgat    3180
cgcgcacgag gttttttctgt ctagtgagca gtgtccaacc tcaaaagaca acatgtgtga    3240
cgacgatgta gcggctcttg tcgtagacaa tggatccggt atgtgcaaag ccggtttcgc    3300
aggagatgac gcacccgtg ccgtcttccc ctcgatcgtc ggtcgcccaa ggcatcaagg    3360
agtcatggtc ggtatgggac aaaaggactc atacgtagga gatgaagccc aaagcaaaag    3420
aggtatcctc accctgaaat accccatcga acacggtatc atcaccaact gggatgagtt    3480
taaaccctct agctgcttta caaagtactg gttccctttc cagcgggatg ctttatctaa    3540
acgcaatgag agaggtattc ctcaggccac atcgcttcct agttccgctg ggatccatcg    3600
ttggcggccg aagccgccat tccatagtga gttctggcgc gcctcatccc agttggtgat    3660
gataccgtgt tcgatggggt atttcagggt gaggatacct cttttgcttt gggcttcatc    3720
tcctacgtat gagtcctttt gtcccatacc gaccatgact ccttgatgcc ttgggcgacc    3780
gacgatcgag gggaagacgg cacggggtgc gtcatctcct gcgaaaccgg ctttgcacat    3840
accggatcca ttgtctacga caagagccgc tacatcgtcg tcacacatgt tgtcttttga    3900
ggttggacac tgctcactag acagaaaaac ctcgtgccgg accgaatacc cggtctgaac    3960
gagggcggcc gcacatgagg atcacccatg tccgcgggct agctaagatc cgctctaacc    4020
gaaaaggaag gagttagaca acctgaagtc taggtcccta tttatttttt tatagttatg    4080
ttagtattaa gaacgttatt tatatttcaa attttctttt tttttctgta cagacgcgtg    4140
tacgcatgta acattatact gaaaaccttg cttgagaagg ttttgggacg ctcgaagatc    4200
cagctgcatt aatgaatcgg ccaacgcgcg gggagaggcg gtttgcgtat tgggcgctct    4260
tccgcttcct cgctcactga ctcgctgcgc tcggtcgttc ggctgcggcg agcggtatca    4320
gctcactcaa aggcggtaat acggttatcc acagaatcag gggataacgc aggaaagaac    4380
atgtgagcaa aaggccagca aaaggccagg aaccgtaaaa aggccgcgtt gctggcgttt    4440
ttccataggc tccgcccccc tgacgagcat cacaaaaatc gacgctcaag tcagaggtgg    4500
cgaaacccga caggactata aagataccag gcgtttcccc ctggaagctc cctcgtgcgc    4560
tctcctgttc cgaccctgcc gcttaccgga tacctgtccg cctttctccc ttcgggaagc    4620
gtggcgcttt ctcatagctc acgctgtagg tatctcagtt cggtgtaggt cgttcgctcc    4680
aagctgggct gtgtgcacga accccccgtt cagcccgacc gctgcgcctt atccggtaac    4740
tatcgtcttg agtccaaccc ggtaagacac gacttatcgc cactggcagc agccactggt    4800
aacaggatta gcagagcgag gtatgtaggc ggtgctacag agttcttgaa gtggtggcct    4860
aactacggct acactagaag gacagtattt ggtatctgcg ctctgctgaa gccagttacc    4920
ttcggaaaaa gagttggtag ctcttgatcc ggcaaacaaa ccaccgctgg tagcggtggt    4980
ttttttgttt gcaagcagca gattacgcgc agaaaaaaag gatctcaaga agatcctttg    5040
atcttttcta cggggtctga cgctcagtgg aacgaaaact cacgttaagg gattttggtc    5100
atgagattat caaaaaggat cttcacctag atccttttaa attaaaaatg aagttttaaa    5160
tcaatctaaa gtatatatga gtaaacttgg tctgacagtt accaatgctt aatcagtgag    5220
gcacctatct cagcgatctg tctatttcgt tcatccatag ttgcctgact ccccgtcgtg    5280
tagataacta cgatacggga gggcttacca tctggcccca gtgctgcaat gataccgcga    5340
gacccacgct caccggctcc agatttatca gcaataaacc agccagccgg aagggccgag    5400
cgcagaagtg gtcctgcaac tttatccgcc tccatccagt ctattaattg ttgccgggaa    5460
```

```
gctagagtaa gtagttcgcc agttaatagt ttgcgcaacg ttgttgccat tgctacaggc   5520
atcgtggtgt cacgctcgtc gtttggtatg gcttcattca gctccggttc ccaacgatca   5580
aggcgagtta catgatcccc catgttgtgc aaaaaagcgg ttagctcctt cggtcctccg   5640
atcgttgtca gaagtaagtt ggccgcagtg ttatcactca tggttatggc agcactgcat   5700
aattctctta ctgtcatgcc atccgtaaga tgcttttctg tgactggtga gtactcaacc   5760
aagtcattct gagaatagtg tatgcggcga ccgagttgct cttgcccggc gtcaatacgg   5820
gataataccg cgccacatag cagaacttta aaagtgctca tcattggaaa acgttcttcg   5880
gggcgaaaac tctcaaggat cttaccgctg ttgagatcca gttcgatgta acccactcgt   5940
gcacccaact gatcttcagc atcttttact ttcaccagcg tttctgggtg agcaaaaaca   6000
ggaaggcaaa atgccgcaaa aaagggaata agggcgacac ggaaatgttg aatactcata   6060
ctcttccttt ttcaatatta ttgaagcatt tatcagggtt attgtctcat gagcggatac   6120
atatttgaat gtatttagaa aaataaacaa ataggggttc cgcgcacatt tccccgaaaa   6180
gtgccacctg aacgaagcat ctgtgcttca ttttgtagaa caaaaatgca acgcgagagc   6240
gctaattttt caaacaaaga atctgagctg cattttttaca gaacagaaat gcaacgcgaa   6300
agcgctattt taccaacgaa gaatctgtgc ttcattttttg taaaacaaaa atgcaacgcg   6360
agagcgctaa ttttttcaaac aaagaatctg agctgcattt ttacagaaca gaaatgcaac   6420
gcgagagcgc tattttacca acaaagaatc tatacttctt ttttgttcta caaaaatgca   6480
tcccgagagc gctattttttc taacaaagca tcttagatta ctttttttttct cctttgtgcg   6540
ctctataatg cagtctcttg ataacttttt gcactgtagg tccgttaagg ttagaagaag   6600
gctactttgg tgtctatttt ctcttccata aaaaagcct gactccactt cccgcgttta   6660
ctgattacta gcgaagctgc gggtgcattt tttcaagata aaggcatccc cgattatatt   6720
ctataccgat gtggattgcg catactttgt gaacagaaag tgatagcgtt gatgattctt   6780
cattggtcag aaaattatga acggtttctt ctatttttgtc tctatatact acgtatagga   6840
aatgtttaca ttttcgtatt gttttcgatt cactctatga atagttctta ctacaatttt   6900
tttgtctaaa gagtaatact agagatatac ataaaaaatg tagaggtcga gtttagatgc   6960
aagttcaagg agcgaaaggt ggatgggtag gttatatagg gatatagcac agagatatat   7020
agcaaagaga tacttttgag caatgtttgt ggaagcggta ttcgcaatat tttagtagct   7080
cgttacagtc cggtgcgttt ttggtttttt gaaagtgcgt cttcagagcg cttttggttt   7140
tcaaaagcgc tctgaagttc ctatactttc tagagaatag gaacttcgga ataggaactt   7200
caaagcgttt ccgaaaacga gcgcttccga aaatgcaacg cgagctgcgc acatacagct   7260
cactgttcac gtcgcaccta tctgcgtgt tgcctgtat atatatatac atgagaagaa   7320
cggcatagtg cgtgtttatg cttaaatgcg tactatatg cgtctattta tgtaggatga   7380
aaggtagtct agtacctcct gtgatattat cccattccat gcggggtatc gtatgcttcc   7440
ttcagcacta ccctttagct gttctatatg ctgccactcc tcaattggat tagtctcatc   7500
cttcaatgct atcatttcct ttgatattgg atcatattaa gaaaccatta ttatcatgac   7560
attaacctat aaaaataggc gtatcacgag gccctttcgt c                       7601
```

<210> SEQ ID NO 43  
<211> LENGTH: 7288  
<212> TYPE: DNA  
<213> ORGANISM: Artificial Sequence  
<220> FEATURE:  
<223> OTHER INFORMATION: Recombinant plasmid pAPSE10443; beta actin stem

```
                loop - coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: promoter
<222> LOCATION: (2162)..(2826)
<223> OTHER INFORMATION: yeast GAL1, 10 bidirectional promoter
<220> FEATURE:
<221> NAME/KEY: misc_feature
<222> LOCATION: (2844)..(2862)
<223> OTHER INFORMATION: bacteriophage MS2 pac sequence
<220> FEATURE:
<221> NAME/KEY: misc_feature
<222> LOCATION: (2863)..(2870)
<223> OTHER INFORMATION: restriction endonuclease AsiSI recognition
      sequence
<220> FEATURE:
<221> NAME/KEY: misc_feature
<222> LOCATION: (2872)..(3165)
<223> OTHER INFORMATION: beta actin sense gene fragment
<220> FEATURE:
<221> NAME/KEY: misc_feature
<222> LOCATION: (3165)..(3172)
<223> OTHER INFORMATION: restriction endonuclease PmeI recognition site
<220> FEATURE:
<221> NAME/KEY: misc_feature
<222> LOCATION: (3329)..(3624)
<223> OTHER INFORMATION: beta actin antisense strand gene fragment
<220> FEATURE:
<221> NAME/KEY: misc_feature
<222> LOCATION: (3660)..(3678)
<223> OTHER INFORMATION: bacteriophage MS2 pac sequence
<220> FEATURE:
<221> NAME/KEY: terminator
<222> LOCATION: (3695)..(3884)
<223> OTHER INFORMATION: yeast CYC1 terminator
<220> FEATURE:
<221> NAME/KEY: misc_feature
<222> LOCATION: (5878)..(7220)
<223> OTHER INFORMATION: yeast 2 micron ori

<400> SEQUENCE: 43
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttcttttt tgccgattaa      360 gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
```

```
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt tttttttggat ggacgcaaag aagtttaata atcatattac   2220
atggcattac caccatatac atatccatat acatatccat atctaatctt acttatatgt   2280
tgtggaaatg taaagagccc cattatctta gcctaaaaaa accttctctt tggaactttc   2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgattttttg atctattaac agatatataa atgcaaaaac   2700
tgcataacca ctttaactaa tactttcaac attttcggtt tgtattactt cttattcaaa   2760
tgtaataaaa gtatcaacaa aaaattgtta atatacctct atactttaac gtcaaggaga   2820
aaaaccccg gatccattta aatacatgag gattacccat gtgcgatcgc gcacgaggtt   2880
tttctgtcta gtgagcagtg tccaacctca aaagacaaca tgtgtgacga cgatgtagcg   2940
gctcttgtcg tagacaatgg atccggtatg tgcaaagccg gtttcgcagg agatgacgca   3000
ccccgtgccg tcttcccctc gatcgtcggt cgcccaaggc atcaaggagt catggtcggt   3060
```

```
atgggacaaa aggactcata cgtaggagat gaagcccaaa gcaaaagagg tatcctcacc    3120
ctgaaatacc ccatcgaaca cggtatcatc accaactggg atgagtttaa accctctagc    3180
tgctttacaa agtactggtt cccttttccag cgggatgctt tatctaaacg caatgagaga   3240
ggtattcctc aggccacatc gcttcctagt tccgctggga tccatcgttg gcggccgaag    3300
ccgccattcc atagtgagtt ctggcgcgcc tcatcccagt tggtgatgat accgtgttcg    3360
atggggtatt tcagggtgag gatacctctt ttgctttggg cttcatctcc tacgtatgag    3420
tccttttgtc ccataccgac catgactcct tgatgccttg ggcgaccgac gatcgagggg    3480
aagacggcac ggggtgcgtc atctcctgcg aaaccggctt tgcacatacc ggatccattg    3540
tctacgacaa gagccgctac atcgtcgtca cacatgttgt cttttgaggt tggacactgc    3600
tcactagaca gaaaaacctc gtgccggacc gaatacccgg tctgaacgag gcggccgca    3660 catgaggatc acccatgtcc gcgggctagc taagatccgc tctaaccgaa aggaaggag    3720 ttagacaacc tgaagtctag gtccctattt attttttat agttatgtta gtattaagaa    3780
cgttatttat atttcaaatt tttctttttt ttctgtacag acgcgtgtac gcatgtaaca    3840
ttatactgaa aaccttgctt gagaaggttt tgggacgctc gaagatccag ctgcattaat    3900
gaatcggcca acgcgcgggg agaggcggtt tgcgtattgg gcgctcttcc gcttcctcgc    3960
tcactgactc gctgcgctcg gtcgttcggc tgcggcgagc ggtatcagct cactcaaagg    4020
cggtaatacg gttatccaca gaatcagggg ataacgcagg aaagaacatg tgagcaaaag    4080
gccagcaaaa ggccaggaac cgtaaaaagg ccgcgttgct ggcgtttttc cataggctcc    4140
gcccccctga cgagcatcac aaaaatcgac gctcaagtca gaggtggcga aacccgacag    4200
gactataaag ataccaggcg tttccccctg gaagctccct cgtgcgctct cctgttccga    4260
ccctgccgct taccggatac ctgtccgcct ttctcccttc gggaagcgtg gcgctttctc    4320
atagctcacg ctgtaggtat ctcagttcgg tgtaggtcgt tcgctccaag ctgggctgtg    4380
tgcacgaacc ccccgttcag cccgaccgct gcgccttatc cggtaactat cgtcttgagt    4440
ccaacccggt aagacacgac ttatcgccac tggcagcagc cactggtaac aggattagca    4500
gagcgaggta tgtaggcggt gctacagagt tcttgaagtg gtggcctaac tacggctaca    4560
ctagaaggac agtatttggt atctgcgctc tgctgaagcc agttaccttc ggaaaaagag    4620
ttggtagctc ttgatccggc aaacaaacca ccgctggtag cggtggtttt tttgtttgca    4680
agcagcagat tacgcgcaga aaaaaggat ctcaagaaga tcctttgatc ttttctacgg    4740
ggtctgacgc tcagtggaac gaaaactcac gttaagggat tttggtcatg agattatcaa    4800
aaaggatctt cacctagatc cttttaaatt aaaaatgaag ttttaaatca atctaaagta    4860
tatatgagta aacttggtct gacagttacc aatgcttaat cagtgaggca cctatctcag    4920
cgatctgtct atttcgttca tccatagttg cctgactccc cgtcgtgtag ataactacga    4980
tacgggaggg cttaccatct ggccccagtg ctgcaatgat accgcgagac ccacgctcac    5040
cggctccaga tttatcagca ataaaccagc cagccggaag ggccgagcgc agaagtggtc    5100
ctgcaacttt atccgcctcc atccagtcta ttaattgttg ccgggaagct agagtaagta    5160
gttcgccagt taatagtttg cgcaacgttg ttgccattgc tacaggcatc gtggtgtcac    5220
gctcgtcgtt tggtatggct tcattcagct ccggttccca acgatcaagg cgagttacat    5280
gatcccccat gttgtgcaaa aaagcggtta gctccttcgg tcctccgatc gttgtcagaa    5340
gtaagttggc cgcagtgtta tcactcatgg ttatggcagc actgcataat tctcttactg    5400
```

-continued

```
tcatgccatc cgtaagatgc tttctgtga ctggtgagta ctcaaccaag tcattctgag    5460
aatagtgtat gcggcgaccg agttgctctt gcccggcgtc aatacgggat aataccgcgc    5520
cacatagcag aactttaaaa gtgctcatca ttggaaaacg ttcttcgggg cgaaaactct    5580
caaggatctt accgctgttg agatccagtt cgatgtaacc cactcgtgca cccaactgat    5640
cttcagcatc ttttactttc accagcgttt ctgggtgagc aaaaacagga aggcaaaatg    5700
ccgcaaaaaa gggaataagg gcgacacgga aatgttgaat actcatactc ttcctttttc    5760
aatattattg aagcatttat cagggttatt gtctcatgag cggatacata tttgaatgta    5820
tttagaaaaa taaacaaata ggggttccgc gcacatttcc ccgaaaagtg ccacctgaac    5880
gaagcatctg tgcttcattt tgtagaacaa aaatgcaacg cgagagcgct aattttcaa    5940 acaaagaatc tgagctgcat ttttacagaa cagaaatgca acgcgaaagc gctattttac    6000
caacgaagaa tctgtgcttc attttgtaa acaaaaatg caacgcgaga gcgctaattt    6060
ttcaaacaaa gaatctgagc tgcatttta cagaacagaa atgcaacgcg agagcgctat    6120
tttaccaaca agaatctat acttctttt tgttctacaa aaatgcatcc cgagagcgct    6180
atttttctaa caaagcatct tagattactt ttttctcct ttgtgcgctc tataatgcag    6240
tctcttgata acttttgca ctgtaggtcc gttaaggtta gaagaaggct actttggtgt    6300
ctattttctc ttccataaaa aaagcctgac tccacttccc gcgttactg attactagcg    6360 aagctgcggg tgcattttt caagataaag gcatccccga ttatattcta taccgatgtg    6420
gattgcgcat actttgtgaa cagaaagtga tagcgttgat gattcttcat tggtcagaaa    6480
attatgaacg gtttcttcta ttttgtctct atatactacg tataggaaat gtttacattt    6540
tcgtattgtt ttcgattcac tctatgaata gttcttacta caatttttt gtctaaagag    6600 taatactaga gataaacata aaaaatgtag aggtcgagtt tagatgcaag ttcaaggagc    6660
gaaaggtgga tgggtaggtt atatagggat atagcacaga gatatatagc aaagagatac    6720
ttttgagcaa tgtttgtgga agcggtattc gcaatatttt agtagctcgt tacagtccgg    6780 tgcgttttg gttttttgaa agtgcgtctt cagagcgctt ttggttttca aaagcgctct    6840
gaagttccta ctttctag agaataggaa cttcggaata ggaacttcaa agcgtttccg    6900
aaaacgagcg cttccgaaaa tgcaacgcga gctgcgcaca tacagctcac tgttcacgtc    6960
gcacctatat ctgcgtgttg cctgtatata tatatacatg agaagaacgg catagtgcgt    7020
gtttatgctt aaatgcgtac ttatatgcgt ctatttatgt aggatgaaag gtagtctagt    7080
acctcctgtg atattatccc attccatgcg gggtatcgta tgcttccttc agcactaccc    7140
tttagctgtt ctatatgctg ccactcctca attggattag tctcatcctt caatgctatc    7200
atttcctttg atattggatc atattaagaa accattatta tcatgacatt aacctataaa    7260
aataggcgta tcacgaggcc ctttcgtc                                        7288
```

<210> SEQ ID NO 44
<211> LENGTH: 7620
<212> TYPE: DNA
<213> ORGANISM: Artificial Sequence
<220> FEATURE:
<223> OTHER INFORMATION: Recombinant plasmid pAPSE10444; beta actin stem
      loop + coat protein
<220> FEATURE:
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)

```
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3194)
<223> OTHER INFORMATION: bacteriophage MS2 pac sequence
<220> FEATURE:
<221> NAME/KEY: misc_feature
<222> LOCATION: (3195)..(3202)
<223> OTHER INFORMATION: restriction endonuclease AsiSI recognition
      sequence
<220> FEATURE:
<221> NAME/KEY: misc_feature
<222> LOCATION: (3204)..(3497)
<223> OTHER INFORMATION: beta actin sense gene fragment
<220> FEATURE:
<221> NAME/KEY: misc_feature
<222> LOCATION: (3497)..(3504)
<223> OTHER INFORMATION: restriction endonuclease PmeI recognition site
<220> FEATURE:
<221> NAME/KEY: misc_feature
<222> LOCATION: (3661)..(3957)
<223> OTHER INFORMATION: beta actin antisense strand gene fragment
<220> FEATURE:
<221> NAME/KEY: misc_feature
<222> LOCATION: (3992)..(4010)
<223> OTHER INFORMATION: bacteriophage MS2 pac sequence
<220> FEATURE:
<221> NAME/KEY: terminator
<222> LOCATION: (4027)..(4216)
<223> OTHER INFORMATION: yeast CYC1 terminator
<220> FEATURE:
<221> NAME/KEY: misc_feature
<222> LOCATION: (6210)..(7552)
<223> OTHER INFORMATION: yeast 2 micron ori

<400> SEQUENCE: 44
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
```

```
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttggggtcg    1500 aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tatttttttt ataacttatt taataataaa   1920
aatcataaat cataagaaat tcgcttattt agaagtgtca acaacgtatc taccaacgat   1980 ttgaccctt tccatctttt cgtaaatttc tggcaaggta gacaagccga caaccttgat   2040
tggagacttg accaaaccc tggcgaagaa ttgttaatta agagctctta ttagtaaatg   2100
ccagagttag cagcgattgc agatgggatc ggattaccgt ctttcagcag gccctgcatt   2160
gccttaacaa tcagttcgca gtcggagttc gtcgcaaaaa tcggaatagt cagttccatg   2220
ttgaggtaag agcgccaggc cgcaactggg agttctacgc cgcctacggt ctgcgttgcg   2280
actttcggta cttcaacttt gatggtgtat ttgcgattct gcgcgctaga ctgacgaacg   2340
gagcacgtga ctttgtaggc ctgagagcgg ctgttagagc taatccattc cgcaacaccg   2400
ttggcgaagt tggacggagc tacggtaacg tcacccgtac cgccgttatc aaccagaacg   2460
aattgggtaa agttagacgc catgaattcg aattttcaaa aattcttact ttttttttgg   2520
atggacgcaa agaagtttaa taatcatatt acatggcatt accaccatat acatatccat   2580
atacatatcc atatctaatc ttacttatat gttgtggaaa tgtaaagagc cccattatct   2640
tagcctaaaa aaaccttctc tttggaactt tcagtaatac gcttaactgc tcattgctat   2700
attgaagtac ggattagaag ccgccgagcg ggtgacagcc ctccgaagga agactctcct   2760
ccgtgcgtcc tcgtcttcac cggtcgcgtt cctgaaacgc agatgtgcct cgcgccgcac   2820
tgctccgaac aataaagatt ctacaatact agcttttatg gttatgaaga ggaaaaattg   2880
gcagtaacct ggccccacaa accttcaaat gaacgaatca aattaacaac cataggatga   2940
taatgcgatt agttttttag ccttatttct ggggtaatta atcagcgaag cgatgatttt   3000
tgatctatta acagatatat aaatgcaaaa actgcataac cactttaact aatactttca   3060
acattttcgg tttgtattac ttcttattca aatgtaataa aagtatcaac aaaaaattgt   3120 taatataccct ctatacttta acgtcaagga gaaaaaaccc cggatccatt taaatacatg   3180
```

-continued

| | |
|---|---|
| aggattaccc atgtgcgatc gcgcacgagg ttttttctgtc tagtgagcag tgtccaacct | 3240 |
| caaaagacaa catgtgtgac gacgatgtag cggctcttgt cgtagacaat ggatccggta | 3300 |
| tgtgcaaagc cggtttcgca ggagatgacg caccccgtgc cgtcttcccc tcgatcgtcg | 3360 |
| gtcgcccaag gcatcaagga gtcatggtcg gtatgggaca aaaggactca tacgtaggag | 3420 |
| atgaagccca agcaaaaga ggtatcctca ccctgaaata ccccatcgaa cacggtatca | 3480 |
| tcaccaactg ggatgagttt aaaccctcta gctgctttac aaagtactgg ttccctttcc | 3540 |
| agcgggatgc tttatctaaa cgcaatgaga gaggtattcc tcaggccaca tcgcttccta | 3600 |
| gttccgctgg gatccatcgt tggcggccga agccgccatt ccatagtgag ttctggcgcg | 3660 |
| cctcatccca gttggtgatg ataccgtgtt cgatgggta tttcagggtg aggatacctc | 3720 |
| ttttgctttg ggcttcatct cctacgtatg agtccttttg tcccataccg accatgactc | 3780 |
| cttgatgcct tgggcgaccg acgatcgagg ggaagacggc acggggtgcg tcatctcctg | 3840 |
| cgaaaccggc tttgcacata ccggatccat tgtctacgac aagagccgct acatcgtcgt | 3900 |
| cacacatgtt gtcttttgag gttggacact gctcactaga cagaaaaacc tcgtgccgga | 3960 |
| ccgaataccc ggtctgaacg agggcggccg cacatgagga tcacccatgt ccgcgggcta | 4020 |
| gctaagatcc gctctaaccg aaaaggaagg agttagacaa cctgaagtct aggtccctat | 4080 |
| ttattttttt atagttatgt tagtattaag aacgttattt atatttcaaa ttttttcttt | 4140 |
| ttttctgtac agacgcgtgt acgcatgtaa cattatactg aaaaccttgc ttgagaaggt | 4200 |
| tttgggacgc tcgaagatcc agctgcatta atgaatcggc caacgcgcgg ggagaggcgg | 4260 |
| tttgcgtatt gggcgctctt ccgcttcctc gctcactgac tcgctgcgct cggtcgttcg | 4320 |
| gctgcggcga gcggtatcag ctcactcaaa ggcggtaata cggttatcca cagaatcagg | 4380 |
| ggataacgca ggaaagaaca tgtgagcaaa aggccagcaa aaggccagga accgtaaaaa | 4440 |
| ggccgcgttg ctggcgtttt tccataggct ccgcccccct gacgagcatc acaaaaatcg | 4500 |
| acgctcaagt cagaggtggc gaaacccgac aggactataa agataccagg cgtttccccc | 4560 |
| tggaagctcc ctcgtgcgct ctcctgttcc gaccctgccg cttaccggat acctgtccgc | 4620 |
| ctttctccct tcgggaagcg tggcgctttc tcatagctca cgctgtaggt atctcagttc | 4680 |
| ggtgtaggtc gttcgctcca agctgggctg tgtgcacgaa ccccccgttc agcccgaccg | 4740 |
| ctgcgcctta tccggtaact atcgtcttga gtccaacccg gtaagacacg acttatcgcc | 4800 |
| actggcagca gccactggta acaggattag cagagcgagg tatgtaggcg gtgctacaga | 4860 |
| gttcttgaag tggtggccta actacggcta cactagaagg acagtatttg gtatctgcgc | 4920 |
| tctgctgaag ccagttacct tcggaaaaag agttggtagc tcttgatccg gcaaacaaac | 4980 |
| caccgctggt agcggtggtt tttttgtttg caagcagcag attacgcgca gaaaaaaagg | 5040 |
| atctcaagaa gatcctttga tcttttctac ggggtctgac gctcagtgga acgaaaactc | 5100 |
| acgttaaggg attttggtca tgagattatc aaaaaggatc ttcacctaga tccttttaaa | 5160 |
| ttaaaaatga agttttaaat caatctaaag tatatatgag taaacttggt ctgacagtta | 5220 |
| ccaatgctta atcagtgagg cacctatctc agcgatctgt ctatttcgtt catccatagt | 5280 |
| tgcctgactc cccgtcgtgt agataactac gatacgggag ggcttaccat ctggccccag | 5340 |
| tgctgcaatg ataccgcgag acccacgctc accggctcca gatttatcag caataaacca | 5400 |
| gccagccgga agggccgagc gcagaagtgg tcctgcaact ttatccgcct ccatccagtc | 5460 |
| tattaattgt tgccgggaag ctagagtaag tagttcgcca gttaatagtt tgcgcaacgt | 5520 |

```
tgttgccatt gctacaggca tcgtggtgtc acgctcgtcg tttggtatgg cttcattcag    5580
ctccggttcc caacgatcaa ggcgagttac atgatcccc  atgttgtgca aaaaagcggt    5640
tagctccttc ggtcctccga tcgttgtcag aagtaagttg gccgcagtgt tatcactcat    5700
ggttatggca gcactgcata attctcttac tgtcatgcca tccgtaagat gcttttctgt    5760
gactggtgag tactcaacca agtcattctg agaatagtgt atgcggcgac cgagttgctc    5820
ttgcccggcg tcaatacggg ataataccgc gccacatagc agaactttaa aagtgctcat    5880
cattggaaaa cgttcttcgg ggcgaaaact ctcaaggatc ttaccgctgt tgagatccag    5940
ttcgatgtaa cccactcgtg cacccaactg atcttcagca tcttttactt tcaccagcgt    6000
ttctgggtga gcaaaaacag gaaggcaaaa tgccgcaaaa aagggaataa gggcgacacg    6060
gaaatgttga atactcatac tcttcctttt tcaatattat tgaagcattt atcagggtta    6120
ttgtctcatg agcggataca tatttgaatg tatttagaaa aataaacaaa tagggggttcc   6180
gcgcacattt ccccgaaaag tgccacctga acgaagcatc tgtgcttcat tttgtagaac    6240
aaaaatgcaa cgcgagagcg ctaatttttc aaacaaagaa tctgagctgc atttttacag    6300
aacagaaatg caacgcgaaa gcgctatttt accaacgaag aatctgtgct tcattttgt     6360
aaaacaaaaa tgcaacgcga gagcgctaat ttttcaaaca aagaatctga gctgcatttt    6420
tacagaacag aaatgcaacg cgagagcgct attttaccaa caagaatct  atacttcttt    6480
tttgttctac aaaaatgcat cccgagagcg ctatttttct aacaaagcat cttagattac    6540
ttttttctc  ctttgtgcgc tctataatgc agtctcttga taacttttg  cactgtaggt    6600
ccgttaaggt tagaagaagg ctactttggt gtctattttc tcttccataa aaaagcctg     6660
actccacttc ccgcgtttac tgattactag cgaagctgcg ggtgcatttt ttcaagataa    6720
aggcatcccc gattatattc tataccgatg tggattgcgc atactttgtg aacagaaagt    6780
gatagcgttg atgattcttc attggtcaga aaattatgaa cggtttcttc tatttgtct    6840
ctatatacta cgtataggaa atgtttacat tttcgtattg ttttcgattc actctatgaa    6900
tagttcttac tacaatttt  ttgtctaaag agtaatacta gagataaaca taaaaatgt    6960
agaggtcgag tttagatgca agttcaagga gcgaaaggtg gatgggtagg ttatataggg    7020
atatagcaca gagatatata gcaaagagat acttttgagc aatgtttgtg gaagcggtat    7080
tcgcaatatt ttagtagctc gttacagtcc ggtgcgtttt tggttttttg aaagtgcgtc    7140
ttcagagcgc ttttggtttt caaaagcgct ctgaagttcc tatactttct agagaatagg    7200
aacttcggaa taggaacttc aaagcgtttc cgaaaacgag cgcttccgaa aatgcaacgc    7260
gagctgcgca catacagctc actgttcacg tcgcacctat atctgcgtgt tgcctgtata    7320
tatatataca tgagaagaac ggcatagtgc gtgtttatgc ttaaatgcgt acttatatgc    7380
gtctatttat gtaggatgaa aggtagtcta gtacctcctg tgatattatc ccattccatg    7440
cggggtatcg tatgcttcct tcagcactac cctttagctg ttctatatgc tgccactcct    7500
caattggatt agtctcatcc ttcaatgcta tcatttcctt tgatattgga tcatattaag    7560
aaaccattat tatcatgaca ttaacctata aaaataggcg tatcacgagg ccctttcgtc    7620
```

<210> SEQ ID NO 45
<211> LENGTH: 7288
<212> TYPE: DNA
<213> ORGANISM: Artificial Sequence
<220> FEATURE:
<223> OTHER INFORMATION: Recpmbinant plasmid pAPSE10445; beta actin stem
      loop - coat protein
<220> FEATURE:

```
<221> NAME/KEY: promoter
<222> LOCATION: (187)..(467)
<223> OTHER INFORMATION: yeast TRP1 promoter
<220> FEATURE:
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: misc_feature
<222> LOCATION: (2152)..(2157)
<223> OTHER INFORMATION: restriction endonuclease EcoRI recognition site
<220> FEATURE:
<221> NAME/KEY: misc_feature
<222> LOCATION: (2162)..(2826)
<223> OTHER INFORMATION: yeast GAL1, 10 bidirectional prmoter
<220> FEATURE:
<221> NAME/KEY: misc_feature
<222> LOCATION: (2844)..(2862)
<223> OTHER INFORMATION: bacteriophage MS2 pac sequence
<220> FEATURE:
<221> NAME/KEY: misc_feature
<222> LOCATION: (2863)..(2870)
<223> OTHER INFORMATION: restriction endonuclease AsiSI recognition
      sequence
<220> FEATURE:
<221> NAME/KEY: misc_feature
<222> LOCATION: (2872)..(3165)
<223> OTHER INFORMATION: beta actin sense gene fragment
<220> FEATURE:
<221> NAME/KEY: misc_feature
<222> LOCATION: (3165)..(3172)
<223> OTHER INFORMATION: restriction endonuclease PmeI recognition site
<220> FEATURE:
<221> NAME/KEY: misc_feature
<222> LOCATION: (3233)..(3251)
<223> OTHER INFORMATION: bacteriophage MS2 pac sequence
<220> FEATURE:
<221> NAME/KEY: misc_feature
<222> LOCATION: (3329)..(3624)
<223> OTHER INFORMATION: beta actin antisense strand gene fragment
<220> FEATURE:
<221> NAME/KEY: misc_feature
<222> LOCATION: (3660)..(3678)
<223> OTHER INFORMATION: bacteriophage MS2 pac sequence
<220> FEATURE:
<221> NAME/KEY: terminator
<222> LOCATION: (3695)..(3884)
<223> OTHER INFORMATION: yeast CYC1 terminator
<220> FEATURE:
<221> NAME/KEY: misc_feature
<222> LOCATION: (5878)..(7220)
<223> OTHER INFORMATION: yeast 2 micron ori

<400> SEQUENCE: 45
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accataaacg acattactat atatataata taggaagcat ttaatagaca gcatcgtaat      240
atatgtgtac tttgcagtta tgacgccaga tggcagtagt ggaagatatt ctttattgaa      300
aaatagcttg tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta      480
atttcacagg tagttctggt ccattggtga aagtttgcgg cttgcagagc acagaggccg      540
cagaatgtgc tctagattcc gatgctgact tgctgggtat tatatgtgtg cccaatagaa      600
```

```
agagaacaat tgacccggtt attgcaagga aaatttcaag tcttgtaaaa gcatatasaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgtta atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg cgaaaaacc    1440
gtctatcagg gcgatggccc actacgtgaa ccatcaccct aatcaagttt ttggggtcg    1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctgaattgga gcgacctcat gctatacctg   1800
agaaagcaac ctgacctaca ggaaagagtt actcaagaat aagaattttc gttttaaaac   1860
ctaagagtca ctttaaaatt tgtatacact tattttttt ataacttatt taataataaa    1920
aatcataaat cataagaaat tcgcttattt agaagtgtca acaacgtatc taccaacgat   1980
ttgacccttt tccatctttt cgtaaatttc tggcaaggta gacaagccga caaccttgat   2040
tggagacttg accaaacctc tggcgaagaa ttgttaatta agagctcaga tcttatcgtc   2100
gtcatccttg taatccatcg atactagtgc ggccgccctt tagtgagggt tgaattcgaa   2160
ttttcaaaaa ttcttacttt ttttttggat ggacgcaaag aagtttaata atcatattac   2220
atggcattac caccatatac atatccatat acatatccat atctaatctt acttatatgt   2280
tgtgaaatg taaagagccc cattatctta gcctaaaaaa accttctctt tggaactttc     2340
agtaatacgc ttaactgctc attgctatat tgaagtacgg attagaagcc gccgagcggg   2400
tgacagccct ccgaaggaag actctcctcc gtgcgtcctc gtcttcaccg gtcgcgttcc   2460
tgaaacgcag atgtgcctcg cgccgcactg ctccgaacaa taaagattct acaatactag   2520
cttttatggt tatgaagagg aaaaattggc agtaacctgg ccccacaaac cttcaaatga   2580
acgaatcaaa ttaacaacca taggatgata atgcgattag ttttttagcc ttatttctgg   2640
ggtaattaat cagcgaagcg atgattttg atctattaac agatatataa atgcaaaaac    2700
tgcataacca cttaactaa tactttcaac attttcggtt tgtattactt cttattcaaa    2760
tgtaataaaa gtatcaacaa aaaattgtta atatacctct atactttaac gtcaaggaga   2820
aaaaaccccg gatccattta aatacatgag gattacccat gtcgatcgc gcacgaggtt    2880
tttctgtcta gtgagcagtg tccaacctca aaagacaaca tgtgtgacga cgatgtagcg   2940
gctcttgtcg tagacaatgg atccggtatg tgcaaagccg gtttcgcagg agatgacgca   3000
```

| | | |
|---|---|---|
| ccccgtgccg tcttccctc gatcgtcggt cgcccaaggc atcaaggagt catggtcggt | 3060 | |
| atgggacaaa aggactcata cgtaggagat gaagcccaaa gcaaagagg tatcctcacc | 3120 | |
| ctgaaatacc ccatcgaaca cggtatcatc accaactggg atgagtttaa accctctagc | 3180 | |
| tgctttacaa agtactggtt cccttccag cgggatgctt tatctaaacg caacatgagg | 3240 | |
| atcacccatg tcgccacatc gcttcctagt tccgctggga tccatcgttg gcggccgaag | 3300 | |
| ccgccattcc atagtgagtt ctggcgcgcc tcatcccagt tggtgatgat accgtgttcg | 3360 | |
| atggggtatt tcagggtgag gatacctctt ttgctttggg cttcatctcc tacgtatgag | 3420 | |
| tccttttgtc ccataccgac catgactcct tgatgccttg ggcgaccgac gatcgagggg | 3480 | |
| aagacggcac ggggtgcgtc atcctgcg aaaccggctt tgcacatacc ggatccattg | 3540 | |
| tctacgacaa gagccgctac atcgtcgtca cacatgttgt cttttgaggt tggacactgc | 3600 | |
| tcactagaca gaaaaaccctc gtgccggacc gaatacccgg tctgaacgag ggcggccgca | 3660 | |
| catgaggatc acccatgtcc gcgggctagc taagatccgc tctaaccgaa aaggaaggag | 3720 | |
| ttagacaacc tgaagtctag gtccctattt attttttat agttatgtta gtattaagaa | 3780 | |
| cgttatttat atttcaaatt tttctttttt ttctgtacag acgcgtgtac gcatgtaaca | 3840 | |
| ttatactgaa aaccttgctt gagaaggttt tgggacgctc gaagatccag ctgcattaat | 3900 | |
| gaatcggcca acgcgcgggg agaggcggtt tgcgtattgg gcgctcttcc gcttcctcgc | 3960 | |
| tcactgactc gctgcgctcg tcgttcggc tgcggcgagc ggtatcagct cactcaaagg | 4020 | |
| cggtaatacg gttatccaca gaatcagggg ataacgcagg aaagaacatg tgagcaaaag | 4080 | |
| gccagcaaaa ggccaggaac cgtaaaaagg ccgcgttgct ggcgttttc cataggctcc | 4140 | |
| gccccctga cgagcatcac aaaaatcgac gctcaagtca gaggtggcga aacccgacag | 4200 | |
| gactataaag ataccaggcg tttccccctg gaagctccct cgtgcgctct cctgttccga | 4260 | |
| ccctgccgct taccggatac ctgtccgcct ttctcccttc gggaagcgtg gcgctttctc | 4320 | |
| atagctcacg ctgtaggtat ctcagttcgg tgtaggtcgt tcgctccaag ctgggctgtg | 4380 | |
| tgcacgaacc ccccgttcag cccgaccgct gcgccttatc cggtaactat cgtcttgagt | 4440 | |
| ccaacccggt aagacacgac ttatcgccac tggcagcagc cactggtaac aggattagca | 4500 | |
| gagcgaggta tgtaggcggt gctacagagt tcttgaagtg gtggcctaac tacggctaca | 4560 | |
| ctagaaggac agtatttggt atctgcgctc tgctgaagcc agttaccttc ggaaaaagag | 4620 | |
| ttggtagctc ttgatccggc aaacaaacca ccgctggtag cggtggtttt tttgtttgca | 4680 | |
| agcagcagat tacgcgcaga aaaaaggat ctcaagaaga tcctttgatc ttttctacgg | 4740 | |
| ggtctgacgc tcagtggaac gaaaactcac gttaagggat tttggtcatg agattatcaa | 4800 | |
| aaaggatctt cacctagatc cttttaaatt aaaaatgaag ttttaaatca atctaaagta | 4860 | |
| tatatgagta aacttggtct gacagttacc aatgcttaat cagtgaggca cctatctcag | 4920 | |
| cgatctgtct atttcgttca tccatagttg cctgactccc cgtcgtgtag ataactacga | 4980 | |
| tacgggaggg cttaccatct ggccccagtg ctgcaatgat accgcgagac ccacgctcac | 5040 | |
| cggctccaga tttatcagca ataaaccagc cagccggaag ggccgagcgc agaagtggtc | 5100 | |
| ctgcaacttt atccgcctcc atccagtcta ttaattgttg ccgggaagct agagtaagta | 5160 | |
| gttcgccagt taatagtttg cgcaacgttg ttgccattgc tacaggcatc gtggtgtcac | 5220 | |
| gctcgtcgtt tggtatggct tcattcagct ccggttccca acgatcaagg cgagttacat | 5280 | |
| gatcccccat gttgtgcaaa aaagcggtta gctccttcgg tcctccgatc gttgtcagaa | 5340 | |

```
gtaagttggc cgcagtgtta tcactcatgg ttatggcagc actgcataat tctcttactg    5400
tcatgccatc cgtaagatgc tttttctgtga ctggtgagta ctcaaccaag tcattctgag    5460
aatagtgtat gcggcgaccg agttgctctt gcccggcgtc aatacgggat aataccgcgc    5520
cacatagcag aactttaaaa gtgctcatca ttggaaaacg ttcttcgggg cgaaaactct    5580
caaggatctt accgctgttg agatccagtt cgatgtaacc cactcgtgca cccaactgat    5640
cttcagcatc ttttactttc accagcgttt ctgggtgagc aaaaacagga aggcaaaatg    5700
ccgcaaaaaa gggaataagg gcgacacgga aatgttgaat actcatactc ttcctttttc    5760
aatattattg aagcatttat cagggttatt gtctcatgag cggatacata tttgaatgta    5820
tttagaaaaa taaacaaata ggggttccgc gcacatttcc ccgaaaagtg ccacctgaac    5880
gaagcatctg tgcttcattt tgtagaacaa aaatgcaacg cgagagcgct aattttcaa     5940 acaaagaatc tgagctgcat ttttacagaa cagaaatgca acgcgaaagc gctatttac     6000 caacgaagaa tctgtgcttc atttttgtaa aacaaaaatg caacgcgaga gcgctaattt    6060
ttcaaacaaa gaatctgagc tgcattttta cagaacagaa atgcaacgcg agagcgctat    6120
tttaccaaca aagaatctat acttctttt tgttctacaa aaatgcatcc cgagagcgct    6180 attttctaa caaagcatct tagattactt tttttctcct ttgtgcgctc tataatgcag    6240
tctcttgata acttttgca ctgtaggtcc gttaaggtta gaagaaggct actttggtgt    6300 ctatttctc ttccataaaa aaagcctgac tccacttccc gcgttactg attactagcg    6360 aagctgcggg tgcatttttt caagataaag gcatccccga ttatattcta taccgatgtg    6420
gattgcgcat acttttgtgaa cagaaagtga tagcgttgat gattcttcat tggtcagaaa    6480
attatgaacg gtttcttcta ttttgtctct atatactacg tataggaaat gtttacattt    6540
tcgtattgtt ttcgattcac tctatgaata gttcttacta caattttttt gtctaaagag    6600
taatactaga gataaacata aaaaatgtag aggtcgagtt tagatgcaag ttcaaggagc    6660
gaaaggtgga tgggtaggtt atataggat atagcacaga gatatatagc aaagagatac    6720
ttttgagcaa tgtttgtgga agcggtattc gcaatatttt agtagctcgt tacagtccgg    6780
tgcgtttttg gttttttgaa agtgcgtctt cagagcgctt ttggttttca aaagcgctct    6840
gaagttccta tactttctag agaataggaa cttcggaata ggaacttcaa agcgtttccg    6900
aaaacgagcg cttccgaaaa tgcaacgcga gctgcgcaca tacagctcac tgttcacgtc    6960
gcacctatat ctgcgtgttg cctgtatata tatatacatg agaagaacgg catagtgcgt    7020
gtttatgctt aaatgcgtac ttatatgcgt ctatttatgt aggatgaaag gtagtctagt    7080
acctcctgtg atattatccc attccatgcg gggtatcgta tgcttccttc agcactaccc    7140
tttagctgtt ctatatgctg ccactcctca attggattag tctcatcctt caatgctatc    7200
atttcctttg atattggatc atattaagaa accattatta tcatgacatt aacctataaa    7260
aataggcgta tcacgaggcc ctttcgtc                                       7288
```

<210> SEQ ID NO 46
<211> LENGTH: 7620
<212> TYPE: DNA
<213> ORGANISM: Artificial Sequence
<220> FEATURE:
<223> OTHER INFORMATION: Recombinant plasmid pAPSE10446; beta actin stem
      loop + coat protein
<220> FEATURE:
<221> NAME/KEY: promoter
<222> LOCATION: (187)..(467)
<223> OTHER INFORMATION: yeast TRP1 promoter
<220> FEATURE:

```
<221> NAME/KEY: gene
<222> LOCATION: (468)..(1142)
<223> OTHER INFORMATION: yeast TRP1 gene
<220> FEATURE:
<221> NAME/KEY: misc_feature
<222> LOCATION: (2082)..(2087)
<223> OTHER INFORMATION: restriction endonuclease SacI recognition site
<220> FEATURE:
<221> NAME/KEY: gene
<222> LOCATION: (2091)..(2480)
<223> OTHER INFORMATION: bacteriophage MS2 coat protein gene
<220> FEATURE:
<221> NAME/KEY: misc_feature
<222> LOCATION: (2484)..(2489)
<223> OTHER INFORMATION: restriction endonuclease EcoRI recognition site
<220> FEATURE:
<221> NAME/KEY: promoter
<222> LOCATION: (2494)..(3158)
<223> OTHER INFORMATION: yeast GAL1, 10 bidirectional promoter
<220> FEATURE:
<221> NAME/KEY: misc_feature
<222> LOCATION: (3176)..(3194)
<223> OTHER INFORMATION: bacteriophage MS2 pac sequence
<220> FEATURE:
<221> NAME/KEY: misc_feature
<222> LOCATION: (3195)..(3202)
<223> OTHER INFORMATION: restriction endonuclease AsiSI recognition
      sequence
<220> FEATURE:
<221> NAME/KEY: misc_feature
<222> LOCATION: (3204)..(3497)
<223> OTHER INFORMATION: beta actin sense gene fragment
<220> FEATURE:
<221> NAME/KEY: misc_feature
<222> LOCATION: (3497)..(3504)
<223> OTHER INFORMATION: restriction endonuclease PmeI recognition site
<220> FEATURE:
<221> NAME/KEY: misc_feature
<222> LOCATION: (3565)..(3583)
<223> OTHER INFORMATION: bacteriophage MS2 pac sequence
<220> FEATURE:
<221> NAME/KEY: misc_feature
<222> LOCATION: (3662)..(3956)
<223> OTHER INFORMATION: beta actin antisense strand gene fragment
<220> FEATURE:
<221> NAME/KEY: misc_feature
<222> LOCATION: (3992)..(4010)
<223> OTHER INFORMATION: bacteriophage MS2 pac sequence
<220> FEATURE:
<221> NAME/KEY: terminator
<222> LOCATION: (4027)..(4216)
<223> OTHER INFORMATION: yeast CYC1 terminator
<220> FEATURE:
<221> NAME/KEY: misc_feature
<222> LOCATION: (6210)..(7552)
<223> OTHER INFORMATION: yeast 2 micron ori

<400> SEQUENCE: 46
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttctttttt tgccgattaa     360
gaattaattc ggtcgaaaaa agaaaaggag agggccaaga ggggggcat tggtgactat     420 tgagcacgtg agtatacgtg attaagcaca caaaggcagc ttggagtatg tctgttatta     480
atttcacagg tagttctggt ccattggtga aagtttgcgg cttgcagagc acagaggccg     540
cagaatgtgc tctagattcc gatgctgact tgctgggtat tatatgtgtg cccaatagaa     600
```

```
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa aagactcgta tttccaaaag      840
actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgg tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttgttaa atcagctcat tttttaacca ataggccgaa      1320
atcggcaaaa tcccttataa atcaaaagaa tagaccgaga tagggttgag tgttgttcca     1380
gtttggaaca agagtccact attaaagaac gtggactcca acgtcaaagg gcgaaaaacc     1440
gtctatcagg gcgatggccc actacgtgaa ccatcaccct aatcaagttt ttggggtcg      1500 aggtgccgta aagcactaaa tcggaaccct aaagggagcc ccgatttag agcttgacgg      1560 ggaaagccgg cgaacgtggc gagaaaggaa gggaagaaag cgaaaggagc gggcgctagg     1620
gcgctggcaa gtgtagcggt cacgctgcgc gtaaccacca cacccgccgc gcttaatgcg     1680
ccgctacagg gcgcgtcgcg ccattcgcca ttcaggctgc gcaactgttg ggaagggcga     1740
tcggtgcggg cctcttcgct attacgccag ctgaattgga gcgacctcat gctataccctg    1800 agaaagcaac ctgacctaca ggaaagagtt actcaagaat aagaattttc gttttaaaac     1860
ctaagagtca cttttaaaatt tgtatacact tatttttttt ataacttatt taataataaa   1920
aatcataaat cataagaaat tcgcttattt agaagtgtca acaacgtatc taccaacgat     1980 ttgaccctt tccatctttt cgtaaatttc tggcaaggta gacaagccga caaccttgat     2040
tggagacttg accaaacctc tggcgaagaa ttgttaatta agagctctta ttagtaaatg     2100
ccagagttag cagcgattgc agatgggatc ggattaccgt ctttcagcag gccctgcatt    2160
gccttaacaa tcagttcgca gtcggagttc gtcgcaaaaa tcggaatagt cagttccatg    2220
ttgaggtaag agcgccaggc cgcaactggg agttctacgc cgcctacggt ctgcgttgcg     2280
actttcggta cttcaacttt gatggtgtat ttgcgattct gcgcgctaga ctgacgaacg     2340
gagcacgtga ctttgtaggc ctgagagcgg ctgttagagc taatccattc cgcaacaccg     2400
ttggcgaagt tggacggagc tacgtaacg tcacccgtac cgccgttatc aaccagaacg      2460
aattgggtaa agttagacgc catgaattcg aattttcaaa aattcttact tttttttgg     2520 atggacgcaa agaagtttaa taatcatatt acatggcatt accaccatat acatatccat     2580
atacatatcc atatctaatc ttacttatat gttgtggaaa tgtaaagagc cccattatct     2640
tagcctaaaa aaaccttctc tttggaactt tcagtaatac gcttaactgc tcattgctat     2700
attgaagtac ggattagaag ccgccgagcg ggtgacagcc ctccgaagga agactctcct     2760
ccgtgcgtcc tcgtcttcac cggtcgcgtt cctgaaacgc agatgtgcct cgcgccgcac     2820
tgctccgaac aataaagatt ctacaatact agctttatg gttatgaaga ggaaaaattg     2880
gcagtaacct ggccccacaa accttcaaat gaacgaatca aattaacaac cataggatga     2940
taatgcgatt agtttttttag ccttatttct ggggtaatta atcagcgaag cgatgatttt     3000
```

```
tgatctatta acagatatat aaatgcaaaa actgcataac cactttaact aatactttca    3060
acattttcgg tttgtattac ttcttattca aatgtaataa aagtatcaac aaaaaattgt    3120
taatatacct ctatacttta acgtcaagga gaaaaaaccc cggatccatt taaatacatg    3180
aggattaccc atgtgcgatc gcgcacgagg ttttctgtc tagtgagcag tgtccaacct     3240
caaaagacaa catgtgtgac gacgatgtag cggctcttgt cgtagacaat ggatccggta    3300
tgtgcaaagc cggtttcgca ggagatgacg cacccgtgc cgtcttcccc tcgatcgtcg     3360
gtcgcccaag gcatcaagga gtcatggtcg gtatgggaca aaaggactca tacgtaggag    3420
atgaagccca aagcaaaaga ggtatcctca ccctgaaata ccccatcgaa cacggtatca    3480
tcaccaactg ggatgagttt aaaccctcta gctgctttac aaagtactgg ttccctttcc    3540
agcgggatgc tttatctaaa cgcaacatga ggatcaccca tgtcgccaca tcgcttccta    3600
gttccgctgg gatccatcgt tggcggccga agccgccatt ccatagtgag ttctggcgcg    3660
cctcatccca gttggtgatg ataccgtgtt cgatggggta tttcagggtg aggataccct    3720
ttttgctttg ggcttcatct cctacgtatg agtccttttg tcccataccg accatgactc    3780
cttgatgcct tgggcgaccg acgatcgagg ggaagacggc acggggtgcg tcatctcctg    3840
cgaaaccggc tttgcacata ccggatccat tgtctacgac aagagccgct acatcgtcgt    3900
cacacatgtt gtcttttgag gttggacact gctcactaga cagaaaaacc tcgtgccgga    3960
ccgaataccc ggtctgaacg agggcggccg cacatgagga tcacccatgt ccgcgggcta    4020
gctaagatcc gctctaaccg aaaaggaagg agttagacaa cctgaagtct aggtccctat    4080 ttatttttt atagttatgt tagtattaag aacgttattt atatttcaaa tttttctttt      4140
ttttctgtac agacgcgtgt acgcatgtaa cattatactg aaaaccttgc ttgagaaggt    4200
tttgggacgc tcgaagatcc agctgcatta atgaatcggc caacgcgcgg ggagaggcgg    4260
tttgcgtatt gggcgctctt ccgcttcctc gctcactgac tcgctgcgct cggtcgttcg    4320
gctgcggcga gcggtatcag ctcactcaaa ggcggtaata cggttatcca cagaatcagg    4380
ggataacgca ggaaagaaca tgtgagcaaa aggccagcaa aaggccagga accgtaaaaa    4440
ggccgcgttg ctggcgtttt tccataggct ccgcccccct gacgagcatc acaaaaatcg    4500
acgctcaagt cagaggtggc gaaacccgac aggactataa agataccagg cgtttccccc    4560
tggaagctcc ctcgtgcgct ctcctgttcc gaccctgccg cttaccggat acctgtccgc    4620
ctttctccct tcgggaagcg tggcgctttc tcatagctca cgctgtaggt atctcagttc    4680
ggtgtaggtc gttcgctcca agctgggctg tgtgcacgaa ccccccgttc agcccgaccg    4740
ctgcgcctta tccggtaact atcgtcttga gtccaacccg gtaagacacg acttatcgcc    4800
actggcagca gccactggta acaggattag cagagcgagg tatgtaggcg gtgctacaga    4860
gttcttgaag tggtggccta actacggcta cactagaagg acagtatttg gtatctgcgc    4920
tctgctgaag ccagttacct tcggaaaaag agttggtagc tcttgatccg gcaaacaaac    4980
caccgctggt agcggtggtt tttttgtttg caagcagcag attacgcgca gaaaaaaagg    5040
atctcaagaa gatcctttga tcttttctac ggggtctgac gctcagtgga acgaaaactc    5100
acgttaaggg attttggtca tgagattatc aaaaaggatc ttcacctaga tccttttaaa    5160
ttaaaaatga agttttaaat caatctaaag tatatatgag taaacttggt ctgacagtta    5220
ccaatgctta atcagtgagg cacctatctc agcgatctgt ctatttcgtt catccatagt    5280
tgcctgactc cccgtcgtgt agataactac gatacgggag ggcttaccat ctggccccag    5340
```

```
tgctgcaatg ataccgcgag acccacgctc accggctcca gatttatcag caataaacca    5400
gccagccgga agggccgagc gcagaagtgg tcctgcaact ttatccgcct ccatccagtc    5460
tattaattgt tgccgggaag ctagagtaag tagttcgcca gttaatagtt tgcgcaacgt    5520
tgttgccatt gctacaggca tcgtggtgtc acgctcgtcg tttggtatgg cttcattcag    5580
ctccggttcc caacgatcaa ggcgagttac atgatccccc atgttgtgca aaaaagcggt    5640
tagctccttc ggtcctccga tcgttgtcag aagtaagttg gccgcagtgt tatcactcat    5700
ggttatggca gcactgcata attctcttac tgtcatgcca tccgtaagat gcttttctgt    5760
gactggtgag tactcaacca agtcattctg agaatagtgt atgcggcgac cgagttgctc    5820
ttgcccggcg tcaatacggg ataataccgc gccacatagc agaactttaa aagtgctcat    5880
cattggaaaa cgttcttcgg ggcgaaaact ctcaaggatc ttaccgctgt tgagatccag    5940
ttcgatgtaa cccactcgtg cacccaactg atcttcagca tcttttactt tcaccagcgt    6000
ttctgggtga gcaaaaacag gaaggcaaaa tgccgcaaaa aagggaataa gggcgacacg    6060
gaaatgttga atactcatac tcttcctttt tcaatattat tgaagcattt atcagggtta    6120
ttgtctcatg agcggataca tatttgaatg tatttagaaa aataaacaaa tagggggttcc    6180
gcgcacattt ccccgaaaag tgccacctga acgaagcatc tgtgcttcat tttgtagaac    6240
aaaaatgcaa cgcgagagcg ctaattttc aaacaaagaa tctgagctgc attttacag    6300
aacagaaatg caacgcgaaa gcgctatttt accaacgaag aatctgtgct tcattttgt    6360
aaaacaaaaa tgcaacgcga gagcgctaat ttttcaaaca aagaatctga gctgcatttt    6420
tacagaacag aaatgcaacg cgagagcgct attttaccaa caaagaatct atacttcttt    6480
tttgttctac aaaaatgcat cccgagagcg ctattttct aacaaagcat cttagattac    6540
tttttttctc ctttgtgcgc tctataatgc agtctcttga taacttttg cactgtaggt    6600
ccgttaaggt tagaagaagg ctactttggt gtctattttc tcttccataa aaaaagcctg    6660
actccacttc ccgcgtttac tgattactag cgaagctgcg ggtgcatttt ttcaagataa    6720
aggcatcccc gattatattc tataccgatg tggattgcgc atactttgtg aacagaaagt    6780
gatagcgttg atgattcttc attggtcaga aaattatgaa cggtttcttc tattttgtct    6840
ctatatacta cgtataggaa atgtttacat tttcgtattg ttttcgattc actctatgaa    6900
tagttcttac tacaattttt ttgtctaaag agtaatacta gagataaaca taaaaatgt    6960
agaggtcgag tttagatgca agttcaagga gcgaaaggtg gatgggtagg ttatataggg    7020
atatagcaca gagatatata gcaaagagat acttttgagc aatgtttgtg gaagcggtat    7080
tcgcaatatt ttagtagctc gttacagtcc ggtgcgtttt tggttttttg aaagtgcgtc    7140
ttcagagcgc ttttggtttt caaaagcgct ctgaagttcc tatactttct agagaatagg    7200
aacttcggaa taggaacttc aaagcgtttc cgaaaacgag cgcttccgaa aatgcaacgc    7260
gagctgcgca catacagctc actgttcacg tcgcacctat atctgcgtgt tgcctgtata    7320
tatatataca tgagaagaac ggcatagtgc gtgtttatgc ttaaatgcgt acttatatgc    7380
gtctatttat gtaggatgaa aggtagtcta gtacctcctg tgatattatc ccattccatg    7440
cggggtatcg tatgcttcct tcagcactac cctttagctg ttctatatgc tgccactcct    7500
caattggatt agtctcatcc ttcaatgcta tcatttcctt tgatattgga tcatattaag    7560
aaaccattat tatcatgaca ttaacctata aaaataggcg tatcacgagg ccctttcgtc    7620
```